(12) United States Patent
Dalby et al.

(10) Patent No.: US 12,240,921 B2
(45) Date of Patent: Mar. 4, 2025

(54) PEPTIDES

(71) Applicant: Teitur Trophics ApS, Aarhus N (DK)

(72) Inventors: Anders Dalby, Aarhus N (DK); Simon Mølgaard Jensen, Aarhus N (DK); Mathias Kaas Ollendorff, Aarhus N (DK); Kristian Strømgaard, Aarhus N (DK); Keld Fosgerau, Aarhus N (DK)

(73) Assignee: Teitur Trophics ApS, Hjortshoj (DK)

( * ) Notice: Subject to any disclaimer, the term of this patent is extended or adjusted under 35 U.S.C. 154(b) by 0 days.

(21) Appl. No.: 18/660,504

(22) Filed: May 10, 2024

(65) Prior Publication Data
US 2024/0301005 A1      Sep. 12, 2024

Related U.S. Application Data

(63) Continuation of application No. PCT/EP2023/053211, filed on Feb. 9, 2023.

(30) Foreign Application Priority Data

Feb. 9, 2022  (EP) .................................. 22155992
Mar. 4, 2022  (EP) .................................. 22160222

(51) Int. Cl.
*C07K 7/64*     (2006.01)
*A61K 38/00*    (2006.01)

(52) U.S. Cl.
CPC .............. *C07K 7/64* (2013.01); *A61K 38/00* (2013.01)

(58) Field of Classification Search
None
See application file for complete search history.

(56) References Cited

U.S. PATENT DOCUMENTS

| | | |
|---|---|---|
| 6,511,824 B1 | 1/2003 | Buchman et al. |
| 6,703,491 B1 | 9/2004 | Homburger et al. |
| 8,066,997 B2 | 11/2011 | Nykjær et al. |
| 8,460,657 B2 | 11/2013 | Nykjær et al. |
| 8,703,125 B2 | 4/2014 | Pedersen et al. |
| 8,815,808 B2 | 8/2014 | Nykjær et al. |
| 8,986,690 B2 | 3/2015 | Nykjær et al. |
| 9,493,522 B2 | 11/2016 | Wells et al. |
| 9,605,073 B2 | 3/2017 | Nykjær et al. |
| 9,670,263 B2 | 6/2017 | Pedersen et al. |
| 11,421,016 B2 | 8/2022 | Nguyen et al. |
| 11,740,237 B2 | 8/2023 | Karlsson et al. |
| 2007/0083334 A1 | 12/2007 | Mintz et al. |
| 2008/0051326 A1 | 2/2008 | Alexander et al. |
| 2013/0336988 A1 | 12/2013 | Hempstead et al. |
| 2017/0158766 A1 | 6/2017 | Nykjær et al. |
| 2017/0240611 A1 | 8/2017 | Pedersen et al. |
| 2019/0345216 A1 | 11/2019 | Jensen et al. |
| 2022/0403007 A1 | 12/2022 | Nguyen et al. |
| 2023/0048732 A1 | 2/2023 | Vigneault et al. |
| 2023/0312652 A1 | 5/2023 | Jensen et al. |

FOREIGN PATENT DOCUMENTS

| | | |
|---|---|---|
| WO | WO2004/056385 A2 | 7/2004 |
| WO | WO2006/110185 A2 | 10/2006 |
| WO | WO2009/155932 A2 | 12/2009 |
| WO | WO2010/021822 A2 | 2/2010 |
| WO | WO2010/069331 A2 | 6/2010 |
| WO | WO2012/068332 A2 | 5/2012 |
| WO | WO2016/172722 A1 | 10/2016 |
| WO | WO2017/101956 A1 | 6/2017 |
| WO | WO2019/211477 A1 | 11/2019 |
| WO | WO2021/242909 A1 | 12/2021 |
| WO | WO2022/029281 A1 | 2/2022 |

OTHER PUBLICATIONS

Van Witteloostuijn et al., "Half-Life Extension of Biopharmaceuticals using Chemical Methods: Alternatives to PEGylation.", *ChemMedChem*, vol. 11, No. 22, (2016): pp. 2474-2495.
Derda and Jafari, "Synthetic Cross-linking of Peptides: Molecular Linchpins for Peptide Cyclization.", *Protein and Peptide Letters*, vol. 25, No. 12, (2018): pp. 1051-1075.
Bech et al., "Chemical Strategies for Half-Life Extension of Biopharmaceuticals: Lipidation and Its Alternatives", *ACS Med. Chem. Lett.*, vol. 9, (2018): pp. 577-580.
Kurtzhals et al., "Derivatization with fatty acids in peptide and protein drug discovery.", *Nature reviews. Drug discovery*, vol. 22, No. 1, (2023): pp. 59-80.
Østergaard et al., "The effect of fatty diacid acylation of human PYY3-36 on Y2 receptor potency and half-life in minipigs.", *Scientific reports*, vol. 11, No. 1, (2021): pp. 21179.
Ward et al., "Peptide lipidation stabilizes structure to enhance biological function.", *Molecular metabolism*, vol. 2, No. 4, (2013): pp. 468-479.
Kowalczyk et al., "Peptide Lipidation—A Synthetic Strategy to Afford Peptide Based Therapeutics.", *Advances in experimental medicine and biology*, vol. 1030, (2017): pp. 185-227.
Rocco et al., "Acyl lipidation of a peptide: effects on activity and epidermal permeability in vitro.", *Drug design, development and therapy*, vol. 10, (2016): pp. 2203-2209.
Database UniProt [Online], XP002767625, "The genome of a songbird".
Database Protein [Online], "hypothetical protein" [*Sphingobium* sp. AP49], XP002767626.
Database UniParc [Online], "hypothetical protein" [Syntrophobacter fumaroxidans] (strain DSM 10017/MPOB), XP002767627.
Rezgaoui et al., "Identification of SorCS2, a novel member of the VPS10 domain containing receptor family, prominently expressed in the developing mouse brain.", *Mechanisms of development*, vol. 100, No. 2, (2001): pp. 335-338.

(Continued)

*Primary Examiner* — Sergio Coffa
(74) *Attorney, Agent, or Firm* — Morgan, Lewis & Bockius LLP

(57) ABSTRACT

SorCS2 related lipidated cyclic peptides, cyclic peptides, lipidated linear peptides, linear peptides which may be of use in medicine, and related aspects.

13 Claims, 53 Drawing Sheets
Specification includes a Sequence Listing.

(56) References Cited

OTHER PUBLICATIONS

Glerup et al., "SorCS2 is required for BDNF-dependent plasticity in the hippocampus.", *Mol Psychiatry*, vol. 21, No. 12, (2016): pp. 1740-1751.

Hermey et al., "Characterization of sorCS1, an alternatively spliced receptor with completely different cytoplasmic domains that mediate different trafficking in cells", *The Journal of Biological Chemistry*, vol. 278, No. 9, (2003): pp. 7390-7396.

Leloup et al., "Structural insights into SorCS2-Nerve Growth Factor complex formation.", *Nature communications*, vol. 9, No. 1, (2018): pp. 2979.

International Search Report and Written opinion issued in corresponding Application No. WO 2023/152229, dated Aug. 17, 2023, 14 pages.

Lau, et al., "Discovery of the Once-Weekly Glucagon-Like Peptide-1 (GLP-1) Analogue Semaglutide," J. Med. Chem, vol. 58, pp. 7370-7380, 2015.

Fig. 7A-B
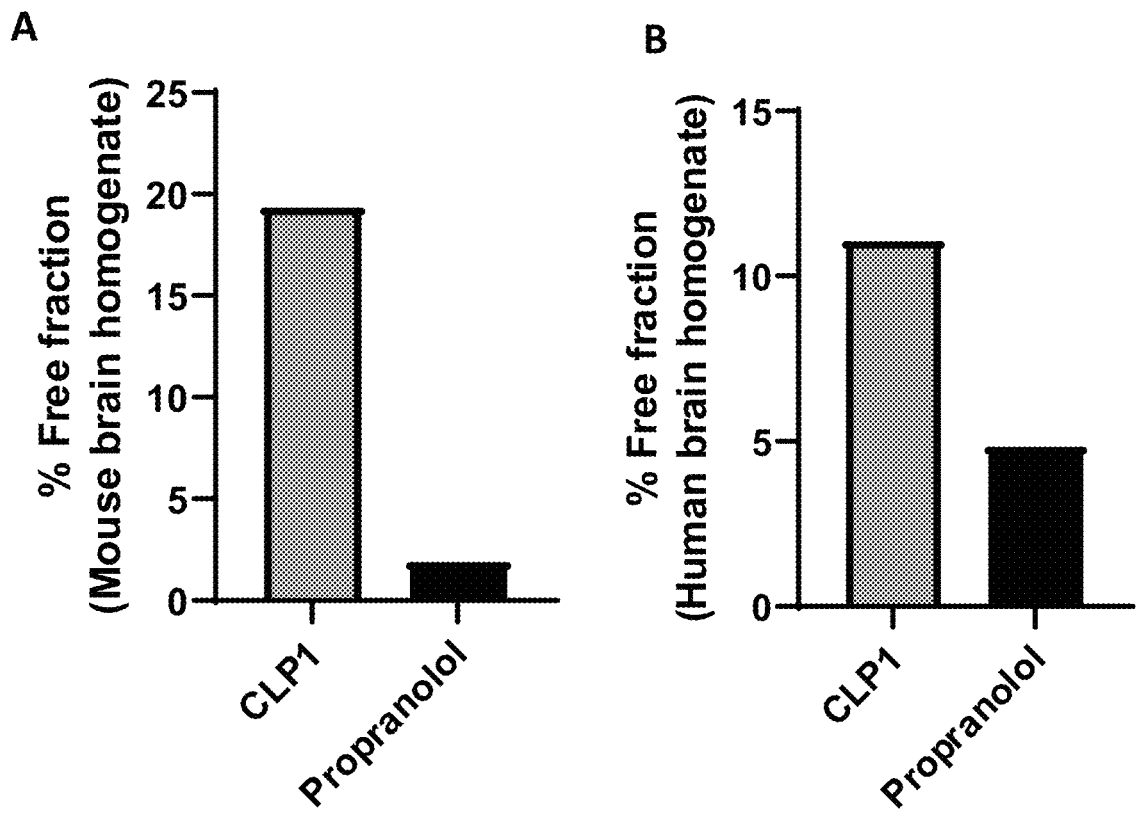
Fig. 8A
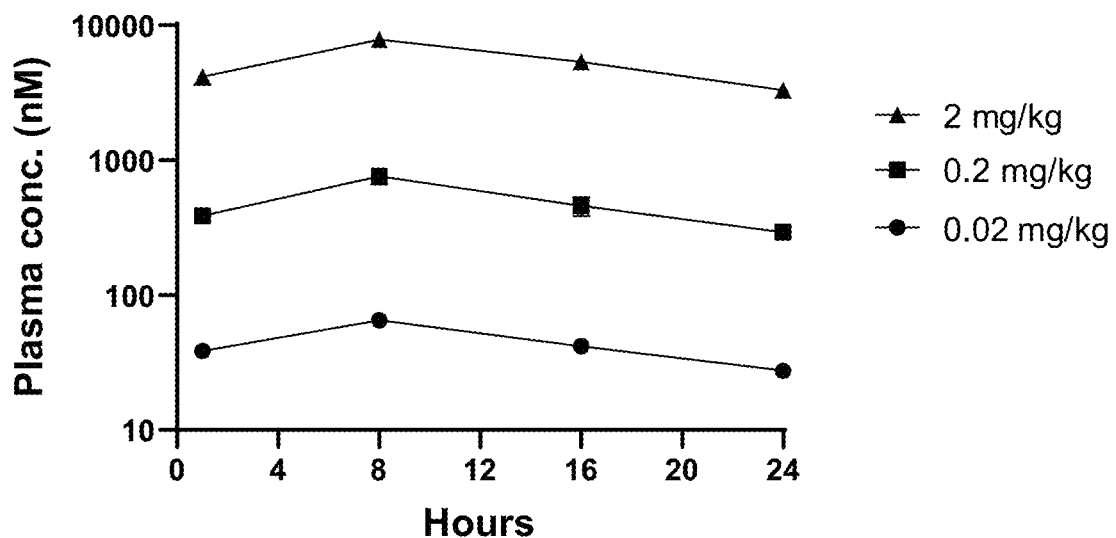

Fig. 9C
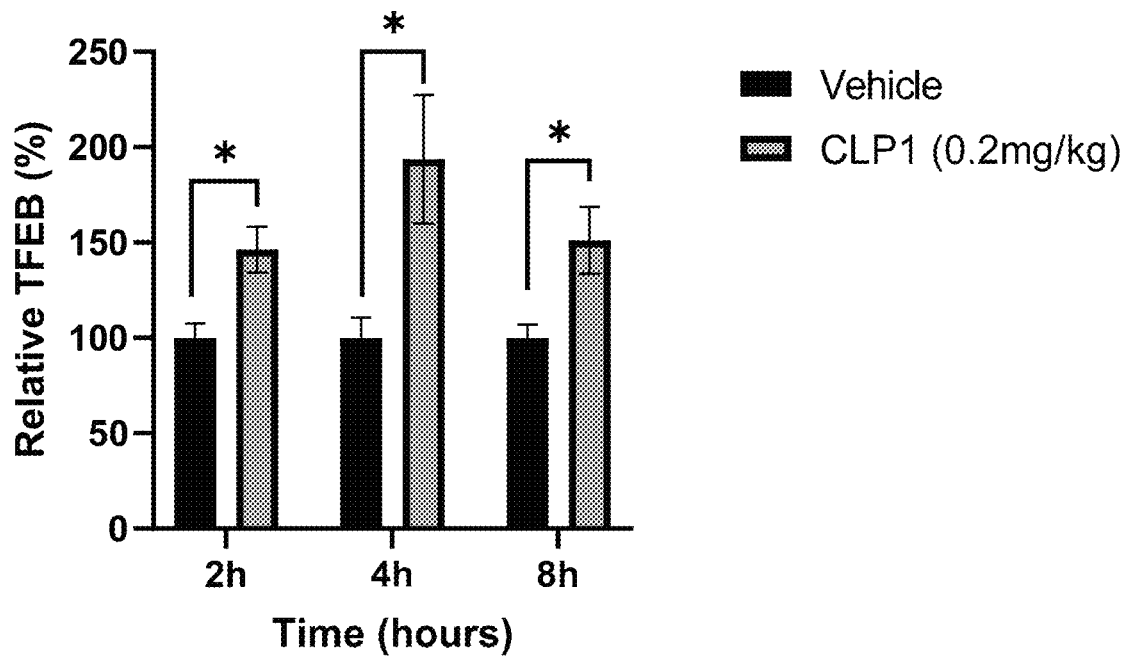
Fig. 10A-B
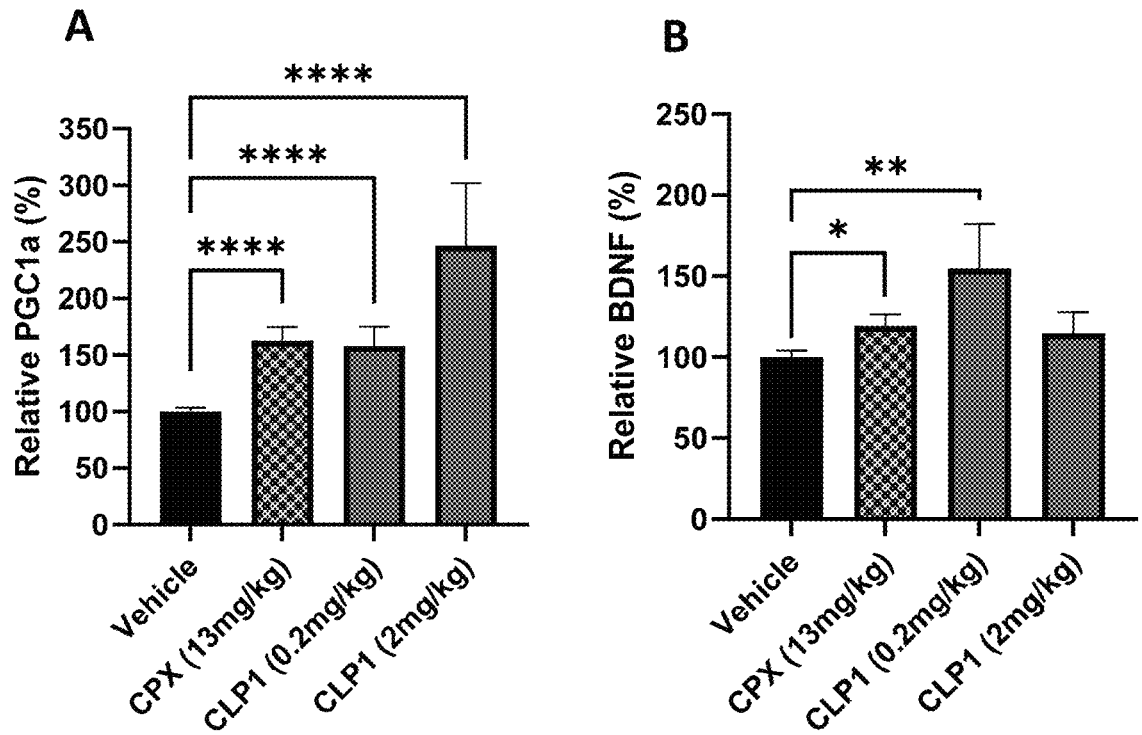

Fig. 11E
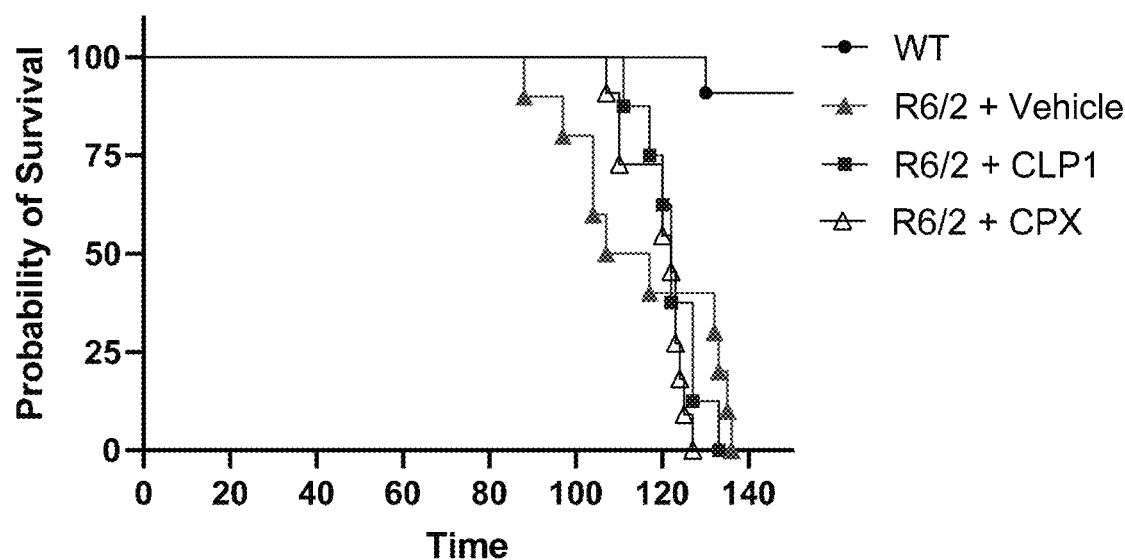
Fig. 11F
| | WT | R6/2 +Vehicle | R6/2 +CLP1 | R6/2 +CPX |
|---|---|---|---|---|
| Mean survival (days) | | 115 | 122 | 118 |
| Median survival (days) | | 109 | 122 | 122 |
Fig. 12A
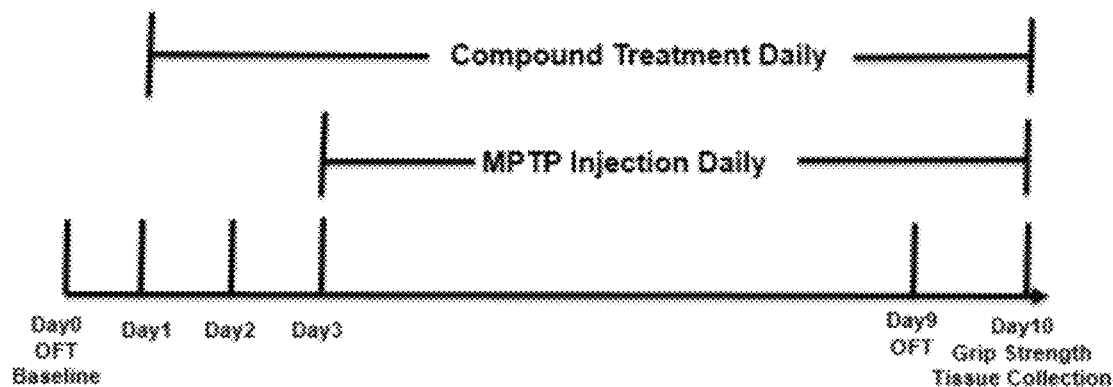

Fig. 12B-C
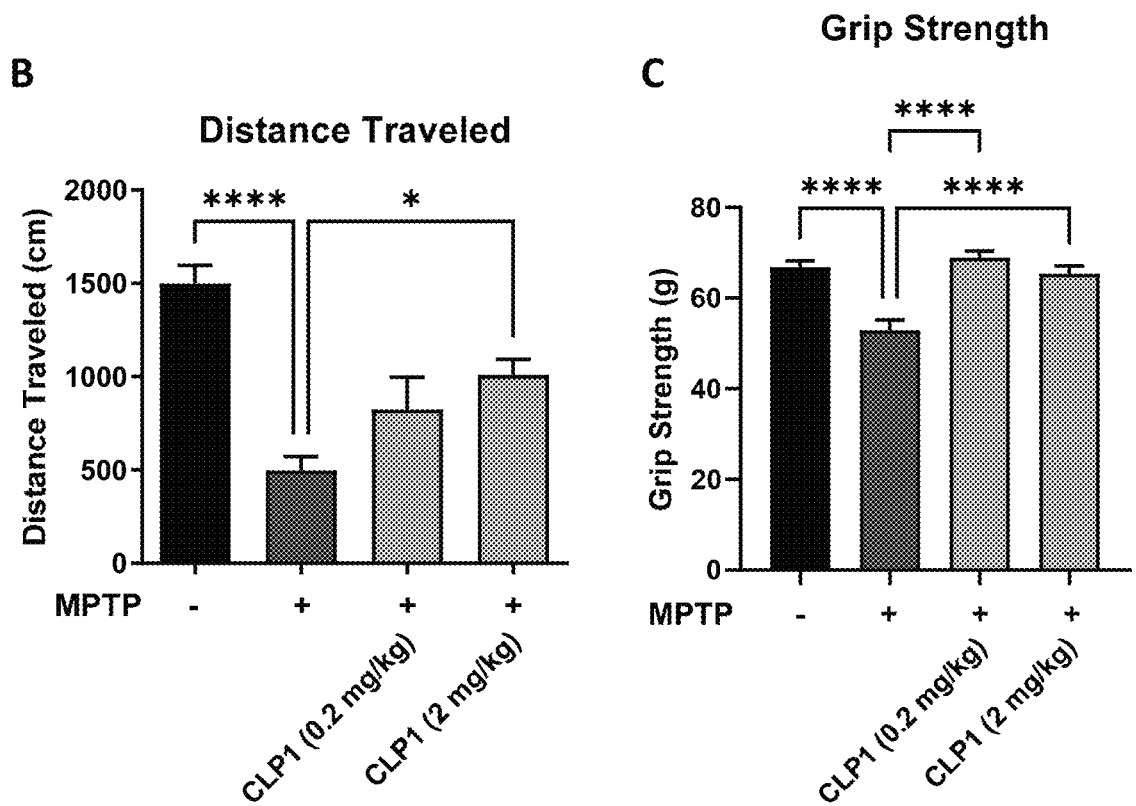
Fig. 12D
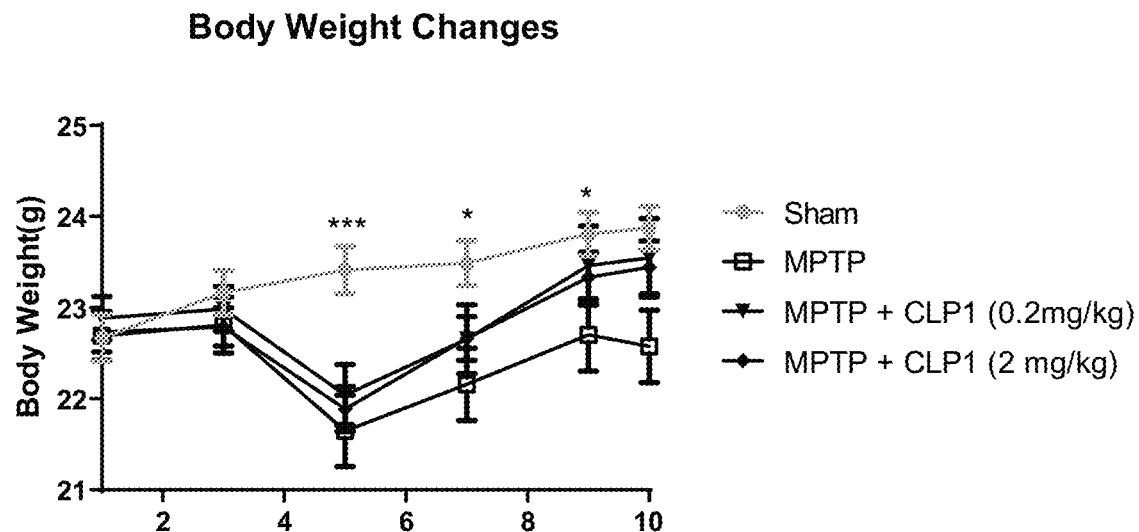

Fig. 13A cont.
MPTP + 0.2mg/kg 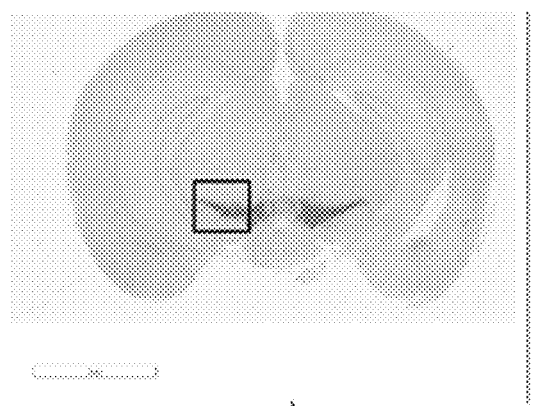
MPTP + 2mg/kg 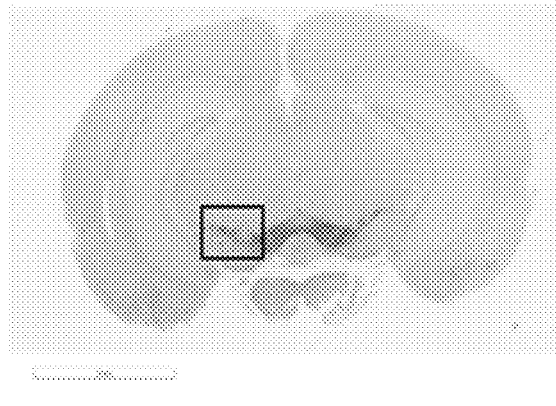
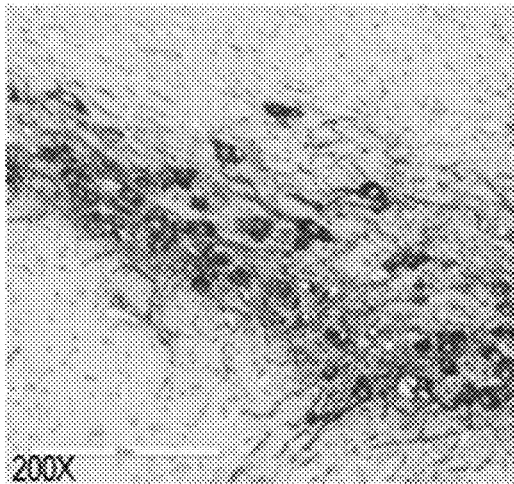
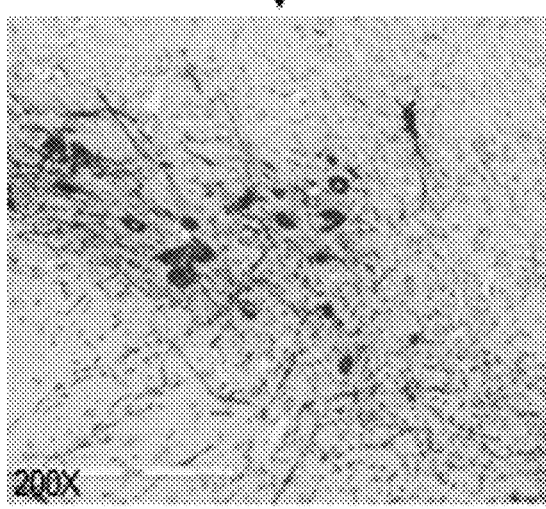

Fig. 14C
Substantia nigra
Untreated
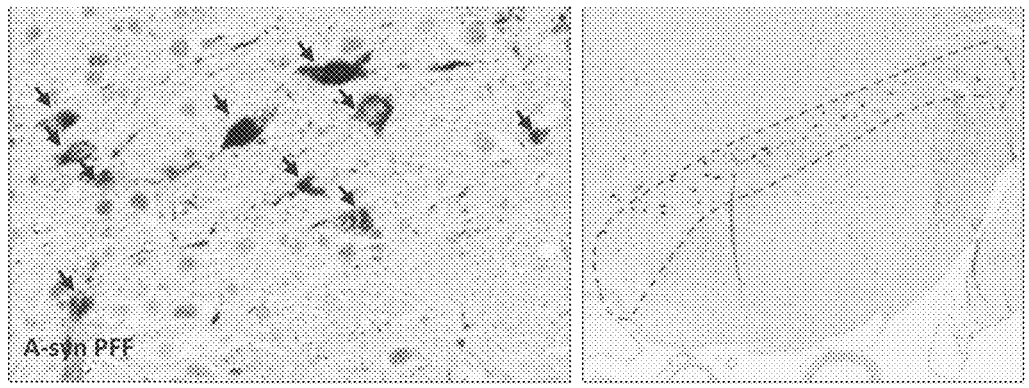
CLP1 (0.2mg/kg)
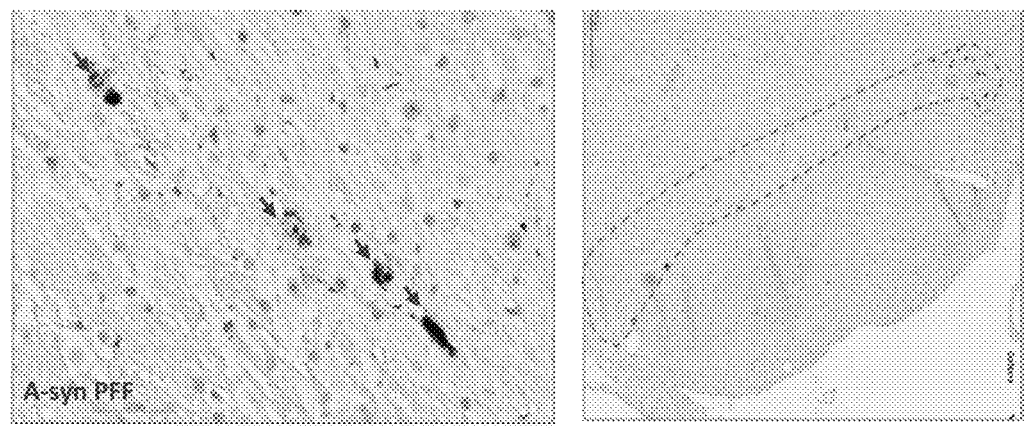

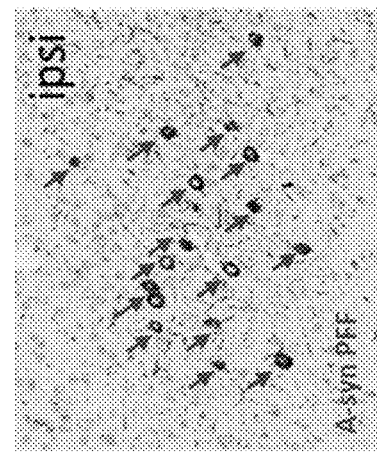
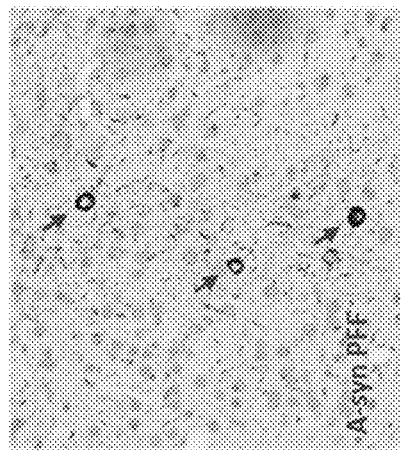
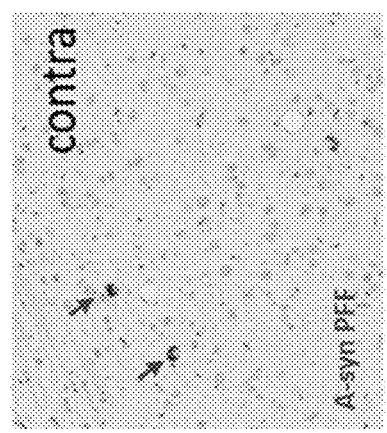
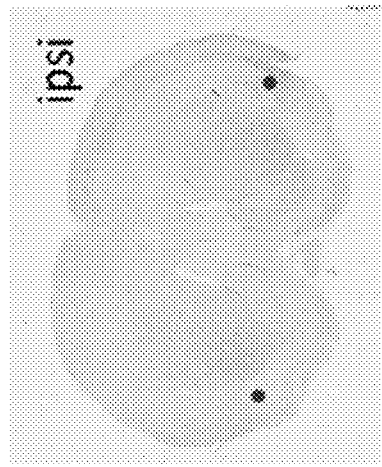
Fig. 14D

Fig. 14E
Amygdala ipsilateral
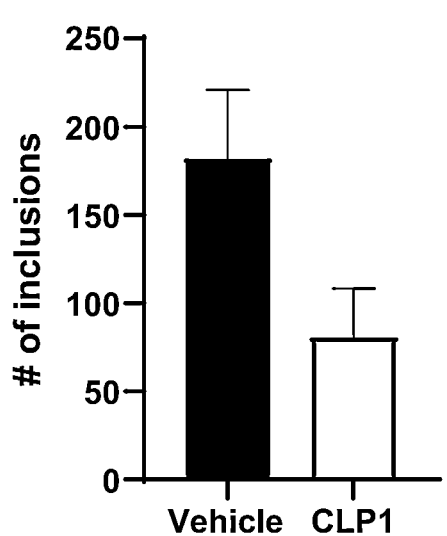
SN ipsilateral
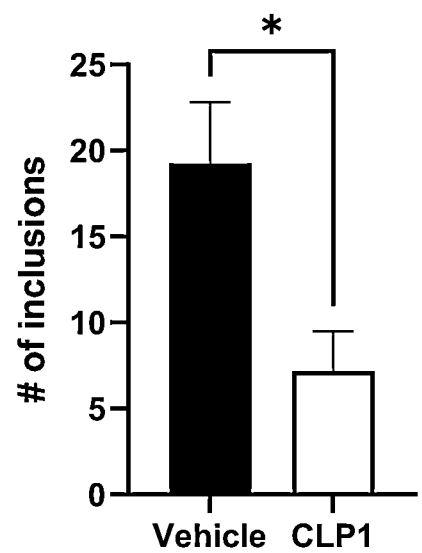
Amygdala contralateral
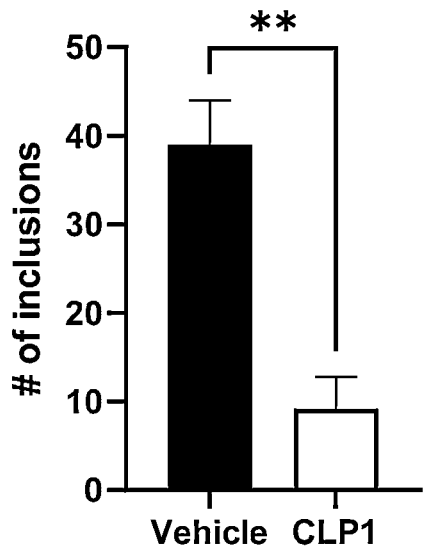

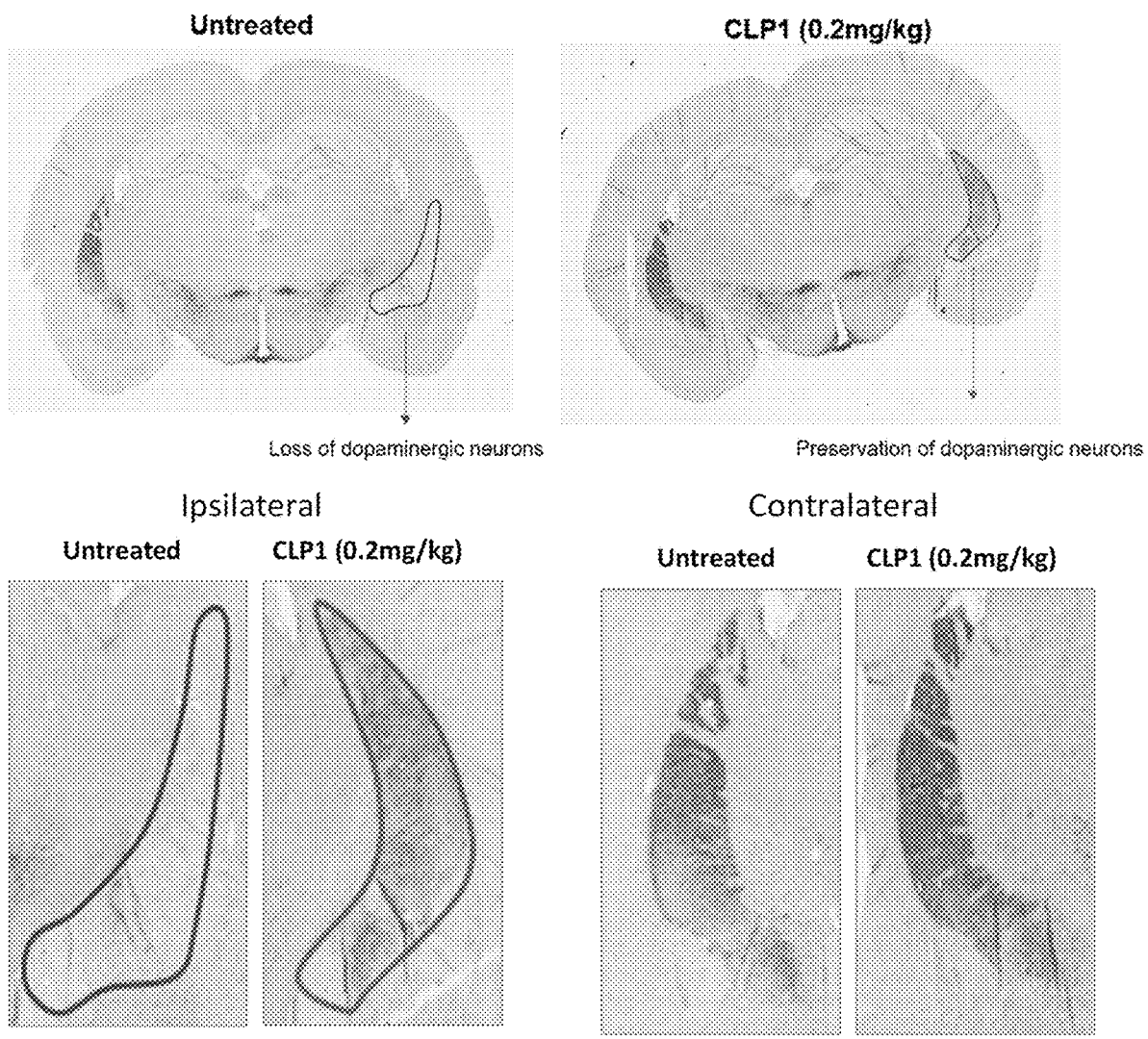

Fig. 16B-E
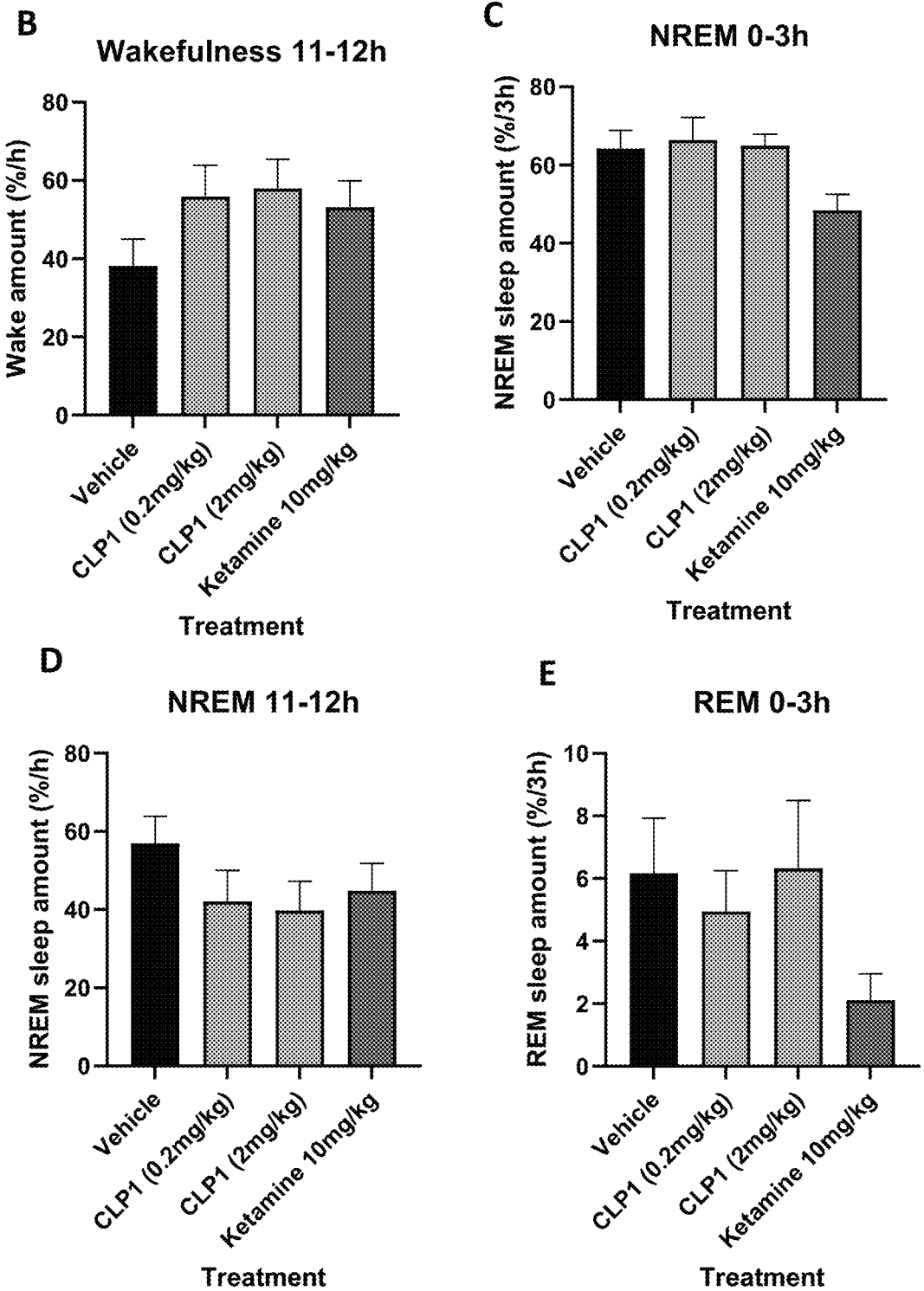

Fig. 18D
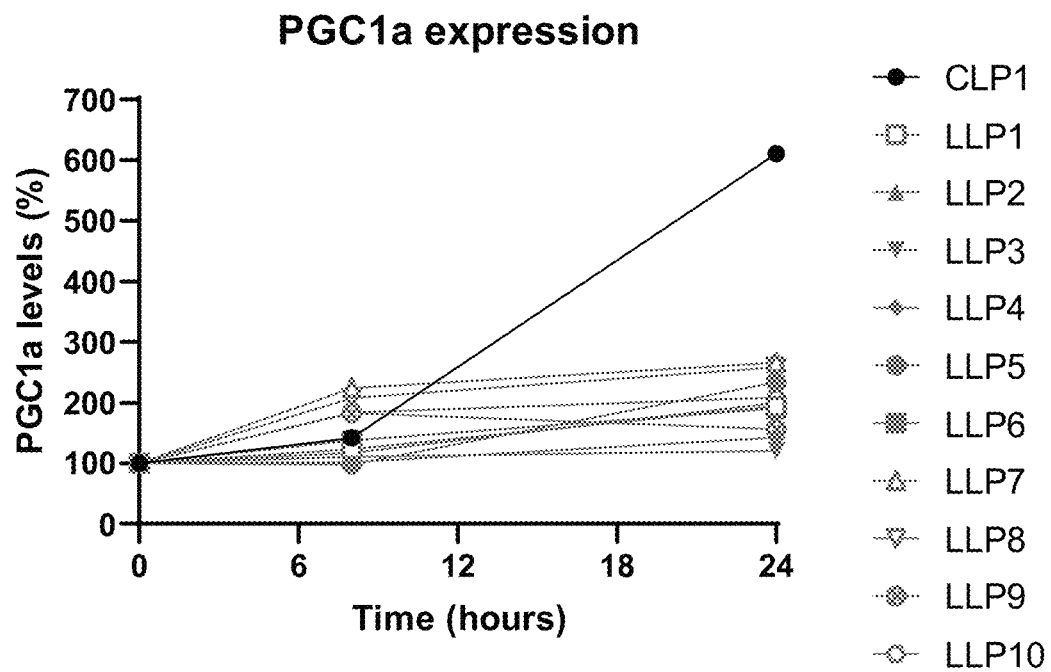
Fig. 19A-B
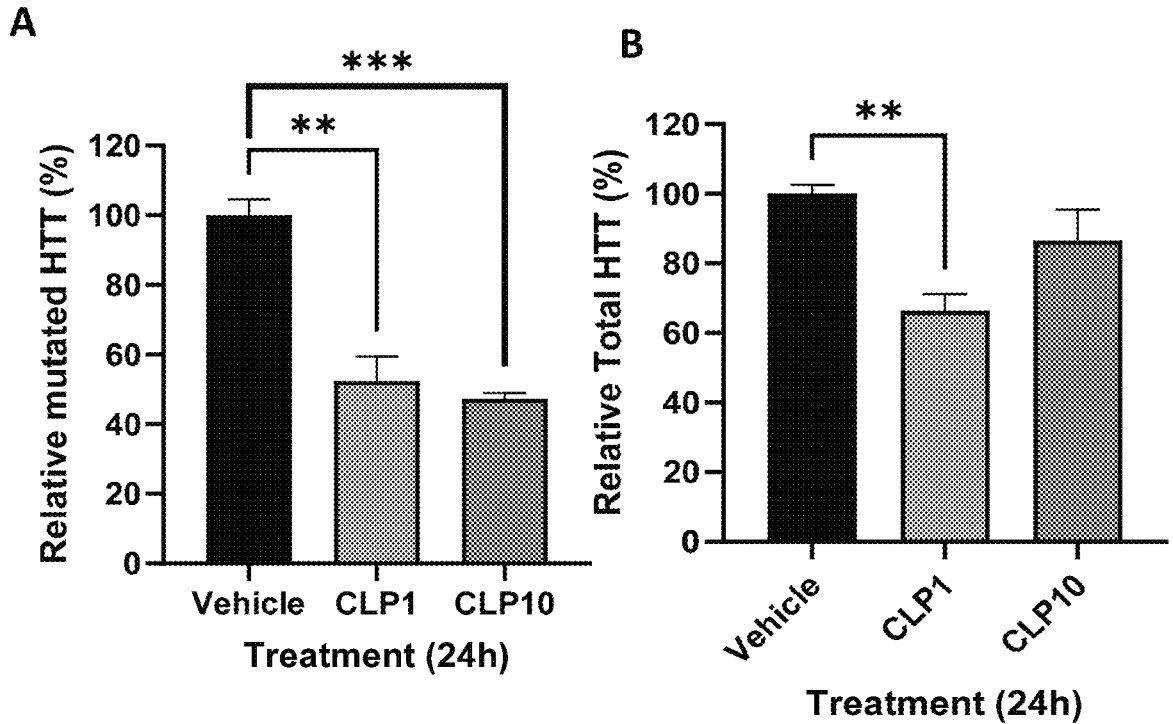

| Compound | t₁/₂ [hrs] | MRT [hrs] | AUC 0-t [μmol/L·h] | C_max [μmol/L] |
|---|---|---|---|---|
| CLP4 | 9.66 | 15.6 | 1,450 | 83.1 |
| CLP5 | 10.41 | 16.8 | 1,194 | 62.7 |
| CLP1 | 8.1 | 15.1 | 935 | 51.4 |
| CLP9 | 9.01 | 16.1 | 1,064 | 53.1 |
| CLP10 | 9.58 | 16.1 | 1,217 | 68.9 |

$t_{1/2}$ = elimination half-life
MRT = mean residence time (the average time a molecule stays in the body (absorption + half-life)
AUC = bioavailability
$C_{max}$ = max drug concentration

| Compound | t₁/₂ [hrs] | AUC 0-t [nmol/L·h] | Cmax [nmol/L] |
|---|---|---|---|
| CLP4 | 10.6 | 11436 | 507 |
| CLP5 | 10.4 | 8709 | 420 |
| CLP1 | 9.4 | 7617 | 423 |
| CLP9 | 10.9 | 8620 | 420 |
| CLP10 | 12.1 | 8923 | 446 |

$t_{1/2}$ = elimination half-life

AUC = bioavailability $C_{max}$ = max drug concentration

Fig. 21A-C
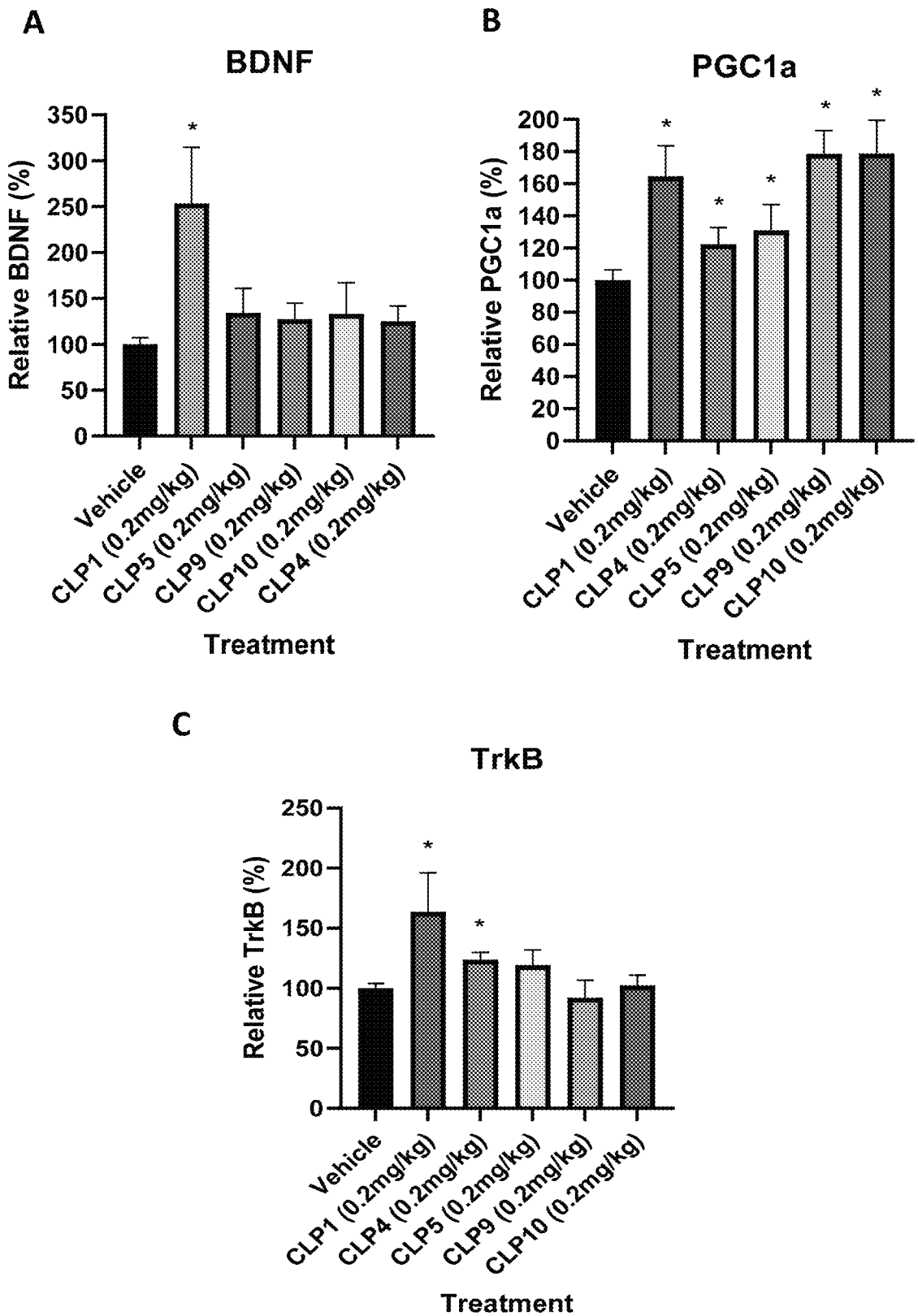

PEPTIDES

CROSS REFERENCE TO RELATED APPLICATIONS

This application is a continuation of International Application No. PCT/EP2023/053211, filed Feb. 9, 2023, which claims the benefit of European Patent Application No. 22155992.5, filed Feb. 9, 2022, and European Patent Application No. 22160222.0, filed Mar. 4, 2022, the entire contents of which are hereby incorporated by reference herein in their entireties.

SEQUENCE LISTING SUBMISSION VIA EFS-WEB

The instant application contains a sequence listing, which has been submitted in XML format via EFS-Web. The contents of the XML copy named "119744-5032-US_Sequence_Listing", which was created on May 10, 2024 and is 114,688 bytes in size, the contents of which are incorporated herein by reference in their entirety.

TECHNICAL FIELD

The present invention concerns novel peptides, uses thereof as medicaments, such as in the treatment or prophylaxis of Alzheimer's disease, Huntington's disease, Parkinson's disease, 5 frontotemporal dementia or depression, and to related aspects.

BACKGROUND

Neurodegenerative diseases designate illnesses in which progressive loss of neuronal functions and synapses leading to apoptosis occurs in distinct brain areas. These include Alzheimer's disease (AD), Parkinson's disease (PD), Huntington's disease (HD), amyotrophic lateral sclerosis (ALS) and frontotemporal dementia (FTD) among others. Hallmarks of neurodegenerative diseases include alack in neurotrophic signaling and aggregation of misfolded proteins, and loss of neurotrophic signaling as a result of aggregates blocking the neurotrophic signaling.

In a healthy neuron, a variety of signalling pathways, initiated by neurotrophic growth factors, converge on the activation of transcription factor cAMP response element-binding protein (CREB) leading to growth, neuronal plasticity and survival (Benito, 2010; Sakamoto, 2011). In line with this, decreased activation of downstream transcription factor CREB is observed in Huntington's, Alzheimer's and FTD (Sugars, 2004; Pugazhenthi, 2011; Ljungberg, 2012).

Interestingly, distinct mutations linked to neurodegenerative diseases attenuate general clearing-mechanisms of misfolded proteins and damaged organelles in cells (Boland, 2018). These include the lysosomal network, the proteasome-system and chaperone-mediated autophagy. For example, in Huntington's Disease, mutations involving abnormal repetitions of CAG-repeats in exon 1 in the HTT gene cause the protein huntingtin to aggregate intranuclearly, which disrupts the autolysosomal network and reduces axonal transport of autophagosomes (Qin, 2004; Wong, 2014). Similarly, heterozygous loss of function mutation in the GRN gene has been linked to FTLD, in which mutations result in lysosomal dysfunction, which leads to aggregation of the protein TDP-43 (van Swieten, 2008; Beel, 2018).

Thus, strategies for treating neurodegenerative diseases may include increasing activation of CREB and increasing clearance of misfolded proteins aggregates.

Recently, the sortilin-related Vps10p domain containing receptor 2 (SorCS2) in the Vps10p-domain receptor family has emerged within neuroscience as it has been shown to be deeply involved with neuronal viability and function (Glerup, 2014; Glerup, 2016; Leloup, 2018; Ma, 2017; Malik, 2019; Yang, 2021). The SorCS2 receptor mediates the sorting and trafficking of a variety of ligands and receptors, which are crucial to neurite formation, synaptic plasticity and axon growth. Large cohort studies have highlighted the clinical relevance of SorCS2, linking it to several neurodegenerative and psychiatric disorders including bipolar disorder, AD, HD, FTD, depression, schizophrenia, and attention deficit/hyperactivity disorder (ADHD) (Baum, 2008; Ollila, 2009; Christoforou, 2011; Alemany, 2015; Reitz, 2015). Additionally, SorCS2 has been functionally linked with the severe neurological proteinopathies of ALS and HD (Mor, 2015; Ma, 2017; Salaiovd, 2021) and also pain-related diseases such as neuropathic pain (Richner, 2012; Ma, 2017; Miki, 2018). In proteinopathies, SorCS2 has been shown to mis-localize to disease-aggregates resulting in its deficiency and acceleration of disease progression.

SorCS2 was further shown to be critical in mediating the signalling by brain-derived neurotrophic factor (BDNF)—a neurotrophin, which initiates survival and synaptic plasticity through activation of CREB (Glerup, 2016). Interestingly, this mediation by SorCS2 was restricted to its intracellular domain. To a similar extent has the cytoplasmic domains of other family members in the VPS10p domain receptor family, SorCS1 and SorCS3-receptors previously been associated with their functions (Savas, 2015; Hermey, 2003; Oetjen, 2014).

Modulators of the SorCS2 pathway may also find utility as diagnostic or investigational tools.

WO2017101956 relates to linear peptides and methods for modulating the phosphorylation of the Vps10 domain-containing receptor SorCS1, SorCS2 or SorCS3.

WO2022029281 describes cyclic peptides and methods for modulating SorCS1, SorCS2 or SorCS3.

There remains a need for alternative or improved modulators of the SorCS2 pathway. Such modulators may be more conveniently manufactured, demonstrate high potency, selectivity, an improved safety profile, or desirable pharmacokinetic parameters, for example high brain availability and/or low clearance rate that reduces the dose or frequency of dosing required for therapeutic effect in vivo.

SUMMARY OF THE INVENTION

In a first aspect is provided a lipidated cyclic peptide comprising the sequence:

|  |  |  |  |  | (SEQ ID No. 51) |
|---|---|---|---|---|---|
| $X_2$— | $X_3$— | E— | H— | $X_4$— | E |
| position 1 | 2 | 3 | 4 | 5 | 6 | wherein:
$X_2$ represents P, D, Q, K, G
$X_3$ represents I, L, A, T, V
$X_4$ represents E, A
or a conservatively substituted variant of said peptide.

In a second aspect is provided cyclic peptide comprising the sequence:

| | | | | | (SEQ ID No. 51) |
|---|---|---|---|---|---|
| $X_2$— | $X_3$— | E— | H— | $X_4$— | E |
| position 1 | 2 | 3 | 4 | 5 | 6 | wherein:

$X_2$ represents P, D, Q, K, G $X_3$ represents I, L, A, T, V $X_4$ represents E, A or a conservatively substituted variant of said peptide, wherein when $X_2$ represents P then $X_3$ is other than V.

In a third aspect is provided a cyclic peptide comprising 10 or fewer amino acid residues within the cycle and comprising the sequence:

| | | | | | (SEQ ID No. 51) |
|---|---|---|---|---|---|
| $X_2$— | $X_3$— | E— | H— | $X_4$— | E |
| position 1 | 2 | 3 | 4 | 5 | 6 | wherein:

$X_2$ represents P, D, Q, K, G $X_3$ represents I, L, A, T, V $X_4$ represents E, A or a conservatively substituted variant of said peptide.

In a fourth aspect is provided a lipidated linear peptide comprising the sequence:

| | | | | | (SEQ ID No. 51) |
|---|---|---|---|---|---|
| $X_2$— | $X_3$— | E— | H— | $X_4$— | E |
| position 1 | 2 | 3 | 4 | 5 | 6 | wherein:

$X_2$ represents P, D, Q, K, G $X_3$ represents I, L, A, T, V $X_4$ represents E, A or a conservatively substituted variant of said peptide.

In a fifth aspect is provided a linear peptide comprising the sequence:

| | | | | | (SEQ ID No. 51) |
|---|---|---|---|---|---|
| $X_2$— | $X_3$— | E— | H— | $X_4$— | E |
| position 1 | 2 | 3 | 4 | 5 | 6 | wherein:

$X_2$ represents P, D, Q, K, G $X_3$ represents I, L, A, T, V $X_4$ represents E, A or a conservatively substituted variant of said peptide, wherein when $X_2$ represents P then $X_3$ is other than V.

In a sixth aspect is provided a linear peptide comprising 10 or fewer amino acid residues within the backbone and comprising the sequence:

| | | | | | (SEQ ID No. 51) |
|---|---|---|---|---|---|
| $X_2$— | $X_3$— | E— | H— | $X_4$— | E |
| position 1 | 2 | 3 | 4 | 5 | 6 | wherein:

$X_2$ represents P, D, Q, K, G $X_3$ represents I, L, A, T, V $X_4$ represents E, A or a conservatively substituted variant of said peptide.

It will be appreciated that peptides of the invention may form salts under appropriate conditions, therefore salts of the peptides of the invention are also provided, in particular pharmaceutically acceptable salts. The peptides and their salts (such as pharmaceutically acceptable salts) may exist in dissociated form in appropriate solvents, such as water.

Modulators of the SorCS2 pathway may have utility in medicine. Consequently, the invention provides the use of the lipidated cyclic peptides, lipidated linear peptides, cyclic peptides and linear peptides described above, and their pharmaceutically acceptable salts, as medicaments, particularly in the treatment or prophylaxis of Alzheimer's disease, Huntington's disease, Parkinson's disease, frontotemporal dementia or depression.

Also provided are protected cyclic peptides, protected linear peptides and linear peptides which when cyclised provide a cyclic peptide as described above, all of which may be of use in the preparation of the cyclic peptides and linear peptides described above.

BRIEF DESCRIPTION OF THE FIGURES

FIG. 7A and FIG. 7B: Brain free fraction of CLP1: brain free fraction of CLP1 in mouse brain (FIG. 7A) and human brain (FIG. 7B) measured by LCMS.

FIG. 8A to FIG. 8C: Pharmacokinetics of CLP1 in wild-type mice: plasma (FIG. 8A), whole brain (FIG. 8B) and cerebrospinal fluid (FIG. 8C) concentrations of CLP1 from 1 to 24 hours post-injection by LCMS/MS.

FIG. 9A to FIG. 9C: Single-injection of CLP1 in wild-type mice: CLP1 showed strong tendency to increase BDNF after 4 hours (FIG. 9A). Post-hoc analysis showed a significant time-dependent effect (p=0.0438) of CLP1 on BDNF levels by two-way ANOVA analysis (not shown). CLP1 significantly increased PGC1a at 2-4 hours post injection (FIG. 9B) and transcription factor EB (TFEB) at 2-8 hours post injection (FIG. 8C). Means±SEM.

FIG. 11A to FIG. 11F: CLP1 improves behavior in R6/2 mouse model of Huntington's disease: a schematic of the PoC study from Example 11 (FIG. 11A). CLP1 and CPX did not change bodyweight (FIG. 11B). CLP1 significantly improved clasping behavior at week 9 and 14 in R6/2 treated mice, while CPX improved clasping at 9 weeks only (FIG. 11C). No significant effects were observed in rotarod (FIG. 11D). Kaplan-Meier curve shows cumulative survival (FIG. 11E), in which CLP1 increased the mean survival of treated R6/2 mice by 7 days and median survival by 13 days (FIG. 11F) in this severe model of Huntington's disease.

FIG. 12A to FIG. 12D: CLP1 improves behavior in a mouse model of Parkinson's (MPTP model): a schematic of the experimental design from Example 12 (FIG. 12A). Behavioral and biochemical analysis was assessed at day 10. Treatment with CLP1 increased distance travelled in the open-field test, significantly for 2 mg/kg (FIG. 12B). CLP1 completely rescued grip strength at both 0.2 and 2 mg/kg dosing (FIG. 12C). Body weight of animals after MPTP injection were reduced at first and gradually increased during the study, while MPTP significantly changed body weight at endpoint from non-treated mice (sham), CLP1 treated mice do not show a significant change in bodyweight at end point compared to sham group (FIG. 12D).

FIG. 14A to FIG. 14F: CLP1 clears and reduces spreading of human α-synuclein PFFs in vivo; a schematic of the experimental design from Example 13 is shown (FIG. 14A). The injection site was amygdala and both ipsilateral and contralateral spread of PFFs in substantia nigra pars compacta and amygdala was assessed after 32-days of treatment (FIG. 14B). Representative images of substantia nigra (FIG. 14C) and amygdala (FIG. 14D) are shown. CLP1 significantly reduced number of PFF inclusions in both substantia nigra (SN) ipsilateral and amygdala contralateral, while showing a clear tendency to reduce ipsilateral inclusion in amygdala as well (FIG. 14E). One brain was immunostained for TH+ neurons and imaged (FIG. 14F). The TH-stain clearly shows loss of dopaminergic striatal dopaminergic terminals in vehicle treated rat, as signal was almost completely lost at site of injection. CLP1-treatment notably preserved the dopaminergic terminals.

FIG. 16A to FIG. 16F: CLP1 increases time spent awake in Wistar Kyoto rats: effect of ketamine and CLP1 on wakefulness (FIG. 16A), NREM (FIG. 16B) and REM (FIG. 16C) sleep between 0-3 hours post injection, and wakefulness (FIG. 16D), NREM (FIG. 16E) and REM (FIG. 16F) sleep between 11-12 hours post injection.

FIG. 18A to FIG. 18D: Effects of CLP1 to CLP10 and LLP1 to LLP10 on CREB-targeted genes: effect on BDNF for CLP1 to CLP10 (FIG. 18A) and CLP1 and LLP1 to LLP10 (FIG. 18B) and PGC1a for CLP1 to CLP10 (FIG. 18C) and CLP1 and LLP1 to LLP10 (FIG. 18D) levels after 8-24 hours of stimulation with respective peptides in primary cortical neurons.

FIG. 19A and FIG. 19B: CLP1 and CLP10 clear soluble mutated HTT in Huntington's patient-derived fibroblasts (GM04719): peptides CLP1 and CLP10 significantly reduced mutated Huntingtin (mHTT) levels in Huntington's patient-derived fibroblasts (GM04719) by 50% after 24 hours of treatment (measured using MW1 antibody specific for polyglutamine stretch) (FIG. 19A) and showed a decrease in total HTT levels (FIG. 19B).

FIG. 21A to FIG. 21C: In vivo efficacy of selected peptides in wild-type mice: CLP1 significantly increased BDNF levels (FIG. 21A) and tropomyosin receptor kinase B (TrkB) levels along with CLP4 (FIG. 21C). All variants significantly increased levels of PGC1a (FIG. 21B).

BRIEF DESCRIPTION OF THE SEQUENCES

Figure 1A:
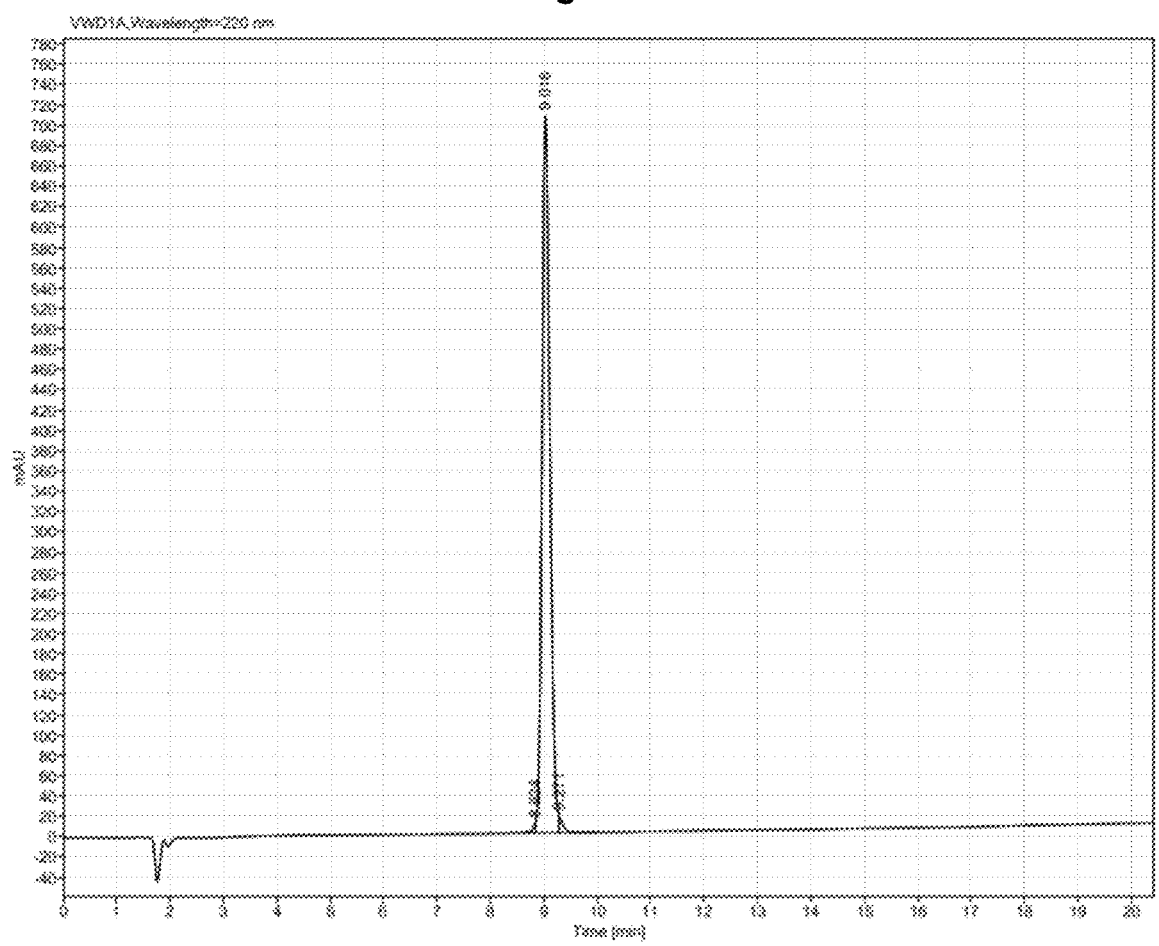
FIG. 1A to FIG. 1C: Purification and qualitative check of CLP1: HPLC chromatogram for CLP1 with UV detection at 220 nm (FIG. 1A), LCMS chromatogram (FIG. 1B) and full scan acquisition positive ion mode spectrum (FIG. 1C).

SEQ ID NO: 1 Cyclic lipidated peptide CLP1
SEQ ID NO: 2 Cyclic lipidated peptide CLP2
SEQ ID NO: 3 Cyclic lipidated peptide CLP3
SEQ ID NO: 4 Cyclic lipidated peptide CLP4
SEQ ID NO: 5 Cyclic lipidated peptide CLP5
SEQ ID NO: 6 Cyclic lipidated peptide CLP6
SEQ ID NO: 7 Cyclic lipidated peptide CLP7
SEQ ID NO: 8 Cyclic lipidated peptide CLP8
SEQ ID NO: 9 Cyclic lipidated peptide CLP9
SEQ ID NO: 10 Cyclic lipidated peptide CLP10
SEQ ID NO: 11 Cyclic lipidated peptide CLP11
SEQ ID NO: 12 Cyclic lipidated peptide CLP12
SEQ ID NO: 13 Cyclic lipidated peptide CLP13
SEQ ID NO: 14 Cyclic lipidated peptide CLP14
SEQ ID NO: 15 Cyclic lipidated peptide CLP15
SEQ ID NO: 16 Linear lipidated peptide LLP1
SEQ ID NO: 17 Linear lipidated peptide LLP2
SEQ ID NO: 18 Linear lipidated peptide LLP3
SEQ ID NO: 19 Linear lipidated peptide LLP4
SEQ ID NO: 20 Linear lipidated peptide LLP5
SEQ ID NO: 21 Linear lipidated peptide LLP6
SEQ ID NO: 22 Linear lipidated peptide LLP7
SEQ ID NO: 23 Linear lipidated peptide LLP8
SEQ ID NO: 24 Linear lipidated peptide LLP9
SEQ ID NO: 25 Linear lipidated peptide LLP10
SEQ ID NO: 26 Linear lipidated peptide LLP11
SEQ ID NO: 27 Linear lipidated peptide LLP12
SEQ ID NO: 28 Cyclic peptide CP1
SEQ ID NO: 29 Cyclic peptide CP2
SEQ ID NO: 30 Cyclic peptide CP3
SEQ ID NO: 31 Cyclic peptide CP4
SEQ ID NO: 32 Cyclic peptide CP5
SEQ ID NO: 33 Cyclic peptide CP6
SEQ ID NO: 34 Cyclic peptide CP7
SEQ ID NO: 35 Cyclic peptide CP8
SEQ ID NO: 36 Cyclic peptide CP9
SEQ ID NO: 37 Cyclic peptide CP10
SEQ ID NO: 38 Cyclic peptide CP11
SEQ ID NO: 39 Cyclic peptide CP12
SEQ ID NO: 40 Cyclic peptide CP13
SEQ ID NO: 41 Cyclic peptide CP14
SEQ ID NO: 42 Cyclic peptide CP15
SEQ ID NO: 43 Cyclic peptide CP16
SEQ ID NO: 44 Cyclic peptide CP17
SEQ ID NO: 45 Cyclic peptide CP18
SEQ ID NO: 46 Cyclic peptide CP19
SEQ ID NO: 47 Cyclic peptide CP20
SEQ ID NO: 48 Cyclic peptide CP21
SEQ ID NO: 49 Cyclic peptide CP22
SEQ ID NO: 50 Native SorCS2 fragment
SEQ ID NO: 51 Variable peptide sequence 1
SEQ ID NO: 52 Variable peptide sequence 2
SEQ ID NO: 53 Variable peptide sequence 3
SEQ ID NO: 54 Variable peptide sequence 4
SEQ ID NO: 55 Variable peptide sequence 5
SEQ ID NO: 56 Variable peptide sequence 6
SEQ ID NO: 57 Variable peptide sequence 7
SEQ ID NO: 58 Variable peptide sequence 8
SEQ ID NO: 59 Variable peptide sequence 9
SEQ ID NO: 60 Variable peptide sequence 10
SEQ ID NO: 61 Variable peptide sequence 11
SEQ ID NO: 62 Variable peptide sequence 12
SEQ ID NO: 63 Cyclic peptide CPX

DETAILED DESCRIPTION OF THE INVENTION

In a first aspect is provided a lipidated cyclic peptide comprising the sequence:

| | | | | | | (SEQ ID No. 51) |
|---|---|---|---|---|---|---|
| $X_2$— | $X_3$— | E— | H— | $X_4$— | E | |
| position | 1 | 2 | 3 | 4 | 5 | 6 | wherein:
$X_2$ represents P, D, Q, K, G
$X_3$ represents I, L, A, T, V
$X_4$ represents E, A
or a salt thereof, or a conservatively substituted variant of said peptide or salt.

The lipidated cyclic peptide may comprise the sequence:

| | | | | | | (SEQ ID No. 51) |
|---|---|---|---|---|---|---|
| $X_2$— | $X_3$— | E— | H— | $X_4$— | E | |
| position | 1 | 2 | 3 | 4 | 5 | 6 | wherein:
$X_2$ represents P, D, Q, K, G
$X_3$ represents I, L, A, T, V
$X_4$ represents E, A
or a salt thereof. In particular wherein the peptide is backbone cyclised and all residues of the peptide backbone are joined exclusively by peptide bonds.

In a second aspect is provided a cyclic peptide comprising the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt, wherein when $X_2$ represents P then $X_3$ is other than V.

The cyclic peptide may comprise the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof, wherein when $X_2$ represents P then $X_3$ is other than V. In particular wherein the peptide is backbone cyclised and all residues of the peptide backbone are joined exclusively by peptide bonds.

In a third aspect is provided a cyclic peptide comprising 10 or fewer amino acid residues within the cycle and comprising the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt.

The cyclic peptide may comprise 10 or fewer amino acid residues within the cycle and comprise the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof. In particular wherein the peptide is backbone cyclised and all residues of the peptide backbone are joined exclusively by peptide bonds.

In a fourth aspect is provided a lipidated linear peptide comprising the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt.

The lipidated linear peptide may comprise the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof. In particular wherein all residues of the peptide backbone are joined exclusively by peptide bonds.

In a fifth aspect is provided a linear peptide comprising the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt, wherein when $X_2$ represents P then $X_3$ is other than V.

The linear peptide may comprise the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt, wherein when $X_2$ represents P then $X_3$ is other than V. In particular wherein all residues of the peptide backbone are joined exclusively by peptide bonds.

In a sixth aspect is provided linear peptide comprising 10 or fewer amino acid residues within the backbone and comprising the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt.

The linear peptide may comprise 10 or fewer amino acid residues within the backbone and comprise the sequence:

| | $X_2$- | $X_3$- | E- | H- | $X_4$- | E | (SEQ ID No. 51) |
|---|---|---|---|---|---|---|---|
| position | 1 | 2 | 3 | 4 | 5 | 6 | | wherein:
$X_2$ represents P, D, Q, K, G
$X_3$ represents I, L, A, T, V
$X_4$ represents E, A
or a salt thereof. In particular wherein all residues of the peptide backbone are joined exclusively by peptide bonds.

Peptide

A "peptide" is a polymer of amino acid residues, typically joined exclusively by peptide bonds.

In some embodiments, the peptides may be modified. Particular modifications include N-terminal acetylation and/or C-terminal amidation. In some embodiments the peptides do not contain side chain modifications. In other embodiments the peptides are not modified.

Certain peptides described herein are cyclic. A peptide can typically be cyclised in four different ways: side chain-to-side chain, tail-to-side chain (i.e. C-terminus to side chain), side chain-to-head (i.e. N-terminus to side chain) and head-to-tail. As used herein, the term "head-to-tail cyclised peptide" is used interchangeably with the term "backbone cyclised peptide".

In one embodiment, the cyclic peptide is a backbone cyclised peptide. In one embodiment, the cyclic peptide is formed by the formation of an amide bond between its N-terminus- and its C-terminus-parts, i.e. head-to tail cyclization. In some embodiments the peptide is cyclised side chain-to-side chain and the backbone of the peptide is joined exclusively by peptide bonds. In some embodiments the peptide is cyclised tail-to-side chain and the backbone of the peptide is joined exclusively by peptide bonds. In some embodiments the peptide is cyclised side chain-to-head and the backbone of the peptide is joined exclusively by peptide bonds.

In some embodiments cyclic peptides comprise 25 or fewer amino acid residues within the cycle, such as 20 or fewer amino acid residues within the cycle (e.g. comprising 20 amino acid residues within the cycle), especially 15 or fewer amino acid residues within the cycle (e.g. comprising 15 amino acid residues within the cycle), in particular 12 or fewer amino acid residues within the cycle (e.g. comprising 12 amino acid residues within the cycle), for example 11 or fewer amino acid residues within the cycle (e.g. comprising 11 amino acid residues within the cycle).

In some embodiments cyclic peptides comprise 6 or more amino acid residues within the cycle, such as 7 or more amino acid residues within the cycle (e.g. comprising 7 amino acid residues within the cycle), especially 8 or more amino acid residues within the cycle (e.g. comprising 8 amino acid residues within the cycle), in particular 9 or more amino acid residues within the cycle (e.g. comprising 9 amino acid residues within the cycle), for example 10 or more amino acid residues within the cycle (e.g. comprising 10 amino acid residues within the cycle). In certain embodiments cyclic peptides comprise 11 or more amino acid residues within the cycle (e.g. comprising 11 amino acid residues within the cycle).

In some embodiments linear peptides comprise 25 or fewer amino acid residues within the backbone, such as 20 or fewer amino acid residues within the backbone (e.g. comprising 20 amino acid residues within the backbone), especially 15 or fewer amino acid residues within the backbone (e.g. comprising 15 amino acid residues within the backbone), in particular 12 or fewer amino acid residues within the backbone (e.g. comprising 12 amino acid residues within the backbone) for example 11 or fewer amino acid residues within the backbone (e.g. comprising 11 amino acid residues within the backbone).

In some embodiments linear peptides comprise 6 or more amino acid residues within the backbone, such as 7 or more amino acid residues within the backbone (e.g. comprising 7 amino acid residues within the backbone), especially 8 or more amino acid residues within the backbone (e.g. comprising 8 amino acid residues within the backbone), in particular 9 or more amino acid residues within the backbone (e.g. comprising 9 amino acid residues within the backbone), for example 10 or more amino acid residues within the backbone (e.g. comprising 10 amino acid residues within the backbone). In certain embodiments linear peptides comprise 11 or more amino acid residues within the backbone (e.g. comprising 11 amino acid residues within the backbone).

In some embodiments peptides comprise the sequence:

| | E- | $X_2$- | $X_3$- | E- | H- | $X_4$- | E | (SEQ ID No. 52) |
|---|---|---|---|---|---|---|---|---|
| position | 0 | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| | E- | $X_2$- | $X_3$- | E- | H- | $X_4$- | E | (SEQ ID No. 52) |
|---|---|---|---|---|---|---|---|---|
| position | 0 | 1 | 2 | 3 | 4 | 5 | 6 | | wherein:
$X_2$ represents P, D, Q, K, G
$X_3$ represents I, L, A, T, V
$X_4$ represents E, A
or a salt thereof.

In some embodiments peptides comprise the sequence:

| | $X_2$- | $X_3$- | E- | H- | $X_4$- | E- | D | (SEQ ID No. 53) |
|---|---|---|---|---|---|---|---|---|
| position | 1 | 2 | 3 | 4 | 5 | 6 | 7 | | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| | $X_2$- | $X_3$- | E- | H- | $X_4$- | E- | D | (SEQ ID No. 53) |
|---|---|---|---|---|---|---|---|---|
| position | 1 | 2 | 3 | 4 | 5 | 6 | 7 | | wherein:
$X_2$ represents P, D, Q, K, G
$X_3$ represents I, L, A, T, V
$X_4$ represents E, A
or a salt thereof.

In some embodiments peptides comprise the sequence:

| | T- | E- | $X_2$- | $X_3$- | E- | H- | $X_4$- | E | (SEQ ID No. 54) |
|---|---|---|---|---|---|---|---|---|---|
| position | -1 | 0 | 1 | 2 | 3 | 4 | 5 | 6 | | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| (SEQ ID No. 54) | | | | | | | | |
|---|---|---|---|---|---|---|---|---|
| | T- | E- | $X_2$- | $X_3$- | E- | H- | $X_4$- | E |
| position | -1 | 0 | 1 | 2 | 3 | 4 | 5 | 6 | wherein:
$X_2$ represents P, D, Q, K, G
$X_3$ represents I, L, A, T, V
$X_4$ represents E, A
or a salt thereof.

In some embodiments peptides comprise the sequence:

| (SEQ ID No. 55) | | | | | | | | |
|---|---|---|---|---|---|---|---|---|
| | E- | $X_2$- | $X_3$- | E- | H- | $X_4$- | E- | D |
| position | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| (SEQ ID No. 55) | | | | | | | | |
|---|---|---|---|---|---|---|---|---|
| | E- | $X_2$- | $X_3$- | E- | H- | $X_4$- | E- | D |
| position | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof.

In some embodiments peptides comprise the sequence:

| (SEQ ID No. 56) | | | | | | | | |
|---|---|---|---|---|---|---|---|---|
| | $X_2$- | $X_3$- | E- | H- | $X_4$- | E- | D- | V |
| position | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| (SEQ ID No. 56) | | | | | | | | |
|---|---|---|---|---|---|---|---|---|
| | $X_2$- | $X_3$- | E- | H- | $X_4$- | E- | D- | V |
| position | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof.

In some embodiments peptides comprise the sequence:

| (SEQ ID No. 57) | | | | | | | | |
|---|---|---|---|---|---|---|---|---|
| | $X_1$- | T- | E- | $X_2$- | $X_3$- | E- | H- | $X_4$- | E |
| position | -2 | -1 | 0 | 1 | 2 | 3 | 4 | 5 | 6 | wherein:
$X_1$ represents M, K
$X_2$ represents P, D, Q, K, G
$X_3$ represents I, L, A, T, V $X_4$ represents E, A or a salt thereof, or a conservatively substituted variant of said peptide or salt.

In some embodiments peptides comprise the sequence:

| (SEQ ID No. 57) | | | | | | | | |
|---|---|---|---|---|---|---|---|---|
| $X_1$- | T- | E- | $X_2$- | $X_3$- | E- | H- | $X_4$- | E |
| position -2 | -1 | 0 | 1 | 2 | 3 | 4 | 5 | 6 | wherein:
$X_1$ represents M, K
$X_2$ represents P, D, Q, K, G
$X_3$ represents I, L, A, T, V
$X_4$ represents E, A
or a salt thereof.

In some embodiments peptides comprise the sequence:

| (SEQ ID No. 58) | | | | | | | | |
|---|---|---|---|---|---|---|---|---|
| T- | E- | $X_2$- | $X_3$- | E- | H- | $X_4$- | E- | D |
| position -1 | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| (SEQ ID No. 58) | | | | | | | | |
|---|---|---|---|---|---|---|---|---|
| T- | E- | $X_2$- | $X_3$- | E- | H- | $X_4$- | E- | D |
| position -1 | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof.

In some embodiments peptides comprise the sequence:

| (SEQ ID No. 59) | | | | | | | | |
|---|---|---|---|---|---|---|---|---|
| E- | $X_2$- | $X_3$- | E- | H- | $X_4$- | E- | D- | V |
| position 0 | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| (SEQ ID No. 59) | | | | | | | | |
|---|---|---|---|---|---|---|---|---|
| E- | $X_2$- | $X_3$- | E- | H- | $X_4$- | E- | D- | V |
| position 0 | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof.

In some embodiments peptides comprise the sequence:

| (SEQ ID No. 60) | | | | | | | | |
|---|---|---|---|---|---|---|---|---|
| $X_1$- | T- | E- | $X_2$- | $X_3$- | E- | H- | $X_4$- | E- | D |
| position -2 | -1 | 0 | 1 | 2 | 3 | 4 | 5 | 6 | 7 | wherein:
$X_1$ represents M, K
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| (SEQ ID No. 60) | | | | | | | | |
|---|---|---|---|---|---|---|---|---|
| $X_1$- | T- | E- | $X_2$- | $X_3$- | E- | H- | $X_4$- | E- | D |
| position -2 | -1 | 0 | 1 | 2 | 3 | 4 | 5 | 6 | 7 | wherein:
$X_1$ represents M, K
$X_2$ represents P, D, Q, K, G
$X_3$ represents I, L, A, T, V
$X_4$ represents E, A
or a salt thereof.

In some embodiments peptides comprise the sequence:

| (SEQ ID No. 61) | | | | | | | | |
|---|---|---|---|---|---|---|---|---|
| T- | E- | $X_2$- | $X_3$- | E- | H- | $X_4$- | E- | D- | V |
| position -1 | 0 | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

In some embodiments peptides comprise the sequence:

| (SEQ ID No. 61) | | | | | | | | |
|---|---|---|---|---|---|---|---|---|
| T- | E- | $X_2$- | $X_3$- | E- | H- | $X_4$- | E- | D- | V |
| position -1 | 0 | 1 | 2 | 3 | 4 | 5 | 6 | 7 | 8 | wherein:
X$_2$ represents P, D, Q, K, G
X$_3$ represents I, L, A, T, V
X$_4$ represents E, A
or a salt thereof.
In some embodiments peptides comprise the sequence:

|  |  |  |  |  |  |  |  |  |  | (SEQ ID No. 62) |
|---|---|---|---|---|---|---|---|---|---|---|
| X$_1$— | T— | E— | X$_2$— | X$_3$— | E— | H— | X$_4$— | E— | D— | V |
| position -2 | -1 | 0 | 1 | 2 | 3 | 4 | 5 | 6 | 7 | 8 | wherein:
X$_1$ represents M, K
X$_2$ represents P, D, Q, K, G
X$_3$ represents I, L, A, T, V
X$_4$ represents E, A
or a salt thereof, or a conservatively substituted variant of said peptide or salt.
In some embodiments peptides comprise the sequence:

|  |  |  |  |  |  |  |  |  |  | (SEQ ID No. 62) |
|---|---|---|---|---|---|---|---|---|---|---|
| X$_1$— | T— | E— | X$_2$— | X$_3$— | E— | H— | X$_4$— | E— | D— | V |
| position -2 | -1 | 0 | 1 | 2 | 3 | 4 | 5 | 6 | 7 | 8 | wherein:
X$_1$ represents M, K
X$_2$ represents P, D, Q, K, G
X$_3$ represents I, L, A, T, V
X$_4$ represents E, A
or a salt thereof.
In some embodiments X$_1$ represents M. In other embodiments X$_1$ represents K.

In some embodiments X$_2$ represents P. In other embodiments X$_2$ represents D. In further embodiments X$_2$ represents Q. In additional embodiments X$_2$ represents K. In certain embodiments X$_2$ represents G.

In some embodiments X$_3$ represents I. In other embodiments X$_3$ represents L. In further embodiments X$_3$ represents A. In additional embodiments X$_3$ represents T. In certain embodiments X$_3$ represents V.

In some embodiments X$_4$ represents E. In further embodiments X$_4$ represents A.

As will be appreciated by the skilled person, certain amino acid residues may be replaced by other amino acid residues without notably impacting function (e.g. stability and/or activity). Such substitutions are generally known as conservative substitutions. Typically a conservatively substituted variant maintains at least 50%, such as at least 80% and especially at least 90% (e.g. at least 100%) of the relevant functional capability of the non-substituted reference sequence. For example, the functional capability to increase BDNF, PGC1a, TFEB and/or phospho-CREB (Ser133), such as using an assay as described herein (e.g. Example 10). Alternatively, the functional capability may be t$_{1/2}$, AUC or C$_{max}$, such as using an assay as described herein (e.g. Example 9), especially t$_{1/2}$ in brain.

A conservatively substituted variant may comprise two conservative substitutions. Alternatively, a conservatively substituted variant may comprise one conservative substitution.

In some embodiments, peptides do not contain conservative substitutions.

Specific conservative substitutions may be determined empirically, although commonly suitable replacements are known, for example as shown in Table 1.

TABLE 1

Common conservative substitutions

| Amino Acid | Common conservative substitution |
|---|---|
| A | D, E, G, S, T |
| C | G, R, S, W, Y |
| D | A, E, G, H, N, V, Y |
| E | A, D, G, K, Q, V |
| F | I, L, Y |
| G | A, C, D, E, R |
| H | D, L, N, P, Q, R, Y |
| I | F, L, M, N, V |
| K | E, M, N, Q, R, T |
| L | F, H, I, M, P, Q, R, V, W |
| M | I, K, L, R, T, V |
| N | D, H, I, K, S, T, Y |
| P | H, L, Q, R, S |
| Q | E, H, K, L, P, R |
| R | C, G, H, K, L, M, P, Q, T, W |
| S | A, C, N, P, T, W, Y |
| T | A, K, M, N, R, S |
| V | D, E, I, L, M |
| W | C, L, R, S |
| Y | C, D, F, H, N, S |

Consequently, in some embodiments a variant comprises a substitution of X, at position -2. X$_1$ may be a replacement for M, such as I, (K), L, R, T, V. Alternatively, X$_1$ may be a replacement for K such as E, (M), N, Q, R, T. X, may be replaced by E, N, Q, R, T I, L or V.

In some embodiments a variant comprises a substitution of T at position -1, such as replacement by A, K, M, N, R or S, especially A, K, M, N or R.

In some embodiments a variant comprises a substitution of E at position 0, such as replacement by A, D, G, K, Q or V, especially G, K, Q or V.

In some embodiments a variant comprises a substitution of X$_2$ at position 1. X$_2$ may be a replacement for P, such as H, L, (Q), R or S, especially H, L, (Q) or R. Alternatively, $X_2$ may be a replacement for D such as A, E, (G), H, N, V or Y. $X_2$ may be a replacement for Q, such as E, H, (K), L, (P) or R. $X_2$ may be a replacement for K, such as E, M, N, (Q), R, T. $X_2$ may be a replacement for G, such as A, C, (D), E or R. $X_2$ may be replaced by A, C, E, H, L, M, N, R, S, T, V or Y, especially A, E, H, L, M, N, R, T, V or Y.

In some embodiments a variant comprises a substitution of $X_3$ at position 2. $X_3$ may be a replacement for I, such as F, (L), M, N or (V). Alternatively, $X_3$ may be a replacement for L such as F, H, (I), M, P, Q, R, (V) or W. $X_3$ may be a replacement for A, such as D, E, G, S or T, especially D, E, G or T. $X_3$ may be a replacement for T, such as (A), K, M, N, R or S, especially (A), K, M, N or R. $X_3$ may be a replacement for V, such as D, E, (I), (L) or M. $X_3$ may be replaced by D, E, F, G, H, K, M, N, P, Q, S or W, especially D, E, F, G, H, K, M, N, P, Q or W.

In some embodiments a variant comprises a substitution of E at position 3, such as replacement by A, D, G, K, Q or V, especially G, K, Q or V.

In some embodiments a variant comprises a substitution of H at position 4, such as replacement by D, L, N, P, Q, R or Y.

In some embodiments a variant comprises a substitution of $X_4$ at position 5. $X_4$ may be a replacement for E, such (A), D, G, K, Q or V. Alternatively, $X_4$ may be a replacement for D such as H, N, or Y. $X_4$ may be a replacement for A, such as D, (E), G, S or T, especially D, E, G or T. $X_4$ may be replaced by G, K, Q, S, T or V, especially G, K, Q, T or V.

In some embodiments a variant comprises a substitution of E at position 6, such as replacement by A, D, G, K, Q or V.

In some embodiments a variant comprises a substitution of D at position 7, such as replacement by A, E, G, H, N, V or Y.

In some embodiments a variant comprises a substitution of V at position 8, such as replacement by D, E, I, L or M.

Suitably the peptide comprises an amino acid sequence selected from any one of SEQ ID No. 1 to 11, 16 to 42 or 49. Such peptides may be in the form of a salt, such as a pharmaceutically acceptable salt.

Suitably the peptide consists of any one of CLP1 to CLP11, LLP1 to LLP12, CP1 to CP15 or CP22 (as described in Tables 2 and 3). Such peptides may be in the form of a salt, such as a pharmaceutically acceptable salt. More suitably, the peptide consists of CLP1 or a salt thereof, such as a pharmaceutically acceptable salt.

TABLE 2

Lipidated peptide overview

| Pep. (SEQ ID No.) | Conformation | Amino acid sequence | | | | | | | | | | |
|---|---|---|---|---|---|---|---|---|---|---|---|---|
| Native SorCS2 fragment (50) | Linear | | M | T | S | P | V | S | H | S | E | D | V |
| CLP1 (1) | Cyclic | | (K* | T | E | Q | I | E | H | E | E | D | V) |
| CLP2 (2) | Cyclic | | (K* | T | E | K | V | E | H | E | E | D | V) |
| CLP3 (3) | Cyclic | | (K* | T | E | K | I | E | H | E | E | D | V) |
| CLP4 (4) | Cyclic | | (K* | T | E | D | V | E | H | E | E | D | V) |
| CLP5 (5) | Cyclic | | (K* | T | E | D | I | E | H | E | E | D | V) |
| CLP6 (6) | Cyclic | | (K* | T | E | Q | V | E | H | E | E | D | V) |
| CLP7 (7) | Cyclic | | (K | T | E | K* | V | E | H | E | E | D | V) |
| CLP8 (8) | Cyclic | | (K | T | E | K* | I | E | H | E | E | D | V) |
| CLP9 (9) | Cyclic | | (M | T | E | K* | V | E | H | E | E | D | V) |
| CLP10 (10) | Cyclic | | (M | T | E | K* | V | E | H | E | E | D | V) |
| CLP11 (11) | Cyclic | | (K* | T | E | P | V | E | H | E | E | D | V) |
| CLP12 (12) | Cyclic | | (K* | T | E | P | V | D | H | E | E | D | V) |
| CLP13 (13) | Cyclic | | (K** | T | E | P | V | E | H | E | E | D | V) |
| CLP14 (14) | Cyclic | | (K*** | T | E | P | V | E | H | E | E | D | V) |
| CLP15 (15) | Cyclic | | (K**** | T | E | P | V | E | H | E | E | D | V) |
| LLP1 (16) | Linear | Ac | K* | T | E | K | V | E | H | E | E | D | V NH$_2$ |
| LLP2 (17) | Linear | Ac | K* | T | E | K | I | E | H | E | E | D | V NH$_2$ |
| LLP3 (18) | Linear | Ac | K* | T | E | D | V | E | H | E | E | D | V NH$_2$ |
| LLP4 (19) | Linear | Ac | K* | T | E | D | I | E | H | E | E | D | V NH$_2$ |
| LLP5 (20) | Linear | Ac | K* | T | E | Q | V | E | H | E | E | D | V NH$_2$ |
| LLP6 (21) | Linear | Ac | K* | T | E | Q | I | E | H | E | E | D | V NH$_2$ |
| LLP7 (22) | Linear | Ac | K | T | E | K* | V | E | H | E | E | D | V NH$_2$ |
| LLP8 (23) | Linear | Ac | K | T | E | K* | I | E | H | E | E | D | V NH$_2$ |
| LLP9 (24) | Linear | Ac | M | T | E | K* | V | E | H | E | E | D | V NH$_2$ |
| LLP10 (25) | Linear | Ac | M | T | E | K* | I | E | H | E | E | D | V NH$_2$ |
| LLP11 (26) | Linear | Ac | K* | T | E | P | V | E | H | E | E | D | V NH$_2$ |
| LLP12 (27) | Linear | | K*EQEM | T | E | P | V | E | H | E | E | D | V NH$_2$ |

\* = C18DA-γGlu-OEG-OEG-

\*\* = C18-γGlu-OEG-OEG-

\*\*\* = C14DA-γGlu-OEG-OEG-

\*\*\*\* = Cholesterol-OEG-OEG-

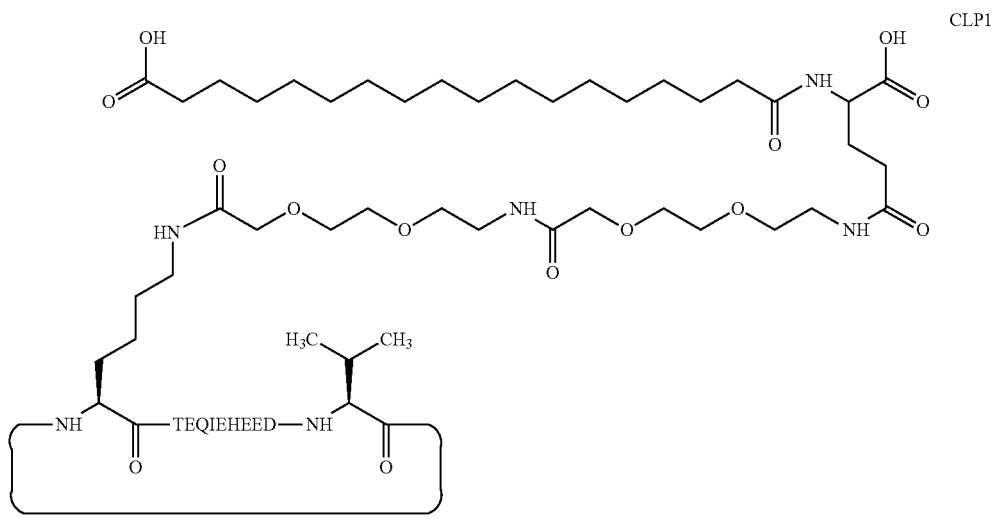

In CLP1, the C18DA-γGlu-OEG-OEG- may be C18DA-L-γGlu-OEG-OEG. Alternatively, in CLP1, the C18DA-γGlu-OEG-OEG- may be C18DA-D-γGlu-OEG-OEG.

TABLE 3

Non-lipidated peptide overview

| Pep. (SEQ ID No.) | Conformation | Amino acid sequence |          |   |   |   |   |   |   |   |   |   |    |
|---|---|---|---|---|---|---|---|---|---|---|---|---|---|
| Native SorCS2 fragment (50) | Linear | M | T | S | P | V | S | H | S | E | D | V |
| CP1 (28) | Cyclic | (M | T | E | P | I | E | H | E | E | D | V) |
| CP2 (29) | Cyclic | (M | T | E | P | L | E | H | E | E | D | V) |
| CP3 (30) | Cyclic | (M | T | E | P | A | E | H | E | E | D | V) |
| CP4 (31) | Cyclic | (M | T | E | P | T | E | H | E | E | D | V) |
| CP5 (32) | Cyclic | (M | T | E | G | V | E | H | E | E | D | V) |
| CP6 (33) | Cyclic | (M | T | E | D | V | E | H | E | E | D | V) |
| CP7 (34) | Cyclic | (M | T | E | K | V | E | H | E | E | D | V) |
| CP8 (35) | Cyclic | (M | T | E | Q | V | E | H | E | E | D | V) |
| CP9 (36) | Cyclic | (M | T | E | Q | I | E | H | E | E | D | V) |
| CP10 (37) | Cyclic | (M | T | E | D | I | E | H | E | E | D | V) |
| CP11 (38) | Cyclic | (M | T | E | Q | L | E | H | E | E | D | V) |
| CP12 (39) | Cyclic | (M | T | E | D | L | E | H | E | E | D | V) |
| CP13 (40) | Cyclic |   | (T | E | P | V | E | H | E | E | D) |   |
| CP14 (41) | Cyclic |   | (T | E | P | V | E | H | E | E) |   |   |
| CP15 (42) | Cyclic |   |   | (E | P | V | E | H | E | E) |   |   |
| CP16 (43) | Cyclic |   |   | (E | P | V | E | H | E) |   |   |   |
| CP17 (44) | Cyclic |   |   |   | (P | V | E | H | E) |   |   |   |
| CP18 (45) | Cyclic | (M | T | E | P | V | D | H | D | E | D | V) |
| CP19 (46) | Cyclic | (M | T | D | P | V | D | H | E | E | D | V) |
| CP20 (47) | Cyclic | (M | T | A | P | V | E | H | E | E | D | V) |
| CP21 (48) | Cyclic | (M | T | E | P | V | A | H | E | E | D | V) |
| CP22 (49) | Cyclic | (M | T | E | P | V | E | H | A | E | D | V) |
| CPX (63)* | Cyclic | (M | T | E | P | V | E | H | E | E | D | V) |

*described in WO2022029281

Desirably, peptides and their conservatively substituted variants demonstrate improved functional capability, for example, the functional capability ability to increase BDNF, PGC1a, TFEB and/or phospho-CREB (Ser133) and/or $t_{1/2}$, AUC or $C_{max}$ (especially all of BDNF, PGC1a, TFEB, phospho-CREB (Ser133), $t_{1/2}$, AUC and $C_{max}$) compared to CPX. Most suitably, peptides and their conservatively substituted variants demonstrate functional capability, for example, the functional capability ability to increase BDNF, PGC1a, TFEB and/or phospho-CREB (Ser133) and/or $t_{1/2}$, AUC and/or $C_{max}$ (especially all of BDNF, PGC1a, TFEB, phospho-CREB (Ser133), $t_{1/2}$, AUC and $C_{max}$) compared at least equivalent to CLP1.

Desirably, peptides of the invention demonstrate one or more (such as all) of the following properties:
- in vitro stability—an absence of fibrillation at pH 6.5 and 7.5, suitably at pH 4.5, pH 6.5 and pH 7.5 (such as by the method of Example 5);
- in vivo stability—a $t_{1/2}$, of at least 1 hr, suitably at least 4 hours, especially at least 8 hours (such as by the method of Example 9). $t_{1/2}$ is desirably determined in the brain.

Lipidation

As described above, certain peptides of the invention are lipidated. Approaches to lipidation have been reviewed in the literature, including: Østergaard, 1993; Bech, 2018; van Witteloostuijn, 2016. Kurtzhals, 2023 provides further information on lipidation.

Although a number of residues can be used for lipidation, including Cys and Tyr, lipidation is conveniently performed at the side chain of a Lys residue. Lipidation is desirably located towards the N-terminus of the peptide. In the present invention a lipidated Lys residue is suitably positioned at $X_1$ (position −2) or $X_2$ (position 1).

Lipidation may involve the replacement of a native amino residue with a residue more amenable to lipidation.

A linking group is generally used to space the lipid chain from the peptide.

A linker may comprise a γGlu residue, in particular an L-γGlu. Alternatively, a linker may comprise (i) L-Asp, L-Glu or D-Glu, especially L-Glu or D-Glu (ii) butanoyl-sulfonamide. A linker may comprise a plurality of residues (e.g. 2, 3, or 4), such as a plurality of L-γGlu (e.g. 2, 3, or 4), but may conveniently comprise one residue, such as one L-γGlu.

A linking group may also contain a spacer, such as OEG units, such as 1 to 4, for example 2. A linking group may contain b-Ala instead of OEG units.

Common lipid chains include carboxylic acids, such as C16, C18, C20 acids, and dicarboxylic acids, such as C18DA, C20DA diacids. However, other chain lengths and types may also be used in some cases, such as carboxylic acid isosteres like sulphonic acid or tetrazoles and the like. Suitably the lipid chain is C16DA, C18DA or C20DA, especially, C18DA or C20DA and in particular C18DA.

Suitably the peptide is lipidated by C18DA-γGlu-OEG-OEG-, such as C18DA-L-γGlu-OEG-OEG or such as C18DA-D-γGlu-OEG-OEG.

Typically the peptide has a single lipidation.

The optimal choice of lipidation type and location may depend on the structure of the specific peptide.

Methods for Preparation of Peptides

The peptides according to the present invention may be prepared by any methods known in the art. Thus, the peptides of may be prepared by standard peptide-preparation techniques, such as solution synthesis or Merrifield-type solid phase synthesis (as illustrated in Examples 1 and 2).

In one embodiment, a peptide according to the invention is synthetically made or produced. The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999. In one embodiment, the peptide or peptide sequences of the invention are produced synthetically, in particular, by the sequence assisted peptide synthesis (SAPS) method, by solution synthesis, by solid-phase peptide synthesis (SPPS) such as Merrifield-type solid phase synthesis After purification of linear peptides, such as by reversed phase HPLC, the linear peptides may be further processed to cyclic peptides. Techniques for cyclizing a peptide and for obtaining a cyclic peptide, for example by using a solid support, are known (as illustrated in Example 2).

In one aspect, the present invention concerns a method of manufacturing a lipidated cyclic peptide of the invention, the method comprising the steps of:

(i) preparing a lipidated linear peptide having an appropriate amino acid sequence, and
(ii) subsequently generating a cyclised peptide from the linear peptide.

In one aspect, the present invention concerns a method of manufacturing a cyclic peptide of the invention, the method comprising the steps of:

(i) preparing a linear peptide having an appropriate amino acid sequence, and
(ii) subsequently generating a cyclised peptide from the linear peptide.

An appropriate amino acid sequence is one which when cyclised provides the intended cyclic peptide (e.g. CLP1 to CLP11, CP1 to CP15 or CP22). A side chain cyclised, head to side chain or tail to side chain cyclised peptide requires a linear sequence in normal N- to C-terminal residue order. However, a backbone cyclised peptide, for example consisting of CP1 may be formed from a linear peptide MTEPIE-HEEDV, VMTEPIEHEED or the like.

A linear peptide will typically be joined exclusively by peptide bonds. A cyclised peptide will typically be joined exclusively by peptide bonds. A cyclised peptide may be backbone cyclised.

Synthetic preparation of a linear peptide may require or benefit from the presence of side chain protecting groups on some or all residues containing side chains which may be reactive, and side chain protecting groups may or may not be removed, or may be removed and reintroduced, depending on the particular sequence, prior to generation of a cyclised peptide, such as a backbone cyclised peptide. If some side chain protection is present during generation of a cyclised peptide, such as a backbone cyclised peptide, this may subsequently be removed to form a deprotected cyclised peptide. In preparation of a non-backbone cyclised peptide, protecting groups may be present at the N- or C-termini as required.

The linear peptide and/or the cyclised peptide (or protected versions thereof as appropriate) may be in the form of a salt, in particular a pharmaceutically acceptable salt.

The present invention provides a linear peptide, or a protected version thereof, which when cyclised provides a cyclic peptide as described herein, or a protected version thereof. The present invention provides a linear peptide, or a side chain protected version thereof, which when cyclised provides a cyclic peptide as described herein, or a side chain protected version thereof.

The present invention provides a lipidated linear peptide, or a protected version thereof, which when cyclised provides a lipidated cyclic peptide as described herein, or a protected version thereof. The present invention provides a lipidated linear peptide, or a side chain protected version thereof, which when cyclised provides a lipidated cyclic peptide as described herein, or a side chain protected version thereof.

Protected cyclic peptides and protected lipidated cyclic peptides also form part of the invention.

Amino acid protecting groups are known to the skilled person and are discussed, for example, in Isidro-Llobet et al, Chem Rev 2009 109 2455-2504 and Chandrudu et al, Molecules 2013 18(4):4373-4388. Common side chain protections include: Arg(Pbf), Asn(Trt), Asp(OtBu), Cys(Trt), Gln(Trt), Glu(OtBu), His(Trt), Lys(Boc), Ser(tBu), Thr(tBu) and Tyr(tBu).

Intermediates of Use in the Preparation of Peptides (i.e the Lipidated Cyclic. Cyclic. Lipidated Linear or Linear and Variants of any Thereof) Include Such Peptides, or a Protected Version Thereof, Covalently Bound to a Solid Support, Covalent Binding to a Solid Support May be Direct with or Through a Spacing Group.

Medical Uses

As demonstrated in the examples herein, the peptides of the present invention can promote clearance of disease-causing aggregates, neuronal survival and improve mitochondrial as well as lysosomal function.

Suitably peptides (lipidated cyclic, cyclic, lipidated linear or linear and variants of any thereof) of the invention or salts thereof, in particular pharmaceutically acceptable salts, are capable of increasing BDNF levels. More suitably, BDNF levels are increased by at least 30% between 0 and 24 hours following administration in the assay of Example 10.

Suitably peptides (lipidated cyclic, cyclic, lipidated linear or linear and variants of any thereof) of the invention or salts thereof, in particular pharmaceutically acceptable salts, are capable of increasing phospho-CREB (Ser133) levels. More suitably, phospho-CREB (Ser133) levels are increased by at least 30% between 0 and 24 hours following administration in the assay of Example 10.

Suitably peptides (lipidated cyclic, cyclic, lipidated linear or linear and variants of any thereof) of the invention or salts thereof, in particular pharmaceutically acceptable salts, are capable of increasing PGC1a levels. More suitably, PGC1a levels are increased by at least 30% between 0 and 24 hours following administration in the assay of Example 10.

Suitably peptides (lipidated cyclic, cyclic, lipidated linear or linear and variants of any thereof) of the invention or salts thereof, in particular pharmaceutically acceptable salts, are capable of increasing TFEB levels. More suitably, TFEB levels are increased by at least 30% between 0 and 24 hours following administration in the assay of Example 10.

Suitably peptides (lipidated cyclic, cyclic, lipidated linear or linear and variants of any thereof) of the invention or salts thereof, in particular pharmaceutically acceptable salts, are capable of decreasing NfL levels. More suitably, NfL levels are decreased by at least 10%, especially at least 20%, in the assay of Example 31.

Neurodegenerative diseases are often linked with blocked neurotrophic-signaling caused by the aggregates of misfolded proteins. In a healthy neuron, a variety of signaling pathways, initiated by neurotrophic growth factors, converge on the activation of transcription factor CREB leading to growth, neuronal plasticity and survival. However, decreased activation of downstream transcription factor CREB is observed in a number of neurodegenerative diseases.

A hallmark of neurodegenerative diseases is aggregation of misfolded proteins. Mutations linked to neurodegenerative diseases have been shown to attenuate general clearing-mechanisms of misfolded proteins and damaged organelles in cells.

The impact of administration of peptides of the invention may be quantified in various ways. For example, in the context of Huntington's the Unified Huntington's Disease Rating Scale (UHDRS) can be applied as a measure of motor function, cognition, behavior abnormalities and functional capacity, which may be improved (improvement typically being relative to the absence of treatment). Other Huntington markers include measuring mutated huntingtin in cerebrospinal fluid (CSF) of a subject, which may be reduced.

Total functional capacity score (TFC) may be improved.

In the context of Parkinsons's disease the Unified Huntington's Disease Rating Scale (UPDRS) or the Movement Disorder Society-Sponsored Revision of the Unified Parkinson's Disease Rating Scale (MDS-UPDRS) can be applied as an assessment of both motor and non-motor symptoms associated with Parkinson's. Such measures may be improved.

In the context of FTD, monitoring of PGRN in the CSF or plasma may be of interest.

CSF or blood plasma levels of neurofilament light-chain (NfL), a biomarker of neuronal loss, may be reduced.

Magnetic Resonance Imaging (MRI) may be used to quantify brain volume, either entire brain or specific regions. Loss of brain volume may be reduced.

In a clinical context, markers of the dopaminergic system function, such as PET radiotracers, might be used to monitor efficacy in humans.

The present invention provides a lipidated cyclic peptide, cyclic peptide, lipidated linear peptide, linear peptide, variant of any thereof and/or a pharmaceutically acceptable salt of any thereof as described herein, for use as a medicament. The present invention also provides CLP1 to CLP11, LLP1 to LLP12, CP1 to CP15 or CP22, or a pharmaceutically acceptable salt of any thereof, for use as a medicament. In particular, the invention provides CLP1, or a pharmaceutically acceptable salt of any thereof, for use as a medicament.

In some embodiments the medicament is for prophylactic use. In other embodiments the medicament is for treatment.

The present invention provides a lipidated cyclic peptide, cyclic peptide, lipidated linear peptide, linear peptide, variant of any thereof and/or a pharmaceutically acceptable salt of any thereof as described herein for the treatment or prophylaxis of a disease or disorder selected from the group consisting of neurodegenerative diseases, proteinopathies, lysosomal storage disorders, mitochondrial disorders, psychiatric disorders and other BDNF-related disorders. The present invention also provides a lipidated cyclic peptide, cyclic peptide, lipidated linear peptide, linear peptide, variant of any thereof and/or a pharmaceutically acceptable salt of any thereof as described herein for the treatment of a disease or disorder selected from the group consisting of neurodegenerative diseases, proteinopathies, lysosomal storage disorders, mitochondrial disorders, psychiatric disorders and other BDNF-related disorders. Further provided a lipidated cyclic peptide, cyclic peptide, lipidated linear peptide, linear peptide, variant of any thereof and/or a pharmaceutically acceptable salt of any thereof as described herein for the prophylaxis of a disease or disorder selected from the group consisting of neurodegenerative diseases, proteinopathies, lysosomal storage disorders, mitochondrial disorders, psychiatric disorders and other BDNF-related disorders.

Additionally provided is the use of a lipidated cyclic peptide, cyclic peptide, lipidated linear peptide, linear peptide, variant of any thereof and/or a pharmaceutically acceptable salt of any thereof as described herein in the manufacture of a medicament for the treatment or prophylaxis of a disease or disorder selected from the group consisting of neurodegenerative diseases, proteinopathies, lysosomal storage disorders, mitochondrial disorders, psychiatric disorders and other BDNF-related disorders. Also provided is the use of a lipidated cyclic peptide, cyclic peptide, lipidated linear peptide, linear peptide, variant of any thereof and/or a pharmaceutically acceptable salt of any thereof as described herein in the manufacture of a medicament for the treatment of a disease or disorder selected from the group consisting of neurodegenerative diseases, proteinopathies, lysosomal storage disorders, mitochondrial disorders, psychiatric disorders and other BDNF-related disorders. The invention provides the use of a lipidated cyclic peptide, cyclic peptide, lipidated linear peptide, linear peptide, variant of any thereof and/or a pharmaceutically acceptable salt of any thereof as described herein in the manufacture of a medicament for the prophylaxis of a disease or disorder selected from the group consisting of neurodegenerative diseases, proteinopathies, lysosomal storage disorders, mitochondrial disorders, psychiatric disorders and other BDNF-related disorders.

Provided is a method of treatment or prophylaxis of a disease or disorder in a subject, wherein the disease or disorder is selected from the group consisting of neurodegenerative diseases, proteinopathies, lysosomal storage disorders, mitochondrial dysfunction disorders, psychiatric disorders and BDNF-related disorders, which method comprises administering to the subject a lipidated cyclic peptide, cyclic peptide, lipidated linear peptide, linear peptide, variant of any thereof and/or a pharmaceutically acceptable salt of any thereof as described herein. Additionally provided is a method of treating a disease or disorder in a subject, wherein the disease or disorder is selected from the group consisting of neurodegenerative diseases, proteinopathies, lysosomal storage disorders, mitochondrial dysfunction disorders, psychiatric disorders and BDNF-related disorders, which method comprises administering to the subject a lipidated cyclic peptide, cyclic peptide, lipidated linear peptide, linear peptide, variant of any thereof and/or a pharmaceutically acceptable salt of any thereof as described herein.

Additionally provided is a method of prophylaxis of a disease or disorder in a subject, wherein the disease or disorder is selected from the group consisting of neurodegenerative diseases, proteinopathies, lysosomal storage disorders, mitochondrial dysfunction disorders, psychiatric disorders and BDNF-related disorders, which method comprises administering to the subject a lipidated cyclic peptide, cyclic peptide, lipidated linear peptide, linear peptide, variant of any thereof and/or a pharmaceutically acceptable salt of any thereof as described herein.

In one embodiment the disease or disorder is a neurodegenerative disease, particularly a neurodegenerative disease associated with reduction of BDNF, rescue with BDNF, mitochondrial dysfunction and/or lysosomal dysfunction.

In one embodiment the disease or disorder is selected from the group consisting of Huntington's disease, Parkinson's disease, Alzheimer's disease, Frontotemporal dementia (especially subjects with GRN-haploinsufficiency), ALS, multiple sclerosis, inherited ataxias, motor neuron disorder and vascular dementia. In one embodiment the disease or disorder is Huntington's disease. In one embodiment the disease or disorder is Parkinson's Disease (PD), such as in a subject with monoallelic mutation in GBA1 (Stoker, 2018—incorporated by reference for its disclosure of specific mutations associated with PD), pathogenic mutations include N370S, L444P, R463C, G10S, N426K, R48W and R257Q. In one embodiment the disease or disorder is Alzheimer's disease. In one embodiment the disease or disorder is Frontotemporal dementia. In one embodiment the disease or disorder is Frontotemporal dementia in subjects with GRN-haploinsufficiency.

In one embodiment the disease or disorder is a proteinopathy, particularly a proteinopathy associated with protein aggregation. In one embodiment, the proteinopathy is selected from the group consisting of prion diseases, Alpha-synucleinopathies, tauopathies, C9orf72-dependent ALS/FTD, dementia with Lewy bodies, dementia with amyloid plaques, Huntington's Disease, TDP-43-positive ALS/FTD and inherited ataxias.

In one embodiment the disease or disorder is a lysosomal storage disorder, in particular a lysosomal storage disorder associated with lysosomal dysfunction. In one embodiment, the lysosomal storage disorder is selected from the group consisting of Nieman-Pick disease and neuronal ceroid lipofuscinose. The lysosomal storage disorder may be Gaucher's Disease, such as in a subject with biallelic mutation in GBA1 (Sheth, 2019—incorporated by reference for its disclosure of specific mutations associated with Gaucher's Disease), in one study p.Leu483Pro was identified as the most commonly occurring Gaucher disease mutation (62% patients), p.Arg535Cys (7% patients) and RecNcil (7% patients).

In one embodiment the disease or disorder is a mitochondrial dysfunction disorder. In one embodiment, the mitochondrial dysfunction disorder is selected from the group consisting of mitochondrial myopathies and Leigh syndrome.

In one embodiment the disease or disorder is a psychiatric disorder, particularly a psychiatric disorder associated with SorCS2 gene or function association, or BDNF or TrkB association. In one embodiment the psychiatric disorder is selected from bipolar disorder, depression, schizophrenia, autism spectrum disorders, anxiety and ADHD. Suitably the disease or disorder is depression.

In one embodiment the disease or disorder is another BDNF related disorder. In one embodiment the BDNF related disorder is selected from the group consisting of WAGR Syndrome (especially BDNF haploinsufficiency), stroke and epilepsy.

The term "treatment" or "treating" as used herein includes the control, mitigation, reduction, or modulation of the disease or disorder or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

Suitably the subject is a human.

In some embodiments, the lipidated cyclic peptide, cyclic peptide, lipidated linear peptide, linear peptide, variant of any thereof and/or a pharmaceutically acceptable salt of any thereof are intended for treatment, i.e. administration to a subject having a condition, disease or disorder.

The therapeutic use may be intended to alleviate or relieve symptoms or complications; delay the progression of the condition, disease or disorder; cure or eliminate the condition, disease or disorder.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 100% improvement in one of more parameters. The change can be based on improvement(s) in the severity of the treated condition in an individual, or on a difference in the frequency of improved conditions in populations of individuals with and without treatment with lipidated cyclic peptide, cyclic peptide, lipidated linear peptide, linear peptide, variant of any thereof and/or a pharmaceutically acceptable salt of any thereof.

Suitably the lipidated cyclic peptide, cyclic peptide, lipidated linear peptide, linear peptide, variant of any thereof and/or a pharmaceutically acceptable salt of any thereof, is administered to a subject in need thereof. Suitably the peptide of the invention, or a pharmaceutically acceptable salt thereof, is administered in a safe and effective amount i.e. an amount providing an acceptable balance of desired benefits and undesired side effects. A "safe and effective amount" is intended to include an amount that is effective to achieve a desirable effect in therapy and/or prophylaxis. A desirable effect is typically clinically significant and/or measurable, for instance in the context of (a) preventing a condition, disease or disorder occurring, in particular, when a subject is predisposed or at risk but has not yet been diagnosed; (b) inhibiting a condition, disease or disorder, i.e., slowing or arresting its development; and/or (c) relieving a condition, disease or disorder, i.e., causing regression of the condition, disease or disorder or a reduction in associated symptoms. The safe and effective amount may be one that is sufficient to achieve the desirable effect either when the peptide of the invention, or a pharmaceutically acceptable salt thereof, is administered alone or alternatively when it is administered in combination with one or more further active pharmaceutical ingredients, which either are further peptides of the invention, or a pharmaceutically acceptable salts thereof, or are different from the peptides of the invention.

In one embodiment of the present invention, the lipidated cyclic peptide, cyclic peptide, lipidated linear peptide, linear peptide, variant of any thereof and/or a pharmaceutically acceptable salt of any thereof is administered in doses of from 1 pg/day to 200 mg/day.

In one embodiment of the present invention, one single dose of peptide is administered and may comprise of from 1 pg/kg body weight to 100 mg/kg body weight, such as 1 pg/kg body weight to 10 mg/kg body weight. A preferred dose is about 0.1 mg/kg to about 10 mg/kg and an especially preferred dose is about 0.1 mg/kg to about 5 mg/kg. A dose according to the present invention may be administered one or several times per day. A dose may also be administered in intermittent intervals, or intervals, whereby a dose is not administered every day. Rather one or more doses may be administered every second day, every third day, every fourth day, every fifth day, every sixth day, every week, every second week, every third week, every fourth week, every fifth week, every sixth week, or intervals within those ranges (such as every 2 to 4 weeks, or 4 to 6 weeks).

It will be appreciated that the preferred route of administration will depend on the general condition and age of the subject to be treated, the nature of the condition to be treated, the location of the tissue to be treated in the body and the peptide of the invention chosen.

In one embodiment of the present invention, the route of administration allows for the lipidated cyclic peptide, cyclic peptide, lipidated linear peptide, linear peptide, variant of any thereof and/or a pharmaceutically acceptable salt of any thereof to cross the blood-brain barrier.

For systemic treatment according to the present invention the route of administration is capable of introducing the lipidated cyclic peptide, cyclic peptide, lipidated linear peptide, linear peptide, variant of any thereof and/or a pharmaceutically acceptable salt of any thereof into the blood stream to ultimately target the sites of desired action. Such routes of administration are any suitable routes, such as a parenteral route (including subcutaneous, intramuscular, intrathecal, intracerebral, intravenous and intradermal administration). Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration.

In one embodiment administration is subcutaneously, such as by injection. In one embodiment administration is intramuscularly, such as by injection. In one embodiment administration is administered intradermally, such as by injection. In one embodiment administration is intravenously, such as by injection.

Pharmaceutical Compositions

Whilst it is possible for the lipidated cyclic peptide, cyclic peptide, lipidated linear peptide, linear peptide, variant of any thereof and/or a pharmaceutically acceptable salt of any thereof of the present invention to be administered as the 'raw' peptide, it is desirable to present them in the form of a pharmaceutical composition. Accordingly, the present invention further provides a pharmaceutical formulation, which comprises a lipidated cyclic peptide, cyclic peptide, lipidated linear peptide, linear peptide, variant of any thereof and/or a pharmaceutically acceptable salt of any thereof of the present invention, and a pharmaceutically acceptable carrier. The pharmaceutical compositions may be prepared by conventional techniques, e.g. as described in Remington: The Science and Practice of Pharmacy 2005, Lippincott, Williams & Wilkins.

Pharmaceutically acceptable carriers include water. For better stability, pharmaceutical compositions may be dry and extemporaneously reconstituted with water (or e.g. saline).

A pharmaceutically acceptable composition for parenteral administration should have a physiologically acceptable pH and should have a physiologically acceptable osmolality.

The pH of an aqueous composition may be adjusted in view of the components of the composition and necessary suitability for administration. The pH is generally at least 4, especially at least 5, in particular at least 5.5 such as at least 6. The pH is generally 9 or less, especially 8.5 or less, in particular 8 or less, such as 7.5 or less. The pH of may be 4 to 9, especially 5 to 8.5, in particular 5.5 to 8, such as 6.5 to 7.4 (e.g. 6.5 to 7.1).

For parenteral administration a physiologically acceptable osmolality is desirable to avoid excessive cell distortion or lysis. A physiologically acceptable osmolality will generally mean that solutions will have an osmolality which is approximately isotonic or mildly hypertonic. Suitably compositions for administration will have an osmolality of 250 to 750 mOsm/kg, especially 250 to 550 mOsm/kg, in particular 270 to 500 mOsm/kg, such as 270 to 400 mOsm/kg.

Other components, such as buffers or stabilizing agents, may also be present.

The phrase "pharmaceutically acceptable" is used herein to refer to those materials, compositions, dosage forms and the like which are, within the scope of sound medical judgment, suitable for use in contact with the tissues of human beings and animals, for example human beings, without excessive toxicity, irritation, allergic response, or other problem or complication, commensurate with a reasonable benefit/risk ratio.

It will be appreciated that for use in medicine the salts of the peptides should be pharmaceutically acceptable. Suitable pharmaceutically acceptable salts will be apparent to those skilled in the art. Pharmaceutically acceptable salts include those *Remington's Pharmaceutical Sciences,* 17th ed., Mack Publishing Company, Easton, P A, 1985, p. 1418. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Pharmaceutically acceptable salts may also be formed with organic bases such as basic amines e.g. with ammonia, meglumine, tromethamine, piperazine, arginine, choline, diethylamine, benzathine or lysine. Salts which are not considered to be pharmaceutically acceptable may still be of use, for example in the preparation of peptides and there pharmaceutically acceptable salts, and as such are included within the scope of this invention.

Certain of peptides may form salts with one or more equivalents of acid or base. The present invention includes within its scope all possible stoichiometric and non-stoichiometric forms.

When the peptides contain a basic group as well as the free acid they may be Zwitterionic.

Pharmaceutical compositions of the present invention may be co-administered with one or more other therapeutic agents. Combined administration of two or more agents may be achieved in a number of different ways. Both may be administered together in a single composition, or they may be administered in separate compositions as part of a combined therapy. For example, one may be administered before or separately, after or sequentially, or concurrently or simultaneously with the other.

The invention is further illustrated by reference to the following clauses:

Clauses of the Invention

The invention is further illustrated by reference to the following clauses:

Clause A1. A lipidated cyclic peptide comprising the sequence:

|  | $X_2$— | $X_3$— | E— | H— | $X_4$— | E |
|---|---|---|---|---|---|---|
| position | 1 | 2 | 3 | 4 | 5 | 6 | wherein:
$X_2$ represents P, D, Q, K, G
$X_3$ represents I, L, A, T, V
$X_4$ represents E, A or a salt thereof, or a conservatively substituted variant of said peptide or salt.

Clause A2. The lipidated cyclic peptide, variant or salt according to clause A1, wherein the peptide is backbone cyclised.

Clause A3. The lipidated cyclic peptide, variant or salt according to clause A2, wherein the peptide is backbone cyclised and all residues of the peptide backbone are joined exclusively by peptide bonds.

Clause A4. The lipidated cyclic peptide, variant or salt according to any one of clauses A1 to A3, comprising 25 or fewer amino acid residues within the cycle.

Clause A5. The lipidated cyclic peptide, variant or salt according to clause A4, comprising 20 or fewer amino acid residues within the cycle, such as comprising 20 amino acid residues within the cycle.

Clause A6. The lipidated cyclic peptide, variant or salt according to clause A5, comprising 15 or fewer amino acid residues within the cycle, such as comprising 15 amino acid residues within the cycle.

Clause A7. The lipidated cyclic peptide, variant or salt according to clause A6, comprising 12 or fewer amino acid residues within the cycle, such as comprising 12 amino acid residues within the cycle.

Clause A8. The lipidated cyclic peptide, variant or salt according to clause A7, comprising 11 or fewer amino acid residues within the cycle.

Clause A9. The lipidated cyclic peptide, variant or salt according to any one of clauses A1 to A8, comprising at least 7 amino acid residues within the cycle, such as comprising 7 amino acid residues within the cycle.

Clause A10. The lipidated cyclic peptide, variant or salt according to clause A9, comprising at least 8 amino acid residues within the cycle, such as comprising 8 amino acid residues within the cycle.

Clause A11. The lipidated cyclic peptide, variant or salt according to clause A10, comprising at least 9 amino acid residues within the cycle, such as comprising 9 amino acid residues within the cycle.

Clause A12. The lipidated cyclic peptide, variant or salt according to clause A11, comprising at least 10 amino acid residues within the cycle, such as comprising 10 amino acid residues within the cycle.

Clause A13. The lipidated cyclic peptide, variant or salt according to clause A12, comprising at least 11 amino acid residues within the cycle.

Clause A14. The lipidated cyclic peptide, variant or salt according to clause A1, comprising 11 amino acid residues within the cycle.

Clause A15. The lipidated cyclic peptide, variant or salt according to any one of clauses A9 to A14, comprising the sequence:

|  | E— | $X_2$— | $X_3$— | E— | H— | $X_4$— | E |
|---|---|---|---|---|---|---|---|
| position | 0 | 1 | 2 | 3 | 4 | 5 | 6 | wherein:
$X_2$ represents P, D, Q, K, G
$X_3$ represents I, L, A, T, V
$X_4$ represents E, A or a salt thereof, or a conservatively substituted variant of said peptide or salt.

Clause A16. The lipidated cyclic peptide, variant or salt according to any one of clauses A9 to A14, comprising the sequence:

|  | $X_2$— | $X_3$— | E— | H— | $X_4$— | E— | D |
|---|---|---|---|---|---|---|---|
| position | 1 | 2 | 3 | 4 | 5 | 6 | 7 | wherein:
$X_2$ represents P, D, Q, K, G
$X_3$ represents I, L, A, T, V
$X_4$ represents E, A or a salt thereof, or a conservatively substituted variant of said peptide or salt.

Clause A17. The lipidated cyclic peptide, variant or salt according to any one of clauses A10 to A14, comprising the sequence:

|  | T— | E— | $X_2$— | $X_3$— | E— | H— | $X_4$— | E |
|---|---|---|---|---|---|---|---|---|
| position | -1 | 0 | 1 | 2 | 3 | 4 | 5 | 6 | wherein:
$X_2$ represents P, D, Q, K, G
$X_3$ represents I, L, A, T, V
$X_4$ represents E, A or a salt thereof, or a conservatively substituted variant of said peptide or salt.

Clause A18. The lipidated cyclic peptide, variant or salt according to any one of clauses A10 to A14, comprising the sequence:

|  | E— | $X_2$— | $X_3$— | E— | H— | $X_4$— | E— | D |
|---|---|---|---|---|---|---|---|---|
| position | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof, or a conservatively substituted variant of said peptide or salt.

Clause A19. The lipidated cyclic peptide, variant or salt according to any one of clauses A10 to A14, comprising the sequence:

|  | $X_2$— | $X_3$— | E— | H— | $X_4$— | E- | D— | V |
|---|---|---|---|---|---|---|---|---|
| position | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

Clause A20. The lipidated cyclic peptide, variant or salt according to any one of clauses A11 to A14, comprising the sequence:

|  | $X_1$— | T— | E— | $X_2$— | $X_3$— | E— | H— | $X_4$— | E |
|---|---|---|---|---|---|---|---|---|---|
| position | -2 | -1 | 0 | 1 | 2 | 3 | 4 | 5 | 6 | wherein:
$X_1$ represents M, K
$X_2$ represents P, D, Q, K, G
$X_3$ represents I, L, A, T, V
$X_4$ represents E, A
or a salt thereof, or a conservatively substituted variant of said peptide or salt.

Clause A21. The lipidated cyclic peptide, variant or salt according to any one of clauses A11 to A14, comprising the sequence:

|  | T— | E— | $X_2$— | $X_3$— | E— | H— | $X_4$— | E— | D |
|---|---|---|---|---|---|---|---|---|---|
| position | -1 | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof, or a conservatively substituted variant of said peptide or salt.

Clause A22. The lipidated cyclic peptide, variant or salt according to any one of clauses A11 to A14, comprising the sequence:

|  | E— | $X_2$— | $X_3$— | E— | H— | $X_4$— | E— | D— | V |
|---|---|---|---|---|---|---|---|---|---|
| position | 0 | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

Clause A23. The lipidated cyclic peptide, variant or salt according to any one of clauses A12 to A14, comprising the sequence:

|  | $X_1$— | T— | E— | $X_2$— | $X_3$— | E— | H— | $X_4$— | E— | D |
|---|---|---|---|---|---|---|---|---|---|---|
| position | -2 | -1 | 0 | 1 | 2 | 3 | 4 | 5 | 6 | 7 | wherein:
$X_1$ represents M, K
$X_2$ represents P, D, Q, K, G
$X_3$ represents I, L, A, T, V
$X_4$ represents E, A
or a salt thereof, or a conservatively substituted variant of said peptide or salt.

Clause A24. The lipidated cyclic peptide, variant or salt according to any one of clauses A12 to A14 comprising the sequence:

|  | T— | E— | $X_2$— | $X_3$— | E— | H— | $X_4$— | E— | D— | V |
|---|---|---|---|---|---|---|---|---|---|---|
| position | -1 | 0 | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

Clause A25. The lipidated cyclic peptide, variant or salt according to any one of clauses A13 to A14, comprising the sequence:

|  | $X_1$— | T— | E— | $X_2$— | $X_3$— | E— | H— | $X_4$— | E— | D— | V |
|---|---|---|---|---|---|---|---|---|---|---|---|
| position | -2 | -1 | 0 | 1 | 2 | 3 | 4 | 5 | 6 | 7 | 8 | wherein:
$X_1$ represents M, K
$X_2$ represents P, D, Q, K, G
$X_3$ represents I, L, A, T, V
$X_4$ represents E, A or a salt thereof, or a conservatively substituted variant of said peptide or salt.

Clause A26. The lipidated cyclic peptide, variant or salt according to any one of clauses A1 to A25, wherein $X_1$ represents M.

Clause A27. The lipidated cyclic peptide, variant or salt according to any one of clauses A1 to A25, wherein $X_1$ represents K.

Clause A28. The lipidated cyclic peptide, variant or salt according to any one of clauses A1 to A27, wherein $X_2$ represents P.

Clause A29. The lipidated cyclic peptide, variant or salt according to any one of clauses A1 to A27, wherein $X_2$ represents D.

Clause A30. The lipidated cyclic peptide, variant or salt according to any one of clauses A1 to A27, wherein $X_2$ represents Q.

Clause A31. The lipidated cyclic peptide, variant or salt according to any one of clauses A1 to A27, wherein $X_2$ represents K.

Clause A32. The lipidated cyclic peptide, variant or salt according to any one of clauses A1 to A27, wherein $X_2$ represents G.

Clause A33. The lipidated cyclic peptide, variant or salt according to any one of clauses A1 to A32, wherein $X_3$ represents I.

Clause A34. The lipidated cyclic peptide, variant or salt according to any one of clauses A1 to A32, wherein $X_3$ represents L.

Clause A35. The lipidated cyclic peptide, variant or salt according to any one of clauses A1 to A32, wherein $X_3$ represents A.

Clause A36. The lipidated cyclic peptide, variant or salt according to any one of clauses A1 to A32, wherein $X_3$ represents T.

Clause A37. The lipidated cyclic peptide, variant or salt according to any one of clauses A1 to A32, wherein $X_3$ represents V.

Clause A38. The lipidated cyclic peptide, variant or salt according to any one of clauses A1 to A37, wherein $X_4$ represents E.

Clause A39. The lipidated cyclic peptide, variant or salt according to any one of clauses A1 to A37, wherein $X_4$ represents A.

Clause A40. The lipidated cyclic peptide, variant or salt according to any one of clauses A13 to A14, comprising the sequence of any one of SEQ ID No. 1 to 11 or a salt thereof, or a conservatively substituted variant of said peptide or salt, such as consisting of the sequence of any one of SEQ ID No. 1 to 11 or a salt thereof, or a conservatively substituted variant of said peptide or salt.

Clause A41. The lipidated cyclic peptide, variant or salt according to any one of clauses A13 to A14, comprising the sequence of SEQ ID No. 1 or a salt thereof, or a conservatively substituted variant of said peptide or salt, such as consisting of the sequence of SEQ ID No. 1 or a salt thereof, or a conservatively substituted variant of said peptide or salt.

Clause A42. The variant or salt thereof according to any one of clauses A1 to A41, comprising two conservative substitutions.

Clause A43. The variant or salt thereof according to any one of clauses A1 to A42, comprising a substitution of X, at position −2, such as replacement by E, N, Q, R, T I, L or V.

Clause A44. The variant or salt thereof according to any one of clauses A1 to A42, comprising a substitution of T at position −1, such as replacement by A, K, M, N, R or S, especially A, K, M, N or R.

Clause A45. The variant or salt thereof according to any one of clauses A1 to A42, comprising a substitution of E at position 0, such as replacement by A, D, G, K, Q or V, especially G, K, Q or V.

Clause A46. The variant or salt thereof according to any one of clauses A1 to A42, comprising a substitution of $X_2$ at position 1, such as replacement by A, C, E, H, L, M, N, R, S, T, V or Y, especially A, E, H, L, M, N, R, T, V or Y.

Clause A47. The variant or salt thereof according to any one of clauses A1 to A42, comprising a substitution of $X_3$ at position 2, such as replacement by D, E, F, G, H, K, M, N, P, Q, S or W, especially D, E, F, G, H, K, M, N, P, Q or W.

Clause A48. The variant or salt thereof according to any one of clauses A1 to A42, comprising a substitution of E at position 3, such as replacement by A, D, G, K, Q or V, especially G, K, Q or V.

Clause A49. The variant or salt thereof according to any one of clauses A1 to A42, comprising a substitution of H at position 4, such as replacement by D, L, N, P, Q, R or Y.

Clause A50. The variant or salt thereof according to any one of clauses A1 to A42, comprising a substitution of $X_4$ at position 5, such as replacement by G, K, Q, S, T or V, especially G, K, Q, T or V.

Clause A51. The variant or salt thereof according to any one of clauses A1 to A42, comprising a substitution of E at position 6, such as replacement by A, D, G, K, Q or V.

Clause A52. The variant or salt thereof according to any one of clauses A1 to A42, comprising a substitution of D at position 7, such as replacement by A, E, G, H, N, V or Y.

Clause A53. The variant or salt thereof according to any one of clauses A1 to A42, comprising a substitution of V at position 8 such as replacement by D, E, I, L or M.

Clause A54. The variant or salt thereof according to any one of clauses A42 to A53, comprising a substitution of X, at position −2, such as replacement by E, N, Q, R, T I, L or V.

Clause A55. The variant or salt thereof according to any one of clauses A42 to A53, comprising a substitution of T at position −1, such as replacement by A, K, M, N, R or S, especially A, K, M, N or R.

Clause A56. The variant or salt thereof according to any one of clauses A42 to A53, comprising a substitution of E at position 0, such as replacement by A, D, G, K, Q or V, especially G, K, Q or V.

Clause A57. The variant or salt thereof according to any one of clauses A42 to A53, comprising a substitution of $X_2$ at position 1, such as replacement by A, C, E, H, L, M, N, R, S, T, V or Y, especially A, E, H, L, M, N, R, T, V or Y.

Clause A58. The variant or salt thereof according to any one of clauses A42 to A53, comprising a substitution of $X_3$ at position 2, such as replacement by D, E, F, G, H, K, M, N, P, Q, S or W, especially D, E, F, G, H, K, M, N, P, Q or W.

Clause A59. The variant or salt thereof according to any one of clauses A42 to A53, comprising a substitution of E at position 3, such as replacement by A, D, G, K, Q or V, especially G, K, Q or V.

Clause A60. The variant or salt thereof according to any one of clauses A42 to A53, comprising a substitution of H at position 4, such as replacement by D, L, N, P, Q, R or Y.

Clause A61. The variant or salt thereof according to any one of clauses A42 to A53, comprising a substitution of X at position 5, such as replacement by G, K, Q, S, T or V, especially G, K, Q, T or V.

Clause A62. The variant or salt thereof according to any one of clauses A42 to A53, comprising a substitution of E at position 6, such as replacement by A, D, G, K, Q or V.

Clause A63. The variant or salt thereof according to any one of clauses A42 to A53, comprising a substitution of D at position 7, such as replacement by A, E, G, H, N, V or Y.

Clause A64. The variant or salt thereof according to any one of clauses A42 to A53, comprising a substitution of V at position 8 such as replacement by D, E, I, L or M.

Clause A65. The variant or salt thereof according to any one of clauses A43 to A53, comprising one conservative substitution.

Clause A66. The lipidated cyclic peptide or salt thereof according to any one of clauses A1 to A41.

Clause A67. The lipidated cyclic peptide, variant or salt according to any one of clauses A1 to A66, which comprises a lipidated K residue.

Clause A68. The lipidated cyclic peptide, variant or salt according to clause A67, wherein the lipidated K residue is $X_2$ position 1.

Clause A69. The lipidated cyclic peptide, variant or salt according to clause A67, wherein the lipidated K residue is X, position −2.

Clause A70. The lipidated cyclic peptide, variant or salt according to any one of clauses A1 to A69, wherein the lipid chain is a C16DA, C18DA or C20DA group.

Clause A71. The lipidated cyclic peptide, variant or salt according to clause A70, wherein the lipid chain is a C18DA group.

Clause A72. The lipidated cyclic peptide, variant or salt according to any one of clauses A1 to A71, wherein the lipid is linked to the K residue via a γGlu.

Clause A73. The lipidated cyclic peptide, variant or salt according to clause A72, wherein the lipid is linked to the K residue via a γGlu and one to four OEG groups.

Clause A74. The lipidated cyclic peptide, variant or salt according to clause A73, wherein the lipid is linked to the K residue via a γGlu and two OEG groups.

Clause A75. The lipidated cyclic peptide, variant or salt according to any one of clauses A1 to A69, wherein the lipid is C18DA-γGlu-OEG-OEG-.

Clause A76. The lipidated cyclic peptide or salt according to any one of clauses A1 to A69, wherein the lipid is C18DA-γGlu-OEG-OEG-.

Clause A77. The lipidated cyclic peptide or salt according to clause A75 or A76, wherein the lipid is C18DA-L-γGlu-OEG-OEG-.

Clause A78. The lipidated cyclic peptide or salt according to clause A75 or A76, wherein the lipid is C18DA-D-γGlu-OEG-OEG-.

Clause A79. The lipidated cyclic peptide or salt according to clause A1 consisting of CLP1 or a salt thereof.

Clause A80. The lipidated cyclic peptide or salt according to clause A1 consisting of CLP1, wherein the lipid is C18DA-L-γGlu-OEG-OEG-, or a salt thereof.

Clause A81. The lipidated cyclic peptide or salt according to clause A1 consisting of CLP1, wherein the lipid is C18DA-D-γGlu-OEG-OEG-, or a salt thereof.

Clause A82. The lipidated cyclic peptide or salt according to clause A1 consisting of CLP2 or a salt thereof.

Clause A83. The lipidated cyclic peptide or salt according to clause A1 consisting of CLP3 or a salt thereof.

Clause A84. The lipidated cyclic peptide or salt according to clause A1 consisting of CLP4 or a salt thereof.

Clause A85. The lipidated cyclic peptide or salt according to clause A1, consisting of CLP5 or a salt thereof.

Clause A86. The lipidated cyclic peptide or salt according to clause A1, consisting of CLP6 or a salt thereof.

Clause A87. The lipidated cyclic peptide or salt according to clause A1, consisting of CLP7 or a salt thereof.

Clause A88. The lipidated cyclic peptide or salt according to clause A1, consisting of CLP8 or a salt thereof.

Clause A89. The lipidated cyclic peptide or salt according to clause A1, consisting of CLP9 or a salt thereof.

Clause A90. The lipidated cyclic peptide or salt according to clause A1, consisting of CLP10 or a salt thereof.

Clause A91. The lipidated cyclic peptide or salt according to clause A1, consisting of CLP11 or a salt thereof.

Clause A92. The lipidated cyclic peptide, variant or salt according to any one of clauses A1 to A91, wherein the salt is a pharmaceutically acceptable salt.

Clause A93. The lipidated cyclic peptide according to any preceding A clause.

Clause A94. The lipidated variant peptide according to any preceding A clause.

Clause A95. The pharmaceutically acceptable salt of a lipidated cyclic peptide according to any preceding A clause.

Clause A96. The pharmaceutically acceptable salt of the lipidated variant peptide according to any preceding A clause.

Clause A97. The lipidated cyclic peptide according to any one of clauses A1 to A96, which is not side chain modified.

Clause A98. The lipidated cyclic peptide according to any one of clauses A1 to A96, which is not modified.

Clause B1. A cyclic peptide comprising the sequence:

|  | $X_2$— | $X_3$— | E— | H— | $X_4$— | E |
|---|---|---|---|---|---|---|
| position | 1 | 2 | 3 | 4 | 5 | 6 | wherein:
$X_2$ represents P, D, Q, K, G
$X_3$ represents I, L, A, T, V
$X_4$ represents E, A
or a salt thereof, or a conservatively substituted variant of said peptide or salt, wherein when $X_2$ represents P then $X_3$ is other than V.

Clause B2. The cyclic peptide, variant or salt according to clause B1, wherein the peptide is backbone cyclised.

Clause B3. The cyclic peptide, variant or salt according to clause B2, wherein the peptide is backbone cyclised and all residues of the peptide backbone are joined exclusively by peptide bonds.

Clause B4. The cyclic peptide, variant or salt according to any one of clauses B1 to B3, comprising 25 or fewer amino acid residues within the cycle.

Clause B5. The cyclic peptide, variant or salt according to clause B4, comprising 20 or fewer amino acid residues within the cycle, such as comprising 20 amino acid residues within the cycle.

Clause B6. The cyclic peptide, variant or salt according to clause B5, comprising 15 or fewer amino acid residues within the cycle, such as comprising 15 amino acid residues within the cycle.

Clause B7. The cyclic peptide, variant or salt according to clause B6, comprising 12 or fewer amino acid residues within the cycle, such as comprising 12 amino acid residues within the cycle.

Clause B8. The cyclic peptide, variant or salt according to clause B7, comprising 11 or fewer amino acid residues within the cycle.

Clause B9. The cyclic peptide, variant or salt according to any one of clauses B1 to B8, comprising at least 7 amino acid residues within the cycle, such as comprising 7 amino acid residues within the cycle.

Clause B10. The cyclic peptide, variant or salt according to clause B9, comprising at least 8 amino acid residues within the cycle, such as comprising 8 amino acid residues within the cycle.

Clause B11. The cyclic peptide, variant or salt according to clause B10, comprising at least 9 amino acid residues within the cycle, such as comprising 9 amino acid residues within the cycle.

Clause B12. The cyclic peptide, variant or salt according to clause B11, comprising at least 10 amino acid residues within the cycle, such as comprising 10 amino acid residues within the cycle.

Clause B13. The cyclic peptide, variant or salt according to clause B12, comprising at least 11 amino acid residues within the cycle.

Clause B14. The cyclic peptide, variant or salt according to clause B1, comprising 11 amino acid residues within the cycle.

Clause B15. The cyclic peptide, variant or salt according to any one of clauses B9 to B14, comprising the sequence:

|  | E— | $X_2$— | $X_3$— | E— | H— | $X_4$— | E— |
| --- | --- | --- | --- | --- | --- | --- | --- |
| position | 0 | 1 | 2 | 3 | 4 | 5 | 6 | wherein:
$X_2$ represents P, D, Q, K, G
$X_3$ represents I, L, A, T, V
$X_4$ represents E, A
or a salt thereof, or a conservatively substituted variant of said peptide or salt.

Clause B16. The cyclic peptide, variant or salt according to any one of clauses B9 to B14, comprising the sequence:

|  | $X_2$— | $X_3$— | E— | H— | $X_4$— | E— | D |
| --- | --- | --- | --- | --- | --- | --- | --- |
| position | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof, or a conservatively substituted variant of said peptide or salt.

Clause B17. The cyclic peptide, variant or salt according to any one of clauses B10 to B14, comprising the sequence:

|  | T— | E— | $X_2$— | $X_3$— | E— | H— | $X_4$— | E |
| --- | --- | --- | --- | --- | --- | --- | --- | --- |
| position | -1 | 0 | 1 | 2 | 3 | 4 | 5 | 6 | wherein:
$X_2$ represents P, D, Q, K, G
$X_3$ represents I, L, A, T, V
$X_4$ represents E, A
or a salt thereof, or a conservatively substituted variant of said peptide or salt.

Clause B18. The cyclic peptide, variant or salt according to any one of clauses B10 to B14, comprising the sequence:

|  | E— | $X_2$— | $X_3$— | E— | H— | $X_4$— | E— | D |
| --- | --- | --- | --- | --- | --- | --- | --- | --- |
| position | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof, or a conservatively substituted variant of said peptide or salt.

Clause B19. The cyclic peptide, variant or salt according to any one of clauses B10 to B14, comprising the sequence:

|  | $X_2$— | $X_3$— | E— | H— | $X_4$— | E— | D— | V |
| --- | --- | --- | --- | --- | --- | --- | --- | --- |
| position | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

Clause B20. The cyclic peptide, variant or salt according to any one of clauses B11 to B14, comprising the sequence:

|  | $X_1$— | T— | E— | $X_2$— | $X_3$— | E— | H— | $X_4$— | E |
| --- | --- | --- | --- | --- | --- | --- | --- | --- | --- |
| position | -2 | -1 | 0 | 1 | 2 | 3 | 4 | 5 | 6 | wherein:
$X_1$ represents M, K
$X_2$ represents P, D, Q, K, G
$X_3$ represents I, L, A, T, V
$X_4$ represents E, A
or a salt thereof, or a conservatively substituted variant of said peptide or salt.

Clause B21. The cyclic peptide, variant or salt according to any one of clauses B11 to B14, comprising the sequence:

|  | T— | E— | $X_2$— | $X_3$— | E— | H— | $X_4$— | E— | D |
| --- | --- | --- | --- | --- | --- | --- | --- | --- | --- |
| position | -1 | 0 | 1 | 2 | 3 | 4 | 5 | 6 | 7 | wherein:
$X_2$ represents P, D, Q, K, G
$X_3$ represents I, L, A, T, V
$X_4$ represents E, A
or a salt thereof, or a conservatively substituted variant of said peptide or salt.

Clause B22. The cyclic peptide, variant or salt according to any one of clauses B11 to B14, comprising the sequence:

|  | E— | $X_2$— | $X_3$— | E— | H— | $X_4$— | E— | D— | V |
| --- | --- | --- | --- | --- | --- | --- | --- | --- | --- |
| position | 0 | 1 | 2 | 3 | 4 | 5 | 6 | 7 | 8 | wherein:
$X_2$ represents P, D, Q, K, G
$X_3$ represents I, L, A, T, V
$X_4$ represents E, A or a salt thereof, or a conservatively substituted variant of said peptide or salt.

Clause B23. The cyclic peptide, variant or salt according to any one of clauses B12 to B14, comprising the sequence:

| | $X_1$— | T— | E— | $X_2$— | $X_3$— | E— | H— | $X_4$— | E— | D |
|---|---|---|---|---|---|---|---|---|---|---|
| position | −2 | −1 | 0 | 1 | 2 | 3 | 4 | 5 | 6 | 7 | wherein:
$X_1$ represents M, K
$X_2$ represents P, D, Q, K, G
$X_3$ represents I, L, A, T, V
$X_4$ represents E, A
or a salt thereof, or a conservatively substituted variant of said peptide or salt.

Clause B24. The cyclic peptide, variant or salt according to any one of clauses B12 to B14, comprising the sequence:

| | T— | E— | $X_2$— | $X_3$— | E— | H— | $X_4$— | E— | D— | V |
|---|---|---|---|---|---|---|---|---|---|---|
| position | −1 | 0 | 1 | 2 | 3 | 4 | 5 | 6 | 7 | 8 | wherein:
$X_2$ represents P, D, Q, K, G
$X_3$ represents I, L, A, T, V
$X_4$ represents E, A
or a salt thereof, or a conservatively substituted variant of said peptide or salt.

Clause B25. The cyclic peptide, variant or salt according to any one of clauses B13 to B14, comprising the sequence:

| | $X_1$— | T— | E— | $X_2$— | $X_3$— | E— | H— | $X_4$— | E— | D— | V |
|---|---|---|---|---|---|---|---|---|---|---|---|
| position | −2 | −1 | 0 | 1 | 2 | 3 | 4 | 5 | 6 | 7 | 8 | wherein:
$X_1$ represents M, K
$X_2$ represents P, D, Q, K, G
$X_3$ represents I, L, A, T, V
$X_4$ represents E, A
or a salt thereof, or a conservatively substituted variant of said peptide or salt.

Clause B26. The cyclic peptide, variant or salt according to any one of clauses B1 to B25, wherein $X_1$ represents M.

Clause B27. The cyclic peptide, variant or salt according to any one of clauses B1 to B25, wherein $X_1$ represents K.

Clause B28. The cyclic peptide, variant or salt according to any one of clauses B1 to B27, wherein $X_2$ represents P.

Clause B29. The cyclic peptide, variant or salt according to any one of clauses B1 to B27, wherein $X_2$ represents D.

Clause B30. The cyclic peptide, variant or salt according to any one of clauses B1 to B27, wherein $X_2$ represents Q.

Clause B31. The cyclic peptide, variant or salt according to any one of clauses B1 to B27, wherein $X_2$ represents K.

Clause B32. The cyclic peptide, variant or salt according to any one of clauses B1 to B27, wherein $X_2$ represents G.

Clause B33. The cyclic peptide, variant or salt according to any one of clauses B1 to B32, wherein $X_3$ represents I.

Clause B34. The cyclic peptide, variant or salt according to any one of clauses B1 to B32, wherein $X_3$ represents L.

Clause B35. The cyclic peptide, variant or salt according to any one of clauses B1 to B32, wherein $X_3$ represents A.

Clause B36. The cyclic peptide, variant or salt according to any one of clauses B1 to B32, wherein $X_3$ represents T.

Clause B37. The cyclic peptide, variant or salt according to any one of clauses B1 to B27 or B29 to B32, wherein $X_3$ represents V.

Clause B38. The cyclic peptide, variant or salt according to any one of clauses B1 to B37, wherein $X_4$ represents E.

Clause B39. The cyclic peptide, variant or salt according to any one of clauses B1 to B37, wherein $X_4$ represents A.

Clause B40. The cyclic peptide, variant or salt according to any one of clauses B13 to B14, comprising the sequence of any one of SEQ ID No. 1 to 10 and 28 to 39, or a salt thereof, or a conservatively substituted variant of said peptide or salt, such as consisting of the sequence of any one of SEQ ID No. 1 to 10 and 28 to 39, or a salt thereof, or a conservatively substituted variant of said peptide or salt.

Clause B41. The cyclic peptide, variant or salt according to any one of clauses B13 to B14, comprising the sequence of SEQ ID No. 1, or a salt thereof, or a conservatively substituted variant of said peptide or salt, such as consisting of the sequence of SEQ ID No. 1, or a salt thereof, or a conservatively substituted variant of said peptide or salt.

Clause B42. The variant or salt thereof according to any one of clauses B1 to B41, comprising two conservative substitutions.

Clause B43. The variant or salt thereof according to any one of clauses B1 to B42, comprising a substitution of X, at position −2, such as replacement by E, N, Q, R, T I, L or V.

Clause B44. The variant or salt thereof according to any one of clauses B1 to B42, comprising a substitution of T at position −1, such as replacement by A, K, M, N, R or S, especially A, K, M, N or R.

Clause B45. The variant or salt thereof according to any one of clauses B1 to B42, comprising a substitution of E at position 0, such as replacement by A, D, G, K, Q or V, especially G, K, Q or V.

Clause B46. The variant or salt thereof according to any one of clauses B1 to B42, comprising a substitution of $X_2$ at position 1, such as replacement by A, C, E, H, L, M, N, R, S, T, V or Y, especially A, E, H, L, M, N, R, T, V or Y.

Clause B47. The variant or salt thereof according to any one of clauses B1 to B42, comprising a substitution of $X_3$ at position 2, such as replacement by D, E, F, G, H, K, M, N, P, Q, S or W, especially D, E, F, G, H, K, M, N, P, Q or W.

Clause B48. The variant or salt thereof according to any one of clauses B1 to B42, comprising a substitution of E at position 3, such as replacement by A, D, G, K, Q or V, especially G, K, Q or V.

Clause B49. The variant or salt thereof according to any one of clauses B1 to B42, comprising a substitution of H at position 4, such as replacement by D, L, N, P, Q, R or Y.

Clause B50. The variant or salt thereof according to any one of clauses B1 to B42, comprising a substitution of $X_4$ at position 5, such as replacement by G, K, Q, S, T or V, especially G, K, Q, T or V.

Clause B51. The variant or salt thereof according to any one of clauses B1 to B42, comprising a substitution of E at position 6, such as replacement by A, D, G, K, Q or V.

Clause B52. The variant or salt thereof according to any one of clauses B1 to B42, comprising a substitution of D at position 7, such as replacement by A, E, G, H, N, V or Y.

Clause B53. The variant or salt thereof according to any one of clauses B1 to B42, comprising a substitution of V at position 8, such as replacement by D, E, I, L or M.

Clause B54. The variant or salt thereof according to any one of clauses B42 to B53, comprising a substitution of X, at position −2, such as replacement by E, N, Q, R, T I, L or V.

Clause B55. The variant or salt thereof according to any one of clauses B42 to B53, comprising a substitution of T at position −1, such as replacement by A, K, M, N, R or S, especially A, K, M, N or R.

Clause B56. The variant or salt thereof according to any one of clauses B42 to B53, comprising a substitution of E at position 0, such as replacement by A, D, G, K, Q or V, especially G, K, Q or V.

Clause B57. The variant or salt thereof according to any one of clauses B42 to B53, comprising a substitution of $X_2$ at position 1, such as replacement by A, C, E, H, L, M, N, R, S, T, V or Y, especially A, E, H, L, M, N, R, T, V or Y.

Clause B58. The variant or salt thereof according to any one of clauses B42 to B53, comprising a substitution of $X_3$ at position 2, such as replacement by D, E, F, G, H, K, M, N, P, Q, S or W, especially D, E, F, G, H, K, M, N, P, Q or W.

Clause B59. The variant or salt thereof according to any one of clauses B42 to B53, comprising a substitution of E at position 3, such as replacement by A, D, G, K, Q or V, especially G, K, Q or V.

Clause B60. The variant or salt thereof according to any one of clauses B42 to B53, comprising a substitution of H at position 4, such as replacement by D, L, N, P, Q, R or Y.

Clause B61. The variant or salt thereof according to any one of clauses B42 to B53, comprising a substitution of X at position 5, such as replacement by G, K, Q, S, T or V, especially G, K, Q, T or V.

Clause B62. The variant or salt thereof according to any one of clauses B42 to B53, comprising a substitution of E at position 6, such as replacement by A, D, G, K, Q or V.

Clause B63. The variant or salt thereof according to any one of clauses B42 to B53, comprising a substitution of D at position 7, such as replacement by A, E, G, H, N, V or Y.

Clause B64. The variant or salt thereof according to any one of clauses B42 to B53, comprising a substitution of V at position 8, such as replacement by D, E, I, L or M.

Clause B65. The variant or salt thereof according to any one of clauses B43 to B53, comprising one conservative substitution.

Clause B66. The cyclic peptide or salt thereof according to any one of clauses B1 to B41.

Clause B67. The cyclic peptide or salt according to clause B1 consisting of SEQ ID No. 1 or a salt thereof.

Clause B68. The cyclic peptide or salt according to clause B1 consisting of SEQ ID No. 2 or a salt thereof.

Clause B69. The cyclic peptide or salt according to clause B1 consisting of SEQ ID No. 3 or a salt thereof.

Clause B70. The cyclic peptide or salt according to clause B1 consisting of SEQ ID No. 4 or a salt thereof.

Clause B71. The cyclic peptide or salt according to clause B1, consisting of SEQ ID No. 5 or a salt thereof.

Clause B72. The cyclic peptide or salt according to clause B1, consisting of SEQ ID No. 6 or a salt thereof.

Clause B73. The cyclic peptide or salt according to clause B1, consisting of SEQ ID No. 7 or a salt thereof.

Clause B74. The cyclic peptide or salt according to clause B1, consisting of SEQ ID No. 8 or a salt thereof.

Clause B75. The cyclic peptide or salt according to clause B1, consisting of SEQ ID No. 9 or a salt thereof.

Clause B76. The cyclic peptide or salt according to clause B1, consisting of SEQ ID No. 10 or a salt thereof.

Clause B77. The cyclic peptide or salt according to clause B1 consisting of CP1 or a salt thereof.

Clause B78. The cyclic peptide or salt according to clause B1 consisting of CP2 or a salt thereof.

Clause B79. The cyclic peptide or salt according to clause B1 consisting of CP3 or a salt thereof.

Clause B80. The cyclic peptide or salt according to clause B1 consisting of CP4 or a salt thereof.

Clause B81. The cyclic peptide or salt according to clause B1, consisting of CP5 or a salt thereof.

Clause B82. The cyclic peptide or salt according to clause B1, consisting of CP6 or a salt thereof.

Clause B83. The cyclic peptide or salt according to clause B1, consisting of CP7 or a salt thereof.

Clause B84. The cyclic peptide or salt according to clause B1, consisting of CP8 or a salt thereof.

Clause B85. The cyclic peptide or salt according to clause B1, consisting of CP9 or a salt thereof.

Clause B86. The cyclic peptide or salt according to clause B1, consisting of CP10 or a salt thereof.

Clause B87. The cyclic peptide or salt according to clause B1, consisting of CP11 or a salt thereof.

Clause B88. The cyclic peptide or salt according to clause B1, consisting of CP12 or a salt thereof.

Clause B89. The cyclic peptide, variant or salt according to any one of clauses B1 to B98, wherein the salt is a pharmaceutically acceptable salt.

Clause B90. The cyclic peptide according to any preceding B clause.

Clause B91. The variant peptide according to any preceding B clause.

Clause B92. The pharmaceutically acceptable salt of a cyclic peptide according to any preceding B clause.

Clause B93. The pharmaceutically acceptable salt of the variant peptide according to any preceding B clause.

Clause B94. The cyclic peptide according to any one of clauses B1 to B93, which is not side chain modified.

Clause B95. The cyclic peptide according to any one of clauses B1 to B93, which is not modified.

Clause C1. A cyclic peptide comprising 10 or fewer amino acid residues within the cycle and comprising the sequence:

|  | $X_2$— | $X_3$— | E— | H— | $X_4$— | E |
|---|---|---|---|---|---|---|
| position | 1 | 2 | 3 | 4 | 5 | 6 | wherein:
$X_2$ represents P, D, Q, K, G
$X_3$ represents I, L, A, T, V
$X_4$ represents E, A
or a salt thereof, or a conservatively substituted variant of said peptide or salt.

Clause C2. The cyclic peptide, variant or salt according to clause C1, wherein the peptide is backbone cyclised.

Clause C3. The cyclic peptide, variant or salt according to clause C2, wherein the peptide is backbone cyclised and all residues of the peptide backbone are joined exclusively by peptide bonds.

Clause C4. The cyclic peptide, variant or salt according to any one of clauses C1 to C3, comprising 6 amino acid residues within the cycle.

Clause C5. The cyclic peptide, variant or salt according to any one of clauses C1 to C3, comprising 7 amino acid residues within the cycle.

Clause C6. The cyclic peptide, variant or salt according to any one of clauses C1 to C3, comprising 8 amino acid residues within the cycle.

Clause C7. The cyclic peptide, variant or salt according to any one of clauses C1 to C3, comprising 9 amino acid residues within the cycle.

Clause C8. The cyclic peptide, variant or salt according to any one of clauses C1 to C3, comprising 10 amino acid residues within the cycle.

Clause C9. The cyclic peptide, variant or salt according to any one of clauses C1 to C3 or C5 to C8, comprising the sequence:

|          | E— | $X_2$— | $X_3$— | E— | H— | $X_4$— | E |
|----------|----|----|----|----|----|----|---|
| position | 0  | 1  | 2  | 3  | 4  | 5  | 6 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause C10. The cyclic peptide, variant or salt according to any one of clauses C1 to C3 or C5 to C8, comprising the sequence:

|          | $X_2$— | $X_3$— | E— | H— | $X_4$— | E— | D |
|----------|----|----|----|----|----|----|---|
| position | 1  | 2  | 3  | 4  | 5  | 6  | 7 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause C11. The cyclic peptide, variant or salt according to any one of clauses C1 to C3 or C6 to C8, comprising the sequence:

|          | T— | E— | $X_2$— | $X_3$— | E— | H— | $X_4$— | E |
|----------|----|----|----|----|----|----|----|---|
| position | -1 | 0  | 1  | 2  | 3  | 4  | 5  | 6 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause C12. The cyclic peptide, variant or salt according to any one of clauses C1 to C3 or C6 to C8, comprising the sequence:

|          | E— | $X_2$— | $X_3$— | E— | H— | $X_4$— | E— | D |
|----------|----|----|----|----|----|----|----|---|
| position | 0  | 1  | 2  | 3  | 4  | 5  | 6  | 7 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause C13. The cyclic peptide, variant or salt according to any one of clauses C1 to C3 or C6 to C8, comprising the sequence:

|          | $X_2$— | $X_3$— | E— | H— | $X_4$— | E— | D— | V |
|----------|----|----|----|----|----|----|----|---|
| position | 1  | 2  | 3  | 4  | 5  | 6  | 7  | 8 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause C14. The cyclic peptide, variant or salt according to any one of clauses C1 to C3 or C7 to C8, comprising the sequence:

|          | $X_1$— | T— | E— | $X_2$— | $X_3$— | E— | H— | $X_4$— | E |
|----------|----|----|----|----|----|----|----|----|---|
| position | -2 | -1 | 0  | 1  | 2  | 3  | 4  | 5  | 6 | wherein:
  $X_1$ represents M, K
  $X_2$ represents P, D, Q, K, G
  $X_3$ represents I, L, A, T, V
  $X_4$ represents E, A
or a salt thereof, or a conservatively substituted variant of said peptide or salt.

Clause C15. The cyclic peptide, variant or salt according to any one of clauses C1 to C3 or C7 to C8, comprising the sequence:

|          | T— | E— | $X_2$— | $X_3$— | E— | H— | $X_4$— | E— | D |
|----------|----|----|----|----|----|----|----|----|---|
| position | -1 | 0  | 1  | 2  | 3  | 4  | 5  | 6  | 7 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause C16. The cyclic peptide, variant or salt according to any one of clauses C1 to C3 or C7 to C8, comprising the sequence:

|          | E— | $X_2$— | $X_3$— | E— | H— | $X_4$— | E— | D— | V |
|----------|----|----|----|----|----|----|----|----|---|
| position | 0  | 1  | 2  | 3  | 4  | 5  | 6  | 7  | 8 | wherein:
- $X_2$ represents P, D, Q, K, G
- $X_3$ represents I, L, A, T, V
- $X_4$ represents E, A or a salt thereof, or a conservatively substituted variant of said peptide or salt.

Clause C17. The cyclic peptide, variant or salt according to any one of clauses C1 to C3 or C8, comprising the sequence:

| $X_1$— | T— | E— | $X_2$— | $X_3$— | E— | H— | $X_4$— | E— | D |
|---|---|---|---|---|---|---|---|---|---|
| position −2 | −1 | 0 | 1 | 2 | 3 | 4 | 5 | 6 | 7 | wherein: T
- $X_1$ represents M, K
- $X_2$ represents P, D, Q, K, G
- $X_3$ represents I, L, A, T, V
- $X_4$ represents E, A or a salt thereof, or a conservatively substituted variant of said peptide or salt.

Clause C18. The cyclic peptide, variant or salt according to any one of clauses C1 to C3 or C8, comprising the sequence:

| T— | E— | $X_2$— | $X_3$— | E— | H— | $X_4$— | E— | D— | V |
|---|---|---|---|---|---|---|---|---|---|
| position −1 | 0 | 1 | 2 | 3 | 4 | 5 | 6 | 7 | 8 | wherein:
- $X_2$ represents P, D, Q, K, G
- $X_3$ represents I, L, A, T, V
- $X_4$ represents E, A or a salt thereof, or a conservatively substituted variant of said peptide or salt.

Clause C19. The cyclic peptide, variant or salt according to any one of clauses C1 to C18, wherein $X_1$ represents M.

Clause C20. The cyclic peptide, variant or salt according to any one of clauses C1 to C18, wherein $X_1$ represents K.

Clause C21. The cyclic peptide, variant or salt according to any one of clauses C1 to C20, wherein $X_2$ represents P.

Clause C22. The cyclic peptide, variant or salt according to any one of clauses C1 to C20, wherein $X_2$ represents D.

Clause C23. The cyclic peptide, variant or salt according to any one of clauses C1 to C20, wherein $X_2$ represents Q.

Clause C24. The cyclic peptide, variant or salt according to any one of clauses C1 to C20, wherein $X_2$ represents K.

Clause C25. The cyclic peptide, variant or salt according to any one of clauses C1 to C20, wherein $X_2$ represents G.

Clause C26. The cyclic peptide, variant or salt according to any one of clauses C1 to C25, wherein $X_3$ represents I.

Clause C27. The cyclic peptide, variant or salt according to any one of clauses C1 to C25, wherein $X_3$ represents L.

Clause C28. The cyclic peptide, variant or salt according to any one of clauses C1 to C25, wherein $X_3$ represents A.

Clause C29. The cyclic peptide, variant or salt according to any one of clauses C1 to C25, wherein $X_3$ represents T.

Clause C30. The cyclic peptide, variant or salt according to any one of clauses C1 to C25, wherein $X_3$ represents V.

Clause C31. The cyclic peptide, variant or salt according to any one of clauses C1 to C30, wherein $X_4$ represents E.

Clause C32. The cyclic peptide, variant or salt according to any one of clauses C1 to C30, wherein $X_4$ represents A.

Clause C33. The cyclic peptide, variant or salt according to any one of clauses C1 to C32, wherein (i) the sequence of the cyclic peptide is a portion of any one of SEQ ID No. 1 to 10 and 28 to 39, or a salt thereof, or (ii) a conservatively substituted variant of said peptide or salt.

Clause C34. The cyclic peptide, variant or salt according to clause C33, wherein (i) the sequence of the cyclic peptide is a portion of SEQ ID No. 1, or a salt thereof, or (ii) a conservatively substituted variant of said peptide or salt.

Clause C35. The cyclic peptide, variant or salt according to any one of clauses C1 to C32, comprising the sequence of any one of SEQ ID No. 40 to 42, or a salt thereof, or a conservatively substituted variant of said peptide or salt, such as consisting of the sequence of any one of SEQ ID No. 40 to 42, or a salt thereof, or a conservatively substituted variant of said peptide or salt.

Clause C36. The variant or salt thereof according to any one of clauses C1 to C35, comprising two conservative substitutions.

Clause C37. The variant or salt thereof according to any one of clauses C1 to C36, comprising a substitution of X, at position −2, such as replacement by E, N, Q, R, T I, L or V.

Clause C38. The variant or salt thereof according to any one of clauses C1 to C36, comprising a substitution of T at position −1, such as replacement by A, K, M, N, R or S, especially A, K, M, N or R.

Clause C39. The variant or salt thereof according to any one of clauses C1 to C36, comprising a substitution of E at position 0, such as replacement by A, D, G, K, Q or V, especially G, K, Q or V.

Clause C40. The variant or salt thereof according to any one of clauses C1 to C36, comprising a substitution of $X_2$ at position 1, such as replacement by A, C, E, H, L, M, N, R, S, T, V or Y, especially A, E, H, L, M, N, R, T, V or Y.

Clause C41. The variant or salt thereof according to any one of clauses C1 to C36, comprising a substitution of $X_3$ at position 2, such as replacement by D, E, F, G, H, K, M, N, P, Q, S or W, especially D, E, F, G, H, K, M, N, P, Q or W.

Clause C42. The variant or salt thereof according to any one of clauses C1 to C36, comprising a substitution of E at position 3, such as replacement by A, D, G, K, Q or V, especially G, K, Q or V.

Clause C43. The variant or salt thereof according to any one of clauses C1 to C36, comprising a substitution of H at position 4, such as replacement by D, L, N, P, Q, R or Y.

Clause C44. The variant or salt thereof according to any one of clauses C1 to C36, comprising a substitution of $X_4$ at position 5, such as replacement by G, K, Q, S, T or V, especially G, K, Q, T or V.

Clause C45. The variant or salt thereof according to any one of clauses C1 to C36, comprising a substitution of E at position 6, such as replacement by A, D, G, K, Q or V.

Clause C46. The variant or salt thereof according to any one of clauses C1 to C36, comprising a substitution of D at position 7, such as replacement by A, E, G, H, N, V or Y.

Clause C47. The variant or salt thereof according to any one of clauses C1 to C36, comprising a substitution of V at position 8, such as replacement by D, E, I, L or M.

Clause C48. The variant or salt thereof according to any one of clauses C36 to C47, comprising a substitution of X, at position −2, such as replacement by E, N, Q, R, T I, L or V.

Clause C49. The variant or salt thereof according to any one of clauses C36 to C47, comprising a substitution of T at position −1, such as replacement by A, K, M, N, R or S, especially A, K, M, N or R.

Clause C50. The variant or salt thereof according to any one of clauses C36 to C47, comprising a substitution of E at position 0, such as replacement by A, D, G, K, Q or V, especially G, K, Q or V.

Clause C51. The variant or salt thereof according to any one of clauses C36 to C47, comprising a substitution of $X_2$ at position 1, such as replacement by A, C, E, H, L, M, N, R, S, T, V or Y, especially A, E, H, L, M, N, R, T, V or Y.

Clause C52. The variant or salt thereof according to any one of clauses C36 to C47, comprising a substitution of $X_3$ at position 2, such as replacement by D, E, F, G, H, K, M, N, P, Q, S or W, especially D, E, F, G, H, K, M, N, P, Q or W.

Clause C53. The variant or salt thereof according to any one of clauses C36 to C47, comprising a substitution of E at position 3, such as replacement by A, D, G, K, Q or V, especially G, K, Q or V.

Clause C54. The variant or salt thereof according to any one of clauses C36 to C47, comprising a substitution of H at position 4, such as replacement by D, L, N, P, Q, R or Y.

Clause C55. The variant or salt thereof according to any one of clauses C36 to C47, comprising a substitution of $X_4$ at position 5, such as replacement by G, K, Q, S, T or V, especially G, K, Q, T or V.

Clause C56. The variant or salt thereof according to any one of clauses C36 to C47, comprising a substitution of E at position 6, such as replacement by A, D, G, K, Q or V.

Clause C57. The variant or salt thereof according to any one of clauses C36 to C47, comprising a substitution of D at position 7, such as replacement by A, E, G, H, N, V or Y.

Clause C58. The variant or salt thereof according to any one of clauses C36 to C47, comprising a substitution of V at position 8, such as replacement by D, E, I, L or M.

Clause C59. The variant or salt thereof according to any one of clauses C37 to C47, comprising one conservative substitution.

Clause C60. The cyclic peptide or salt thereof according to any one of clauses C1 to C35.

Clause C61. The cyclic peptide or salt according to clause C1, consisting of CP13 or a salt thereof.

Clause C62. The cyclic peptide or salt according to clause C1, consisting of CP14 or a salt thereof.

Clause C63. The cyclic peptide or salt according to clause C1, consisting of CP15 or a salt thereof.

Clause C64. The cyclic peptide, variant or salt according to any one of clauses C1 to C63, wherein the salt is a pharmaceutically acceptable salt.

Clause C65. The cyclic peptide according to any preceding C clause.

Clause C66. The variant peptide according to any preceding C clause.

Clause C67. The pharmaceutically acceptable salt of a cyclic peptide according to any preceding C clause.

Clause C68. The pharmaceutically acceptable salt of the variant peptide according to any preceding C clause.

Clause C69. The cyclic peptide according to any one of clauses C1 to C68, which is not side chain modified.

Clause C70. The cyclic peptide according to any one of clauses C1 to C68, which is not modified.

Clause D1. A lipidated linear peptide comprising the sequence:

| | $X_2$— | $X_3$— | E— | H— | $X_4$— | E |
|---|---|---|---|---|---|---|
| position | 1 | 2 | 3 | 4 | 5 | 6 | wherein:
$X_2$ represents P, D, Q, K, G
$X_3$ represents I, L, A, T, V
$X_4$ represents E, A
or a salt thereof, or a conservatively substituted variant of said peptide or salt.

Clause D2. The lipidated linear peptide, variant or salt according to clause D1, wherein all residues of the peptide backbone are joined exclusively by peptide bonds.

Clause D3. The lipidated linear peptide, variant or salt according to clause D1 or D2, comprising 25 or fewer amino acid residues within the backbone.

Clause D4. The lipidated linear peptide, variant or salt according to clause D3, comprising 20 or fewer amino acid residues within the backbone, such as comprising 20 amino acid residues within the backbone.

Clause D5. The lipidated linear peptide, variant or salt according to clause D4, comprising 15 or fewer amino acid residues within the backbone, such as comprising 15 amino acid residues within the backbone.

Clause D6. The lipidated linear peptide, variant or salt according to clause D5, comprising 12 or fewer amino acid residues within the backbone, such as comprising 12 amino acid residues within the backbone.

Clause D7. The lipidated linear peptide, variant or salt according to clause D6, comprising 11 or fewer amino acid residues within the backbone.

Clause D8. The lipidated linear peptide, variant or salt according to any one of clauses D1 to D7, comprising at least 7 amino acid residues within the backbone, such as comprising 7 amino acid residues within the backbone.

Clause D9. The lipidated linear peptide, variant or salt according to clause D8, comprising at least 8 amino acid residues within the backbone, such as comprising 8 amino acid residues within the backbone.

Clause D10. The lipidated linear peptide, variant or salt according to clause D9, comprising at least 9 amino acid residues within the backbone, such as comprising 9 amino acid residues within the backbone.

Clause D11. The lipidated linear peptide, variant or salt according to clause D10, comprising at least 10 amino acid residues within the backbone, such as comprising 10 amino acid residues within the backbone.

Clause D12. The lipidated linear peptide, variant or salt according to clause D11, comprising at least 11 amino acid residues within the backbone Clause D13. The lipidated linear peptide, variant or salt according to clause D12, comprising 11 amino acid residues within the backbone.

Clause D14. The lipidated linear peptide, variant or salt according to any one of clauses D8 to D13, comprising the sequence:

| | E— | $X_2$— | $X_3$— | E— | H— | $X_4$— | E |
|---|---|---|---|---|---|---|---|
| position | 0 | 1 | 2 | 3 | 4 | 5 | 6 | wherein:
$X_2$ represents P, D, Q, K, G
$X_3$ represents I, L, A, T, V
$X_4$ represents E, A or a salt thereof, or a conservatively substituted variant of said peptide or salt.

Clause D15. The lipidated linear peptide, variant or salt according to any one of clauses D8 to D13, comprising the sequence:

|  | X₂— | X₃— | E— | H— | X₄— | E— | D |
|---|---|---|---|---|---|---|---|
| position | 1 | 2 | 3 | 4 | 5 | 6 | 7 | wherein:
X₂ represents P, D, Q, K, G
X₃ represents I, L, A, T, V
X₄ represents E, A
or a salt thereof, or a conservatively substituted variant of said peptide or salt.

Clause D16. The lipidated linear peptide, variant or salt according to any one of clauses D9 to D13, comprising the sequence:

|  | T— | E— | X₂— | X₃— | E— | H— | X₄— | E |
|---|---|---|---|---|---|---|---|---|
| position | −1 | 0 | 1 | 2 | 3 | 4 | 5 | 6 | wherein:
X₂ represents P, D, Q, K, G
X₃ represents I, L, A, T, V
X₄ represents E, A
or a salt thereof, or a conservatively substituted variant of said peptide or salt.

Clause D17. The lipidated linear peptide, variant or salt according to any one of clauses D9 to D13, comprising the sequence:

|  | E— | X₂— | X₃— | E— | H— | X₄— | E— | D |
|---|---|---|---|---|---|---|---|---|
| position | 0 | 1 | 2 | 3 | 4 | 5 | 6 | 7 | wherein:
X₂ represents P, D, Q, K, G
X₃ represents I, L, A, T, V
X₄ represents E, A
or a salt thereof, or a conservatively substituted variant of said peptide or salt.

Clause D18. The lipidated linear peptide, variant or salt according to any one of clauses D9 to D13, comprising the sequence:

|  | X₂— | X₃— | E— | H— | X₄— | E— | D— | V |
|---|---|---|---|---|---|---|---|---|
| position | 1 | 2 | 3 | 4 | 5 | 6 | 7 | 8 | wherein:
X₂ represents P, D, Q, K, G
X₃ represents I, L, A, T, V
X₄ represents E, A
or a salt thereof, or a conservatively substituted variant of said peptide or salt.

Clause D19. The lipidated linear peptide, variant or salt according to any one of clauses D10 to D13, comprising the sequence:

|  | X₁— | T— | E— | X₂— | X₃— | E— | H— | X₄— | E |
|---|---|---|---|---|---|---|---|---|---|
| position | −2 | −1 | 0 | 1 | 2 | 3 | 4 | 5 | 6 | wherein:
X₁ represents M, K
X₂ represents P, D, Q, K, G
X₃ represents I, L, A, T, V
X₄ represents E, A
or a salt thereof, or a conservatively substituted variant of said peptide or salt.

Clause D20. The lipidated linear peptide, variant or salt according to any one of clauses D10 to D13 comprising the sequence:

|  | T— | E— | X₂— | X₃— | E— | H— | X₄— | E— | D |
|---|---|---|---|---|---|---|---|---|---|
| position | −1 | 0 | 1 | 2 | 3 | 4 | 5 | 6 | 7 | wherein:
X₂ represents P, D, Q, K, G
X₃ represents I, L, A, T, V
X₄ represents E, A
or a salt thereof, or a conservatively substituted variant of said peptide or salt.

Clause D21. The lipidated linear peptide, variant or salt according to any one of clauses D10 to D13, comprising the sequence:

|  | E— | X₂— | X₃— | E— | H— | X₄— | E— | D— | V |
|---|---|---|---|---|---|---|---|---|---|
| position | 0 | 1 | 2 | 3 | 4 | 5 | 6 | 7 | 8 | wherein:
X₂ represents P, D, Q, K, G
X₃ represents I, L, A, T, V
X₄ represents E, A
or a salt thereof, or a conservatively substituted variant of said peptide or salt.

Clause D22. The lipidated linear peptide, variant or salt according to any one of clauses D11 to D23, comprising the sequence:

|  | X₁— | T— | E— | X₂— | X₃— | E— | H— | X₄— | E— | D |
|---|---|---|---|---|---|---|---|---|---|---|
| position | −2 | −1 | 0 | 1 | 2 | 3 | 4 | 5 | 6 | 7 | wherein:
 $X_1$ represents M, K
 $X_2$ represents P, D, Q, K, G
 $X_3$ represents I, L, A, T, V
 $X_4$ represents E, A
 or a salt thereof, or a conservatively substituted variant of said peptide or salt.

Clause D23. The lipidated linear peptide, variant or salt according to any one of clauses D11 to D13, comprising the sequence:

| | T— | E— | $X_2$— | $X_3$— | E— | H— | $X_4$— | E— | D— | V |
|---|---|---|---|---|---|---|---|---|---|---|
| position | −1 | 0 | 1 | 2 | 3 | 4 | 5 | 6 | 7 | 8 | wherein:
 $X_2$ represents P, D, Q, K, G
 $X_3$ represents I, L, A, T, V
 $X_4$ represents E, A
 or a salt thereof, or a conservatively substituted variant of said peptide or salt.

Clause D24. The lipidated linear peptide, variant or salt according to any one of clauses D12 to D13, comprising the sequence:

| | $X_1$— | T— | E— | $X_2$— | $X_3$— | E— | H— | $X_4$— | E— | D— | V |
|---|---|---|---|---|---|---|---|---|---|---|---|
| position | −2 | −1 | 0 | 1 | 2 | 3 | 4 | 5 | 6 | 7 | 8 | wherein:
 $X_1$ represents M, K
 $X_2$ represents P, D, Q, K, G
 $X_3$ represents I, L, A, T, V
 $X_4$ represents E, A
 or a salt thereof, or a conservatively substituted variant of said peptide or salt.

Clause D25. The lipidated linear peptide, variant or salt according to any one of clauses D1 to D24, wherein $X_1$ represents M.

Clause D26. The lipidated linear peptide, variant or salt according to any one of clauses D1 to D24, wherein $X_1$ represents K.

Clause D27. The lipidated linear peptide, variant or salt according to any one of clauses D1 to D26, wherein $X_2$ represents P.

Clause D28. The lipidated linear peptide, variant or salt according to any one of clauses D1 to D26, wherein $X_2$ represents D.

Clause D29. The lipidated linear peptide, variant or salt according to any one of clauses D1 to D26, wherein $X_2$ represents Q.

Clause D30. The lipidated linear peptide, variant or salt according to any one of clauses D1 to D26, wherein $X_2$ represents K.

Clause D31. The lipidated linear peptide, variant or salt according to any one of clauses D1 to D26, wherein $X_2$ represents G.

Clause D32. The lipidated linear peptide, variant or salt according to any one of clauses D1 to D31, wherein $X_3$ represents I.

Clause D33. The lipidated linear peptide, variant or salt according to any one of clauses D1 to D31, wherein $X_3$ represents L.

Clause D34. The lipidated linear peptide, variant or salt according to any one of clauses D1 to D31, wherein $X_3$ represents A.

Clause D35. The lipidated linear peptide, variant or salt according to any one of clauses D1 to D31, wherein $X_3$ represents T.

Clause D36. The lipidated linear peptide, variant or salt according to any one of clauses D1 to D31, wherein $X_3$ represents V.

Clause D37. The lipidated linear peptide, variant or salt according to any one of clauses D1 to D36, wherein $X_4$ represents E.

Clause D38. The lipidated linear peptide, variant or salt according to any one of clauses D1 to D36, wherein $X_4$ represents A.

Clause D39. The lipidated linear peptide, variant or salt according to any one of clauses D13 to D14, comprising the sequence of any one of SEQ ID No. 1 to 11 or a salt thereof, or a conservatively substituted variant of said peptide or salt, such as consisting of the sequence of any one of SEQ ID No. 1 to 11 or a salt thereof, or a conservatively substituted variant of said peptide or salt.

Clause D40. The lipidated linear peptide, variant or salt according to any one of clauses D13 to D14, comprising the sequence of SEQ ID No. 1 or a salt thereof, or a conservatively substituted variant of said peptide or salt, such as consisting of the sequence of SEQ ID No. 1 or a salt thereof, or a conservatively substituted variant of said peptide or salt.

Clause D41. The lipidated linear peptide, variant or salt according to any one of clauses D13 to D14, comprising the sequence of any one of LLP1 to LLP12 or a salt thereof, or a conservatively substituted variant of said peptide or salt, such as consisting of the sequence of any one of LLP1 to LLP12 or a salt thereof, or a conservatively substituted variant of said peptide or salt.

Clause D42. The variant or salt thereof according to any one of clauses D1 to D41, comprising two conservative substitutions.

Clause D43. The variant or salt thereof according to any one of clauses D1 to D42, comprising a substitution of X, at position −2, such as replacement by E, N, Q, R, T I, L or V.

Clause D44. The variant or salt thereof according to any one of clauses D1 to D42, comprising a substitution of T at position −1, such as replacement by A, K, M, N, R or S, especially A, K, M, N or R.

Clause D45. The variant or salt thereof according to any one of clauses D1 to D42, comprising a substitution of E at position 0, such as replacement by A, D, G, K, Q or V, especially G, K, Q or V.

Clause D46. The variant or salt thereof according to any one of clauses D1 to D42, comprising a substitution of $X_2$ at position 1, such as replacement by A, C, E, H, L, M, N, R, S, T, V or Y, especially A, E, H, L, M, N, R, T, V or Y.

Clause D47. The variant or salt thereof according to any one of clauses D1 to D42, comprising a substitution of $X_3$ at position 2, such as replacement by D, E, F, G, H, K, M, N, P, Q, S or W, especially D, E, F, G, H, K, M, N, P, Q or W.

Clause D48. The variant or salt thereof according to any one of clauses D1 to D42, comprising a substitution of E at position 3, such as replacement by A, D, G, K, Q or V, especially G, K, Q or V.

Clause D49. The variant or salt thereof according to any one of clauses D1 to D42, comprising a substitution of H at position 4, such as replacement by D, L, N, P, Q, R or Y.

Clause D50. The variant or salt thereof according to any one of clauses D1 to D42, comprising a substitution of $X_4$ at position 5, such as replacement by G, K, Q, S, T or V, especially G, K, Q, T or V.

Clause D51. The variant or salt thereof according to any one of clauses D1 to D42, comprising a substitution of E at position 6, such as replacement by A, D, G, K, Q or V.

Clause D52. The variant or salt thereof according to any one of clauses D1 to D42, comprising a substitution of D at position 7, such as replacement by A, E, G, H, N, V or Y.

Clause D53. The variant or salt thereof according to any one of clauses D1 to D42, comprising a substitution of V at position 8, such as replacement by D, E, I, L or M.

Clause D54. The variant or salt thereof according to any one of clauses D42 to D53, comprising a substitution of X, at position −2, such as replacement by E, N, Q, R, T I, L or V.

Clause D55. The variant or salt thereof according to any one of clauses D42 to D53, comprising a substitution of T at position −1, such as replacement by A, K, M, N, R or S, especially A, K, M, N or R.

Clause D56. The variant or salt thereof according to any one of clauses D42 to D53, comprising a substitution of E at position 0, such as replacement by A, D, G, K, Q or V, especially G, K, Q or V.

Clause D57. The variant or salt thereof according to any one of clauses D42 to D53, comprising a substitution of $X_2$ at position 1, such as replacement by A, C, E, H, L, M, N, R, S, T, V or Y, especially A, E, H, L, M, N, R, T, V or Y.

Clause D58. The variant or salt thereof according to any one of clauses D42 to D53, comprising a substitution of $X_3$ at position 2, such as replacement by D, E, F, G, H, K, M, N, P, Q, S or W, especially D, E, F, G, H, K, M, N, P, Q or W.

Clause D59. The variant or salt thereof according to any one of clauses D42 to D53, comprising a substitution of E at position 3, such as replacement by A, D, G, K, Q or V, especially G, K, Q or V.

Clause D60. The variant or salt thereof according to any one of clauses D42 to D53, comprising a substitution of H at position 4, such as replacement by D, L, N, P, Q, R or Y.

Clause D61. The variant or salt thereof according to any one of clauses D42 to D53, comprising a substitution of X at position 5, such as replacement by G, K, Q, S, T or V, especially G, K, Q, T or V.

Clause D62. The variant or salt thereof according to any one of clauses D42 to D53, comprising a substitution of E at position 6, such as replacement by A, D, G, K, Q or V.

Clause D63. The variant or salt thereof according to any one of clauses D42 to D53, comprising a substitution of D at position 7, such as replacement by A, E, G, H, N, V or Y.

Clause D64. The variant or salt thereof according to any one of clauses D42 to D53, comprising a substitution of V at position 8, such as replacement by D, E, I, L or M.

Clause D65. The variant or salt thereof according to any one of clauses D43 to D53, comprising one conservative substitution.

Clause D66. The lipidated linear peptide or salt thereof according to any one of clauses D1 to D41.

Clause D67. The lipidated linear peptide, variant or salt according to any one of clauses D1 to D66, which comprises a lipidated K residue.

Clause D68. The lipidated linear peptide, variant or salt according to clause D67, wherein the lipidated K residue is $X_2$ position 1.

Clause D69. The lipidated linear peptide, variant or salt according to clause D67, wherein the lipidated K residue is X, position −2.

Clause D70. The lipidated linear peptide, variant or salt according to any one of clauses D1 to D69, wherein the lipid chain is a C16DA, C18DA or C20DA group.

Clause D71. The lipidated linear peptide, variant or salt according to clause D70, wherein the lipid chain is a C18DA group.

Clause D72. The lipidated linear peptide, variant or salt according to any one of clauses D1 to D71, wherein the lipid is linked to the K residue via a γGlu.

Clause D73. The lipidated linear peptide, variant or salt according to clause D72, wherein the lipid is linked to the K residue via a γGlu and one to four OEG groups.

Clause D74. The lipidated linear peptide, variant or salt according to clause D73, wherein the lipid is linked to the K residue via a γGlu and two OEG groups.

Clause D75. The lipidated linear peptide, variant or salt according to any one of clauses D1 to D69, wherein the lipid is C18DA-γGlu-OEG-OEG-.

Clause D76. The lipidated linear peptide or salt according to any one of clauses D1 to D69, wherein the lipid is C18DA-γGlu-OEG-OEG-.

Clause D77. The lipidated linear peptide or salt according to either clause D75 or D76, wherein the lipid is C18DA-L-γGlu-OEG-OEG-.

Clause D78. The lipidated linear peptide or salt according to either clause D75 or D76, wherein the lipid is C18DA-D-γGlu-OEG-OEG-.

Clause D79. The lipidated linear peptide, variant or salt according to any one of clauses D1 to D78, which is N-terminally acetylated.

Clause D80. The lipidated linear peptide, variant or salt according to any one of clauses D1 to D78, which is not N-terminally modified.

Clause D81. The lipidated linear peptide, variant or salt according to any one of clauses D1 to D80, which is C-terminally amidated.

Clause D82. The lipidated linear peptide, variant or salt according to any one of clauses D1 to D80, which is not C-terminally modified.

Clause D83. The lipidated linear peptide or salt according to clause D1 consisting of LLP1 or a salt thereof.

Clause D84. The lipidated linear peptide or salt according to clause D1 consisting of LLP2 or a salt thereof.

Clause D85. The lipidated linear peptide or salt according to clause D1 consisting of LLP3 or a salt thereof.

Clause D86. The lipidated linear peptide or salt according to clause D1 consisting of LLP4 or a salt thereof.

Clause D87. The lipidated linear peptide or salt according to clause D1, consisting of LLP5 or a salt thereof.

Clause D88. The lipidated linear peptide or salt according to clause D1, consisting of LLP6 or a salt thereof.

Clause D89. The lipidated linear peptide or salt according to clause D1, consisting of LLP7 or a salt thereof.

Clause D90. The lipidated linear peptide or salt according to clause D1, consisting of LLP8 or a salt thereof.

Clause D91. The lipidated linear peptide or salt according to clause D1, consisting of LLP9 or a salt thereof.

Clause D92. The lipidated linear peptide or salt according to clause D1, consisting of LLP10 or a salt thereof.

Clause D93. The lipidated linear peptide or salt according to clause D1, consisting of LLP11 or a salt thereof.

Clause D94. The lipidated linear peptide or salt according to clause D1, consisting of LLP12 or a salt thereof.

Clause D95. The lipidated linear peptide, variant or salt according to any one of clauses D1 to D95, wherein the salt is a pharmaceutically acceptable salt.

Clause D96. The lipidated linear peptide according to any preceding D clause.

Clause D97. The lipidated variant peptide according to any preceding D clause.

Clause D98. The pharmaceutically acceptable salt of a lipidated linear peptide according to any preceding D clause.

Clause D99. The pharmaceutically acceptable salt of the lipidated variant peptide according to any preceding D clause.

Clause D100. The lipidated linear peptide according to any one of clauses D1 to D99, which is not side chain modified.

Clause D101. The lipidated linear peptide according to any one of clauses D1 to D99, which is not modified.

Clause E1. A linear peptide comprising the sequence:

| | $X_2$— | $X_3$— | E— | H— | $X_4$— | E |
|---|---|---|---|---|---|---|
| position | 1 | 2 | 3 | 4 | 5 | 6 | wherein:
- $X_2$ represents P, D, Q, K, G
- $X_3$ represents I, L, A, T, V
- $X_4$ represents E, A
- or a salt thereof, or a conservatively substituted variant of said peptide or salt, wherein when $X_2$ represents P then $X_3$ is other than V.

Clause E2. The linear peptide, variant or salt according to clause E1, wherein all residues of the peptide backbone are joined exclusively by peptide bonds.

Clause E3. The linear peptide, variant or salt according to clause E1 or E2, comprising 25 or fewer amino acid residues within the backbone.

Clause E4. The linear peptide, variant or salt according to clause E3, comprising 20 or fewer amino acid residues within the backbone, such as comprising 20 amino acid residues within the backbone.

Clause E5. The linear peptide, variant or salt according to clause E4, comprising 15 or fewer amino acid residues within the backbone, such as comprising 15 amino acid residues within the backbone.

Clause E6. The linear peptide, variant or salt according to clause E5, comprising 12 or fewer amino acid residues within the backbone, such as comprising 12 amino acid residues within the backbone.

Clause E7. The linear peptide, variant or salt according to clause E6, comprising 11 or fewer amino acid residues within the backbone.

Clause E8. The linear peptide, variant or salt according to any one of clauses E1 to E7, comprising at least 7 amino acid residues within the backbone, such as comprising 7 amino acid residues within the backbone.

Clause E9. The linear peptide, variant or salt according to clause E8, comprising at least 8 amino acid residues within the backbone, such as comprising 8 amino acid residues within the backbone.

Clause E10. The linear peptide, variant or salt according to clause E9, comprising at least 9 amino acid residues within the backbone, such as comprising 9 amino acid residues within the backbone.

Clause E11. The linear peptide, variant or salt according to clause E10, comprising at least 10 amino acid residues within the backbone, such as comprising 10 amino acid residues within the backbone.

Clause E12. The linear peptide, variant or salt according to clause E11, comprising at least 11 amino acid residues within the backbone Clause E13. The linear peptide, variant or salt according to clause E12, comprising 11 amino acid residues within the backbone.

Clause E14. The linear peptide, variant or salt according to any one of clauses E8 to E13, comprising the sequence:

| | E— | $X_2$— | $X_3$— | E— | H— | $X_4$— | E |
|---|---|---|---|---|---|---|---|
| position | 0 | 1 | 2 | 3 | 4 | 5 | 6 | wherein:
- $X_2$ represents P, D, Q, K, G
- $X_3$ represents I, L, A, T, V
- $X_4$ represents E, A
- or a salt thereof, or a conservatively substituted variant of said peptide or salt.

Clause E15. The linear peptide, variant or salt according to any one of clauses E8 to E13, comprising the sequence:

| | $X_2$— | $X_3$— | E— | H— | $X_4$— | E— | D |
|---|---|---|---|---|---|---|---|
| position | 1 | 2 | 3 | 4 | 5 | 6 | 7 | wherein:
- $X_2$ represents P, D, Q, K, G
- $X_3$ represents I, L, A, T, V
- $X_4$ represents E, A
- or a salt thereof, or a conservatively substituted variant of said peptide or salt.

Clause E16. The linear peptide, variant or salt according to any one of clauses E9 to E13, comprising the sequence:

| | T— | E— | $X_2$— | $X_3$— | E— | H— | $X_4$— | E |
|---|---|---|---|---|---|---|---|---|
| position | −1 | 0 | 1 | 2 | 3 | 4 | 5 | 6 | wherein:
- $X_2$ represents P, D, Q, K, G
- $X_3$ represents I, L, A, T, V
- $X_4$ represents E, A
- or a salt thereof, or a conservatively substituted variant of said peptide or salt.

Clause E17. The linear peptide, variant or salt according to any one of clauses E9 to E13, comprising the sequence:

| | E— | $X_2$— | $X_3$— | E— | H— | $X_4$— | E— | D |
|---|---|---|---|---|---|---|---|---|
| position | 0 | 1 | 2 | 3 | 4 | 5 | 6 | 7 | wherein:
X$_2$ represents P, D, Q, K, G
X$_3$ represents I, L, A, T, V
X$_4$ represents E, A
or a salt thereof, or a conservatively substituted variant of said peptide or salt.

Clause E18. The linear peptide, variant or salt according to any one of clauses E9 to E13, comprising the sequence:

| | X$_2$— | X$_3$— | E— | H— | X$_4$— | E— | D— | V |
|---|---|---|---|---|---|---|---|---|
| position | 1 | 2 | 3 | 4 | 5 | 6 | 7 | 8 | wherein:
X$_2$ represents P, D, Q, K, G
X$_3$ represents I, L, A, T, V
X$_4$ represents E, A
or a salt thereof, or a conservatively substituted variant of said peptide or salt.

Clause E19. The linear peptide, variant or salt according to any one of clauses E10 to E13, comprising the sequence:

| | X$_1$— | T— | E— | X$_2$— | X$_3$— | E— | H— | X$_4$— | E |
|---|---|---|---|---|---|---|---|---|---|
| position | −2 | −1 | 0 | 1 | 2 | 3 | 4 | 5 | 6 | wherein:
X$_1$ represents M, K
X$_2$ represents P, D, Q, K, G
X$_3$ represents I, L, A, T, V
X$_4$ represents E, A
or a salt thereof, or a conservatively substituted variant of said peptide or salt.

Clause E20. The linear peptide, variant or salt according to any one of clauses E10 to E13, comprising the sequence:

| | T— | E— | X$_2$— | X$_3$— | E— | H— | X$_4$— | E— | D |
|---|---|---|---|---|---|---|---|---|---|
| position | −1 | 0 | 1 | 2 | 3 | 4 | 5 | 6 | 7 | wherein:
X$_2$ represents P, D, Q, K, G
X$_3$ represents I, L, A, T, V
X$_4$ represents E, A
or a salt thereof, or a conservatively substituted variant of said peptide or salt.

Clause E21. The linear peptide, variant or salt according to any one of clauses E10 to E13, comprising the sequence:

| | E— | X$_2$— | X$_3$— | E— | H— | X$_4$— | E— | D— | V |
|---|---|---|---|---|---|---|---|---|---|
| position | 0 | 1 | 2 | 3 | 4 | 5 | 6 | 7 | 8 | wherein:
X$_2$ represents P, D, Q, K, G
X$_3$ represents I, L, A, T, V
X$_4$ represents E, A
or a salt thereof, or a conservatively substituted variant of said peptide or salt.

Clause E22. The linear peptide, variant or salt according to any one of clauses E11 to E13, comprising the sequence:

| | X$_1$— | T— | E— | X$_2$— | X$_3$— | E— | H— | X$_4$— | E— | D |
|---|---|---|---|---|---|---|---|---|---|---|
| position | −2 | −1 | 0 | 1 | 2 | 3 | 4 | 5 | 6 | 7 | wherein:
X$_1$ represents M, K
X$_2$ represents P, D, Q, K, G
X$_3$ represents I, L, A, T, V
X$_4$ represents E, A
or a salt thereof, or a conservatively substituted variant of said peptide or salt.

Clause E23. The linear peptide, variant or salt according to any one of clauses E11 to E13, comprising the sequence:

| | T— | E— | X$_2$— | X$_3$— | E— | H— | X$_4$— | E— | D— | V |
|---|---|---|---|---|---|---|---|---|---|---|
| position | −1 | 0 | 1 | 2 | 3 | 4 | 5 | 6 | 7 | 8 | wherein:
X$_2$ represents P, D, Q, K, G
X$_3$ represents I, L, A, T, V
X$_4$ represents E, A
or a salt thereof, or a conservatively substituted variant of said peptide or salt.

Clause E24. The linear peptide, variant or salt according to any one of clauses E12 to E13, comprising the sequence:

| | X$_1$— | T— | E— | X$_2$— | X$_3$— | E— | H— | X$_4$— | E— | D— | V |
|---|---|---|---|---|---|---|---|---|---|---|---|
| position | −2 | −1 | 0 | 1 | 2 | 3 | 4 | 5 | 6 | 7 | 8 | wherein:
X$_1$ represents M, K
X$_2$ represents P, D, Q, K, G
X$_3$ represents I, L, A, T, V
X$_4$ represents E, A
or a salt thereof, or a conservatively substituted variant of said peptide or salt.

Clause E25. The linear peptide, variant or salt according to any one of clauses E1 to E24, wherein X$_1$ represents M.

Clause E26. The linear peptide, variant or salt according to any one of clauses E1 to E24, wherein X$_1$ represents K.

Clause E27. The linear peptide, variant or salt according to any one of clauses E1 to E25, wherein X$_2$ represents P.

Clause E28. The linear peptide, variant or salt according to any one of clauses E1 to E25, wherein X$_2$ represents D.

Clause E29. The linear peptide, variant or salt according to any one of clauses E1 to E25, wherein X$_2$ represents Q.

Clause E30. The linear peptide, variant or salt according to any one of clauses E1 to E25, wherein X$_2$ represents K.

Clause E31. The linear peptide, variant or salt according to any one of clauses E1 to E25, wherein X$_2$ represents G.

Clause E32. The linear peptide, variant or salt according to any one of clauses E1 to E31, wherein X$_3$ represents I.

Clause E33. The linear peptide, variant or salt according to any one of clauses E1 to E31, wherein X$_3$ represents L.

Clause E34. The linear peptide, variant or salt according to any one of clauses E1 to E31, wherein X$_3$ represents A.

Clause E35. The linear peptide, variant or salt according to any one of clauses E1 to E31, wherein X$_3$ represents T.

Clause E36. The linear peptide, variant or salt according to any one of clauses E1 to E26 or E28 to E31, wherein X$_3$ represents V.

Clause E37. The linear peptide, variant or salt according to any one of clauses E1 to E36, wherein X$_4$ represents E.

Clause E38. The linear peptide, variant or salt according to any one of clauses E1 to E36, wherein X$_4$ represents A.

Clause E39. The linear peptide, variant or salt according to any one of clauses E12 to E13, comprising the sequence of any one of SEQ ID No. 1 to 10 and 16 to 39, or a salt thereof, or a conservatively substituted variant of said peptide or salt, such as consisting of the sequence of any one of SEQ ID No. 1 to 10 and 16 to 39, or a salt thereof, or a conservatively substituted variant of said peptide or salt.

Clause E40. The linear peptide, variant or salt according to any one of clauses E12 to E13, comprising the sequence of SEQ ID No. 1, or a salt thereof, or a conservatively substituted variant of said peptide or salt, such as consisting of the sequence of SEQ ID No. 1, or a salt thereof, or a conservatively substituted variant of said peptide or salt.

Clause E41. The variant or salt thereof according to any one of clauses E1 to E40, comprising two conservative substitutions.

Clause E42. The variant or salt thereof according to any one of clauses E1 to E41, comprising a substitution of X, at position −2, such as replacement by E, N, Q, R, T I, L or V.

Clause E43. The variant or salt thereof according to any one of clauses E1 to E41, comprising a substitution of T at position −1, such as replacement by A, K, M, N, R or S, especially A, K, M, N or R.

Clause E44. The variant or salt thereof according to any one of clauses E1 to E41, comprising a substitution of E at position 0, such as replacement by A, D, G, K, Q or V, especially G, K, Q or V.

Clause E45. The variant or salt thereof according to any one of clauses E1 to E41, comprising a substitution of X$_2$ at position 1, such as replacement by A, C, E, H, L, M, N, R, S, T, V or Y, especially A, E, H, L, M, N, R, T, V or Y.

Clause E46. The variant or salt thereof according to any one of clauses E1 to E41, comprising a substitution of X$_3$ at position 2, such as replacement by D, E, F, G, H, K, M, N, P, Q, S or W, especially D, E, F, G, H, K, M, N, P, Q or W.

Clause E47. The variant or salt thereof according to any one of clauses E1 to E41, comprising a substitution of E at position 3, such as replacement by A, D, G, K, Q or V, especially G, K, Q or V.

Clause E48. The variant or salt thereof according to any one of clauses E1 to E41, comprising a substitution of H at position 4, such as replacement by D, L, N, P, Q, R or Y.

Clause E49. The variant or salt thereof according to any one of clauses E1 to E41, comprising a substitution of X$_4$ at position 5, such as replacement by G, K, Q, S, T or V, especially G, K, Q, T or V.

Clause E50. The variant or salt thereof according to any one of clauses E1 to E41, comprising a substitution of E at position 6, such as replacement by A, D, G, K, Q or V.

Clause E51. The variant or salt thereof according to any one of clauses E1 to E41, comprising a substitution of D at position 7, such as replacement by A, E, G, H, N, V or Y.

Clause E52. The variant or salt thereof according to any one of clauses E1 to E41, comprising a substitution of V at position 8, such as replacement by D, E, I, L or M.

Clause E53. The variant or salt thereof according to any one of clauses E41 to E52, comprising a substitution of X, at position −2, such as replacement by E, N, Q, R, T I, L or V.

Clause E54. The variant or salt thereof according to any one of clauses E41 to E52, comprising a substitution of T at position −1, such as replacement by A, K, M, N, R or S, especially A, K, M, N or R.

Clause E55. The variant or salt thereof according to any one of clauses E41 to E52, comprising a substitution of E at position 0, such as replacement by A, D, G, K, Q or V, especially G, K, Q or V.

Clause E56. The variant or salt thereof according to any one of clauses E41 to E52, comprising a substitution of X$_2$ at position 1, such as replacement by A, C, E, H, L, M, N, R, S, T, V or Y, especially A, E, H, L, M, N, R, T, V or Y.

Clause E57. The variant or salt thereof according to any one of clauses E41 to E52, comprising a substitution of X$_3$ at position 2, such as replacement by D, E, F, G, H, K, M, N, P, Q, S or W, especially D, E, F, G, H, K, M, N, P, Q or W.

Clause E58. The variant or salt thereof according to any one of clauses E41 to E52, comprising a substitution of E at position 3, such as replacement by A, D, G, K, Q or V, especially G, K, Q or V.

Clause E59. The variant or salt thereof according to any one of clauses E41 to E52, comprising a substitution of H at position 4, such as replacement by D, L, N, P, Q, R or Y.

Clause E60. The variant or salt thereof according to any one of clauses E41 to E52, comprising a substitution of X$_4$ at position 5, such as replacement by G, K, Q, S, T or V, especially G, K, Q, T or V.

Clause E61. The variant or salt thereof according to any one of clauses E41 to E52, comprising a substitution of E at position 6, such as replacement by A, D, G, K, Q or V.

Clause E62. The variant or salt thereof according to any one of clauses E41 to E52, comprising a substitution of D at position 7, such as replacement by A, E, G, H, N, V or Y.

Clause E63. The variant or salt thereof according to any one of clauses E41 to E52, comprising a substitution of V at position 8, such as replacement by D, E, I, L or M.

Clause E64. The variant or salt thereof according to any one of clauses E42 to E52, comprising one conservative substitution.

Clause E65. The linear peptide or salt thereof according to any one of clauses E1 to E40.

Clause E66. The linear peptide, variant or salt according to any one of clauses E1 to E65, which is N-terminally acetylated.

Clause E67. The linear peptide, variant or salt according to any one of clauses E1 to E65, which is not N-terminally modified.

Clause E68. The linear peptide, variant or salt according to any one of clauses E1 to E67, which is C-terminally amidated.

Clause E69. The linear peptide, variant or salt according to any one of clauses E1 to E67, which is not C-terminally modified.

Clause E70. The linear peptide or salt according to clause E1 consisting of SEQ ID No. 1 or a salt thereof.

Clause E71. The linear peptide or salt according to clause E1 consisting of SEQ ID No. 2 or a salt thereof.

Clause E72. The linear peptide or salt according to clause E1 consisting of SEQ ID No. 3 or a salt thereof.

Clause E73. The linear peptide or salt according to clause E1 consisting of SEQ ID No. 4 or a salt thereof.

Clause E74. The linear peptide or salt according to clause E1, consisting of SEQ ID No. 5 or a salt thereof.

Clause E75. The linear peptide or salt according to clause E1, consisting of SEQ ID No. 6 or a salt thereof.

Clause E76. The linear peptide or salt according to clause E1, consisting of SEQ ID No. 7 or a salt thereof.

Clause E77. The linear peptide or salt according to clause E1, consisting of SEQ ID No. 8 or a salt thereof.

Clause E78. The linear peptide or salt according to clause E1, consisting of SEQ ID No. 9 or a salt thereof.

Clause E79. The linear peptide or salt according to clause E1, consisting of SEQ ID No. 10 or a salt thereof.

Clause E80. The linear peptide or salt according to clause E1 consisting of SEQ ID No. 16 or a salt thereof.

Clause E81. The linear peptide or salt according to clause E1 consisting of SEQ ID No. 17 or a salt thereof.

Clause E82. The linear peptide or salt according to clause E1 consisting of SEQ ID No. 18 or a salt thereof.

Clause E83. The linear peptide or salt according to clause E1 consisting of SEQ ID No. 19 or a salt thereof.

Clause E84. The linear peptide or salt according to clause E1, consisting of SEQ ID No. 20 or a salt thereof.

Clause E85. The linear peptide or salt according to clause E1, consisting of SEQ ID No. 21 or a salt thereof.

Clause E86. The linear peptide or salt according to clause E1, consisting of SEQ ID No. 22 or a salt thereof.

Clause E87. The linear peptide or salt according to clause E1, consisting of SEQ ID No. 23 or a salt thereof.

Clause E88. The linear peptide or salt according to clause E1, consisting of SEQ ID No. 24 or a salt thereof.

Clause E89. The linear peptide or salt according to clause E1, consisting of SEQ ID No. 25 or a salt thereof.

Clause E90. The linear peptide or salt according to clause E1, consisting of SEQ ID No. 26 or a salt thereof.

Clause E91. The linear peptide or salt according to clause E1 consisting of SEQ ID No. 27 or a salt thereof.

Clause E92. The linear peptide or salt according to clause E1 consisting of SEQ ID No. 28 or a salt thereof.

Clause E93. The linear peptide or salt according to clause E1 consisting of SEQ ID No. 29 or a salt thereof.

Clause E94. The linear peptide or salt according to clause E1, consisting of SEQ ID No. 30 or a salt thereof.

Clause E95. The linear peptide or salt according to clause E1, consisting of SEQ ID No. 31 or a salt thereof.

Clause E96. The linear peptide or salt according to clause E1, consisting of SEQ ID No. 32 or a salt thereof.

Clause E97. The linear peptide or salt according to clause E1, consisting of SEQ ID No. 33 or a salt thereof.

Clause E98. The linear peptide or salt according to clause E1, consisting of SEQ ID No. 34 or a salt thereof.

Clause E99. The linear peptide or salt according to clause E1, consisting of SEQ ID No. 35 or a salt thereof.

Clause E100. The linear peptide or salt according to clause E1, consisting of SEQ ID No. 36 or a salt thereof.

Clause E101. The linear peptide or salt according to clause E1, consisting of SEQ ID No. 37 or a salt thereof.

Clause E102. The linear peptide or salt according to clause E1, consisting of SEQ ID No. 38 or a salt thereof.

Clause E103. The linear peptide, variant or salt according to any one of clauses E1 to E102, wherein the salt is a pharmaceutically acceptable salt.

Clause E104. The linear peptide according to any preceding E clause.

Clause E105. The variant peptide according to any preceding E clause.

Clause E106. The pharmaceutically acceptable salt of a linear peptide according to any preceding E clause.

Clause E107. The pharmaceutically acceptable salt of the variant peptide according to any preceding E clause.

Clause E108. The linear peptide according to any one of clauses E1 to E107, which is not side chain modified.

Clause E109. The linear peptide according to any one of clauses E1 to E107, which is not modified.

Clause F1. A linear peptide comprising 10 or fewer amino acid residues within the backbone and comprising the sequence:

| | $X_2$— | $X_3$— | E— | H— | $X_4$— | E |
|---|---|---|---|---|---|---|
| position | 1 | 2 | 3 | 4 | 5 | 6 | wherein:
$X_2$ represents P, D, Q, K, G
$X_3$ represents I, L, A, T, V
$X_4$ represents E, A or a salt thereof, or a conservatively substituted variant of said peptide or salt.

Clause F2. The linear peptide, variant or salt according to clause F1, wherein all residues of the peptide backbone are joined exclusively by peptide bonds.

Clause F3. The linear peptide, variant or salt according to clause F1 or F2, comprising 6 amino acid residues within the backbone.

Clause F4. The linear peptide, variant or salt according to clause F1 or F2, comprising 7 amino acid residues within the backbone.

Clause F5. The linear peptide, variant or salt according to clause F1 or F2, comprising 8 amino acid residues within the backbone.

Clause F6. The linear peptide, variant or salt according to clause F1 or F2, comprising 9 amino acid residues within the backbone.

Clause F7. The linear peptide, variant or salt according to clause F1 or F2, comprising 10 amino acid residues within the backbone.

Clause F8. The linear peptide, variant or salt according to any one of clauses F1, F2 or F4 to

| | E— | $X_2$— | $X_3$— | E— | H— | $X_4$— | E |
|---|---|---|---|---|---|---|---|
| position | 0 | 1 | 2 | 3 | 4 | 5 | 6 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F9. The linear peptide, variant or salt according to any one of clauses F1, F2 or F4 to F7, comprising the sequence:

| | $X_2$— | $X_3$— | E— | H— | $X_4$— | E— | D |
|---|---|---|---|---|---|---|---|
| position | 1 | 2 | 3 | 4 | 5 | 6 | 7 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F10. The linear peptide, variant or salt according to any one of clauses F1, F2 or F5 to F7, comprising the sequence:

| | T— | E— | $X_2$— | $X_3$— | E— | H— | $X_4$— | E |
|---|---|---|---|---|---|---|---|---|
| position | -1 | 0 | 1 | 2 | 3 | 4 | 5 | 6 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F11. The linear peptide, variant or salt according to any one of clauses F1, F2 or F5 to F7, comprising the sequence:

| | E— | $X_2$— | $X_3$— | E— | H— | $X_4$— | E— | D |
|---|---|---|---|---|---|---|---|---|
| position | 0 | 1 | 2 | 3 | 4 | 5 | 6 | 7 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F12. The linear peptide, variant or salt according to any one of clauses F1, F2 or F6 to F7, comprising the sequence:

| | $X_2$— | $X_3$— | E— | H— | $X_4$— | E— | D— | V |
|---|---|---|---|---|---|---|---|---|
| position | 1 | 2 | 3 | 4 | 5 | 6 | 7 | 8 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F13. The linear peptide, variant or salt according to any one of clauses F1, F2, F6 or F7, comprising the sequence:

| | $X_1$— | T— | E— | $X_2$— | $X_3$— | E— | H— | $X_4$— | E |
|---|---|---|---|---|---|---|---|---|---|
| position | -2 | -1 | 0 | 1 | 2 | 3 | 4 | 5 | 6 | wherein:
  $X_1$ represents M, K
  $X_2$ represents P, D, Q, K, G
  $X_3$ represents I, L, A, T, V
  $X_4$ represents E, A
or a salt thereof, or a conservatively substituted variant of said peptide or salt.

Clause F14. The linear peptide, variant or salt according to any one of clauses F1, F2, F6 or F7, comprising the sequence:

| | T— | E— | $X_2$— | $X_3$— | E— | H— | $X_4$— | E— | D |
|---|---|---|---|---|---|---|---|---|---|
| position | -1 | 0 | 1 | 2 | 3 | 4 | 5 | 6 | 7 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F15. The linear peptide, variant or salt according to any one of clauses F1, F2, F6 or F7, comprising the sequence:

| | E— | $X_2$— | $X_3$— | E— | H— | $X_4$— | E— | D— | V |
|---|---|---|---|---|---|---|---|---|---|
| position | 0 | 1 | 2 | 3 | 4 | 5 | 6 | 7 | 8 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F16. The linear peptide, variant or salt according to any one of clauses F1, F2 or F7, comprising the sequence:

| | $X_1$— | T— | E— | $X_2$— | $X_3$— | E— | H— | $X_4$— | E— | D |
|---|---|---|---|---|---|---|---|---|---|---|
| position | -2 | -1 | 0 | 1 | 2 | 3 | 4 | 5 | 6 | 7 | wherein:
  $X_1$ represents M, K
  $X_2$ represents P, D, Q, K, G
  $X_3$ represents I, L, A, T, V
  $X_4$ represents E, A
or a salt thereof, or a conservatively substituted variant of said peptide or salt.

Clause F17. The linear peptide, variant or salt according to any one of clauses F1, F2 or F7, comprising the sequence:

| | T— | E— | $X_2$— | $X_3$— | E— | H— | $X_4$— | E— | D— | V |
|---|---|---|---|---|---|---|---|---|---|---|
| position | −1 | 0 | 1 | 2 | 3 | 4 | 5 | 6 | 7 | 8 | wherein:
  $X_2$ represents P, D, Q, K, G
  $X_3$ represents I, L, A, T, V
  $X_4$ represents E, A
or a salt thereof, or a conservatively substituted variant of said peptide or salt.

Clause F18. The linear peptide, variant or salt according to any one of clauses F1 to F17, wherein $X_1$ represents M.

Clause F19. The linear peptide, variant or salt according to any one of clauses F1 to F17, wherein $X_1$ represents K.

Clause F20. The linear peptide, variant or salt according to any one of clauses F1 to F19, wherein $X_2$ represents P.

Clause F21. The linear peptide, variant or salt according to any one of clauses F1 to F19, wherein $X_2$ represents D.

Clause F22. The linear peptide, variant or salt according to any one of clauses F1 to F19, wherein $X_2$ represents Q.

Clause F23. The linear peptide, variant or salt according to any one of clauses F1 to F19, wherein $X_2$ represents K.

Clause F24. The linear peptide, variant or salt according to any one of clauses F1 to F19, wherein $X_2$ represents G.

Clause F25. The linear peptide, variant or salt according to any one of clauses F1 to F24, wherein $X_3$ represents I.

Clause F26. The linear peptide, variant or salt according to any one of clauses F1 to F24, wherein $X_3$ represents L.

Clause F27. The linear peptide, variant or salt according to any one of clauses F1 to F24, wherein $X_3$ represents A.

Clause F26. The linear peptide, variant or salt according to any one of clauses F1 to F24, wherein $X_3$ represents T.

Clause F29. The linear peptide, variant or salt according to any one of clauses F1 to F24, wherein $X_3$ represents V.

Clause F30. The linear peptide, variant or salt according to any one of clauses F1 to F29, wherein $X_4$ represents E.

Clause F31. The linear peptide, variant or salt according to any one of clauses F1 to F29, wherein $X_4$ represents A.

Clause F32. The linear peptide, variant or salt according to any one of clauses F1 to F31, comprising the sequence of any one of SEQ ID No. 40 to 42, or a salt thereof, or a conservatively substituted variant of said peptide or salt.

Clause F33. The linear peptide, variant or salt according to clause F32, consisting of the sequence of any one of SEQ ID No. 40 to 42, or a salt thereof, or a conservatively substituted variant of said peptide or salt.

Clause F34. The variant or salt thereof according to any one of clauses F1 to F33, comprising two conservative substitutions.

Clause F35. The variant or salt thereof according to any one of clauses F1 to F34, comprising a substitution of X, at position −2, such as replacement by E, N, Q, R, T I, L or V.

Clause F36. The variant or salt thereof according to any one of clauses F1 to F34, comprising a substitution of T at position −1, such as replacement by A, K, M, N, R or S, especially A, K, M, N or R.

Clause F37. The variant or salt thereof according to any one of clauses F1 to F34, comprising a substitution of E at position 0, such as replacement by A, D, G, K, Q or V, especially G, K, Q or V.

Clause F38. The variant or salt thereof according to any one of clauses F1 to F34, comprising a substitution of $X_2$ at position 1, such as replacement by A, C, E, H, L, M, N, R, S, T, V or Y, especially A, E, H, L, M, N, R, T, V or Y.

Clause F39. The variant or salt thereof according to any one of clauses F1 to F34, comprising a substitution of $X_3$ at position 2, such as replacement by D, E, F, G, H, K, M, N, P, Q, S or W, especially D, E, F, G, H, K, M, N, P, Q or W.

Clause F40. The variant or salt thereof according to any one of clauses F1 to F34, comprising a substitution of E at position 3, such as replacement by A, D, G, K, Q or V, especially G, K, Q or V.

Clause F41. The variant or salt thereof according to any one of clauses F1 to F34, comprising a substitution of H at position 4, such as replacement by D, L, N, P, Q, R or Y.

Clause F42. The variant or salt thereof according to any one of clauses F1 to F34, comprising a substitution of $X_4$ at position 5, such as replacement by G, K, Q, S, T or V, especially G, K, Q, T or V.

Clause F43. The variant or salt thereof according to any one of clauses F1 to F34, comprising a substitution of E at position 6, such as replacement by A, D, G, K, Q or V.

Clause F44. The variant or salt thereof according to any one of clauses F1 to F34, comprising a substitution of D at position 7, such as replacement by A, E, G, H, N, V or Y.

Clause F45. The variant or salt thereof according to any one of clauses F1 to F34, comprising a substitution of V at position 8, such as replacement by D, E, I, L or M.

Clause F46. The variant or salt thereof according to any one of clauses F34 to F45, comprising a substitution of X, at position −2, such as replacement by E, N, Q, R, T I, L or V.

Clause F47. The variant or salt thereof according to any one of clauses F34 to F45, comprising a substitution of T at position −1, such as replacement by A, K, M, N, R or S, especially A, K, M, N or R.

Clause F48. The variant or salt thereof according to any one of clauses F34 to F45, comprising a substitution of E at position 0, such as replacement by A, D, G, K, Q or V, especially G, K, Q or V.

Clause F49. The variant or salt thereof according to any one of clauses F34 to F45, comprising a substitution of $X_2$ at position 1, such as replacement by A, C, E, H, L, M, N, R, S, T, V or Y, especially A, E, H, L, M, N, R, T, V or Y.

Clause F50. The variant or salt thereof according to any one of clauses F34 to F45, comprising a substitution of $X_3$ at position 2, such as replacement by D, E, F, G, H, K, M, N, P, Q, S or W, especially D, E, F, G, H, K, M, N, P, Q or W.

Clause F51. The variant or salt thereof according to any one of clauses F34 to F45, comprising a substitution of E at position 3, such as replacement by A, D, G, K, Q or V, especially G, K, Q or V.

Clause F52. The variant or salt thereof according to any one of clauses F34 to F45, comprising a substitution of H at position 4, such as replacement by D, L, N, P, Q, R or Y.

Clause F53. The variant or salt thereof according to any one of clauses F34 to F45, comprising a substitution of X at position 5, such as replacement by G, K, Q, S, T or V, especially G, K, Q, T or V.

Clause F54. The variant or salt thereof according to any one of clauses F34 to F45, comprising a substitution of E at position 6, such as replacement by A, D, G, K, Q or V.

Clause F55. The variant or salt thereof according to any one of clauses F34 to F45, comprising a substitution of D at position 7, such as replacement by A, E, G, H, N, V or Y.

Clause F56. The variant or salt thereof according to any one of clauses F34 to F45, comprising a substitution of V at position 8, such as replacement by D, E, I, L or M.

Clause F57. The variant or salt thereof according to any one of clauses F35 to F45, comprising one conservative substitution.

Clause F58. The linear peptide, variant or salt according to any one of clauses F1 to F57, which is N-terminally acetylated.

Clause F59. The linear peptide, variant or salt according to any one of clauses F1 to F57, which is not N-terminally modified.

Clause F60. The linear peptide, variant or salt according to any one of clauses F1 to F59, which is C-terminally amidated.

Clause F61. The linear peptide, variant or salt according to any one of clauses F1 to F59, which is not C-terminally modified.

Clause F62. The linear peptide or salt thereof according to any one of clauses F1 to F33.

Clause F63. The linear peptide or salt according to clause F1, consisting of SEQ ID No. 40 or a salt thereof.

Clause F64. The linear peptide or salt according to clause F1, consisting of SEQ ID No. 41 or a salt thereof.

Clause F65. The linear peptide or salt according to clause F1, consisting of SEQ ID No. 42 or a salt thereof.

Clause F66. The linear peptide, variant or salt according to any one of clauses F1 to F65, wherein the salt is a pharmaceutically acceptable salt.

Clause F67. The linear peptide according to any preceding F clause.

Clause F68. The variant peptide according to any preceding F clause.

Clause F69. The pharmaceutically acceptable salt of a linear peptide according to any preceding F clause.

Clause F70. The pharmaceutically acceptable salt of the variant peptide according to any preceding F clause.

Clause F71. The linear peptide according to any one of clauses F1 to F70, which is not side chain modified.

Clause F72. The linear peptide according to any one of clauses F1 to F70, which is not modified.

Clause G1. A protected cyclic peptide, comprising a cyclic peptide as described in any one of clauses A1 to A98, B1 to B95 or C1 to C70 wherein at least one reactive amino acid side chain is protected.

Clause G2. The protected cyclic peptide according to clause G1, wherein all reactive amino acid side chains are protected.

Clause H1. A protected linear peptide, comprising a linear peptide as described in any one of clauses D1 to D101, E1 to E109 or F1 to F72 wherein at least one reactive group is protected.

Clause H2. The protected linear peptide according to clause H1, wherein at least one reactive amino acid side chains is protected.

Clause H3. The protected linear peptide according to clause H2, wherein all reactive amino acid side chains are protected.

Clause H4. The protected linear peptide according to any one of clauses H1 to H3, wherein the N-terminus is protected.

Clause H5. The protected linear peptide according to any one of clauses H1 to H4, wherein the C-terminus is protected.

Clause 11. A linear peptide which when cyclised provides a cyclic peptide as described in any one of clauses A1 to A98, B1 to B95 or C1 to C70.

Clause J1. A protected linear peptide which when cyclised provides a protected cyclic peptide as described in either clause G1 or G2.

Clause K. A method for the manufacture of a peptide as described herein.

Clause L1. The lipidated cyclic peptide, cyclic peptide, lipidated linear peptide, linear peptide, variant of any thereof and/or of any thereof according to any one of clauses A1 to A98, B1 to B99, C1 to C70, D1 to D101, E1 to E109 or F1 to F72 which is capable of increasing BDNF levels.

Clause L2. The lipidated cyclic peptide, cyclic peptide, lipidated linear peptide, linear peptide, variant of any thereof and/or of any thereof according to clause J1 which is capable of increasing BDNF levels by at least 20% between 0 and 24 hours following administration in the assay of Example 10.

Clause M1. The lipidated cyclic peptide, cyclic peptide, lipidated linear peptide, linear peptide, variant of any thereof and/or salt of any thereof according to any one of clauses A1 to A98, B1 to B95, C1 to C70, D1 to D101, E1 to E109 or F1 to F72 which is capable of increasing phosphor-CREB (Ser133) levels.

Clause M2. The lipidated cyclic peptide, cyclic peptide, lipidated linear peptide, linear peptide, variant of any thereof and/or salt of any thereof according to clause M1 which is capable of increasing CREB levels by at least 30% between 0 and 24 hours following administration in the assay of Example 10.

Clause N1. The lipidated cyclic peptide, cyclic peptide, lipidated linear peptide, linear peptide, variant of any thereof and/or salt of any thereof according to any one of clauses A1 to A99, B1 to B95, C1 to C70, D1 to D101, E1 to E109 or F1 to F72 which is capable of increasing PGC1a levels.

Clause N2. The lipidated cyclic peptide, cyclic peptide, lipidated linear peptide, linear peptide, variant of any thereof and/or of any thereof according to clause M1 which is capable of increasing PGC1a levels by at least 30% between 0 and 24 hours following administration in the assay of Example 10.

Clause O1. The lipidated cyclic peptide, cyclic peptide, lipidated linear peptide, linear peptide, variant of any thereof and/or salt of any thereof according to any one of clauses A1 to A99, B1 to B95, C1 to C70, D1 to D101, E1 to E109 or F1 to F72 which is capable of increasing TFEB levels.

Clause O2. The lipidated cyclic peptide, cyclic peptide, lipidated linear peptide, linear peptide, variant of any thereof and/or salt of any thereof according to clause O1 which is capable of increasing TFEB levels by at least 30% between 0 and 24 hours following administration in the assay of Example 10.

Clause P1. The lipidated cyclic peptide, cyclic peptide, lipidated linear peptide, linear peptide, variant of any thereof and/or salt of any thereof according to any one of clauses A1 to A99, B1 to B95, C1 to C70, D1 to D101, E1 to E109 or F1 to F72 which is capable of decreasing NfL levels.

Clause P2. The lipidated cyclic peptide, cyclic peptide, lipidated linear peptide, linear peptide, variant of any thereof and/or salt of any thereof according to clause P1 which is capable of decreasing NfL levels by at least 10% between in the assay of Example 31.

Clause Q1. The peptide or variant thereof and/or salt thereof according to any preceding clause which has improved ability to increase BDNF, PGC1a, TFEB and/or phospho-CREB (Ser133) as compared to CPX.

Clause Q2. The peptide or variant thereof and/or salt thereof according to any preceding clause which has improved $t_{1/2}$, AUC or $C_{max}$, particularly in the brain, as compared to CPX.

Clause Q3. The peptide or variant thereof and/or salt thereof according to any preceding clause which has improved $t_{1/2}$ in the brain, as compared to CPX.

Clause Q4. The peptide or variant thereof and/or salt thereof according to any preceding clause which has ability to increase BDNF, PGC1a, TFEB and/or phospho-CREB (Ser133) at least equivalent to CLP1.

Clause Q5. The peptide or variant thereof and/or salt thereof according to any preceding clause which has $t_{1/2}$, AUC or $C_{max}$, particularly in the brain, at least equivalent to CLP1.

Clause Q6. The peptide or variant thereof and/or salt thereof according to any preceding clause which has $t_{1/2}$ particularly in the brain, at least equivalent to CLP1.

Clause Q7. The peptide or variant thereof and/or salt thereof according to any preceding clause which demonstrates an absence of fibrillation at pH 6.5 and 7.5, suitably at pH 4.5, pH 6.5 and pH 7.5 (such as by the method of Example 5).

Clause Q8. The peptide or variant thereof and/or salt thereof according to any preceding clause which demonstrates a $t_{1/2}$ of at least 1 hr, suitably at least 4 hours, especially at least 8 hours (such as by the method of Example 9).

Clause Q9. The peptide or variant thereof and/or salt thereof according to clause Q8 which demonstrates a $t_{1/2}$ in the brain of at least 1 hr, suitably at least 4 hours, especially at least 8 hours (such as by the method of Example 9).

Clause R1. A pharmaceutical composition comprising a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 and a pharmaceutically acceptable carrier or excipient.

Clause R2. The pharmaceutical composition according to clause R1, which is a solid.

Clause R3. The pharmaceutical composition according to clause R2, which is a liquid.

Clause R4. The pharmaceutical composition according to clause R3, wherein the pharmaceutically acceptable carrier or excipient is water.

Clause R5. The pharmaceutical composition according to any one of clauses R1 to R4, which is in unit dose form.

Clause R6. The pharmaceutical composition according to clause R5, wherein the unit dose form contains 0.005 mg to 100 mg, more suitably 0.05 mg to 50 mg.

Clause R7. The lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 for use as a medicament.

Clause R8. Use of a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 in the manufacture of a medicament.

Clause R9. The lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 for use in increasing BDNF levels.

Clause R10. Use of a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 in the manufacture of a medicament for increasing BDNF levels.

Clause R11. A method of increasing BDNF levels in a subject, which method comprises administering to a subject a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9.

Clause R12. The lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 for use in increasing phospho-CREB (Ser133) levels.

Clause R13. Use of a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 in the manufacture of a medicament for increasing phospho-CREB (Ser133) levels.

Clause R14. A method of increasing CREB levels in a subject, which method comprises administering to a subject a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9.

Clause R15. The lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 for use in increasing PGC1a levels.

Clause R16. Use of a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 in the manufacture of a medicament for increasing PGC1a levels.

Clause R17. A method of increasing PGC1a levels in a subject, which method comprises administering to a subject a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9.

Clause R18. The lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 for use in increasing TFEB levels.

Clause R19. Use of a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 in the manufacture of a medicament for increasing TFEB levels.

Clause R20. A method of increasing TFEB levels in a subject, which method comprises administering to a subject a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9.

Clause R21. The lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 for use in decreasing NfL levels.

Clause R22. Use of a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 in the manufacture of a medicament for decreasing NfL levels.

Clause R23. A method of decreasing NfL levels in a subject, which method comprises administering to a subject a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9.

Clause R24. The lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9 for use in the treatment or prophylaxis of a disease or disorder selected from the group consisting of neurodegenerative diseases, proteionopathies, lysosomal storage disorders, mitochondrial disorders, psychiatric disorders and other BDNF-related disorders.

Clause R25. Use of a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, O1 to O9 in the manufacture of a medicament for the treatment or prophylaxis of a disease or disorder selected from the group consisting of neurodegenerative diseases, proteionopathies, lysosomal storage disorders, mitochondrial disorders, psychiatric disorders and other BDNF-related disorders.

Clause R26. A method of the treatment or prophylaxis of a disease or disorder selected from the group consisting of neurodegenerative diseases, proteionopathies, lysosomal storage disorders, mitochondrial disorders, psychiatric disorders and other BDNF-related disorders in a subject, which method comprises administering to the subject a lipidated cyclic peptide, cyclic peptide, lipidated linear peptide, linear peptide, variant of any thereof and/or a pharmaceutically acceptable salt of any thereof according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9.

Clause R27. The peptide, use or method according to any one of clauses R24 to R26, for the treatment or prophylaxis of a neurodegenerative disease, particularly a neurodegenerative disease associated with reduction of BDNF, rescue with BDNF, mitochondrial dysfunction and/or lysosomal dysfunction.

Clause R28. The peptide, use or method according to any one of clauses R24 to R26, for the treatment or prophylaxis of Huntington's disease, Parkinson's disease, Alzheimer's disease, Frontotemporal dementia (especially subjects with GRN-haploinsufficiency), ALS, multiple sclerosis, inherited ataxias, motor neuron disorder or vascular dementia.

Clause R29. The peptide, use or method according to clause R28, for the treatment or prophylaxis of Huntington's disease.

Clause R30. The peptide, use or method according to clause R29, wherein the UHDRS is improved (relative to the absence of treatment).

Clause R31. The peptide, use or method according to clause R28, for the treatment or prophylaxis of Parkinson's disease.

Clause R32. The peptide, use or method according to clause R31, in a subject with monoallelic mutation in GBA1.

Clause R33. The peptide, use or method according to clause R32, in a subject with N370S, L444P, R463C, G10S, N426K, R48W and/or R257Q mutations.

Clause R34. The peptide, use or method according to any one of clauses R31 to R33, wherein the UPDRS is improved (relative to the absence of treatment).

Clause R35. The peptide, use or method according to any one of clauses R31 to R34, wherein the MDS-UPDRS is improved (relative to the absence of treatment).

Clause R36. The peptide, use or method according to clause R28, for the treatment or prophylaxis of Alzheimer's disease.

Clause R37. The peptide, use or method according to clause R28, for the treatment or prophylaxis of, Frontotemporal dementia, especially subjects with GRN-haploinsufficiency.

Clause R38. The peptide, use or method according to any one of clauses R24 to R26, for the treatment or prophylaxis of a proteinopathy, particularly a proteinopathy associated with protein aggregation.

Clause R39. The peptide, use or method according to any one of clauses R24 to R26, for the treatment or prophylaxis of prion diseases, Alpha-synucleinopathies, tauopathies, C9orf72-dependent ALS/FTD, dementia with Lewy bodies, dementia with amyloid plaques, Huntington's Disease, TDP-43-positive ALS/FTD or inherited ataxias.

Clause R40. The peptide, use or method according to any one of clauses R24 to R26, for the treatment or prophylaxis of a lysosomal storage disorder, in particular a lysosomal storage disorder associated with lysosomal dysfunction.

Clause R41. The peptide, use or method according to clause R40, in a subject with Gaucher's Disease.

Clause R42. The peptide, use or method according to clause R41, in a subject with biallelic mutation in GBA1.

Clause R43. The peptide, use or method according to clause R42, in a subject with p.Leu483Pro, p.Arg535Cys and/or RecNcil mutations.

Clause R44. The peptide, use or method according to any one of clauses R24 to R26, for the treatment or prophylaxis of Nieman-Pick disease or neuronal ceroid lipofuscinose.

Clause R45. The peptide, use or method according to any one of clauses R24 to R26, for the treatment or prophylaxis of a mitochondrial dysfunction disorder.

Clause R46. The peptide, use or method according to any one of clauses R24 to R26, for the treatment or prophylaxis of mitochondrial myopathies or Leigh syndrome.

Clause R47. The peptide, use or method according to any one of clauses R24 to R26, for the treatment or prophylaxis of a psychiatric disorder, particularly a psychiatric disorder associated with SorCS2 gene or function association, or BDNF or TrkB association.

Clause R48. The peptide, use or method according to any one of clauses R24 to R26, for the treatment or prophylaxis of bipolar disorder, depression, schizophrenia, autism spectrum disorders, anxiety or ADHD.

Clause R49. The peptide, use or method according to any one of clauses R24 to R26, for the treatment or prophylaxis of depression.

Clause R50. The peptide, use or method according to any one of clauses R24 to R26, for the treatment or prophylaxis of another BDNF related disorder.

Clause R51. The peptide, use or method according to any one of clauses R24 to R26, for the treatment or prophylaxis of WAGR Syndrome (especially BDNF haploinsufficiency), stroke or epilepsy.

Clause R52. The peptide, use or method according to any one of clauses R7 to R51, for use in treatment.

Clause R53. The peptide, use or method according to any one of clauses R7 to R51, for use in prophylaxis.

Clause R54. The peptide, use or method according to any one of clauses R7 to R53, for use in a human subject.

Clause R55. The peptide, use or method according to any one of clauses R7 to R54, wherein the lipidated cyclic peptide, cyclic peptide, lipidated linear peptide, linear peptide, variant of any thereof and/or a pharmaceutically acceptable salt of any thereof is provided in the form of a pharmaceutical composition according to any one of clauses R1 to R7.

Clause S1. A peptide according to any one of clauses A1 to A98, B1 to B95, C1 to C70, D1 to D101, E1 to E109, F1 to F72, L1 or L2, M1 or M2, N1 or N2, O1 or O2, P1 or P2, Q1 to Q9, or a protected peptide according to any one of clauses G1 and G2, H1 to H5, I1 or J1 which is covalently bound to a solid support.

The present invention is also described in more detail with reference to the Examples which follow, but is not limited thereto. The examples may be modified without departing from the scope of the invention.

In addition, as used in this specification and the appended claims, the singular forms "a", "an", and "the" include plural referents unless the content clearly dictates otherwise. Thus, for example, reference to "a peptide" includes two or more such peptides, and the like.

All publications, patents and patent applications cited herein, whether supra or infra, are hereby incorporated by reference in their entirety.

EXAMPLES

Statistics

Unless otherwise indicated, two-tailed Student's t-test was used to assess significance. Error bars indicate S.E.M. *$p<0.05$, $p<0.01$, $p<0.001$, **$p<0.0001$.

Example 1: Peptide Synthesis

Linear peptides were synthesized using standard Fmoc (fluorenylmethyloxycarbonyl) chemistry.
Resin Preparation:
Fmoc-Pro-OH (0.2 mmol, 1 eq) and N,N-diisopropylethylamine (DIPEA) (0.14 mL, 4 eq) were added to 2-CTC Resin (0.2 mmol, 1.00 eq, Sub 1.05 mmol/g) in dichloromethane (DCM) (10 mL). The mixture was agitated with $N_2$ for 2 h at 20° C., then methanol (MeOH) (0.5 mL) added and agitated with $N_2$ bubbling for another 30 min. The resin was washed three times with dimethylformamide (DMF) (15 mL).
Deprotection:
Fmoc removal was performed using 20% piperidine in DMF (15 mL) added and to the resin and agitated with $N_2$ for 30 min. The resin was washed with DMF four times (15 mL) and filtered.
Coupling:
The consecutive amino acid couplings were performed using a solution of 2-(1H-benzotriazole-1-yl)-1,1,3,3tetramethyluronium hexafluorophosphate (HBTU) (2.85 eq), DIPEA (6 eq) and Fmoc-protected amino acids (3 eq) in DMF (5 mL) added to the resin and agitated with $N_2$ for 30 min at 20° C. The resin was then washed four times with DMF (15 mL). Fmoc deprotection and coupling steps were repeated for each of the subsequent amino acids until the desired peptide sequence was achieved. The resin was then washed four times with dimethylformamide (DMF) (15 mL). Fmoc removal and coupling steps were repeated until the desired peptide sequence was achieved. The resultant sidechain protected and resin bound linear peptide was used directly in the next step.

The Fmoc-protected amino acid building blocks used were: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln (Trt)-OH, FmocGlu(OtBu)-OH, Fmoc-Gly-OH, Fmoc-His (Trt)-OH, Fmoc-Ile-OH, Fmoc-Leu-OH, Fmoc-Lys(Boc) OH, Fmoc-Met-OH, Fmoc-Phe-OH, Fmoc-Pro-OH, Fmoc-Ser(tBu)-OH, Fmoc-Thr(tBu)-OH, Fmoc-Tyr(tBu)-OH, and Fmoc-L-Val-OH. If nothing else is specified, the natural L-form of the amino acids were used. Addition of lipids on lysine-residues was carried out using orthogonally protected Lys (Dde-Lys(Fmoc)-OH), in which the Dde is placed on alpha amine, while Fmoc is placed on sidechain amine. After coupling of the protected Lys, the Fmoc was first removed, then the lipid was coupled to the resulting exposed amine. Dde was subsequently removed and the peptide chain was elongated using Fmoc chemistry as usual.

Example 2: Peptide Cleavage, Cyclisation and Purification

After final amino acid coupling and Fmoc removal, the resin from Example 1 was washed with DMF 5 times, with MeOH 3 times, and dried under vacuum. To develop cyclic peptides, the peptide resin was then treated with the cleavage cocktail (1% trifluoroacetic acid (TFA)/99% DCM) (15 mL) for 15 min and the peptide containing TFA-DCM mixture was collected. The cleavage was repeated three times. In relation to linear peptides, these were cleaved and directly deprotected using strong acid (95% TFA). In relation to cyclic peptides, the peptide (in 1% TFA/99% DCM) was diluted in DCM (200 mL) together with 2-(1H-benzotriazole-1-yl)-1,1,3,3-tetramethylaminium tetrafluoroborate (TBTU) (2 eq) and 1-hydroxybenzotriazole hydrate (HOBT) (2 eq) and DIPEA (6 eq) to couple the head to tail of the peptide. The mixture was stirred at 20° C. for 1 h. Cyclisation was monitored by LC-MS.

After stirring, the mixture was washed with 1 M hydrochloric acid (HCl) (30 mL) twice and dried under reduced pressure. 5 mL of cleavage buffer (92.5% TFA/2.5% 3-mercaptopropionic acid/2.5% triisopropyl silane/2.5% $H_2O$) was added to the flask containing the sidechain protected cyclic peptide and the mixture was stirred for 2 h at 20° C. The peptide was precipitated with ice cold tert-butyl methyl ether (40 mL) and centrifuged (2 min at 3000 rpm) and washed two times with ice cold tert-butyl methyl ether (40 mL). The crude peptide was dried under vacuum for 2 hours and purified by prep-HPLC and the target peptide fraction freeze dried to give a white solid:

Prep-HPLC method: (system: Gilson GX-281; column: Gemini, C18, 110 Å, 5 μm or Luna, C18, 100 Å, 10 μm; gradient: gradient run-time 50 minutes; 0 to 50 min 7 to 37% B; flow rate: 20 mL/min; column temperature: 30° C.; diode array: 220/254 nm; solvent A: 0.075% TFA in water; solvent B: acetonitrile.

Figure 1B:
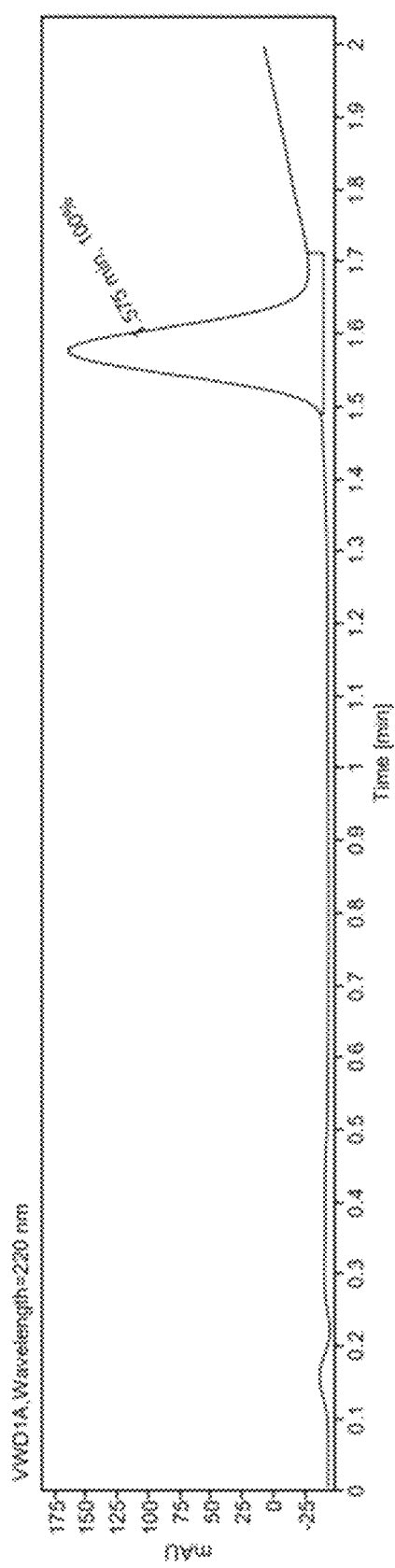
Figure 1C:
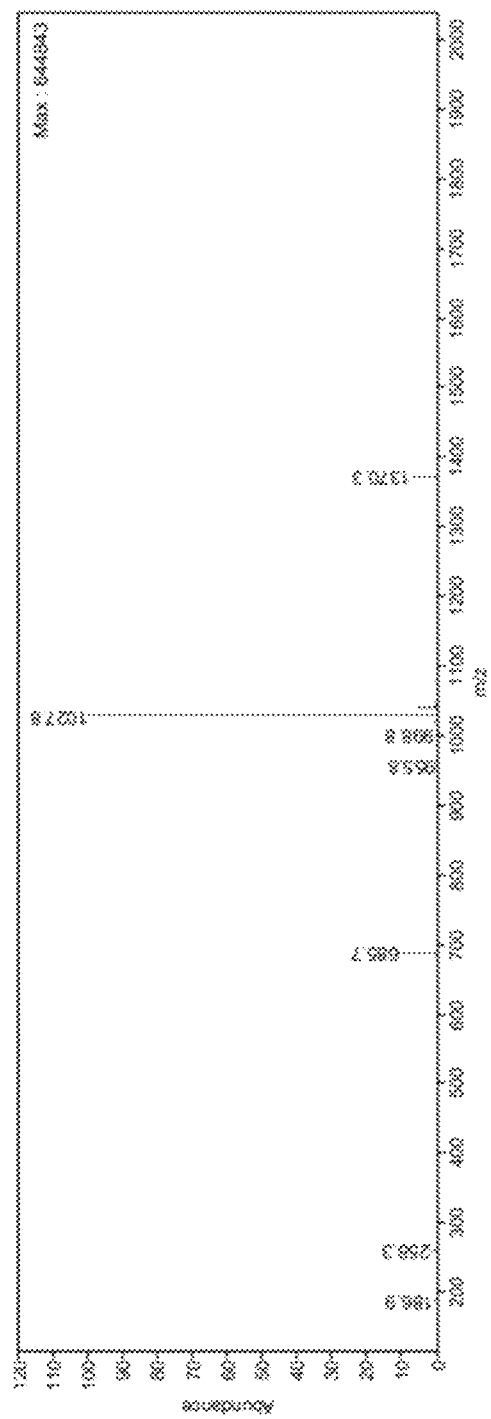

A qualitative analysis of the peptides was conducted by HPLC and LCMS (see FIG. 1):

HPLC: Column: Gemini C18, 110 Å, 5 μm, 150×4.6 mm; gradient: gradient run-time 20 minutes; 0.00-20.00 min 15-45% B, 20.10-23.00 min 95% B, 23.00-23.10 min 95-15% B, 23.10-28.00 min 15% B; flow rate: 1.0 mL/min; diode array, 220/254 nm; column temperature: 30° C.; solvent A: 0.1% TFA in water; solvent B: 0.075% TFA in acetonitrile).

LCMS method for final products: (system: Agilent Infinity 111260 HPLC series; column: Xbridge C18, 130 Å, 3.5 μm, 2.1×30 mm; detector: Agilent LCMS (G6125C), single quadrupole TIC scan; scanning range: m/z min 100, m/z max. 2000, positive mode, electrospray; gradient: gradient run-time 1 minutes; 0.00-1.00 min 10-80% B; column cleaning and equilibration; 1.00-1.01 80-95% B, 1.01-1.60 min 95% B, 1.60-1.61 min 95-10% B, 1.61-2.00 min 10% B; flow rate: 1.2 mL/min; diode array: 215 or 220 nm; column temperature: room temperature; solvent A: 0.1% TFA in water; solvent B: 0.075% TFA in acetonitrile Results A summary of data on LC-MS and HPLC purity is shown in the table below, with exemplary chromatograms and mass spectrum for CLP1 shown in FIG. 1A to FIG. 10C.

TABLE 4

Summary of peptide HPLC purification and MS characterisation

| Pep. (SEQ) | LCMS RT (min) | HPLC purity | Sum formula | Calc. mass* | Calc. average mass | Mass found m/z z = 1 | m/z z = 2 | m/z z = 3 | m/z z = 4 |
|---|---|---|---|---|---|---|---|---|---|
| CLP1 (1) | 1.575 | 98.3 | C91H148N18O35 | 2053.035 | 2054.252 | | 1027.8 | 685.7 | |
| CLP2 (2) | 1.552 | 96.0 | C91H150N18O34 | 2039.056 | 2040.269 | | 1021.0 | 681.1 | |
| CLP3 (3) | 1.557 | 90.1 | C92H152N18O34 | 2053.072 | 2054.296 | | 1028.0 | 685.7 | |
| CLP4 (4) | 1.561 | 95.4 | C89H143N17O36 | 2025.988 | 2027.184 | | 1014.4 | 676.8 | |
| CLP5 (5) | 1.573 | 96.5 | C90H145N17O36 | 2040.004 | 2041.211 | | 1021.5 | 681.4 | |
| CLP6 (6) | 1.579 | 98.2 | C90H146N18O35 | 2039.020 | 2040.226 | | 1020.8 | 681.1 | |
| CLP7 (7) | 1.541 | 99.1 | C91H150N18O34 | 2039.056 | 2040.269 | | 1020.9 | 681.0 | |
| CLP8 (8) | 1.551 | 97.7 | C92H152N18O34 | 2053.072 | 2054.296 | | 1027.9 | 685.6 | |
| CLP9 (1) | 1.595 | 99.6 | C90H147N17O34S | 2042.002 | 2043.292 | | 1022.4 | 682.0 | |
| CLP10 (10) | 1.603 | 96.3 | C91H149N17O34S | 2056.017 | 2057.319 | | 1029.4 | 666.7 | |
| CLP11 (11) | 1.555 | 95.1 | C90H145N17O34 | 2008.014 | 2009.212 | | 1005.4 | 670.8 | |
| CLP12 (12) | 1.557 | 96.85 | C87H139N17O34 | 1965.967 | 1967.132 | | 984.2 | 656.5 | |
| CLP13 (13) | 1.763 | 95.05 | C90H147N17O32 | 1978.040 | 1979.229 | | 990.8 | 660.7 | |
| CLP14 (14) | 1.661 | 95.24 | C86H137N17O34 | 1951.951 | 1953.105 | | 977.2 | 652.1 | |
| CLP15 (15) | 1.724 | 95.56 | C95H150N16O30 | 1995.070 | 1996.301 | | 998.7 | | |

TABLE 4-continued

Summary of peptide HPLC purification and MS characterisation

| | LCMS | | | | Calc. | Mass found | | | |
|---|---|---|---|---|---|---|---|---|---|
| Pep. (SEQ) | RT (min) | HPLC purity | Sum formula | Calc. mass* | average mass | m/z z = 1 | m/z z = 2 | m/z z = 3 | m/z z = 4 |
| LLP1 (16) | 1.538 | 98.7 | C93H155N19O35 | 2098.093 | 2099.336 | | | 1050.5 | 700.7 |
| LLP2 (17) | 1.536 | 98.3 | C94H157N19O35 | 2112.109 | 2113.363 | | | 1057.5 | 705.5 |
| LLP3 (18) | 1.556 | 96.7 | C91H148N18O37 | 2085.025 | 2086.251 | | | 1043.9 | 696.3 |
| LLP4 (19) | 1.559 | 95.3 | C92H150N18O37 | 2099.041 | 2100.278 | | | 1050.9 | 701.3 |
| LLP5 (20) | 1.551 | 97.2 | C92H151N19O36 | 2098.057 | 2099.293 | | | 1050.5 | 700.7 |
| LLP6 (21) | 1.559 | 97.5 | C93H153N19O36 | 2112.073 | 2113.320 | | | 1057.5 | 705.4 |
| LLP7 (22) | 1.527 | 99.1 | C93H155N19O35 | 2098.093 | 2099.336 | | | 1050.5 | 700.7 |
| LLP8 (23) | 1.533 | 98.0 | C94H157N19O35 | 2112.109 | 2113.363 | | | 1057.5 | 705.3 |
| LLP9 (24) | 1.574 | 95.3 | C92H152N18O35S | 2101.039 | 2102.360 | | | 1051.9 | 701.7 |
| LLP10 (25) | 1.581 | 95.2 | C93H154N18O35S | 2115.054 | 2116.386 | | | 1058.9 | 706.3 |
| LLP11 (26) | 1.55 | 98.0 | C92H150N18O35 | 2067.051 | 2068.279 | | | 1034.9 | 690.3 |
| LLP12 (27) | 1.74 | 95.6 | C110H179N23O43S | 2542.225 | 2543.796 | | | 1272.5 | 848.9 |
| CP1 (28) | 1.495 | 94.5 | C55H83N13O22S | 1309.550 | 1310.389 | 1310.8 | 656.1 | | |
| CP2 (29) | 1.516 | 98.3 | C55H83N13O22S | 1309.550 | 1310.389 | 1310.9 | 656.0 | | |
| CP3 (30) | 1.423 | 95.6 | C52H77N13O22S | 1267.503 | 1268.309 | 1268.7 | 635.0 | | |
| CP4 (31) | 1.426 | 97.1 | C53H79N13O23S | 1297.513 | 1298.335 | 1298.8 | 650.1 | | |
| CP5 (32) | 1.445 | 97.2 | C51H77N13O22S | 1255.503 | 1256.298 | 1256.8 | 629.0 | | |
| CP6 (33) | 1.46 | 94.1 | C53H79N13O24S | 1313.503 | 1314.334 | 1314.8 | 658.0 | | |
| CP7 (34) | 1.427 | 98.3 | C55H86N14O22S | 1326.576 | 1327.419 | 1327.9 | 664.5 | | |
| CP8 (35) | 1.433 | 95.5 | C54H82N14O23S | 1326.540 | 1327.376 | 1327.8 | 664.5 | | |
| CP9 (36) | 1.463 | 94.0 | C55H84N14O23S | 1340.555 | 1341.403 | 1341.8 | 671.6 | | |
| CP10 (37) | 1.482 | 94.3 | C54H81N13O24S | 1327.524 | 1328.361 | 1328.8 | 665.1 | | |
| CP11 (38) | 1.462 | 98.3 | C55H84N14O23S | 1340.555 | 1341.403 | 1341.8 | 671.6 | | |
| CP12 (39) | 1.484 | 95.7 | C54H81N13O24S | 1327.524 | 1328.361 | 1328.8 | 665.0 | | |
| CP13 (40) | 1.367 | 98.52 | C44H63N11O20 | 1065.425 | 1066.035 | 1066.5 | 533.9 | | |
| CP14 (41) | 1.339 | 98.79 | C40H58N10O17 | 950.398 | 950.947 | 951.5 | 476.4 | | |
| CP15 (42) | 1.392 | 98.28 | C36H51N9O15 | 849.350 | 849.843 | 850.5 | 425.9 | | |
| CP16 (43) | 1.382 | 92.67 | C31H44N8O12 | 720.308 | 720.729 | 721.6 | | | |
| CP17 (44) | 1.412 | 99.23 | C26H37N7O9 | 591.265 | 591.615 | 592.5 | | | |
| CP18 (45) | 1.471 | 99.63 | C52H77N13O22S | 1267.503 | 1268.309 | 1268.6 | 635 | | |
| CP19 (46) | 1.473 | 98.7 | C52H77N13O22S | 1267.503 | 1268.309 | 1268.6 | 635 | | |
| CP20 (47) | 1.483 | 98.57 | C52H79N13O20S | 1237.529 | 1238.326 | 1238.7 | 620 | | |
| CP21 (48) | 1.485 | 99.84 | C52H79N13O20S | 1237.529 | 1238.326 | 1238.6 | 620 | | |
| CP22 (49) | 1.475 | 97.55 | C52H79N13O20S | 1237.529 | 1238.326 | 1238.6 | 620 | | |

*monoisotopic

Example 3: CLP1 Treatment Leads to Increase in CREB-Targeted Genes

SorCS2 has recently been established to play a critical role in BDNF/TrkB signaling by being indispensable in the activation of downstream kinases (Glerup, 2016). A major mediator of the neurotrophin responses to BDNF results from the activation of transcription factor CREB (Finkbeiner, 1997; Walton, 2000; Benito, 2010; Sakamoto, 2011). Activation of CREB is well-known to improve survival, synaptic formation and growth in neurons. A critical mediator of this is the production of BDNF itself, by CREB (Tao, 1998), thereby establishing a positive feedback loop. Similarly has CREB activation been described to induce mitochondrial biogenesis through the upregulation of master regulator PGC1a (Wu, 2006; Kang, 2017). Indeed, the cyclized peptide-mimetic of the SorCS2 receptor fragment, CPX, increases BDNF levels after 4 hours of stimulation in wild-type neurons (WO2022029281). As CLP1 is a cyclised lipidated peptide-mimetic of the SorCS2 receptor-fragment important for the BDNF-signal transduction, whether CLP1 treatment leads to increased BDNF and PGC1a production in wild-type neurons as a consequence of CREB activation was assessed. The effects of cyclised and stabilised lipidated peptide CLP1 were compared with those of cyclised peptide CPX.

Cortical neurons were isolated from p0 wild-type mice and seeded in a density of 200,000 per well (24-well tray). After 7 days in vitro the neurons were stimulated with 1 uM CLP1 or CPX in neurobasal A 15 media and incubated at 37° C. and 5% $CO_2$ for 8, 16 or 24 hours. Hereafter, the neurons were lysed in RIPA lysis buffer containing cOmplete cocktail protease inhibitor. BDNF and PGC1a levels were analysed by western blotting normalized to beta-actin.

Figure 2A:
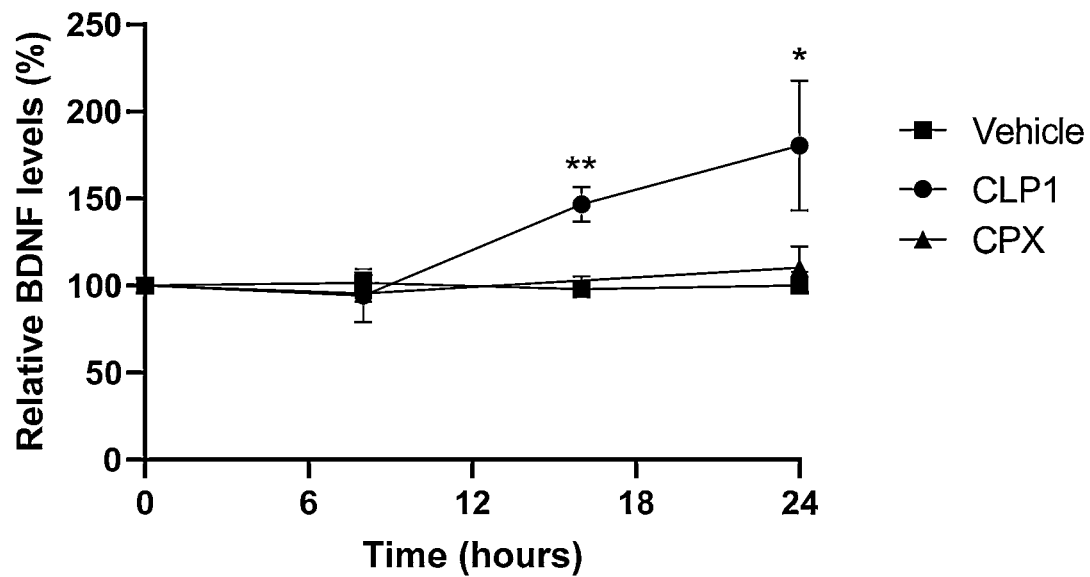
FIG. 2A and FIG. 2B: CLP1 increases levels of CREB transcriptional targets: 1 uM of peptide CLP1 significantly increased the levels of downstream targets of CREB: neurotrophic factor BDNF (FIG. 2A), mitochondrial master regulator PGC1a (FIG. 2B) in mouse primary neurons after 16- and 24-hours. Peptide CPX showed no effect at these timepoints. Means±SEM.
Figure 2B:
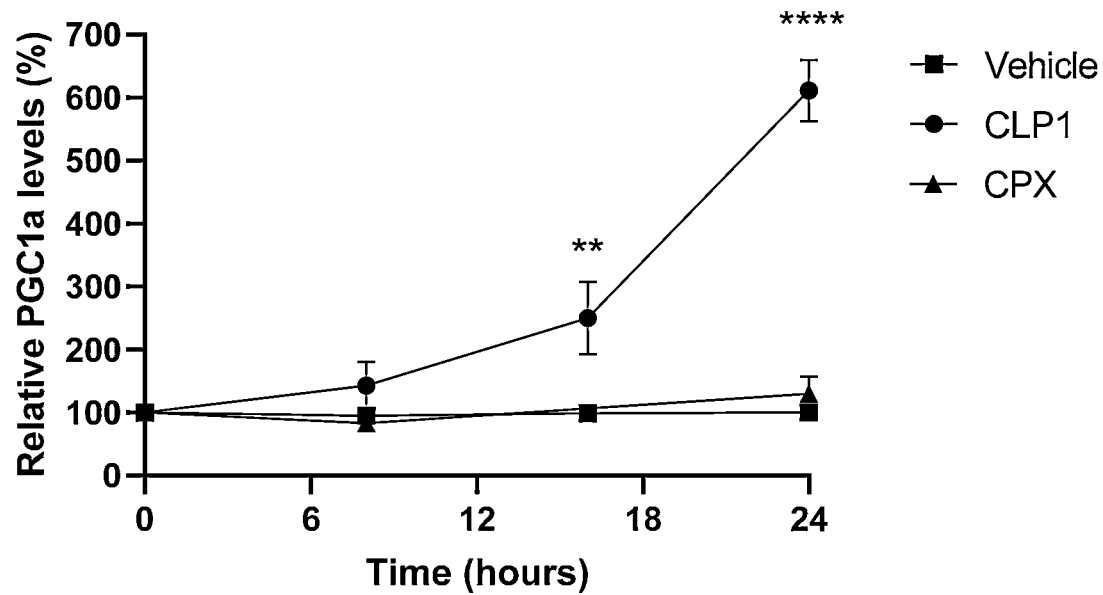

As shown in FIG. 2A and FIG. 2B, CLP1 significantly upregulated both of the assessed CREB-downstream target genes of BDNF by 180% (p=0.0174) and PGC1a by 611% (p<0.0001) after 24 hours of stimulation. CPX did not increase the levels of either BDNF or PGC1a, possibly due to the fact that its effect is elicited prior to the assessed timepoints. This indicates prolonged signaling of CLP1 compared to CPX.

Figure 3A:
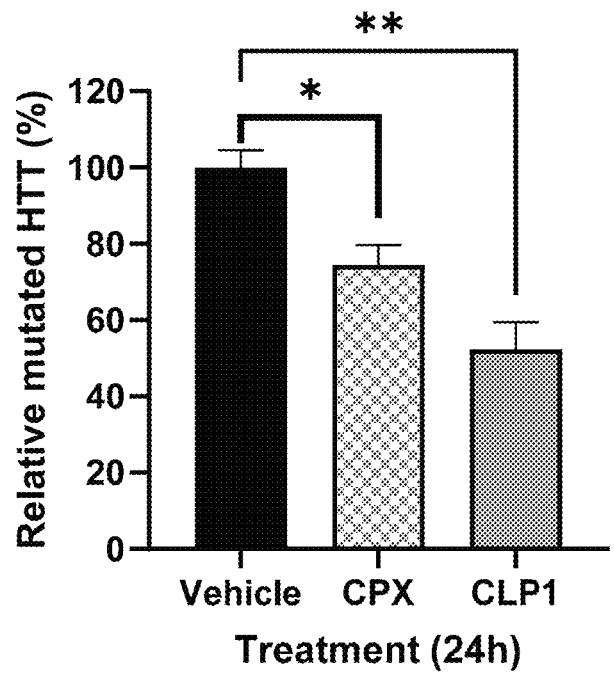
FIG. 3A and FIG. 3B: CLP1 clears soluble mutated HTT in Huntington's patient-derived fibroblasts (GM04719): peptides CLP1 and CPX significantly reduced mutated Huntingtin (mHTT) levels in Huntington's patient-derived fibroblasts (GM04719) by 50% and 25%, respectively, after 24 hours of treatment (FIG. 3A). A significant decrease in total HTT levels was also observed (FIG. 3B).
Figure 3B:
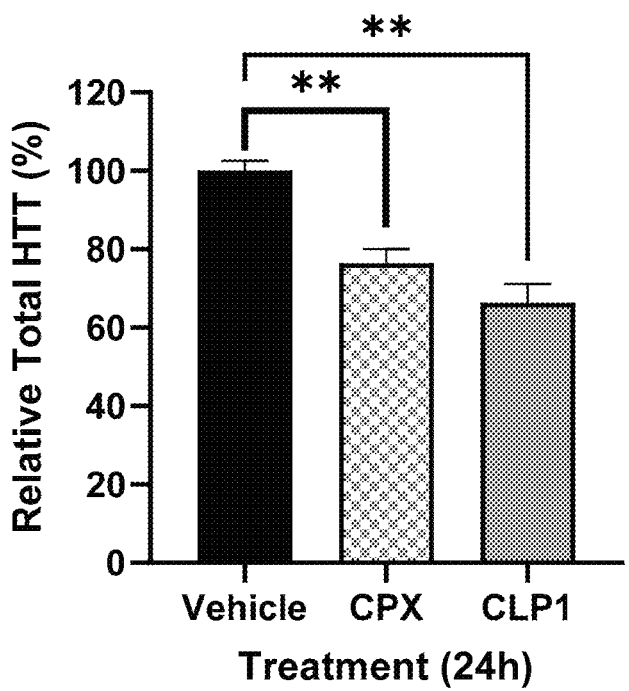
Figure 4A:
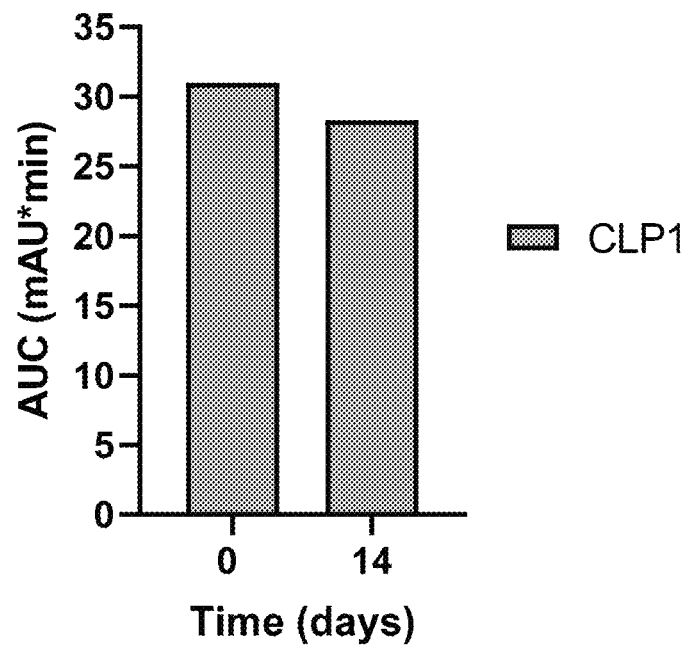
FIG. 4A to FIG. 4G: Chemical and physical stability of CLP1 in three buffers: the stability of CLP1 in buffer systems with pH 4.5 (FIG. 4A), pH 6.5 (FIG. 4B) and pH 7.5 (FIG. 4C) after 14 days at 40° C. CLP1 did not show any fibrillation in any of the buffers using ThT assay, demonstrating good physical stability at pH 4.5 (FIG. 4D), pH 6.5 (FIG. 4E) and pH 7.5 (FIG. 4F) relative to positive control (FIG. 4G).
Figure 4B:
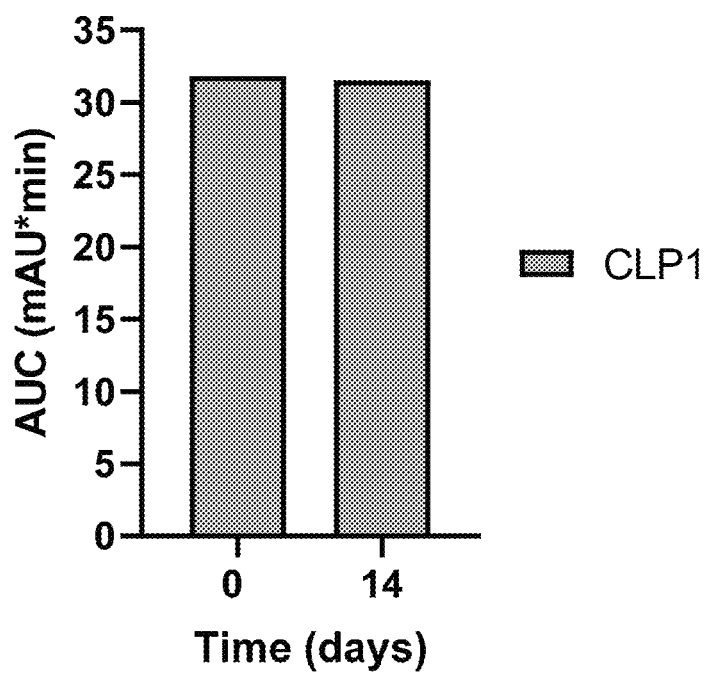
Figure 4C:
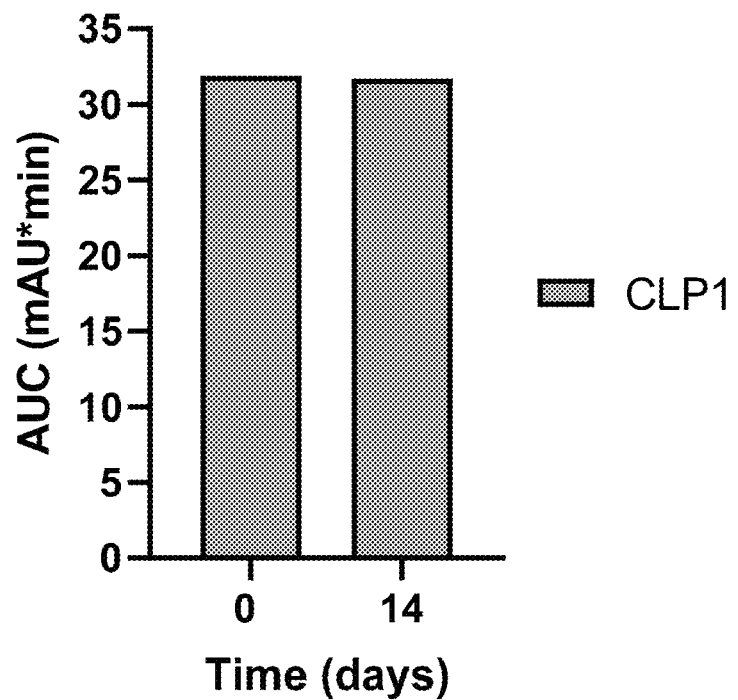
Figure 4D:
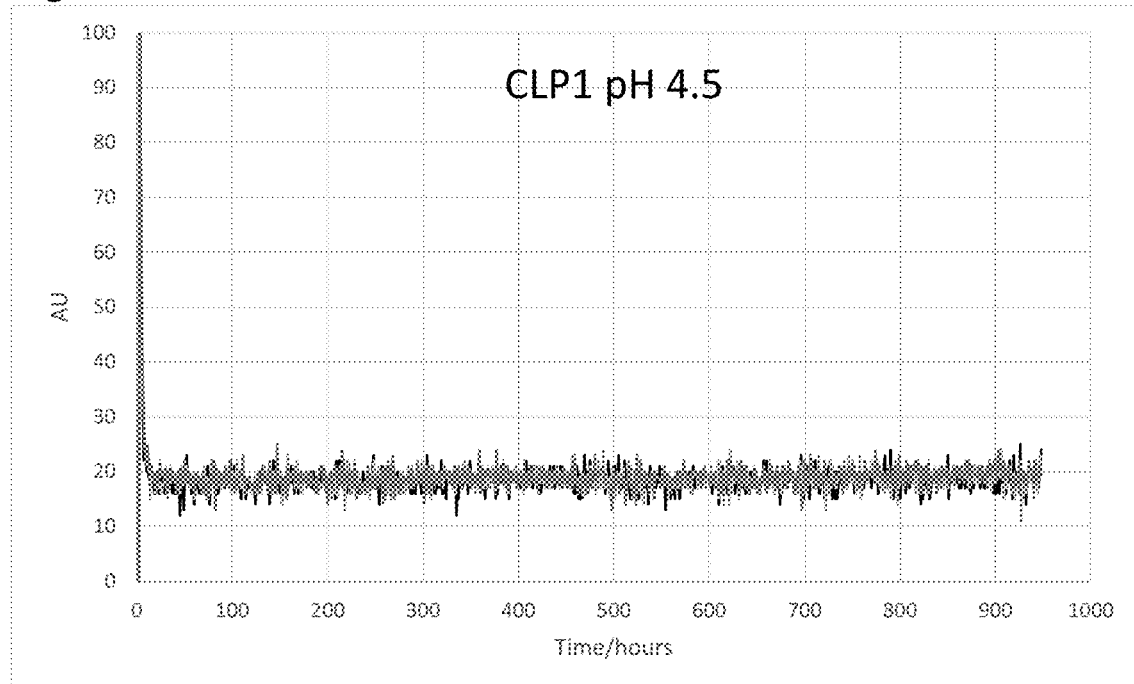
Figure 4E:
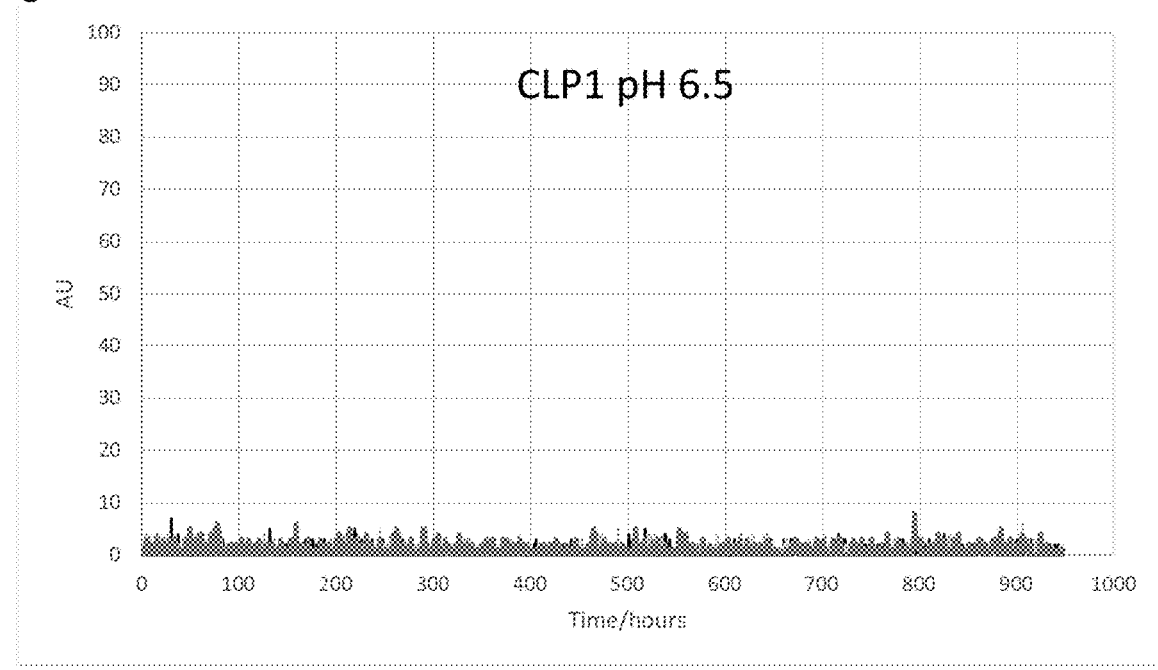
Figure 4F:
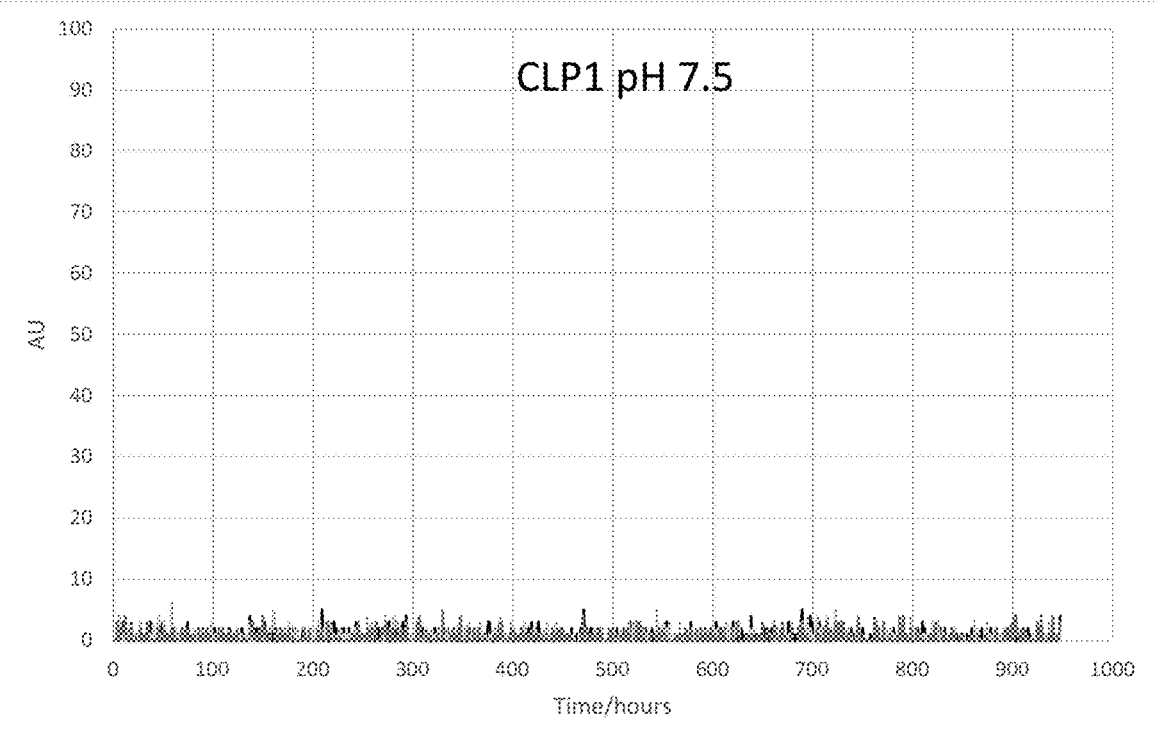
Figure 4G:
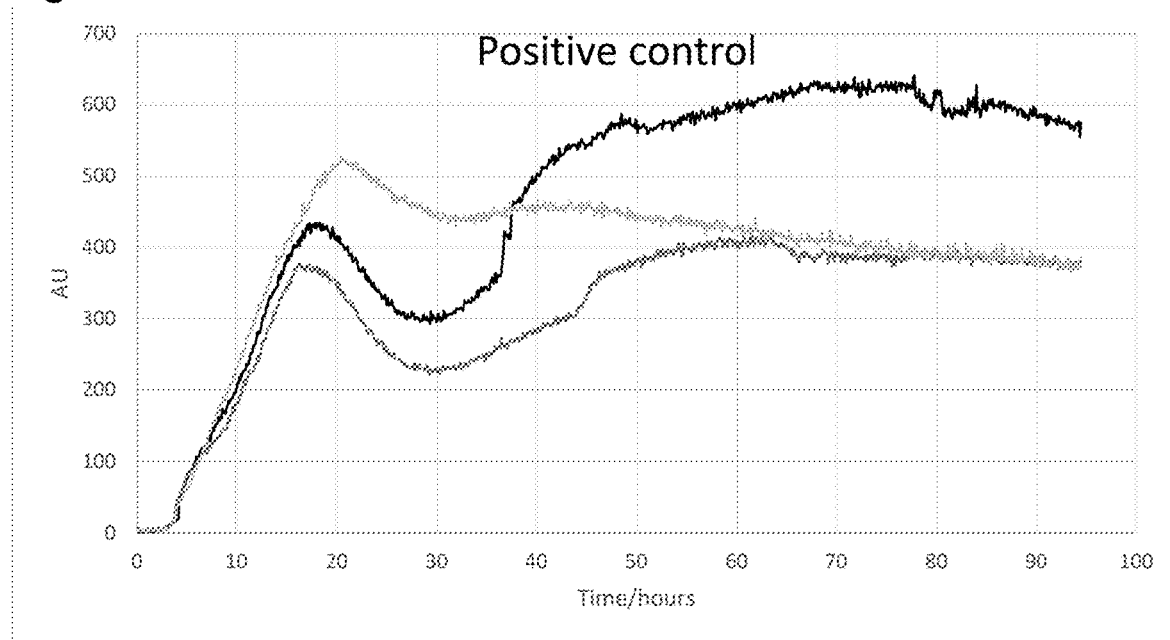
Figure 5A:
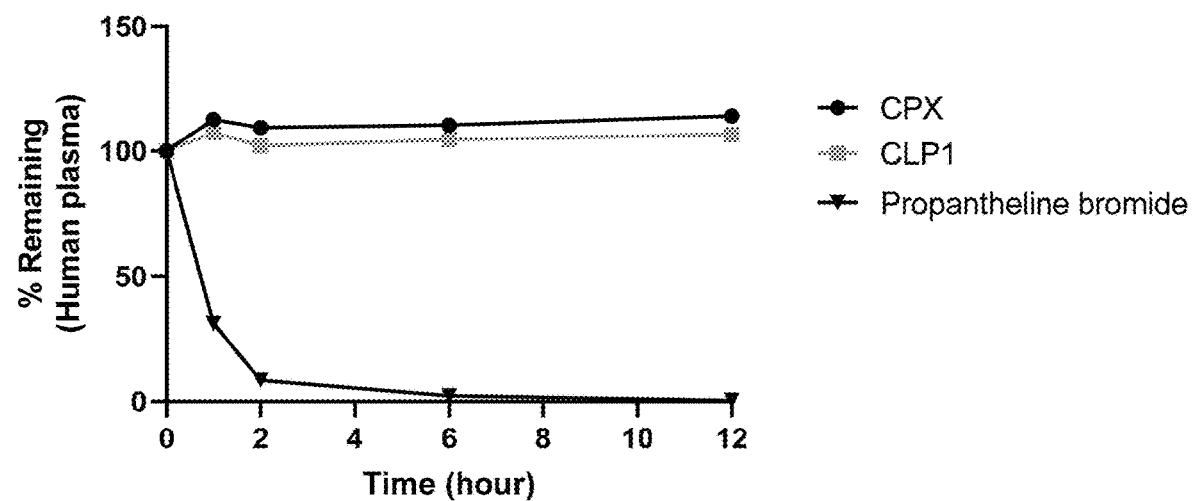
FIG. 5A to FIG. 5C: CLP1 is stable in plasma and brain homogenates: CLP1 and CPX demonstrated limited degradation in human plasma (FIG. 5A), mouse plasma (FIG. 5B). CLP1 displayed higher stability than CPX in mouse brain homogenate (FIG. 5C).
Figure 5B:
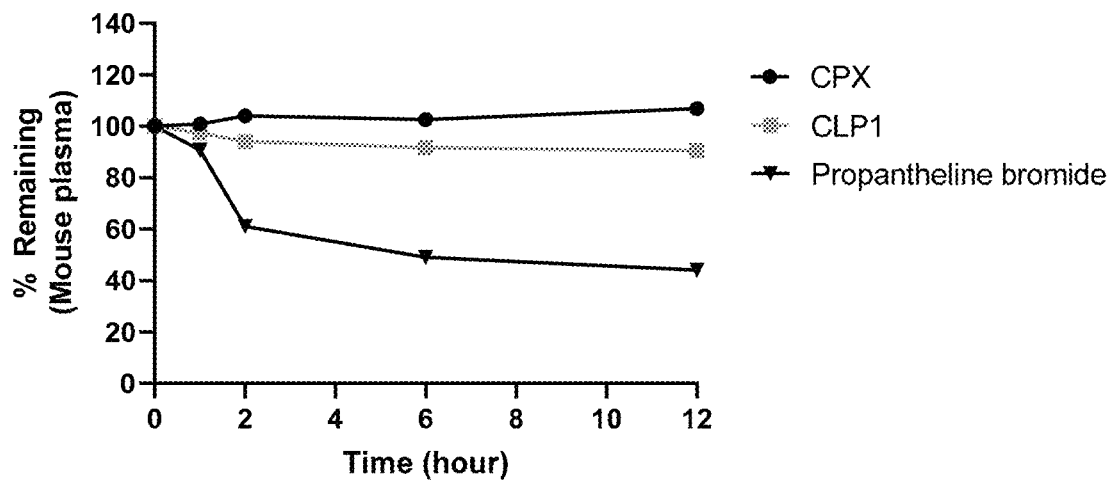
Figure 5C:
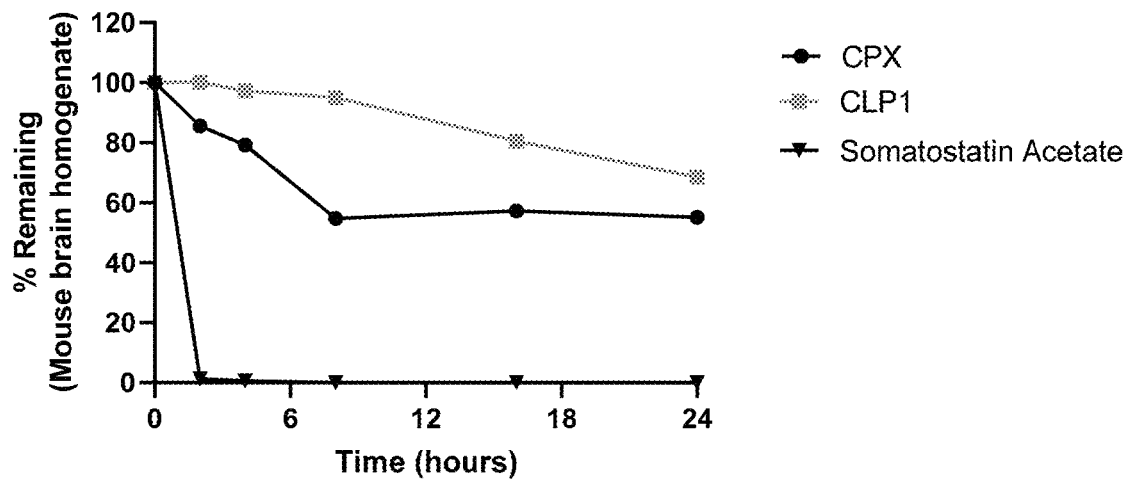

Example 4: CLP1 Clears Soluble mHTT in Huntington's Peent-Derived Fibroblasts Autophagy is the process of clearing misfolded proteins, aggregates or damaged organelles. In addition to driving mitochondrial biogenesis, PGC1a, has been shown to promote lysosomal biogenesis through regulation of TFEB (master regulator of lysosomal biogenesis) (Ghosh, 2015; Lynch, 2020). CLP1-induced decrease of mHTT (mutated Huntingtin) protein expressed from the disease-causing gene in HD, as a cause of PGC1a upregulation and regulation of TFEB, was assessed. CPX, which has previously shown to reduce mutated HTT levels (WO2022029281), was included to compare efficacy. Patient-derived fibroblasts GM04476 (from Coriell Biobank) were seeded at 30,000-50,000 per well in a 96-well plate. The following day, the cells were treated with 1 uM of CLP1 or CPX and incubated at 37° C. and 5% $CO_2$ for 24 hours. Hereafter, the cells were lysed in RIPA lysis buffer containing cOmplete cocktail protease inhibitor. Total Huntingtin levels were analysed by antibody mab2166 (Sigma-Aldrich) and mutated Huntingtin levels were measured by antibody (MW1 ab), which only detects the mutated-allele in western blotting. The levels were normalized to beta-actin. As shown in FIG. 3A and FIG. 3B, both CLP1 and CPX reduced levels of mutated Huntingtin to 50% (p=0.0048) and 75% (p=0.0209), respectively, while reducing total levels of Huntingtin (mutated and healthy allele) to ~65% (p=0.0036) for CLP1 and 75% for CPX (p=0.0056). This demonstrates increased efficacy of CLP1 compared to CPX in addition to CLP1 eliciting degradation more specifically towards the mutated Huntingtin protein than healthy, thereby providing a valuable opportunity as a therapeutic drug for HD patients.

Example 5: Chemical and Physical Stability of CLP1

To better understand the chemical basis of CLP1 stability and degradation the chemical and physical stability of CLP1 in three buffer systems was evaluated. Solutions of CLP1 were prepared in three buffer systems with different pH-values and the samples were incubated at 40° C. without agitation. Chemical stability was assessed by means of UPLC-UV on the day of preparation (10) and after two weeks of incubation (t14). The physical stability was assessed by means of a Thioflavin T (ThT) assay over the course of four days with agitation at 40° C.

For each assay the samples were dissolved to a peptide concentration of 1 mg/mL either in 25% acetonitrile (ACN) (for analytical standard solutions) or in one of the three buffer systems (50 mM sodium acetate buffer, pH 4.5 (22.5 mM sodium acetate+27.5 mM glacial acetic acid); 50 mM L-Histidine buffer, pH 6.5; 50 mM sodium phosphate buffer, pH 7.5 (40.6 mM $Na_2HPO_4$+9.4 mM $NaH_2PO_4$)). All buffers were prepared in ultrapure water (Milli-Q® Reference A+ System, Merck) with a resistivity of 18.2 MΩ·cm. The samples were centrifuged at 13300 rpm (17000 g) for 10 min prior to UPLC-UV measurements. For the physical stability study, the samples were filtered through 0.22 um cellulose filters (13 Ø, Frisenette) prior to setting up the ThT assay.

UPLC-UV method for chemical stability assay: column: Kinetex 1.7 µm C18 100 Å 150×2.1 mm from Phenomenex; mobile phase A: Ultrapure water+0.1% TFA; mobile phase B: Acetonitrile+0.1% TFA; injection volume: 2 µL of CLP1; flow rate: 0.3 mL/min detection wavelength: 220

Gradient:

| Time | % B | Curve |
|---|---|---|
| 0.00 | 5 | 5 |
| 17.0 | 80 | 5 |
| 17.5 | 5 | 1 |
| 23.0 | 5 | |

Platereader settings for ThT assay: Excitation wavelength: 450 nm; dicroic filter: 465 nm; emission wavelength: 486 nm; focal height: 3.5 mm; gain: 1000; number of cycles: 1000; cycle time: 360 s; number of flashes per well: 20; shaking: 300 rpm, 5 s on, 5 s off between cycles; temperature: 40° C.

The results (FIG. 4A to FIG. 4C) show that the highest degradation was seen at pH 4.5 for CLP1 (9% decrease in AUC). CLP1 showed equally good chemical stability at pH 6.5 and 7.5 (1% decrease in AUC). The physical stability was assessed by a ThT assay to evaluate the fibrillation behavior over the course of 96 hours. CLP1 did not show any fibrillation in any of the buffers, demonstrating good physical stability (FIG. 4D to FIG. 4G). Each line represents an individual replicate.

Example 6: CLP1 Free Fraction and Stability

An important aspect of drug-development is pharmacokinetics, including absorption, distribution, metabolism and excretion (ADME). The stability of CLP1 was assessed in both human and mouse plasma and mouse brain homogenate samples. As CLP1 has been stabilized by substitution of two amino acids compared to CPX, CPX was included as a reference in these stability assays. The stability of CLP1 was likewise assessed in liver S9 fractions from mouse, dog, rat, human and monkey. Brain binding (free fraction) in both mouse and human brain homogenates was also evaluated.

Plasma Stability

Frozen mouse or human plasma were thawed in a water bath at 37° C. prior to use. Plasma was centrifuged at 4000 rpm for 5 min and clots were removed (if any). Mouse or human plasma were incubated with 2 uM of CLP1 or CPX or 2 uM of propantheline bromide (positive control for degradation) and left at 37° C. in a water bath. At each time point, stop solution (200 ng/mL tolbutamide and 200 ng/mL labetalol in MeOH) was added to precipitate the protein and after mixing and centrifugation, supernatant was used for LCMS analysis. As demonstrated by FIG. 5A and FIG. 5B, CLP1 and CPX had a half-life (t1/2) of more than 28.9 hours. This demonstrates high plasma stability. % Remaining=100×(PAR at appointed incubation time/PAR at T0 time), where PAR is peak area ratio of analyte versus internal standard (IS) and half-life was calculated by $t_{1/2}=0.693\ k$.

Mouse Brain Stability

Frozen mouse brain homogenate was thawed in a water bath at 37° C. prior to use. Mouse brain homogenate was incubated with 1 uM of CLP1 or CPX or 2 uM of 7-ethoxycoumarin (positive control of degradation) and left at 37° C. in a water bath. At each time point, stop solution (200 ng/mL tolbutamide and 200 ng/mL labetalol in MeOH) was added to precipitate the protein and after mixing and centrifugation, supernatant was used for LCMS analysis. As demonstrated by FIG. 5C, CLP1 had a half-life (t1/2) of 40.7 hours, compared to 28.9 hours for CPX. This demonstrates high brain stability of CLP1, which is improved when compared to CPX.

Example 7: CLP1 Metabolic Stability in Liver Fractions

As the majority of drug metabolism occurs in the liver, liver in vitro preparations may serve as models to evaluate metabolic stability of drugs. To test metabolic stability, S9 fractions are often used, which contains a mixture of unfractionated microsomes and cytosol with a wide variety of drug-metabolizing enzymes. Liver S9 fractions are commonly used as a preferred test system for in vitro ADME.

Liver S9 Stability

Figure 6A:
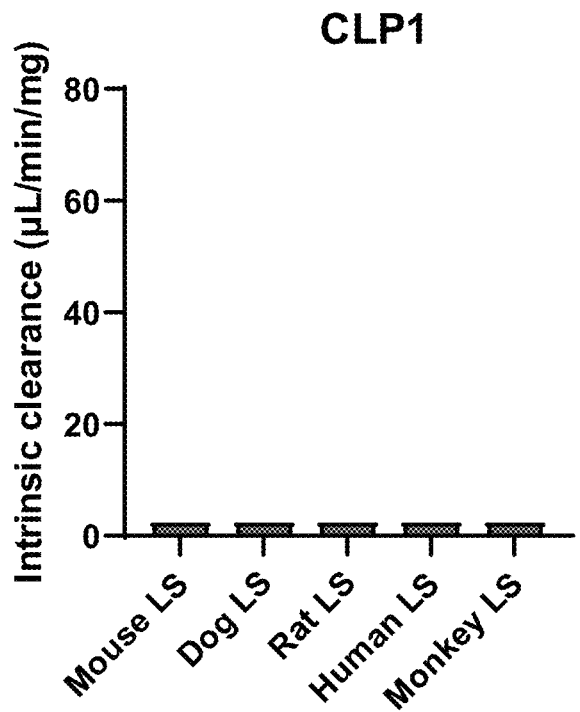
FIG. 6A to FIG. 6D: CLP1 metabolic stability in liver S9 fractions: stability of CLP1 in Liver S9 fractions from 5 different species—intrinsic clearance of CLP1 (FIG. 6A), intrinsic clearance of 7-ethoxycoumarin positive control (FIG. 6B), remaining percentage of CLP1 (FIG. 6C) and remaining percentage of 7-ethoxycoumarin positive control (FIG. 6D).
Figure 6B:
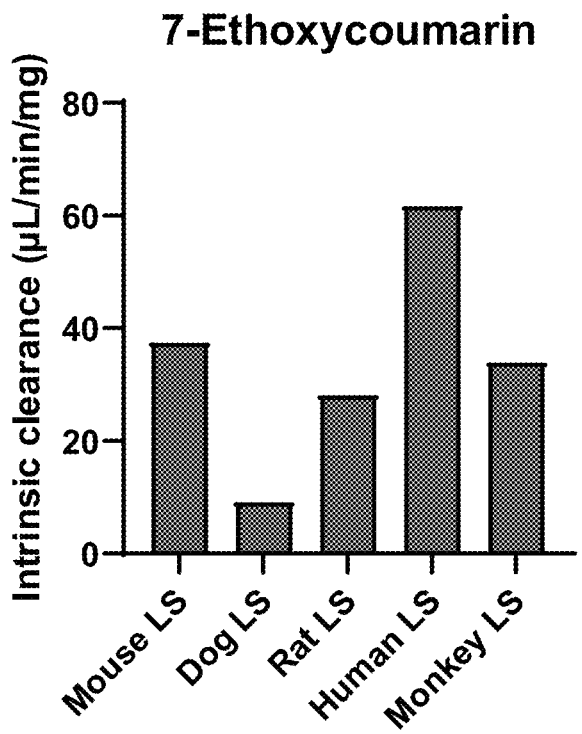
Figure 6C:
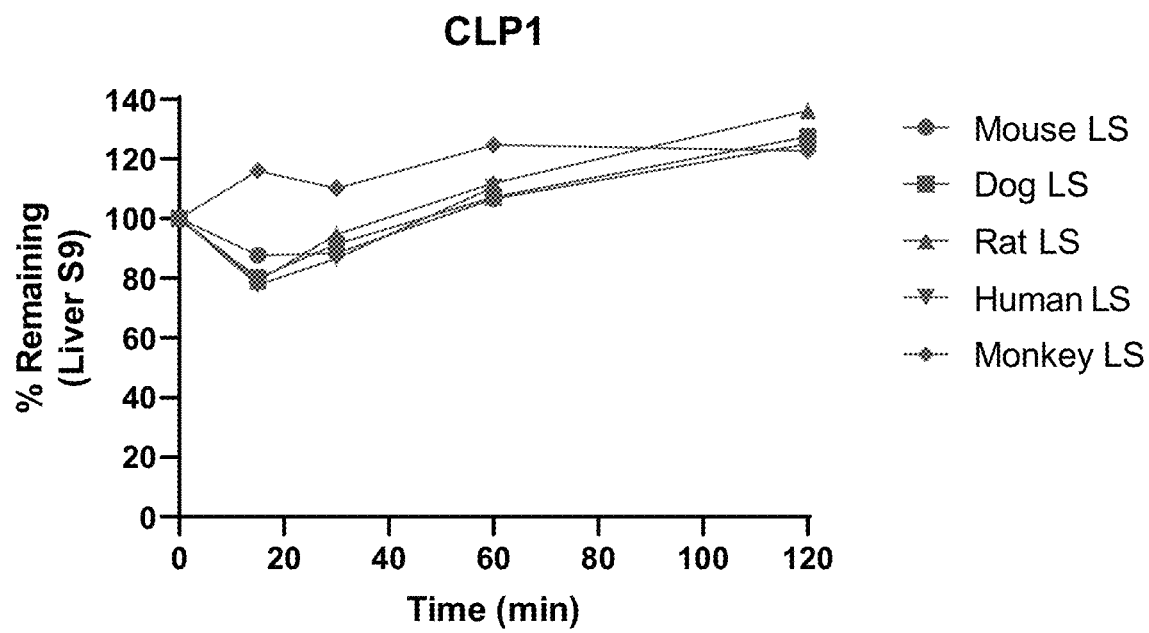
Figure 6D:
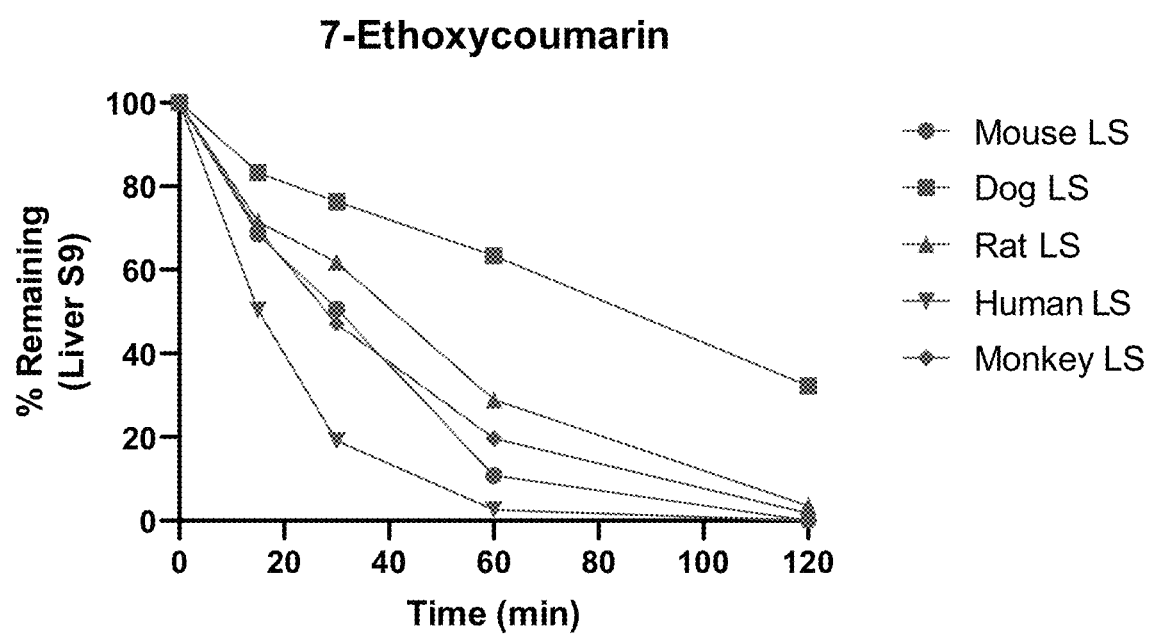

CLP1 was added to Human liver S9, CD-1 Mouse liver S9, Sprague Dawley Rat liver S9, Beagle Dog liver S9 and Cynomolgus Monkey liver S9 solutions (1 mg protein/mL) in 100 mM potassium phosphate buffer to a final concentration of 1 uM. 7-ethoxycoumarin (1 uM) was used as a positive control for clearance. A cofactor regenerating system was added to initiate reaction containing nicotinamide adenine dinucleotide phosphate (NADP) (1.3 mM), glucose 6-phosphate (G6P) (3.3 mM), glucose-6-phosphate dehydrogenase (G6PDH) (0.4 U/mL), uridine diphosphate glucuronic acid (UDPGA) (2.5 mM), 3'-Phosphoadenosine-5'-phosphosulfate (PAPS) (0.1 mM), glutathione (GSH) (5 mM), $MgCl_2$ (3.3 mM) in 100 mM phosphate buffer. Reactions were carried out at different timepoints between 0 to 2 hours, before terminated using stop solution. After shaking and centrifugation of the plate supernatant was used for LCMS analysis. As demonstrated by FIG. 6A (intrinsic clearance rate) and FIG. 6C (% remaining), CLP1 shows very low clearance of <2.4 µL/min/mg in all species and a half-life (t1/2) of at least 289 min. T½ was calculated as: $T\frac{1}{2}=Ln2/k_e=0.693/k_e$. The intrinsic clearance was calculated as: CLint(S9)=0.693/T1/2/mg S9 protein per mL, where T1/2 is half-life and CL is the intrinsic clearance. This demonstrates high metabolic stability. 7-ethoxycoumarin controls are shown in FIG. 6B (intrinsic clearance rate) and FIG. 6D (% remaining).

Example 8: Brain Fee Fraction of CLP1

Measuring the total concentration of a drug in the brain has limited correlation with its pharmacodynamic readout. To obtain a better correlation, the drug concentration within the brain must be corrected for the fraction of the drug which is unbound and bound. The brain-free fraction of CLP1 in both human and mouse brain homogenates was therefore assessed. On the day of experiment, the brain homogenate was thawed by running under cold tap water. CLP1 and control compound (propranolol) were dissolved in $H_2O$ to achieve 10 mM stock solutions in DMSO. Working solutions (400 uM) were prepared by diluting 10 uL of stock solutions with 240 uL of $H_2O$.

Ultracentrifugation Procedure:

Buffer Preparation

A basic solution was made by dissolving 14.2 g/L $Na_2HPO_4$ and 8.77 g/L NaCl in deionized water. An acidic solution was made by dissolving 15.6 g/L $NaH_2PO_4 \cdot 2H_2O$ and 8.77 g/L NaCl in deionized water. The basic was titrated with the acidic solution to pH 7.4±0.1. Mouse brains were homogenised in buffer and loaded with (2 uM) of CLP1 and control compound (Propanolol, 2 uM) were prepared by diluting 6 uL of working solutions with 1194 uL of blank matrix (no compound added). The concentration of DMSO from compound stock solutions in the final solutions was 0.5

To prepare the time zero (T0) samples to be used for remaining determination, 30 uL of loading matrix were transferred (n=2) to sample collection plate. The samples were immediately added 30 uL of buffer to obtain a final volume of 60 uL with a volume ratio of plasma-buffer (1:1, v:v) in each well. 60 uL of 4% $H_3PO_4$ in $H_2O$ and 480 uL of stop solution containing internal standards were added. They were then stored at 2-8° C. pending further processes along with other samples. To prepare the protein-free samples (referred to as F samples) to be used for unbound determination, an aliquot of 400 uL of the pre-incubated brain homogenates containing either CLP1 or control compound was transferred to ultracentrifuge tubes (n=2) and subjected to ultracentrifugation at 37° C., 47000×g (115000 rpm) for 2 hr to generate the F samples. At the end of the ultracentrifugation, 30 uL of samples were taken from the second layer (beneath top layer) of the supernatant of the F samples. To prepare samples to be used for unbound and remaining measurement (referred to as T samples), at the same time of ultracentrifugation, the residual aliquot of pre-incubated spiked plasma was placed into the same incubator (n=1) and continued to be incubated at 37° C. for 2 hr. The samples were transferred into new 96 well plates. Each sample was added with equal volume of opposite blank matrix (buffer or plasma) to reach a final volume of 60 uL with volume ratio of plasma:buffer at 1:1 (v:v) in each well. All samples were added 60 uL of 4% $H_3PO_4$ in $H_2O$ and 480 uL of stop solution containing internal standards, respectively. The mixture was vortexed and centrifuged at 4000 rpm for about 20 minutes. An aliquot of 100 uL of supernatant of all the samples was then removed for LC-MS/MS analysis.

The % Unbound, % Undiluted Unbound, % Undiluted Bound and % Remaining were calculated by the following equations: % Unbound (free fraction)=100*F/T4.5; where F is the analyte concentration or peak area ratio of analyte/internal standard of protein-free sample after ultracentrifugation, T4.5 is the analyte concentration or peak area ratio of analyte/internal standard in matrix after incubation for 4.5 h. As demonstrated in FIG. 7A and Fig. B, CLP1 has a free-fraction in mouse brain homogenates of 19% and 11% in human brain homogenates.

Example 9: Pharmacokinetics of CLP1

The pharmacokinetics of CLP1 in wild-type mice were assessed. 10-fold serial dilutions of CLP1 (2 mg/kg, 0.2 mg/kg and 0.02 mg/kg) were subcutaneously (SC) injected into wild-type mice (Male C57BL/6J) in 4.38 mM L-His, 140 mM NaCl, 0.2% Tween-20 and 1500 IU hyaluronidase (pH 6.15). Both plasma, whole brain and cerebrospinal fluid concentrations were determined at different timepoints from 1 to 24 hours by LC-MS/MS.

Plasma Processing Procedure:

Aliquots of 40 uL of an unknown sample, a calibration standard, a quality control, a dilute quality control, single blank and double blank were added to the 96-well plate. Each sample (except the double blank) was quenched with 160 uL IS1 (internal standard in MeOH: 100 ng/mL of each Labetalol, tolbutamide, Verapamil, dexamethasone, glyburide & Celecoxib), respectively (double blank sample was quenched with 160 uL MeOH), and then the mixture was vortex-mixed for 10 min at 800 rpm and centrifuged for 15 min at 3220 g (4000 rpm), 4° C. 50 uL supernatant was transferred to another clean 96-well plate and centrifuged for 5 min at 3220 g, 4° C., then the supernatant was directly injected for LC-MS/MS analysis.

Brain Processing Procedure:

Tissue homogenate was prepared by homogenizing tissue with 5 volumes (w:v) of cold homogenizing solution (MeOH/15 mM PBS (1-2, v:v)). Aliquots of 40 uL of an unknown sample, a calibration standard, a quality control, a dilute quality control, single blank and double blank were added to the 96-well plate; then 40 uL Male C57BL/6J Mouse Plasma (EDTA-K2) was added, vortex-mixed well (at least 5 min) with vortexer. Each sample (except the double blank) was quenched with 320 uL IS1 respectively (double blank sample was quenched with 320 uL MeOH), and then the mixture was vortex-mixed for 10 min at 800 rpm and centrifuged for 15 min at 3220 g (4000 rpm), 4° C. 50 uL supernatant was transferred to another clean 96-well plate and centrifuged for 5 min at 3220 g, 4° C., then the supernatant was directly injected for LC-MS/MS analysis. The process was carried out on ice.

CSF Processing Procedure:

The CSF samples and blank matrix were added with equal volume of plasma and mixed well and proteins was precipitated using 1.5 mL tube. An aliquot of 20 uL calibration standard, quality control and dilution quality control, single blank and double blank samples were added to the 1.5 mL tube; Each sample (except the double blank) was quenched with 400 uL IS1 respectively (double blank sample was quenched with 400 uL MeOH), and then the mixture was vortex-mixed well (at least 15 s) with vortexer and centrifuged for 15 min at 12000×g, 4° C.; All mixed unknown samples were quenched with 20-times IS1, and then the mixture was vortex-mixed well (at least 15 s) with vortexer and centrifuged for 15 min at 12000×g, 4° C.; An aliquot of 50 μL supernatant was transferred to the 96-well plate and centrifuged for 5 min at 3220×g, 4° C., then the supernatant was directly injected for LC-MS/MS analysis. The process was done on the wet ice. The process was done in low binding EP tubes and low binding 96-well plates.

Figure 8B:
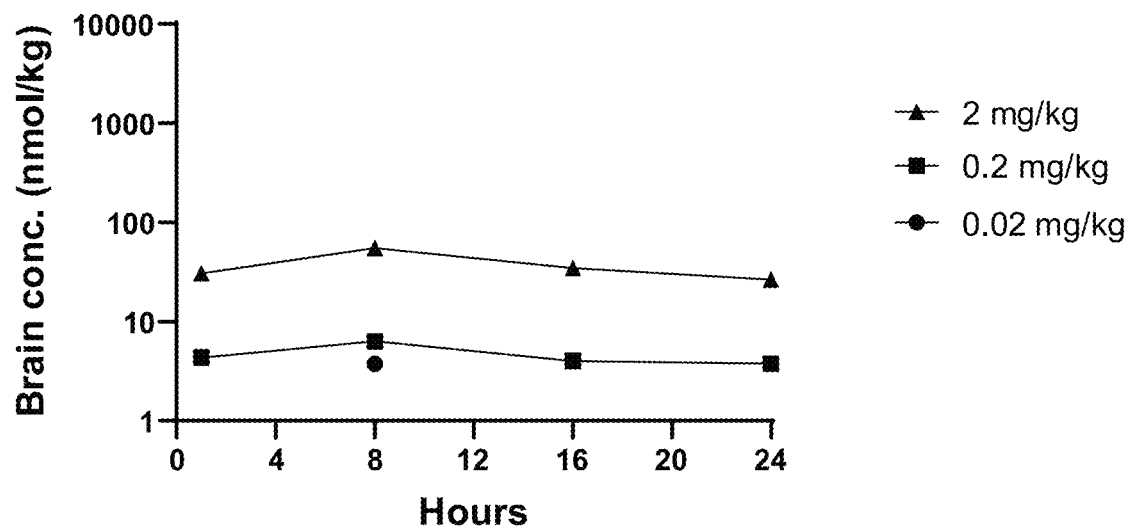
Figure 8C:
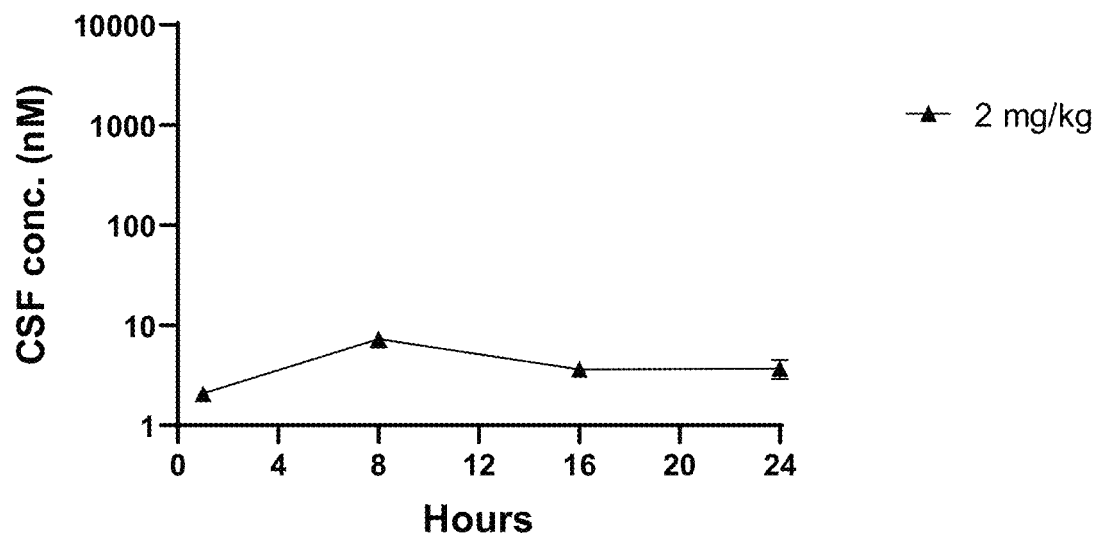

FIG. 8A to FIG. 8C display measured concentrations of CLP1 at the different timepoints. The PK parameters of CLP1 are listed below. These results demonstrate that CLP1 reaches the brain and CSF following SC injection. In addition, CLP1 demonstrates stable levels in the brain for at least 24 hours at both 0.2 mg/kg and 2 mg/kg. In comparison, 13 mg/kg of CPX has previously shown to be cleared from the brain 1 hour post subcutaneous injection (WO2022029281). Thus, CLP1 demonstrates a superior stability profile within the brain following subcutaneous delivery.

The parameters were calculated using WinNonlin software, in which the maximum observed concentration is Cmax, $T\frac{1}{2}$ (hours)=$\ln(2)/\Delta z$. The definition of $\Delta z$ (Lambda_z) is the first order rate constant associated with the terminal (log-linear) portion of the curve (estimated by linear regression of time vs. log concentration). AUC 0-t was calculated using linear/log trapezoidal method. Linear function was used for fitting before Tmax, and log function was used for fitting after Tmax.

Plasma

| Concentration | $T\frac{1}{2}$ (hours) | $C_{max}$ (nmol/L) | AUC 0-t (nmol/L * h) |
|---|---|---|---|
| 2 mg/kg | 12.8 | 7833 | 130170 |
| 0.2 mg/kg | 11.7 | 759 | 11943 |

| Concentration | $T\frac{1}{2}$ (hours) | $C_{max}$ (nmol/L) | AUC 0-t (nmol/L * h) |
|---|---|---|---|
| 2 mg/kg | 15.1 | 55.4 | 915 |
| 0.2 mg/kg | 21.6 | 6.32 | 111 |

CSF

| Concentration | $T\frac{1}{2}$ (hours) | $C_{max}$ (nmol/L) | AUC 0-t (nmol/L * h) |
|---|---|---|---|
| 2 mg/kg | 16.3 | 7.33 | 106 |

Example 10: In Vivo Efficacy of CLP1 in Wild-Type Mice

Previous Examples show that CLP1 reaches the brain (at measurable levels) following SC administration when injecting both 2 mg/kg and 0.2 mg/kg. The ability of CLP1 to increase downstream targets of CREB following a single dose injection was evaluated.

Single Dose Administration

Figure 9A:
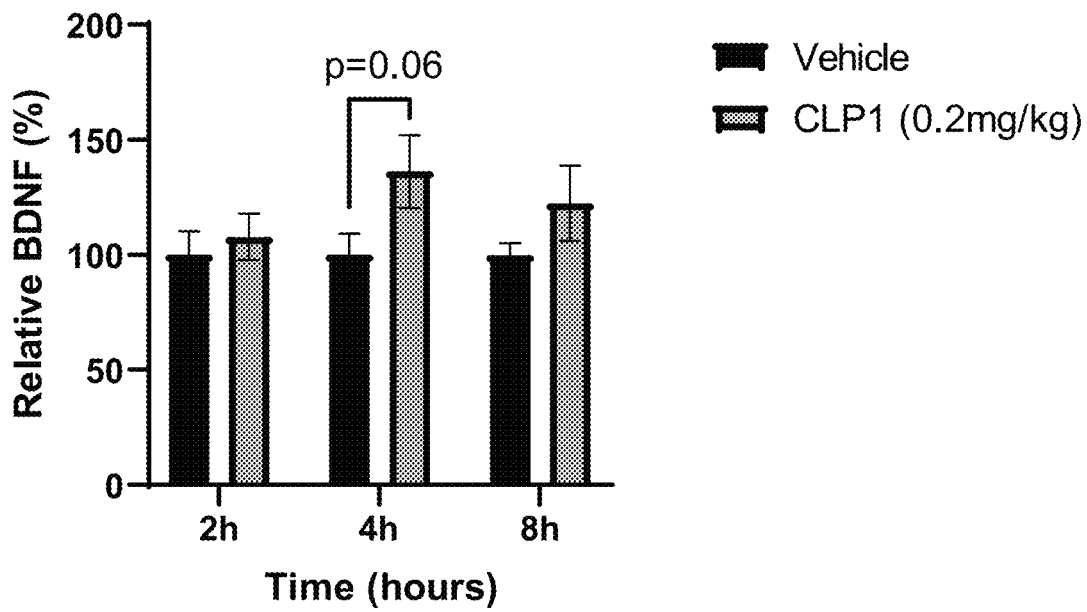
Figure 9B:
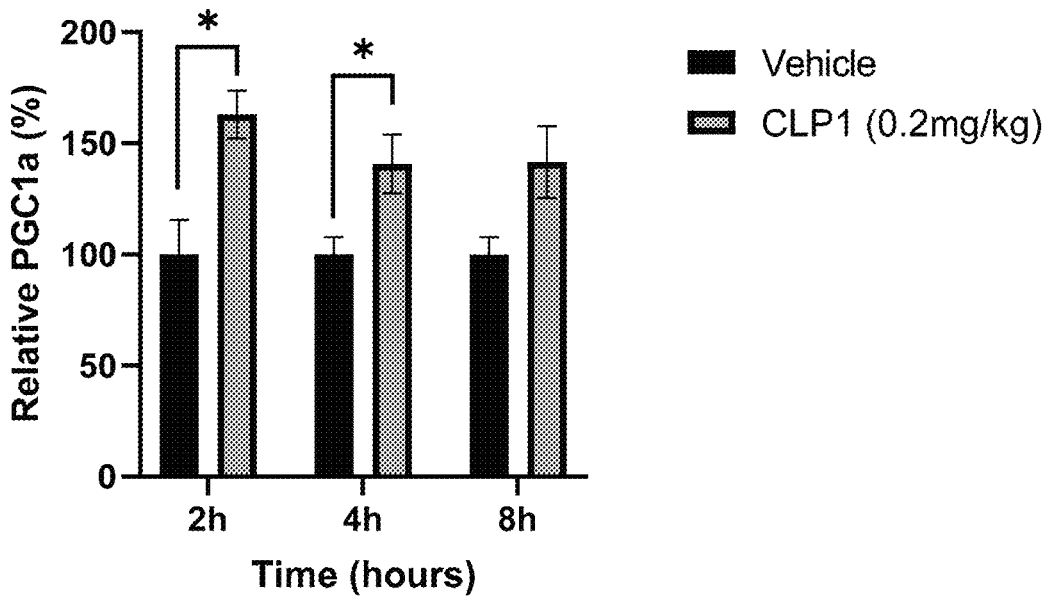

Wild-type mice were injected with 0.2 mg/kg of CLP1 subcutaneously in 4.38 mM L-His, 140 mM NaCl, 0.2% Tween-20 and 1500 IU hyaluronidase (pH 6.15). The mice were sacrificed at timepoints between 2-8 hours after injection. Striatal tissue was isolated, and the tissue was lysed using a TissueLyser in RIPA lysis buffer containing cOmplete and phosSTOP. Levels of BDNF, PGC1a and lysosomal master regulator, TFEB, were validated by western blotting. All proteins were normalized to beta-actin levels. As shown in FIG. 9A to FIG. 9C, CLP1 had a strong tendency to increase BDNF levels 4 hours after SC delivery (p-value 0.06), while significantly increasing both PGC1a and TFEB at 2-4 hours and 2-8 hours post injection, respectively. Posthoc analysis, using two-way ANOVA, revealed a significant time-dependent effect on BDNF levels and an overall significant effect of treatment on PGC1a and TFEB levels by CLP1. Thus, CLP1 showed target engagement in vivo in the striatum of wild-type mice following a single dose SC administration.

Daily Treatment (7 Days)

In a separate study, whether continuous daily administration (SC) of CLP1 or CPX would lead to increased levels of CREB-target genes was evaluated. In addition, as TFEB has been shown to drive the expression of the lysosomal protein, GRN (Tanaka, 2013), we assessed the efficacy of CLP1 or CPX to increase GRN levels. Heterozygous loss of function mutations in the GRN gene have been linked to the neurodegenerative disease frontotemporal dementia (FTD), in which mutations result in lysosomal dysfunction. Therefore, increasing levels of GRN is considered a therapeutic approach in FTD.

Wild-type mice were injected once daily with 0.2 mg/kg or 2 mg/kg of CLP1 or 13 mg/kg of CPX subcutaneously in 4.38 mM L-His, 140 mM NaCl, 0.2% Tween-20 and 1500 IU hyaluronidase (pH 6.15). The mice were sacrificed at day 8, 24 hours after last injection. Striatal tissue was isolated and the tissue was lysed using a TissueLyser in RIPA lysis buffer containing cOmplete and phosSTOP. Levels of BDNF, PGC1a and GRN were validated by western blotting. All proteins were normalized to beta-actin levels.

Figure 10C:
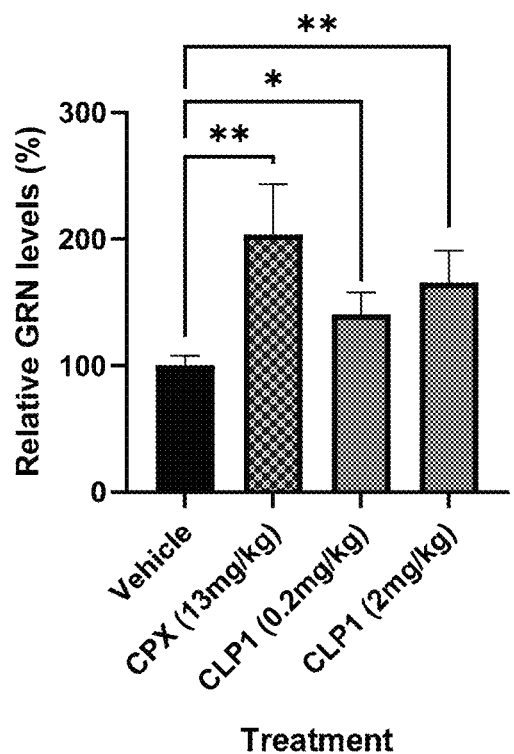
FIG. 10A and FIG. 10B: 7-day daily treatment of CLP1 in wild-type mice: CLP1 and CPX significantly increased PGC1a at both 0.2 mg/kg and 2 mg/kg daily doses for CLP1 and 13 mg/kg for CPX (FIG. 10A) and GRN at both 0.2 mg/kg and 2 mg/kg daily doses for CLP1 and 13 mg/kg for CPX (FIG. 10C). CLP1 (0.2 mg/kg) and CPX (13 mg/kg) significantly increased BDNF-levels following single subcutaneous dose per day (FIG. 10B).

As shown in FIG. 10A to FIG. 10C, CLP1 and CPX significantly increased both PGC1a and GRN at both 0.2 mg/kg and 2 mg/kg dose after daily injections for 7 days. Interestingly, BDNF levels only significantly increased using the 0.2 mg/kg dose of CLP1, and to a higher extent than CPX, while no significant effect was observed using 2 mg/kg CLP1. This demonstrates the therapeutic value of CLP1 in FTD patients carrying heterozygous GRN mutations and other neurodegenerative disorders.

Example 11: CLP1 Improves Behavior in R6/2 Mouse Model of Huntington's

Central to pathobiology of Huntington's Disease is loss of BDNF transportation in cortico-striatal circuitry leading to striatal neuronal death (Strand, 2007; Zuccato, 2007; Conforti, 2013). 0.2 mg/kg daily dosing scheme was chosen for treatment of an R6/2 mouse model of Huntington's over the entire period of the experiment.

The purpose of the study was to measure the effect of CLP1 during motoric testing in the R6/2 (B6CBA-R6/2 (CAG 120+/−5) mice of Huntington's disease, with a major parameter of lifespan in the treatment group according to the Kaplan-Meier Scale. CPX (13 mg/kg) was included to compare efficacy. 20 R6/2 mice (B6CBA-R6/2 (CAG 120+/−5) and 10 aged match WT littermates at the age of 5-weeks were used for experiments. Animals are housed at a standard temperature (22±1° C.) and in a light-controlled environment (lights on from 7 am to 8 pm) with ad libitum access to food and water. Administration was by daily subcutaneous (SC) injections of CLP1 or CPX in 4.38 mM L-His, 140 mM NaCl, 0.2% Tween-20 and 1500 IU hyaluronidase (pH 6.15), starting at 5 weeks of age and continuing until 25 weeks (endpoint). Weighing of each mouse was carried out each week in addition to motor behavior tests (clasping and rotarod).

Rotarod Measurement

Mice were tested during the diurnal phase over 2 consecutive days at 4 (baseline), 6, 9 and, 12 weeks of age. Each daily session includes a training trial of 5 min at 4 RPM on the rotarod apparatus (AccuScan Instruments, Columbus, USA). One hour later, the animals were tested for 3 consecutive accelerating trials of 6 min with the speed changing from 0 to 40 RPM over 360 seconds and an inter-trial interval at least 30 min. The latency to fall from the rod was recorded. Mice remaining on the rod for more than 360 s were removed and their time scored as 360 sec.

Clasping

Mice were tested during the diurnal phase at 4 (baseline), 6, 9 and, 12 weeks of age. The mice were suspended by their tails from a height of 50 cm for 30 seconds, and a limb-clasping response was defined as the withdrawal of any limb to the torso for more than 1 second. Each testing session consists of three trials with a clasping score ranging from 0 to 4, with 0 representing the absence of clasping, 1 representing a withdrawal of any single limb, 2 representing the withdrawal of any two limbs, 3 representing the withdrawal of any three limbs, and 4 representing the withdrawal of all four limbs. The limb-clasping response scores are averaged for each testing session for each animal.

Figure 11A:
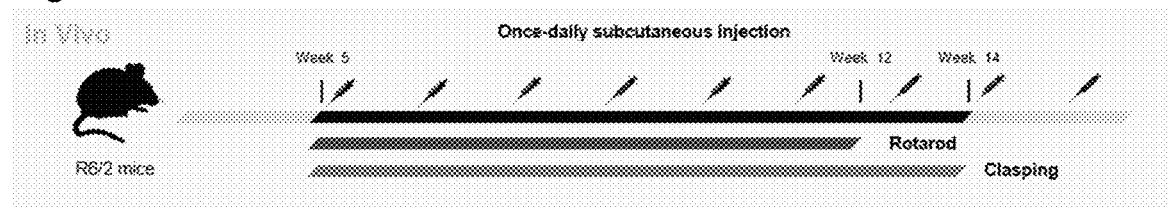
Figure 11B:
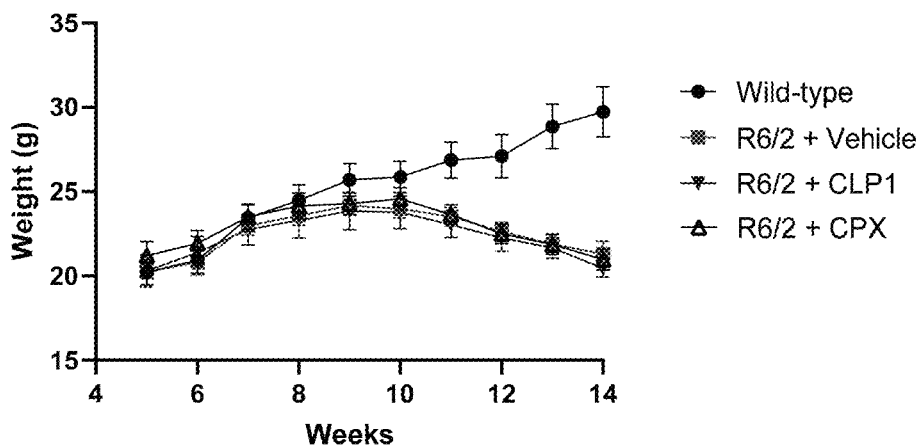
Figure 11C:
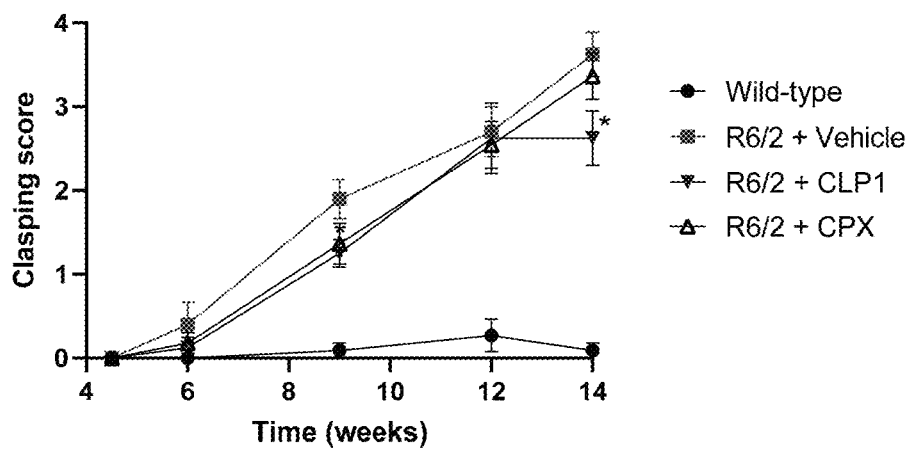
Figure 11D:
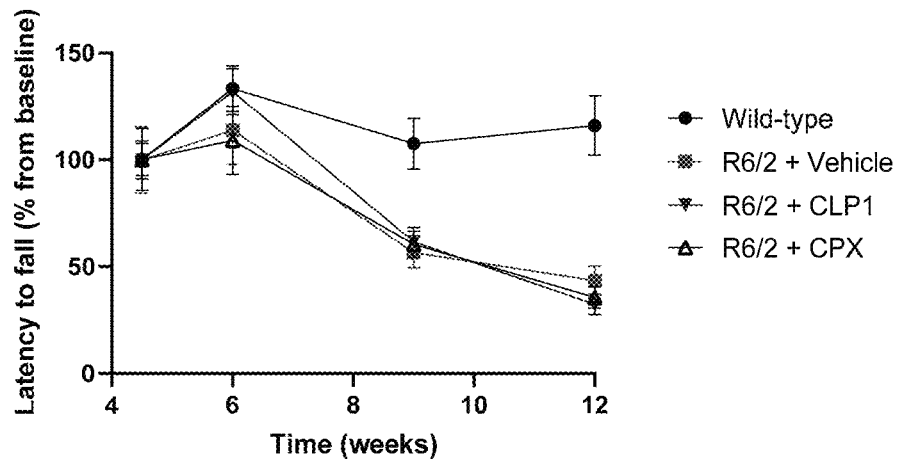

FIG. 11A displays a schematic of the study in R6/2 mice. As shown in FIG. 11B, both CLP1 and CPX did not have an impact on the weight of the mice. However, CLP1 significantly improved clasping at 9 and 14 weeks of age, while CPX treatment only improved at 9 weeks of age (FIG. 11B). Rotarod performance (latency to fall) is shown in 11D. CLP1 and CPX increased the mean survival of treated R6/2 mice, by 8 days for CLP1 and 3 days for CPX, and median survival by 13 days for both CLP1 and CPX (FIG. 11E & FIG. 11F). These results demonstrate a beneficial effect of CLP1 in this challenging mouse model of Huntington's.

Example 12: CLP1 Improves Behavior in Mouse Model of Parkinson's (MPTP Model)

Many neurodegenerative diseases demonstrate mitochondrial dysfunctions, energy failure and oxidative stress as a consequence of this (Sawa, 2001; Oliveira, 2007; Chaturvedi, 2013; Naia, 2017; Pinho, 2020). A mouse model of mitochondrial dysfunction is the 1-methyl-4-phenyl-1,2,3,6-tetrahydropyridine (MPTP) model, which has been used as a Parkinson's Disease (PD) model as the neurotoxic effects of MPTP lead to specific damage in the dopaminergic neurons in the substantia nigra pars compacta and striatum, two highly affected areas in PD. Injection of MPTP leads to production of the neurotoxin MPP+, which interferes with complex I of the electron transport chain (component of mitochondrial metabolism) causing permanent symptoms of PD.

The PD animal model was established by intraperitoneal injection of MPTP in C57BL/6 mice, and the ameliorative effect of CLP1 in doses of 0.2 mg/kg and 2 mg/kg on MPTP-induced hypoactivity and decreased number of neurons in the substania nigra compact was detected.

A total of 48 animals were randomly divided into 4 groups. The animals were on a 12-hour light/dark (6:00 am/6:00 pm) cycle. Animals were acclimated for 1 week prior to the study. 2 days prior to MPTP dosing, the mice were administered subcutaneously with CLP1 (2 mg/kg or 0.2 mg/kg) in 4.38 mM L-His, 140 mM NaCl, 0.2% Tween-20 and 1500 IU hyaluronidase (pH 6.15). Other groups received buffer only. The mice were treated once daily by subcutaneous administration throughout the entire experiment. At day 0, group 1 mice were additionally injected with a once daily SC dose of saline throughout the rest of the experiment. Group 2 to 4 mice were injected with a once daily SC dose of MPTP (30 mg/kg/day) through the rest of the experiment. The whole study period was 10 days.

A series of end point assays were performed including body weight, total distance traveled, vertical counts, grip strength and immunostaining of tyrosine hydroxylase. A schematic outlining behavioral testing and treatment is shown in FIG. 12A.

Behavior Test

At day 9 of the study, 6 hours after MPTP injection, the animals were placed in the open field to detect changes in motor behavior (main indicators: total distance traveled and vertical counts) within 10 minutes. At day 10 of the study, 6 hours after MPTP injection, for gripping force measurements, mice were allowed to grip the metal grids of a grip meter with their forelimbs, and they were gently pulled backwards by the tail until they could no longer hold the grids. The average grip strength observed in 10 trials were recorded and calculated.

Tissue Sampling and Immunostaining

At the end of the study, brain tissues were collected. 6 brains from each group were perfusion fixed for immunostaining of tyrosine hydroxylase. Coronal sections of mouse brain tissues were embedded in paraffin using standard histological methods: 3 slide sections per mouse, 4 um thickness, 50 um apart were cut. Slides were deparaffinized and dehydrated in 3% hydrogen peroxide solution at room temperature. Antigen retrieval citrate buffer (pH6.0) was used. To avoid nonspecific staining, the sections were then incubated in blocking serum (DAKO #X0909) for 15 mins at room temperature, followed by using primary tyrosine hydroxylase (TH) antibodies (Abcam #ab112) in 1:400 dilution for 1 hour. Then secondary goat polyclonal antibodies conjugated to HRP (DAKO #K4003) were added. For image analysis of neurons, TH stained sections were used and scanned by Leica Aperio CS2 Scanner. Images were opened with HALO, TH-positive neurons of SNpc on both sides were counted. The number of positive cells was expressed as average of three brain sections. Statistics were carried out using one-way ANOVA (or Kruskal-Wallis test).

In this study, the body weight of animals after MPTP injection were reduced first and gradually increased during the study, while MPTP significantly changed body weight at endpoint from non-treated mice (sham), CLP1 treated mice did not show a significant change in bodyweight at end point compared to sham group (FIG. 12D). Open field test and grip strength test showed, distance traveled, vertical counts and grip strength of model group decreased significantly compared with control group. 2 mg/kg treatment with CLP1 significantly increased distance traveled and vertical counts in open field test compared with model group (FIG. 12B), while both 0.2 mg/kg and 2 mg/kg treatment significantly increased grip strength compared with MPTP non-treated group (FIG. 12C).

Figure 13A:
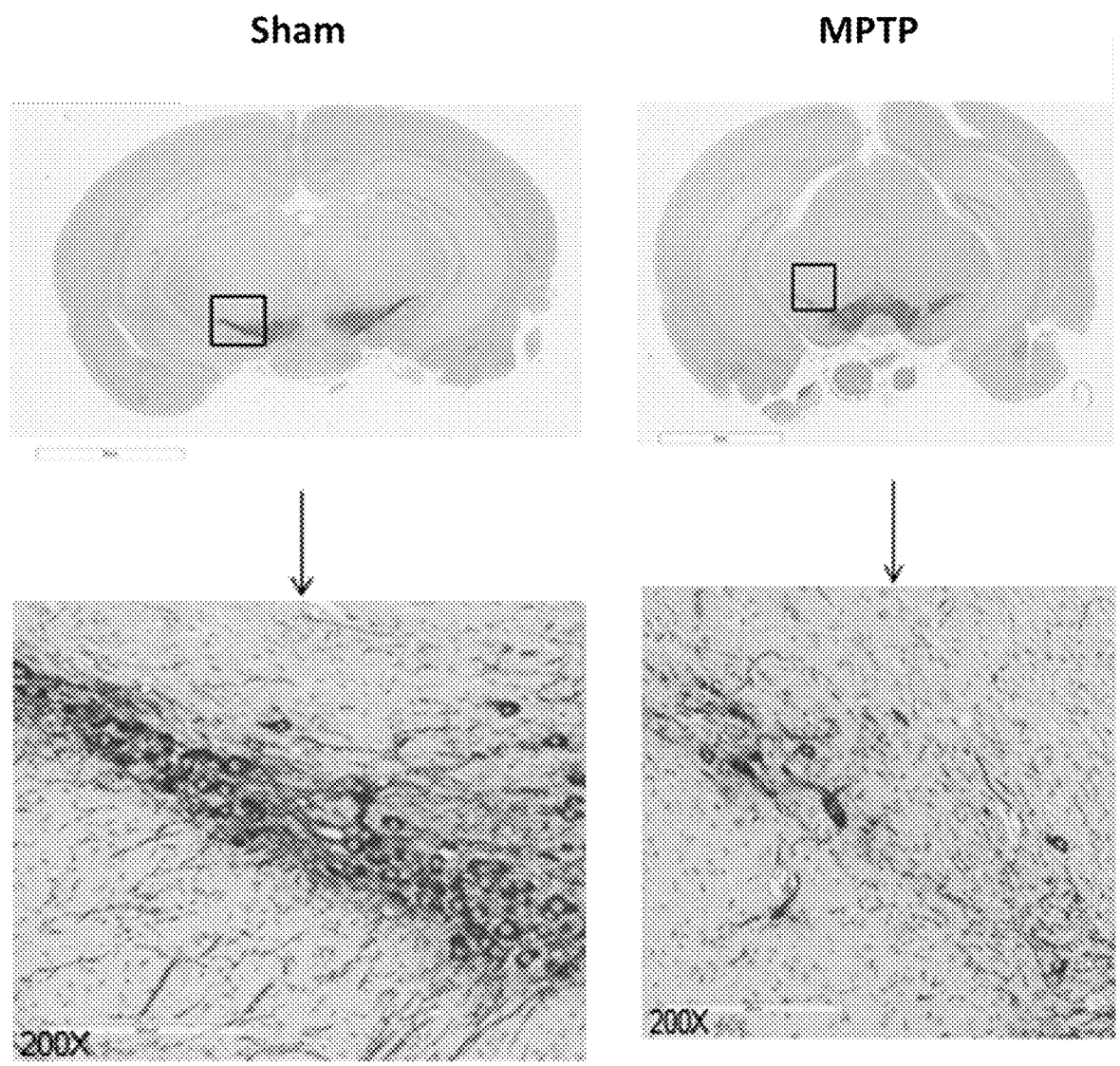
FIG. 13A and FIG. 13B: CLP1 increases neuronal survival in a mouse model of Parkinson's (MPTP model): Tyrosine hydroxylase (TH)+ neurons in the substantia nigra pars *compacta* (SNpc) from 6 mice were immunostained and counted as a measure of dopaminergic neuronal survival. The number of positive cells was expressed as average of three brain sections. Representative images from each group are shown (FIG. 13A). TH-stain quantifications show a significant effect of CLP1 (0.2 mg/kg) on survival of TH+ neurons (FIG. 13B).
Figure 13B:
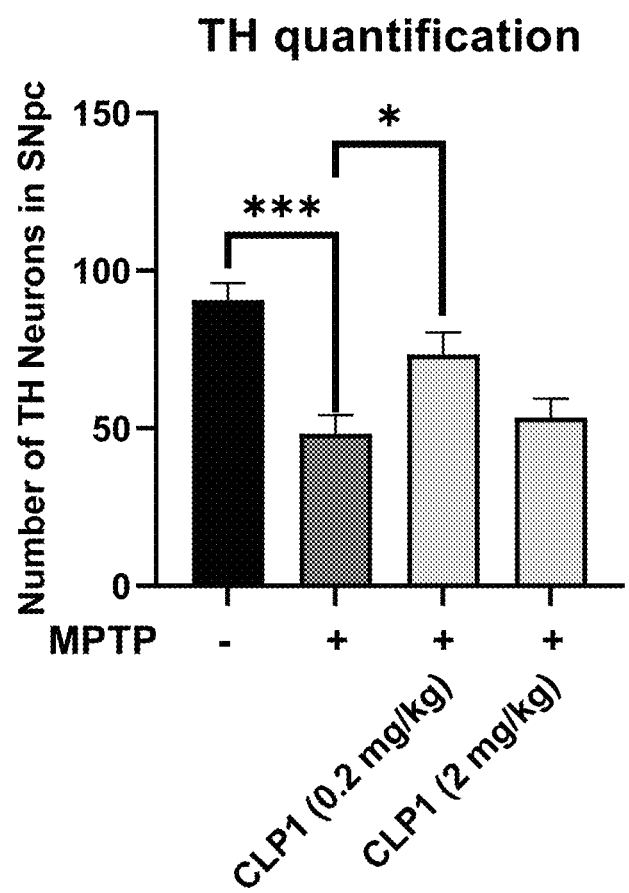

As a measure of dopaminergic neuronal survival tyrosine hydroxylase (TH)+ neurons in the substantia nigra pars compacta (SNpc) were counted. The MPTP non-treated group showed a significantly decrease of neurons after MPTP injection. Dosing of 0.2 mg/kg of CLP1 significantly increased TH+ neurons compared with model group, demonstrating increased levels of live dopaminergic neurons (FIG. 13A and FIG. 13B).

This demonstrates the potential of using CLP1 as treatment approach in Parkinson's Disease and other neurodegenerative diseases with mitochondrial dysfunctions.

Example 13: CLP1 Clears and Reduces Spreading of Human α-Synuclein PFFs in Injected Wild-Type Rats and Prevents Dopaminergic Neuronal Loss As CLP1 was able to increase TFEB expression, the master regulator of lysosomal proteins, and induce autophagy, CLP1 therapeutic efficacy was assessed in a PD rat-model injected with human α-synuclein pre-formed fibrils to induce α-synuclein pathology. The amygdala was chosen as injection site for several reasons as it is: (1) the most commonly affected region in human PD patients, and in some instances, the only affected structure in the entire brain of incidental Lewy body disease cases (Beach, 2009; Beach, 2010; Adler, 2016) suggesting that PD may often start in this structure; (2) the amygdala is the second CNS structure affected subsequently to an initial olfactory bulb start; (3) the amygdala has a broad input-output connectome making this brain region suitable to investigate trans-neuronal spread; and (4) it is monosynaptically connected to the olfactory bulb and other important brainstem structures, which are all severely affected in PD.

Rats and Injections

Given that age is the greatest risk factor for human PD, it seems likely that older experimental animals could yield the most relevant and reliable findings. Therefore, elderly wild-type rats (fourteen-month-old at the time of injection) were used for the experiment, as age is a crucial factor for alpha-synuclein aggregation and complete propagation to heart, stomach and skin, similar to patients.

Figure 14A:
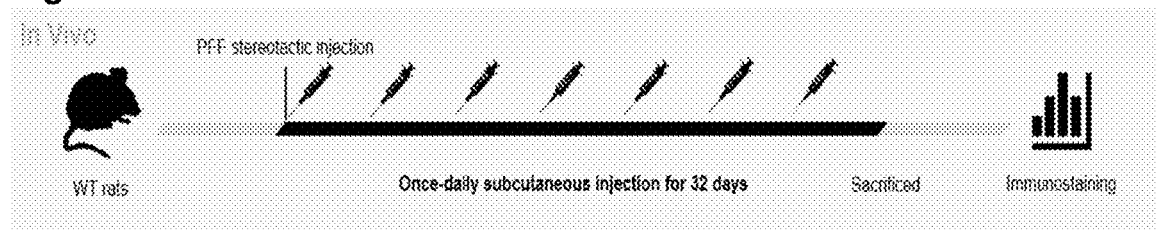

The injections in rats were carried out using a 10 ul Hamilton syringe (25-gauge needle). 9 ug of α-synuclein fibrils (pre-formed fibrils, PFF) were unilaterally divided over the basolateral and central amygdala (3 ul of 1 ug/ul PFFs at each location) localized by means of standardized stereotactic coordinates (ML −4.45, AP −2.4, DVcentral −7.95, DVbasolateral,1 −8.6, DVbasolateral,2 −9.15). The stereotactic coordinates were based on the Paxinos & Watson rat brain atlas and three pilot trials. For each group, a control group received intracerebral injection with saline. The rats were treated with a daily SC injection of CLP1 (0.2 mg/kg) in 4.38 mM L-His, 140 mM NaCl, 0.2% Tween-20 and 1500 IU hyaluronidase (pH 6.15) for 32 days. A schematic outlining experiment procedure are shown in FIG. 14A.

Tissue Collection and Immunohistochemistry 24 hours after final administration, the rats were sedated and perfused transcardially with PBS and phosphate-buffered 4% formaldehyde. The brains were sampled to study α-syn pathology propagation through the brain. In addition, one brain (n=1) was assessed for tyrosine hydroxylase (TH) levels to assess dopaminergic neuronal loss. The tissue was processed and cut. Sections (4-um thick, 10-um thick if skin) from several subjects (three to six subjects depending on section size) were randomized and mounted on one tissue slide. Tissue sections were deparaffinized and stained for PFF inclusions or TH.

Quantification Assessment of Immunoreactivity

Figure 14B:
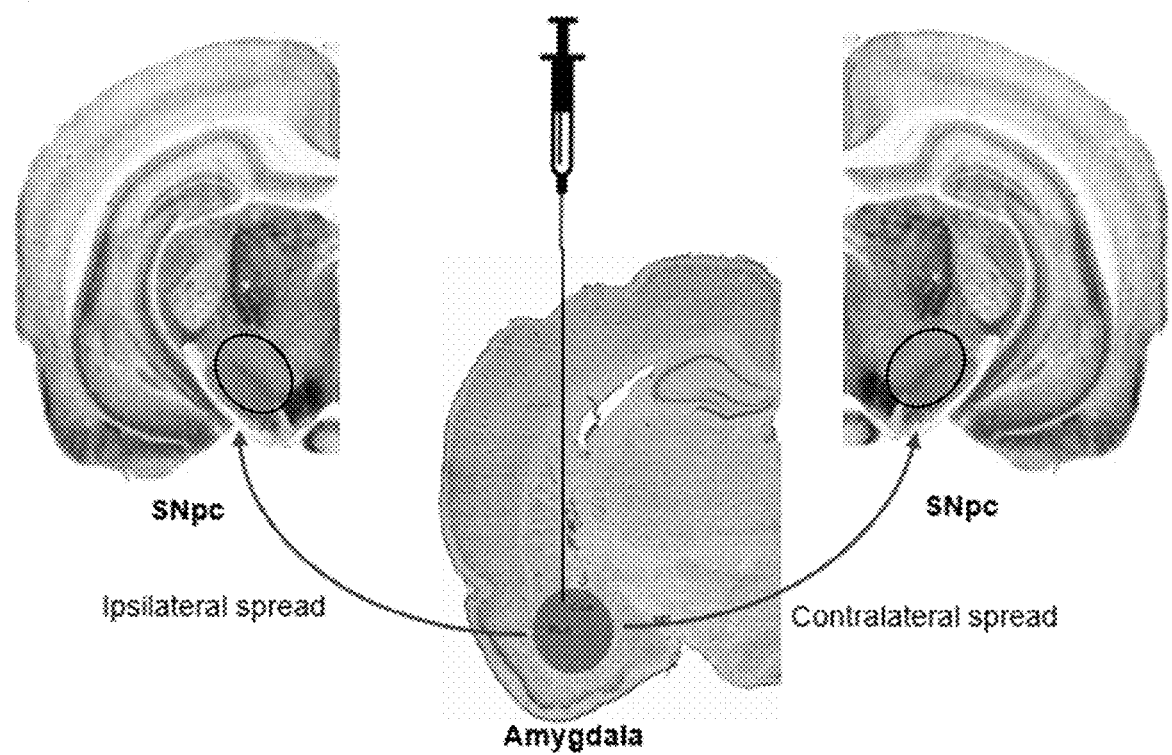

Images were collected from 4-um thick sections using the Olympus VS120 automated slide-scanning microscope. Quantification of immunoreactive density in brain tissue was performed. To get an idea of spreading, the rat brains were perfusion fixed and stained for PFFs. PFF positive neurons were counted in area of amygdala both ipsilaterally, at injection site, and contralaterally to evaluate spread. Furthermore, PFF positive neurons were counted in substantia nigra pars compacta (SNpc). Injection site and brain areas analysed are shown in FIG. 14B.

Representative pictures of both SNpc and amygdala are shown in FIG. 14C and FIG. 14D at both ipsilateral and contralateral site. The number of inclusions is displayed in FIG. 14E. Striatal dopaminergic staining (TH-staining) are shown in FIG. 14F. CLP1 significantly decreased the number of inclusions in SN ipsilateral and amygdala contralateral while also trending to decrease inclusion in amygdala ipsilaterally. In addition, CLP1 completely preserved striatal dopaminergic terminals compared to a non-CLP1 treated rat, which showed complete loss of striatal dopamine signal. This shows an effect of CLP1 on both spreading and clearance of α-synuclein, a central aspect in treatment of PD with a therapeutic effect of preventing striatal dopamine terminal denervation and cell loss. Furthermore, this highlights the potential of using clinically validated biomarkers of the dopaminergic system, such as certain PET radiotracers, as a clinical biomarker for efficacy in humans.

Example 14: FSL Rats

BDNF has been associated with depression as postmortem samples of patients suffering from mood disorders display reduced BDNF levels, particularly in brain regions of hippocampus and amygdala (Dwivedi, 2003; Thompson, 2011; Guilloux, 2012). In addition, antidepressant drugs have been shown to induce expression of BDNF or act on targets in the BDNF pathway (Chen, 2001; Casarotto, 2021).

The therapeutic potential of CLP1 in a rat model of depression, The Flinders Sensitive Line (FSL) characterized by reduced BDNF levels in hippocampus along with reduced locomotor activity, reduced body weight, increased REM sleep and cognitive (learning) difficulties, was therefore evaluated (Shiromani, 1988; Shiromani, 1991; Overstreet, 1993). Flinders Resistant Line (FRL) rats was used as control (healthy) rats. The rats were treated with a once daily SC injection of ketamine (10 mg/kg) as positive control, CLP1 (0.2 mg/kg or 2 mg/kg dosing) or CPX (13 mg/kg dosing) in 4.38 mM L-His, 140 mM NaCl, 0.2% Tween-20 and 1500 IU hyaluronidase (pH 6.15) for 8 days.

Molecular Analysis of BDNF Levels

Figure 15:
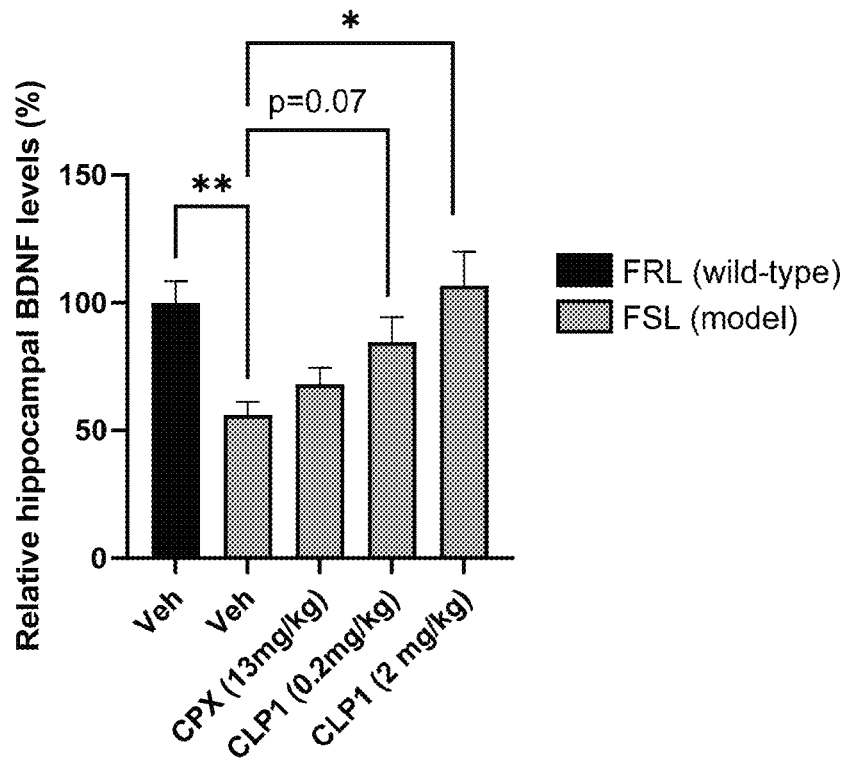
FIG. 15: FSL data: 8-week old FSL rats were treated once per day with 0.2 mg/kg or 2 mg/kg of CLP1 or 13 mg/kg of CPX for 8 days in 4.38 mM L-His, 140 mM NaCl, 0.2% Tween-20 and 1500 IU hyaluronidase (pH 6.15). After treatment, the levels of BDNF in the hippocampus were evaluated by western blotting normalized to beta-actin. The graph depicts the densitometric quantification of western blot bands. BDNF levels were normalised to BDNF levels in control rats (FRL).

Each rat was anesthetized using pentobarbital and subsequently sacrificed by cervical dislocation and striatal, hippocampal and cortical tissue was dissected and flash frozen in floating nitrogen. The tissue samples were lysed in RIPA buffer containing cOmplete protease inhibitor cocktail in a TissueLyser and levels of BDNF were validated by western blotting. Hippocampal BDNF levels are shown in FIG. 15. As expected, FSL rats demonstrated significantly lower BDNF levels than wild-type control rats (FRL, p=0.041). Rats treated with both dosages of CLP1 displayed increased hippocampal BDNF levels in which 2 mg/kg totally restored these to normal levels (p=0.0147). CPX appeared to have a more limited effect compared to vehicle, which was not significant. This shows a potential therapeutic value of CLP1 in restoring BDNF levels of patients suffering from depression.

Example 15: CLP1 Increase Time Spent Awake in Rat Model of Depression (Wistar Kyoto)

The therapeutic potential of CLP1 in a rat model of depression, Wistar Kyoto (WKY) characterized by elevated anxiety- and depression-like behavior was evaluated. This model has been shown to display abnormal sleep-wake characteristics that are often associated with depression, including EEG and EMG-measurable parameters such as reduced wakefulness and increased REM and non-REM sleep (nREM) (Dugovic, 2000).

EEG and EMG in WKY rats treated with 0.2 mg/kg or 2 mg/kg of CLP1 following single injections in 4.38 mM L-His, 140 mM NaCl, 0.2% Tween-20 and 1500 IU hyaluronidase (pH 6.15) were evaluated. Ketamine (10 mg/kg), a N-methyl-D-aspartate-receptor antagonist, was used as positive control. All rats received all treatments 2 h after light onset in a pseudo randomized crossover fashion with a minimum period of 3 days between treatments. The rats were placed individually in recording boxes, and sleep-wake behaviour was recorded for 24 h. EEG/EMG signals were amplified, analogue filtered (0.5-100 Hz), digitized (500 Hz), and then digitally filtered (EEG: 0.5-100 Hz and EMG: 70-100 Hz). EEG/EMG recordings were semi-automatically scored as wake, non-REM (NREM) sleep, or REM sleep in 10 s epochs using SleepSign. Sleep stages were defined as below:

| Sleep Stage | Definition |
| --- | --- |
| Wake | a. Activity integral ≥65,000 AU or |
|  | b. EMG integral >4.5 uV-sec |
| NREM sleep | a. EEG delta (0.65-4.5 Hz) power ≥ 900 $uV^2$ and EMG integral <11.5 uV-sec or |
|  | b. EEG delta oscillations/10 s ≥29% and EMG integral <6.5 uV-sec |
| REM sleep | a. EEG theta (6-10 Hz) power ratio ≥31% and EMG integral <2 uV-sec or |
|  | b. EEG theta oscillations / 10 s ≥ 29% and EMG integral <4.5 uV-sec |

Figure 16A:
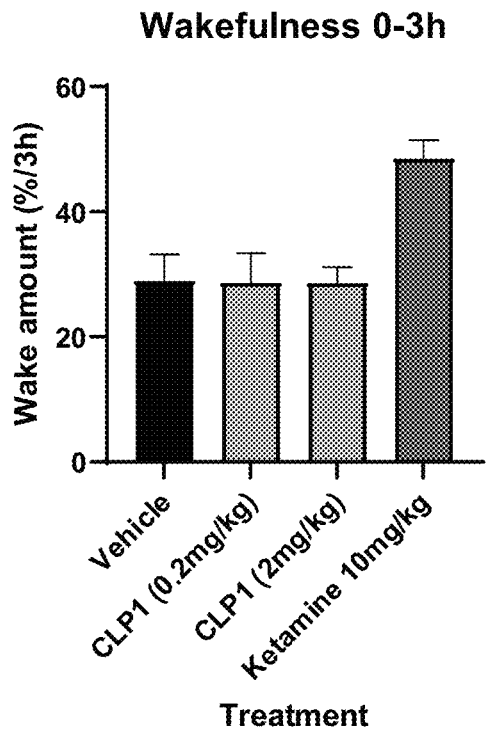
Figure 16F:
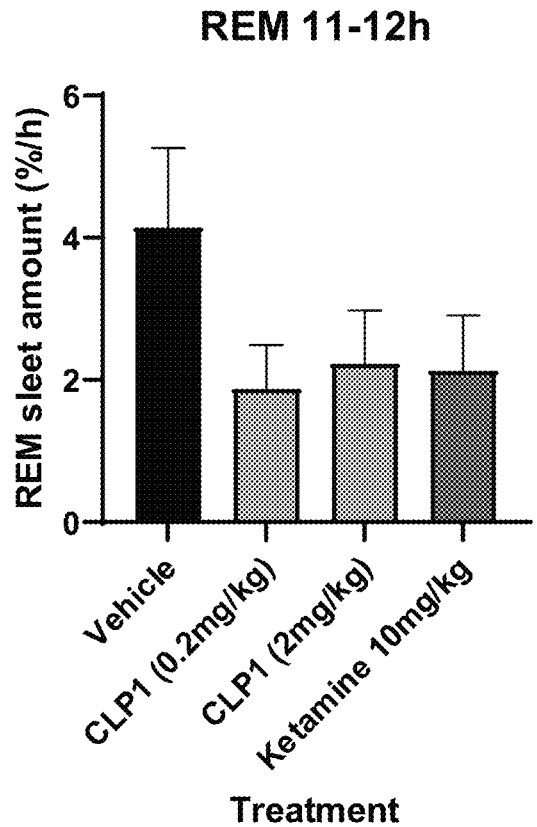

EEG and EMG recordings at timepoints of 0-3 h & 11-12 h post dosing are shown in FIG. 16 and all other timepoints have been excluded as no differences between treated and control rats were observed. As expected, ketamine increased time spent awake (FIG. 16A, FIG. 16C and FIG. 16E), at the expense of REM & NREM sleep, 0-3 h post dosing. A similar trend was seen for ketamine at 11-12 h post dosing (dark onset starts here and thus timepoint when rodents become active). CLP1 likewise increased wakefulness and decreased REM and NREM sleep at 11-12 h post dosing (FIG. 16B, FIG. 16D and FIG. 16F). This demonstrates a potential therapeutic effect of CLP1 for patients suffering from mood disorders, such as depression.

Example 16: Brain and Plasma Stability of Variants of CLP1

A range of variants CLP2 to CLP10 and LLP1 to LLP10 prepared in Examples 1 and 2 were investigated:
  variants CLP2 to CLP6 are cyclic sequences and feature up to two residue replacements at positions 4 and/or 5 relative to CLP1.

variants CLP7 to CLP10 are cyclic sequences and feature (i) different lipidation location and (ii) up to two additional residue replacements at positions 1 and/or 5 relative to CLP1.

variants LLP1 to LLP6 are linear sequences and feature up to two residue replacements at positions 4 and/or 5 relative to CLP1.

variants LLP7 to LLP10 are linear sequences and feature (i) different lipidation location and (ii) up to two additional residue replacements at positions 1 and/or 5 relative to CLP1.

These variants were tested for their stability in both mouse brain homogenates and plasma similarly to procedure in Example 6.

Figure 17A:
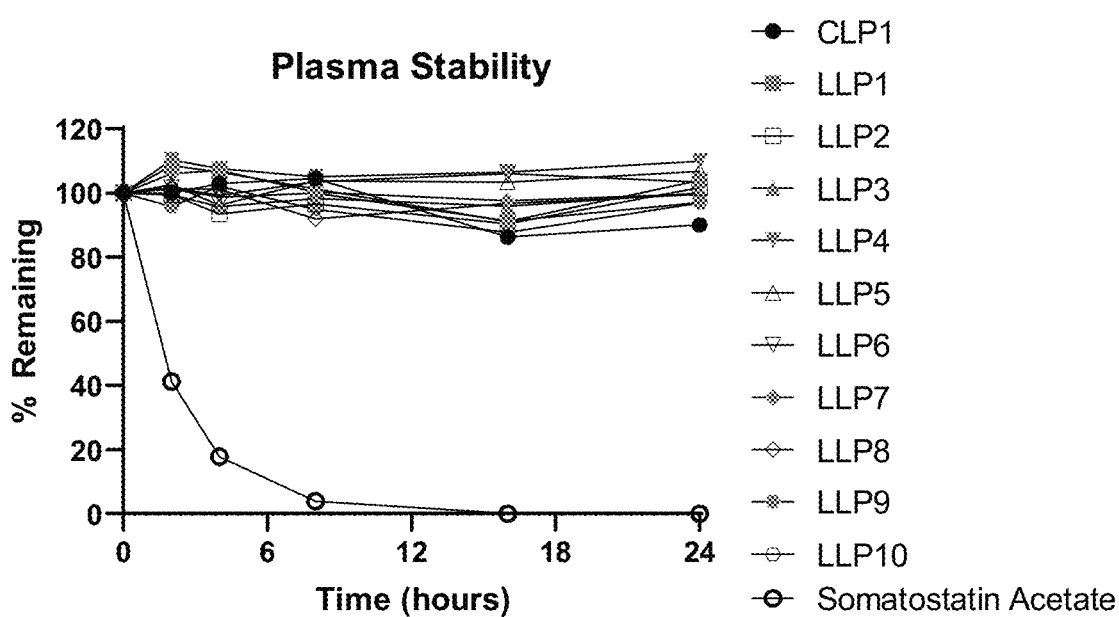
FIG. 17A to FIG. 17D: Brain and plasma-stability of CLP1 to CLP10 and LLP1 to LLP10: the stability of peptides CLP1 and LLP1 to LLP10 in plasma (FIG. 17A) and mouse brain homogenate (FIG. 17C) and stability of peptides CLP1 to CLP10 in plasma (FIG. 17B) and mouse brain homogenate (FIG. 17D).
Figure 17B:
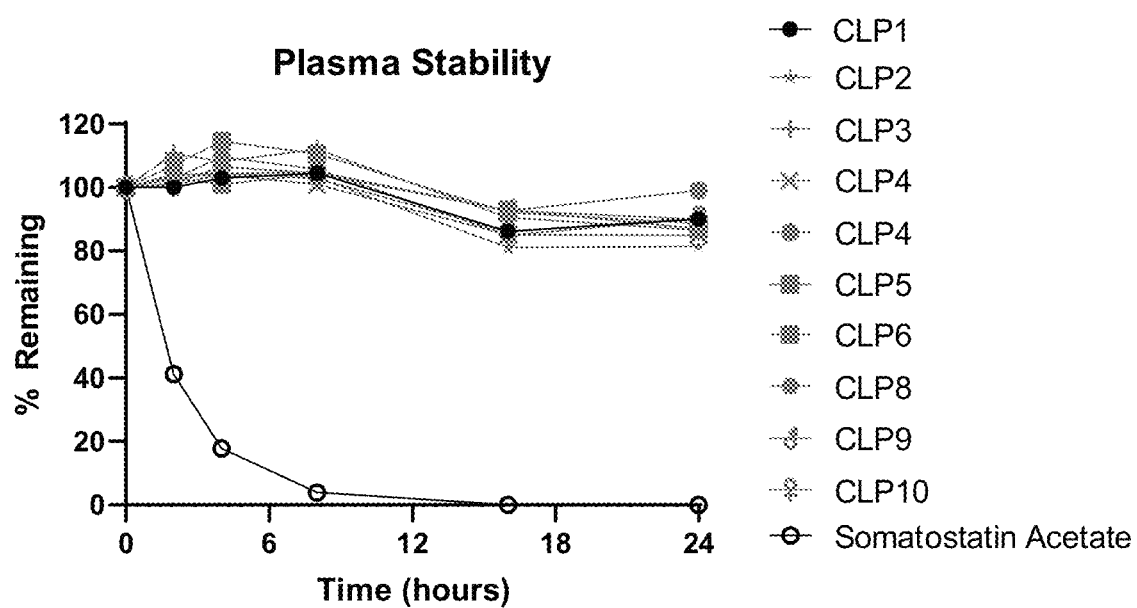
Figure 17C:
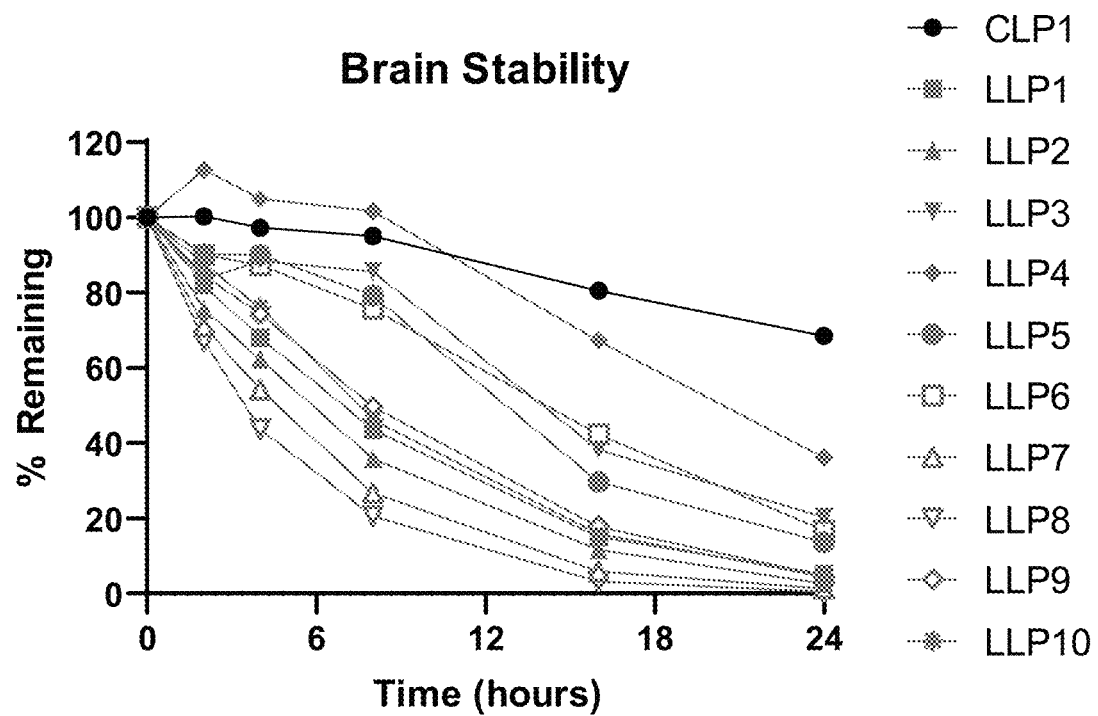
Figure 17D:
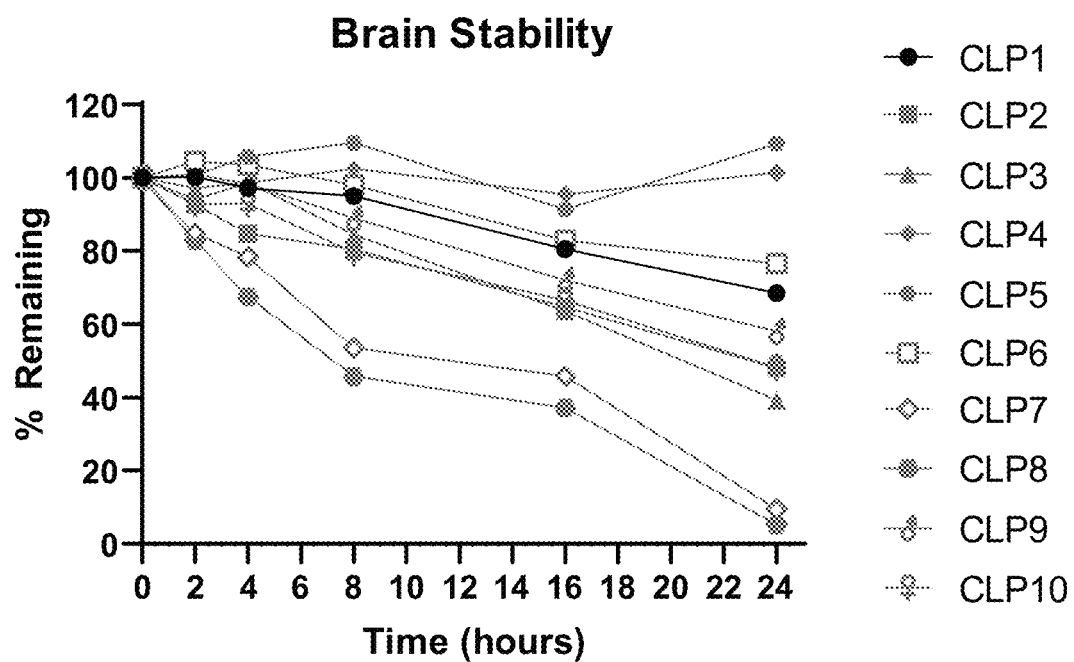
Figure 18A:
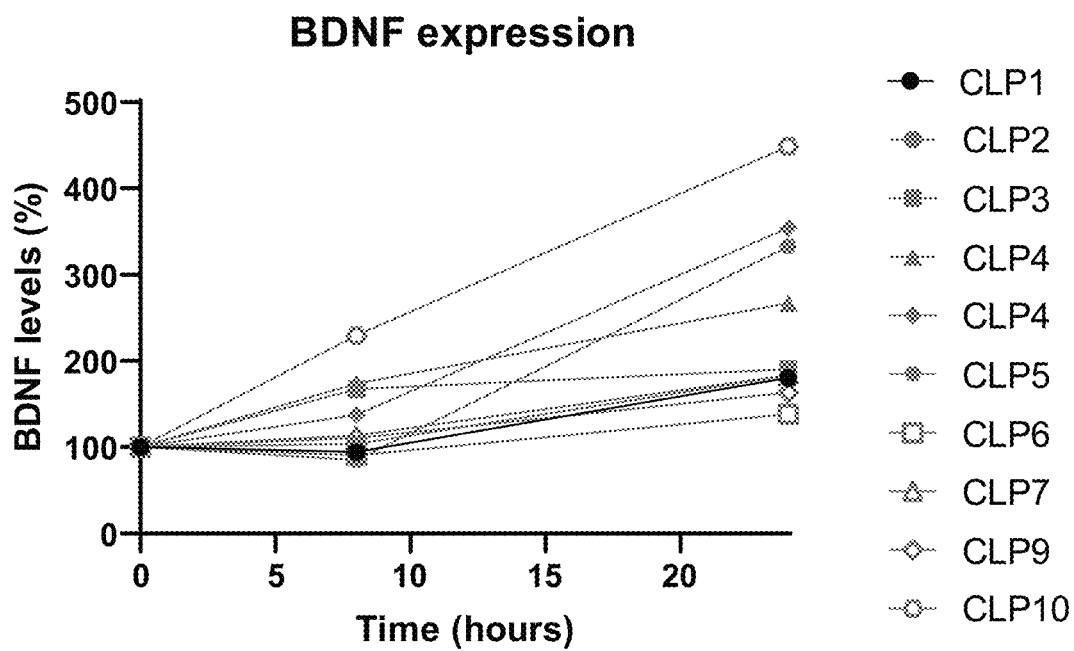
Figure 18B:
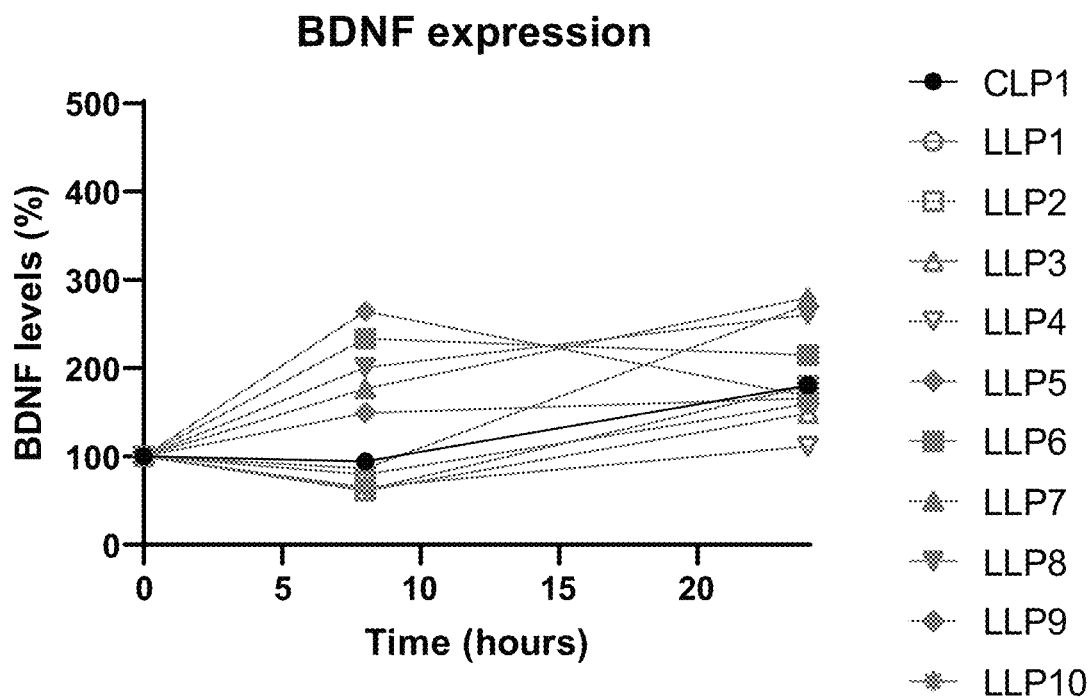
Figure 18C:
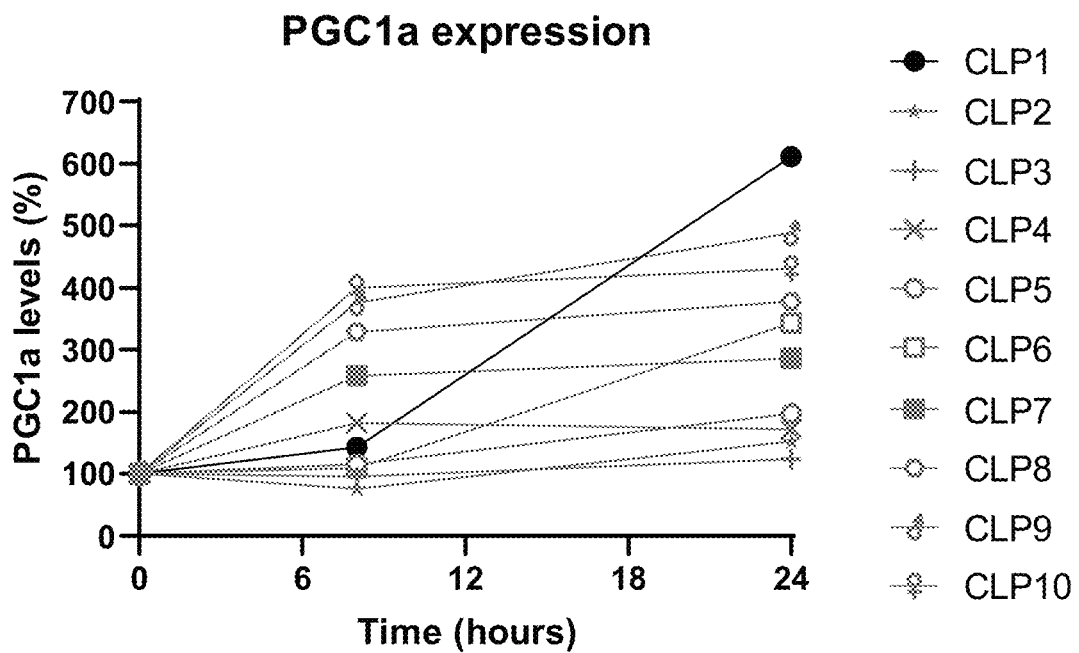
Figures 20A, 20B:
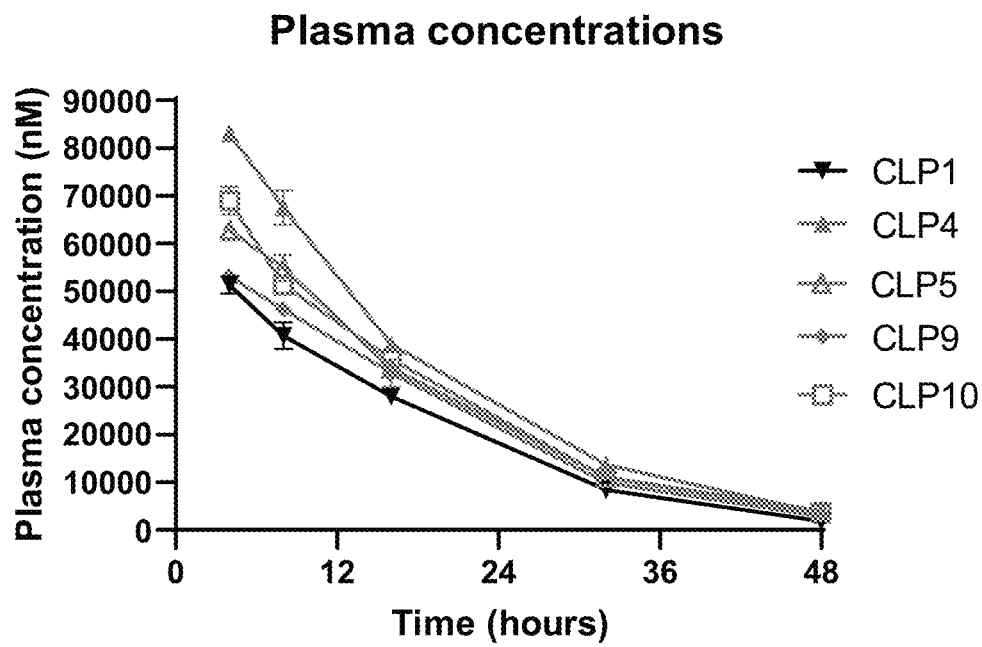
FIG. 20A to FIG. 20D: Pharmacokinetics of selected peptides in wild-type mice: plasma (FIG. 20A) and whole brain (FIG. 20C) concentrations of cyclic peptides from 1 to 48 hours by LCMS/MS. Calculated PK measures for plasma (FIG. 20B) and brain (FIG. 20D).
Figures 20C, 20D:
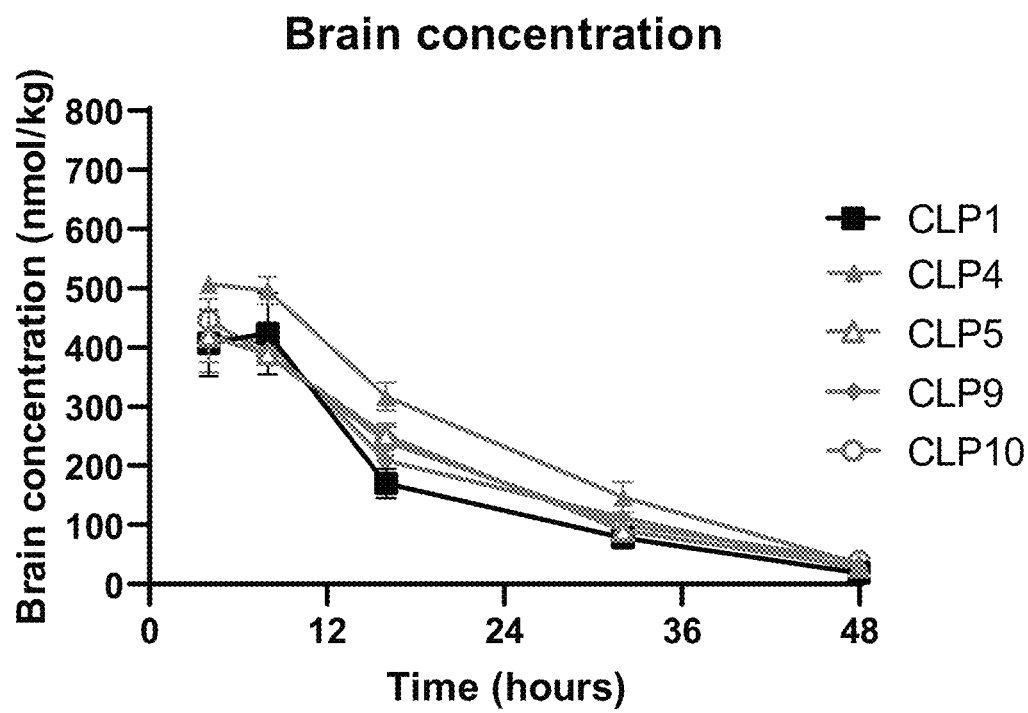

As shown in FIG. 17A and FIG. 17B, both cyclic and linear cyclic peptides showed high stability in mouse plasma. Linear lipidated peptides LLP1 to LLP10 demonstrated shorter half-lives in brain homogenates than CLP1 (FIG. 16C). Data for stability of cyclic lipidated peptides CLP2 to CLP10 are shown in FIG. 16D. A number of cyclic lipidated peptide show good stability, with CLP4, CLP5 and CLP6 improving on the stability of CLP1.

Example 17: Effects of Variants on CREB-Targeted Genes

Variants CLP2 to CLP10 and LLP1 to LLP10 were tested for their ability to increase CREB-targeted genes BDNF and PGC1a. The assay was carried out according to Example 3.

Results are provided in FIG. 18A to FIG. 18D. The most potent peptides were the CLPs compared to LLPs on both BDNF and PGC1a expression. CLP10 behaved well by both increasing BDNF the most and PGC1a to a relatively high extent.

Example 18: CLP10 Clears Soluble mHTT in Huntington's Patient-Derived Fibroblasts Efficacy of CLP10 in removing mutated huntingtin in patient-derived fibroblasts was assessed in a similar way as described in Example 4. As shown in FIG. 19A, CLP10 significantly reduced mHTT. Total HTT levels were not reduced significantly (FIG. 19B).

Example 19: Pharmacokinetics of Selected Novel Candidates

Variants CLP4, CLP5, CLP9 and CLP10, together with CLP1 for reference, were selected for a pharmacokinetic (PK) study in mice. The PK study was carried out as described in Example 9.

As demonstrated in FIG. 20A to FIG. 20D all of the novel variants showed good half-lives, bioavailability and $C_{max}$ values in both plasma and mouse brain following SC injection.

Example 20: In Vivo Efficacy of Selected Candidates in Wild-Type Mice

Variants CLP4, CLP5, CLP9 and CLP10 were evaluated for their ability to increase downstream targets of CREB following continuous daily administration (SC) in wild-type mice.

This was carried out similarly to the method described in Example 10. BDNF and PGC1a levels were validated by western blotting. In addition to this, TrkB levels were assessed to see whether any changes in the receptor system of BDNF occurred. CLP1 was the only peptide, which significantly increased striatal BDNF levels (FIG. 21B). However, all of the peptides increased PGC1a levels (FIG. 21B). CLP1 also significantly increased TrkB levels, along with CLP4, while no significant effects were observed for other peptides (FIG. 21C). Importantly, this demonstrates that none of the peptides decrease the BDNF-receptor, TrkB, crucial for maintaining BDNF/TrkB signaling and, interestingly, CLP1 in fact was found to boost this system both on ligand and receptor levels.

Example 21: Physical Stability of CLP10

Figure 22A:
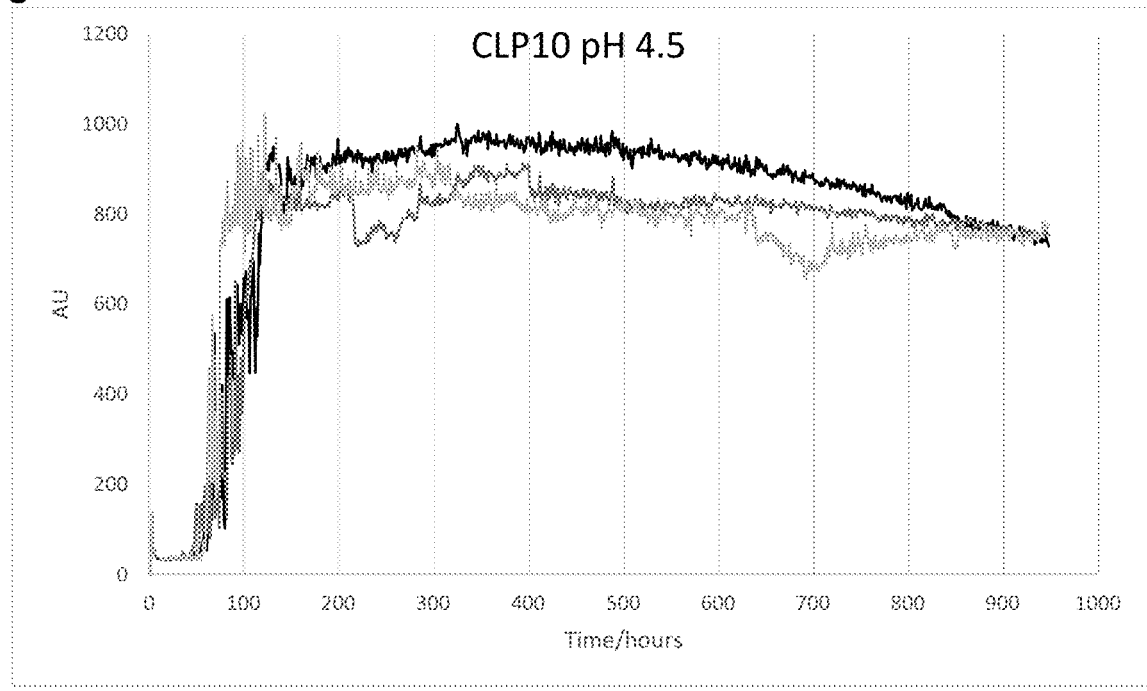
FIG. 22A to FIG. 22D: Physical stability of CLP10 in three buffers: CLP10 demonstrated fibrillation in buffer at pH 4.5 (FIG. 22A) while being stable in both pH 6.5 (FIG. 22B) and pH 7.5 (FIG. 22C) buffer systems using ThT assay. Positive control is shown in FIG. 22D.
Figure 22B:
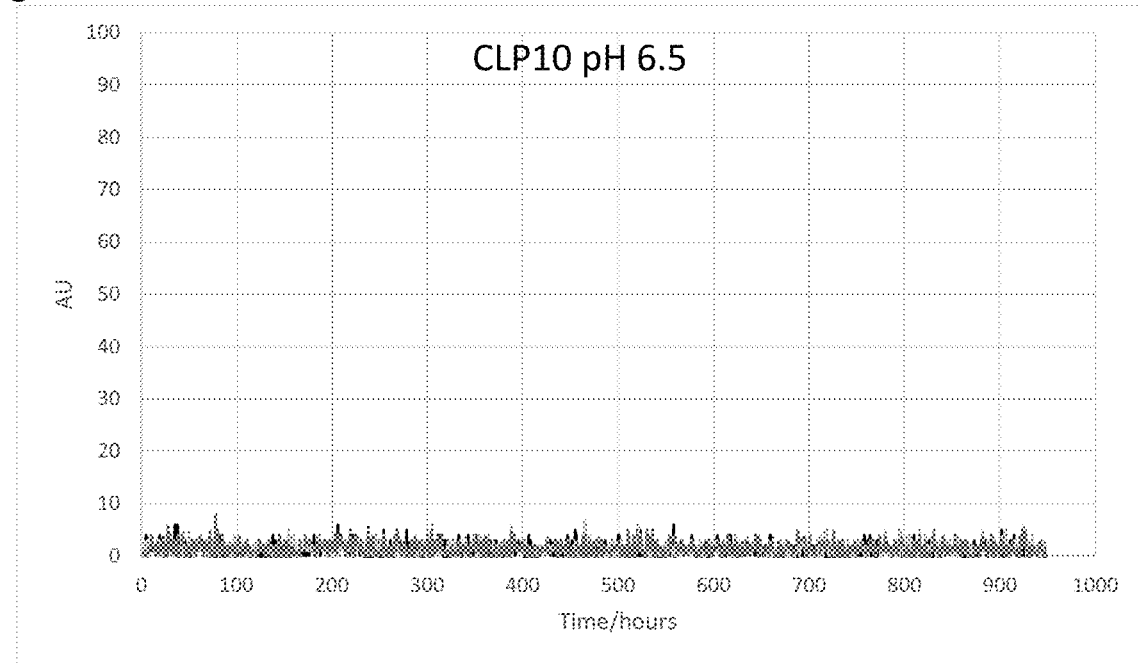
Figure 22C:
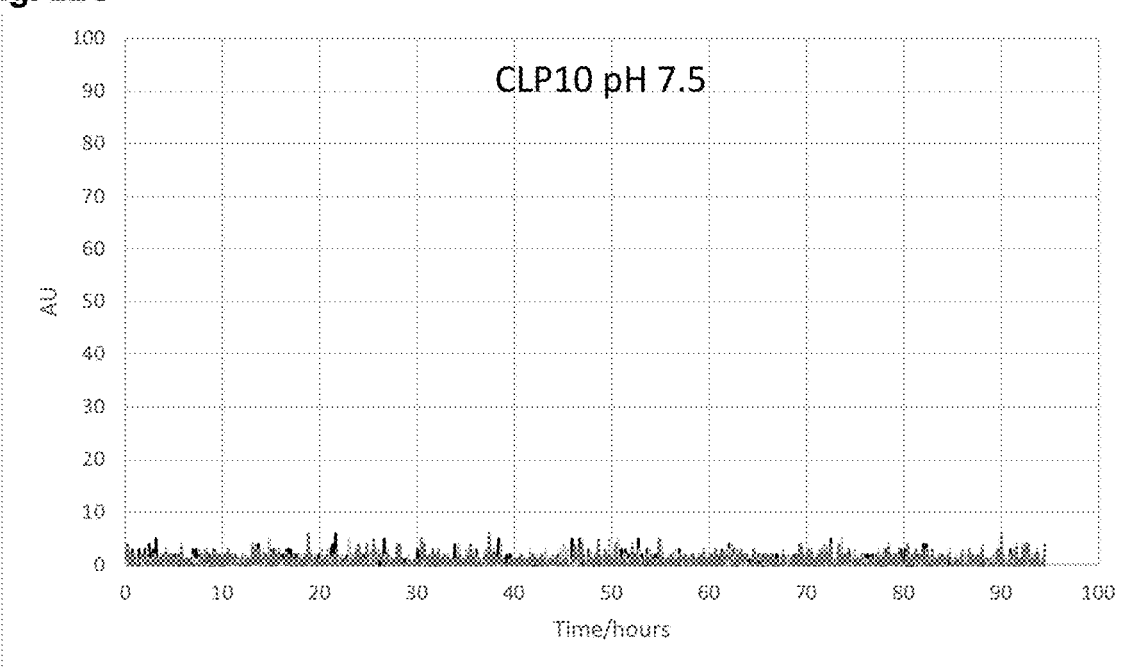
Figure 22D:
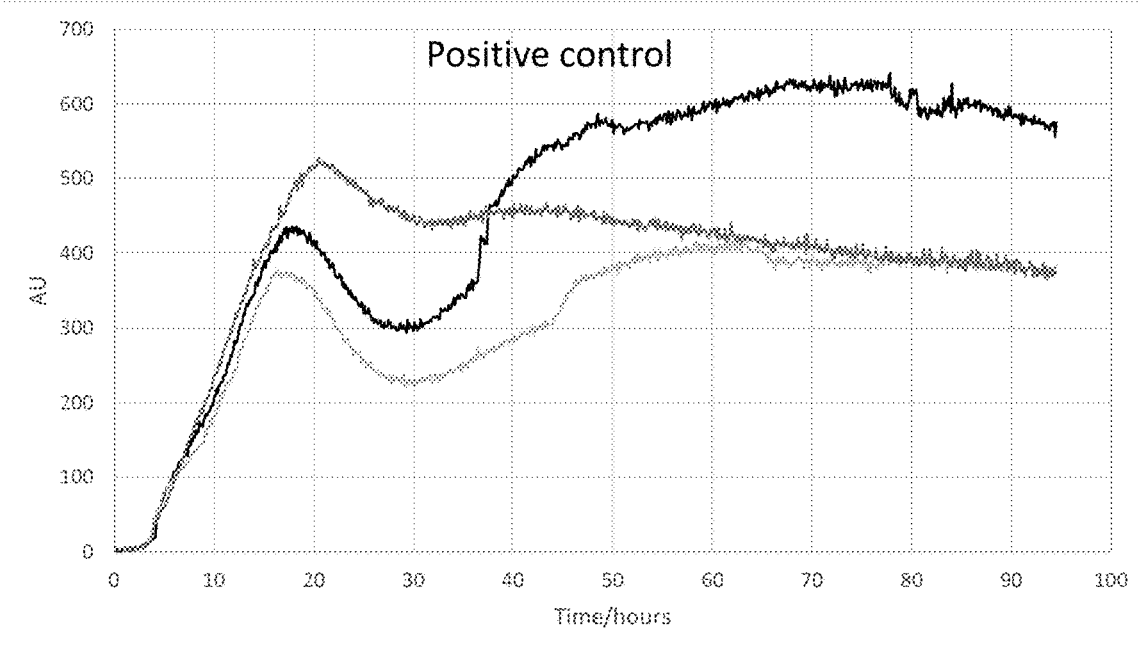

Physical stability of CLP10 was assessed similarly to Example 5, in the three same buffer systems. CLP10 did not show any fibrillation in buffers with pH 6.5 and 7.5 (FIG. 22B and FIG. 22C). However, CLP10 did show fibrillation at pH 4.5 (FIG. 22A).

Example 22: Brain Free Fraction of CLP10

Figure 23A:
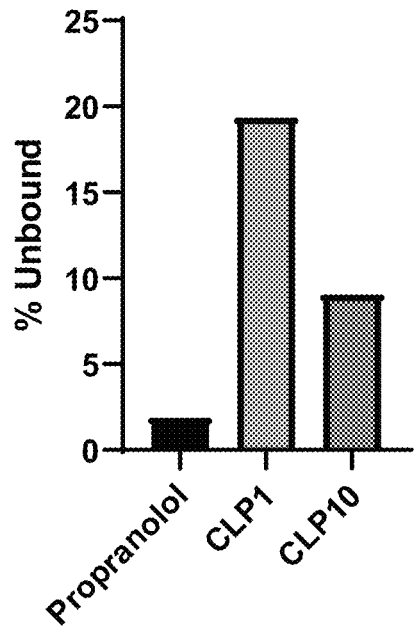
FIG. 23A and FIG. 23B: Brain free fraction of CLP1 and CLP10: brain free fraction of CLP1 and CLP10 in mouse brain (FIG. 23A) and human brain (FIG. 23B) measured by LCMS.
Figure 23B:
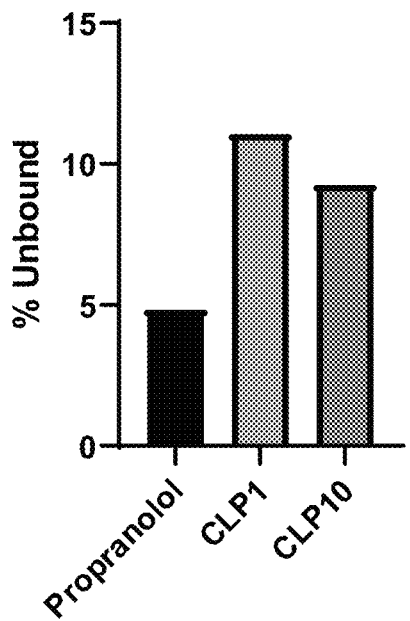

Brain free fraction of CLP10 was assessed in mouse and human homogenates, similarly to Example 10. In this experiment CLP10 showed similar brain free fraction in both mouse and human brain homogenates of ~9% (FIG. 23A and FIG. 23B).

Example 23: Pharmacokinetics of CLP10

Pharmacokinetics of CLP10 in wild-type mice was assessed. 10-fold serial dilutions of CLP10 (2 mg/kg, 0.2 mg/kg and 0.02 mg/kg) were injected SC into wild-type mice (Male C57BL/6J) in 4.38 mM L-His, 140 mM NaCl, 0.2% Tween-20 and 1500 IU hyaluronidase (pH 6.15). Both plasma, whole brain and cerebrospinal fluid concentrations were determined at different timepoints from 1 to 24 hours by LC-MS/MS. The procedure for plasma and brain processing was as described in Example 9.

Figure 24A:
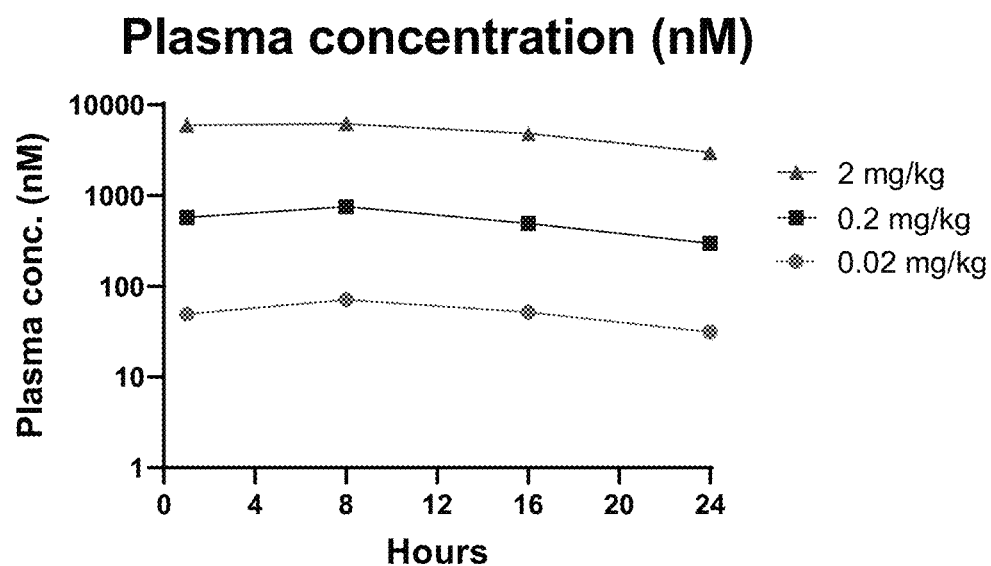
FIG. 24A and FIG. 24B: Pharmacokinetics of CLP10: CLP10 levels are stable in both plasma (FIG. 24A) and brain (FIG. 24B) 24 hours post injection.
Figure 24B:
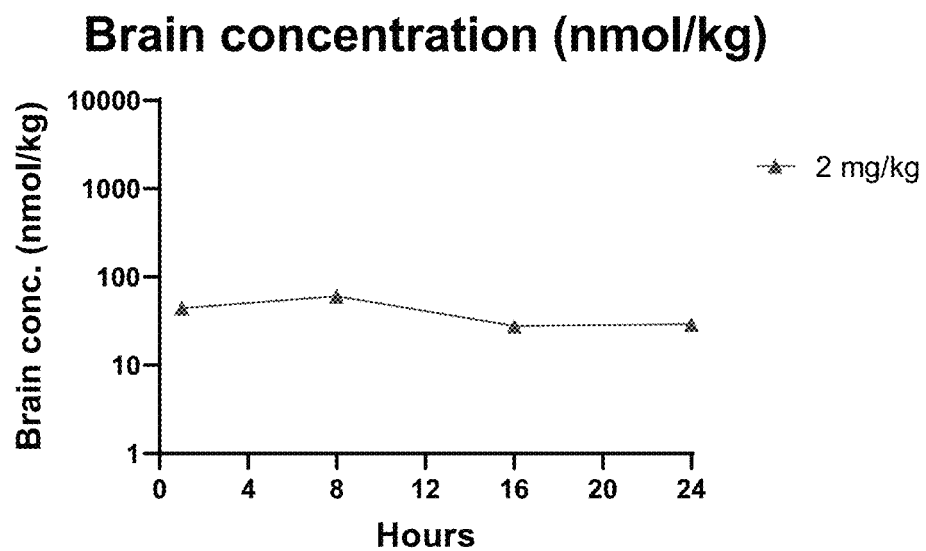

FIG. 24A (plasma) and FIG. 24B (brain) display measured concentrations of CLP10 at the different timepoints. Concentrations of CLP10 in CSF was below lowest limit of detection and thus no results were obtained for CSF samples. CLP10 was measurable in the brain following 2 mg/kg administration, which demonstrates that CLP10 reaches the brain and CSF following SC injection, however to a lower slightly lower degree than CLP1 as it was not measurable at 0.2 mg/kg. The PK parameters of CLP10 are listed below.

Plasma

| Concentration | T½ (hours) | $C_{max}$ (nmol/L) | AUC 0-t (nmol/L * h) |
|---|---|---|---|
| 2 mg/kg | 15.3 | 6179 | 120293 |
| 0.2 mg/kg | 11.9 | 757 | 12953 |

Brain

| Concentration | T½ (hours) | $C_{max}$ (nmol/L) | AUC 0-t (nmol/L * h) |
|---|---|---|---|
| 2 mg/kg | 15.1 | 60.7 | 955 |

Example 24: Lipidated Variants Increase BDNF In Vivo

In a further experiment in vivo efficacy of both cyclic lipidated variant CLP11 and linear variants LLP11 and LLP12 was investigated.

variant CLP11 is a cyclic sequence and features two residue replacements at positions 4 and 5 relative to CLP1 (corresponding to reversion from CLP1 to native SorCS2 residues at these positions).

variant LLP11 is a linear sequence and features two residue replacements at positions 4 and 5 relative to CLP1 (corresponding to reversion from CLP1 to native SorCS2 residues at these positions).

variant LLP12 is a linear sequence and features (i) two residue replacements at positions 4 and 5 relative to CLP1 (corresponding to reversion from CLP1 to native SorCS2 residues at these positions) (ii) inclusion of 4 additional residues from the native SorCS2 sequence between positions 1 and 2 of CLP1.

The experiment was carried out similarly to Example 10 using single subcutaneous dose administration of LLP11 (21 mg/kg), LLP12 (26 mg/kg) and CLP11 (21 mg/kg) in wild-type mice in 4.38 mM L-His, 140 mM NaCl, 0.2% Tween-20 and 1500 IU hyaluronidase (pH 6.15) followed by BDNF measurement. 4 and 8 hour timepoints were chosen.

Figure 25:
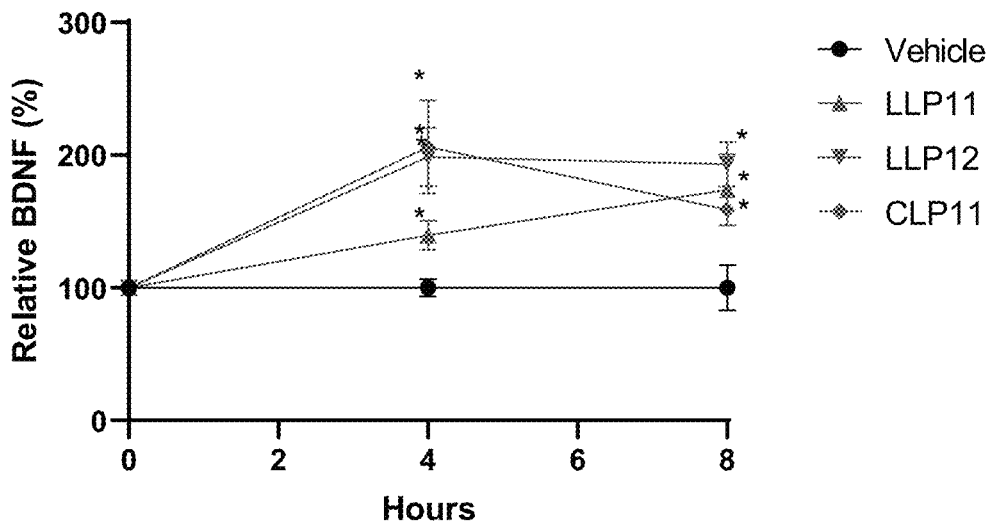
FIG. 25: Lipidated peptides LLP11. LLP12 and CLP11 increase BDNF in vivo: BDNF levels in wild-type mice between 4-8 hours post-injection.

As shown in FIG. 25, all peptides resulted in a statistically significant increase in BDNF levels after both 4 and 8 hours.

Example 25: Identification of Minimal Sequence with Activity

In a further experiment, in vitro efficacy of a set of peptide variants based on the native SorCS2 sequence was investigated. The aim of this in vitro efficacy assay was to identify minimal sequences within the native SorCS2 sequence with activity. The variants included cyclic peptides CP13 to CP17.

Variant CP13 is a non-lipidated cyclic sequence and features two residue replacements at positions 4 and 5 relative to CLP1 (corresponding to reversion from CLP1 to native SorCS2 residues at these positions) with shortening of N-terminally M and c-terminal V.

Variant CP14 is a non-lipidated cyclic sequence and features two residue replacements at positions 4 and 5 relative to CLP1 (corresponding to reversion from CLP1 to native SorCS2 residues at these positions) with shortening of N-terminally M and c-terminal DV.

Variant CP15 is a non-lipidated cyclic sequence and features two residue replacements at positions 4 and 5 relative to CLP1 (corresponding to reversion from CLP1 to native SorCS2 residues at these positions) with shortening of N-terminally MT and c-terminal DV.

Variant CP16 is a non-lipidated cyclic sequence and features two residue replacements at positions 4 and 5 relative to CLP1 (corresponding to reversion from CLP1 to native SorCS2 residues at these positions) with shortening of N-terminally MT and c-terminal EDV.

Variant CP17 is a non-lipidated cyclic sequence and features two residue replacements at positions 4 and 5 relative to CLP1 (corresponding to reversion from CLP1 to native SorCS2 residues at these positions) with shortening of N-terminally MTE and c-terminal EDV.

These variants were tested for their ability to increase BDNF levels in primary neurons and the experiment was carried out similarly to Example 3 using 1 uM final concentration of each peptide and stimulated for 6 hours. CPX was included for comparison.

Figure 26:
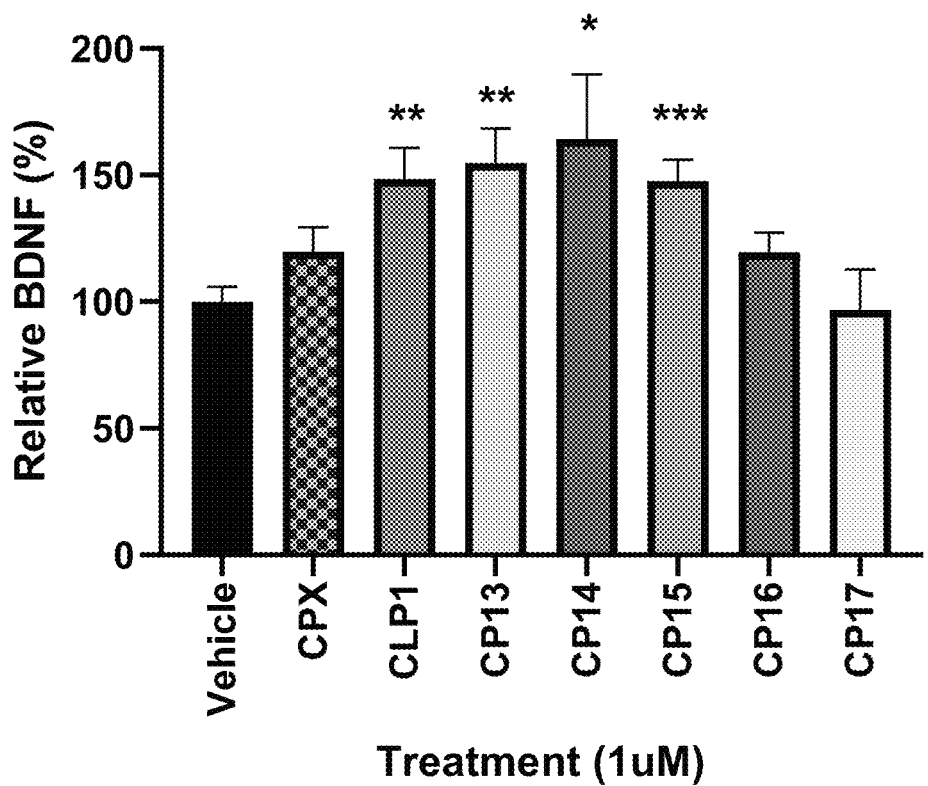
FIG. 26: Identification of shorter sequences with activity (CP13 to CP17): the activity of CLP1 and non-lipidated cyclic peptides (CP13 to CP17 and CPX).

As shown in FIG. 26 CP13, CP14 and CP15 significantly increase BDNF levels, whereas CP16 had tendency (p=0.563) and CP17 did not. Excessive shortening of the peptide derived from native SorCS2 sequence decreases the activity and 5 amino acid length completely abolishes activity.

Example 26: Brain and Plasma Stability of Cyclic Non-Lipidated Variants

Figure 27A:
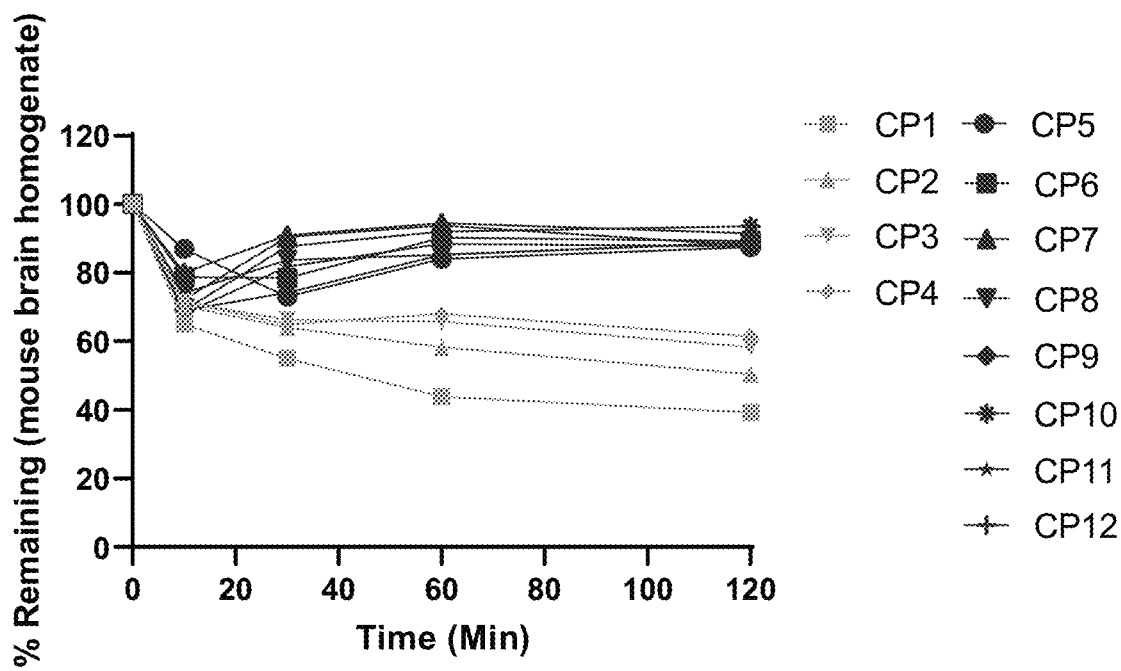
FIG. 27A and FIG. 27B: Stability of cyclic non-lipidated peptides CP1 to CP12: stability of peptides in mouse brain (FIG. 27A) and plasma (FIG. 27B).
Figure 27B:
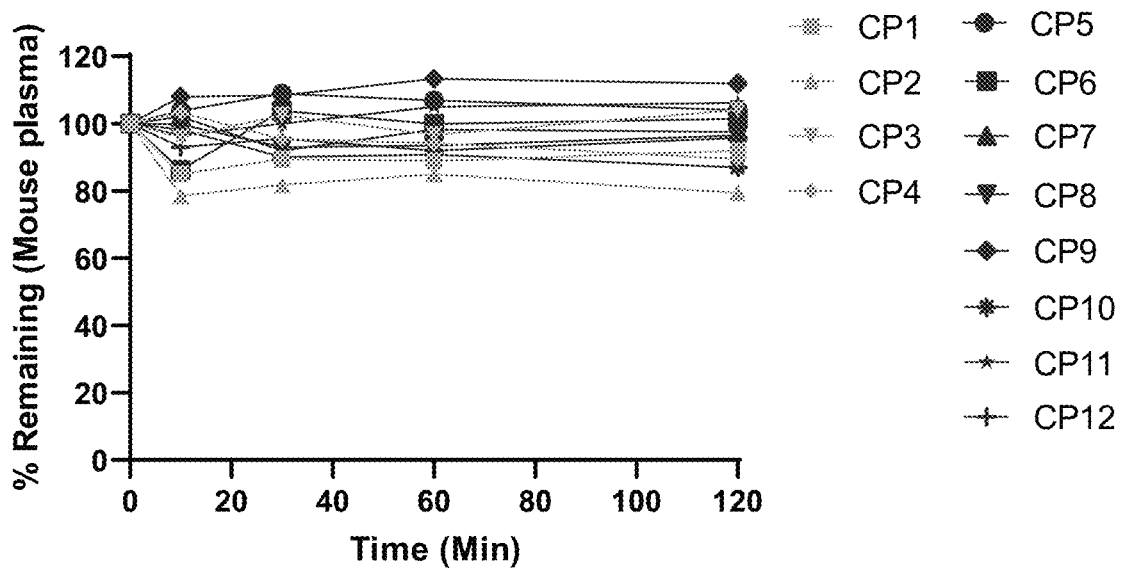

Similar to Example 16, we analysed novel set of peptide variants with differences in position of amino acid or amino acid substitution around the "QI" site of CLP1—the stabilized position compared to natural SorCS2 fragment. However, these were "naked" peptides with no lipidation attached. The novel variants were all cyclic forms (cyclic peptide, CP). These variants were tested for their stability in both mouse brain homogenates and plasma similarly to procedure in Example 6. As shown in FIG. 27 B, all of the cyclic peptides showed high stability in plasma of mouse. CPs with Q→P aa substitutions CLP1 sequence, displayed less stability in brain homogenates (CP1-CP4). This shows that adding proline to the sequence decrease stability in mouse brain homogenate.

Example 27: In Vivo Efficacy of Non-Lipidated Cyclic Peptides

The ex vivo brain-stable variants efficacy of increasing CREB-target genes in vivo was tested. The experiment was carried out similarly to Example 10 using single subcutaneous dose administration of CP5-12 (13 mg/kg) in wild-type in 4.38 mM L-His, 140 mM NaCl, 0.2% Tween-20 and 1500 IU hyaluronidase (pH 6.15) followed by BDNF-, TFEB- and PGC1a-level measurement. 4-hour timepoint were chosen.

Figure 28A:
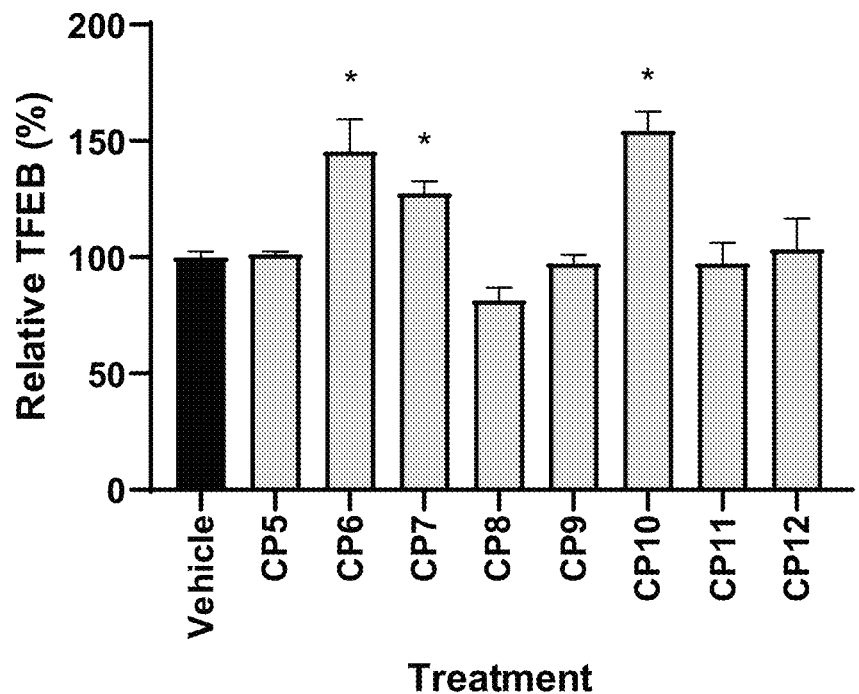
FIG. 28A to FIG. 28C: In vivo efficacy of non-lipidated cyclic peptides CP5 to CP12: CP6, CP7 and CP10 significantly increased TFEB (FIG. 28A). CP5, CP7 and CP9 significantly increased BDNF (FIG. 28B). CP5, CP6, CP7, CP8 and CP10 significantly increased PGC1a levels (FIG. 28C).
Figure 28B:
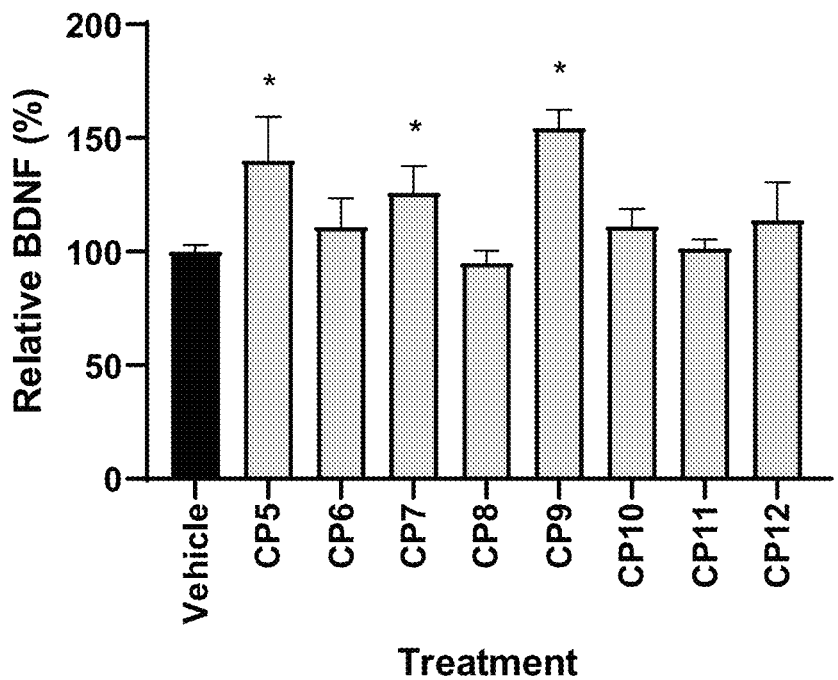
Figure 28C:
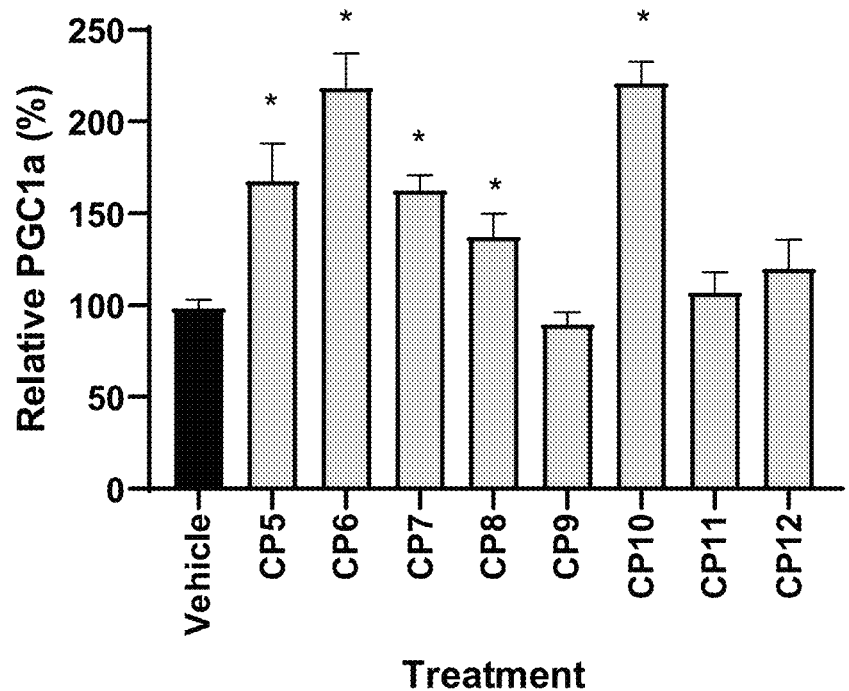

As shown in FIG. 28A, CP6, CP7 and CP10 increased TFEB significantly. CP5, CP7, CP9 increased BDNF (FIG. 28B). CP5, CP6, CP7, CP8 and CP10 significantly increased PGC1a levels (FIG. 28C). In summary, peptide C5-C7 and C10 demonstrated improvement in two of the three CREB-regulated proteins, whereas C7 significantly increased all three protein levels.

Example 28: Identification of Amino Acids Important for Activity

In a further experiment, in vitro efficacy of cyclic variants CP18 to CP22 was investigated.

Variant CP18 is a cyclic sequence and features four residue replacements at positions 4 and 5 relative to CLP1 (corresponding to reversion from CLP1 to native SorCS2 residues at these positions) and position 6 and 8 (E→D residue replacements) relative to CLP1.

Variant CP19 is a cyclic sequence and features four residue replacements at positions 4 and 5 relative to CLP1 (corresponding to reversion from CLP1 to native SorCS2 residues at these positions) and position 3 and 6 (E→D residue replacements) relative to CLP1.

Variant CP20 is a cyclic sequence and features three residue replacements at positions 4 and 5 relative to CLP1 (corresponding to reversion from CLP1 to native SorCS2 residues at these positions) and position 3 (E→A residue replacement) relative to CLP1.

Variant CP21 is a cyclic sequence and features three residue replacements at positions 4 and 5 relative to CLP1 (corresponding to reversion from CLP1 to native SorCS2 residues at these positions) and position 6 (E→A residue replacement) relative to CLP1.

Variant CP22 is a cyclic sequence and features three residue replacements at positions 4 and 5 relative to CLP1 (corresponding to reversion from CLP1 to native SorCS2 residues at these positions) and position 8 (E→A residue replacement) relative to CLP1.

Figure 29:
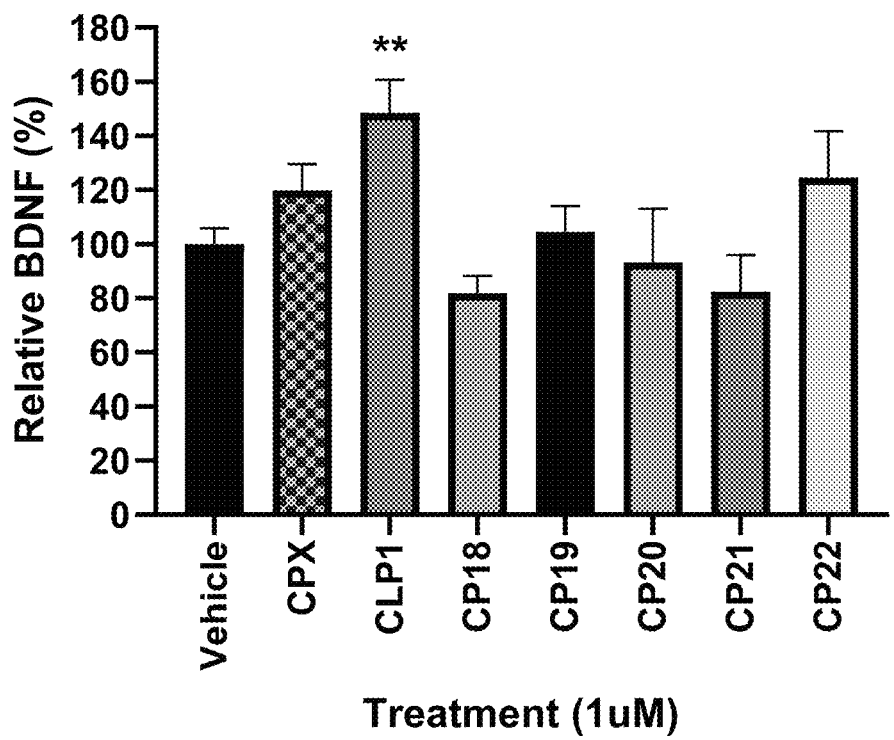
FIG. 29: Impact of amino acid variation on activity (CP18 to CP22): BDNF levels of primary cortical neurons after treatment with non-lipidated cyclic peptides (CP18 to CP22 and CPX) compared to CLP1.

The experiment was carried out similarly to Example 3 using 1 uM final concentration of each peptide for treating primary neurons. The neurons were for treated for a total of 6 hours. CPX was included as comparison. As shown in FIG. 29 none of the peptides significantly increase BDNF levels, however CP22 showed a trend to increase BDNF levels (p=0.13).

Example 29: Assessment of Different Lipidations for Activity

In further experiment in vitro efficacy of cyclic lipidated variant CLP12 to CLP15 was investigated.

Variant CLP12 is a cyclic sequence and features three E→D residue replacements at positions 3, 6 and 8 relative to CLP1.

Variant CLP13 is a cyclic sequence and features a C18-γGlu-OEG-OEG- lipid of which the diacid group on C18 have been removed relative to CLP1.

Variant CLP14 is a cyclic sequence and features a C14DA-γGlu-OEG-OEG lipid of which the chain length have been shortened to C14 relative to CLP1.

Variant CLP15 is a cyclic sequence and features a Cholesterol-OEG-OEG- lipid replacement relative to CLP1.

Figure 30:
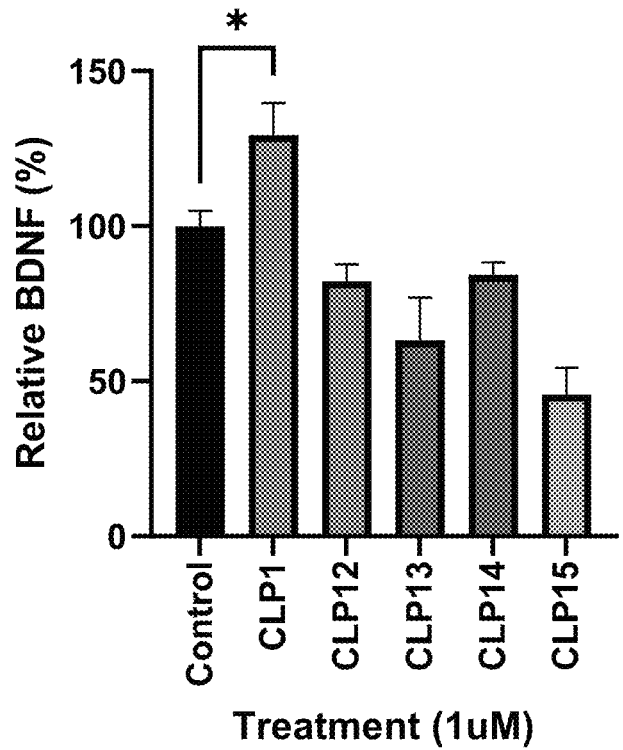
FIG. 30: Impact of different lipidations on activity (CLP12 to CLP15): BDNF levels of primary cortical neurons after treatment with lipidated cyclic peptides (CLP12 to CP15) compared to CLP1.

The experiment was carried out similarly to Example 3 using 1 uM final concentration of each peptide for treating primary neurons, however treating neurons for 24 hours. As shown in FIG. 30 none of the peptides significantly increased BDNF levels under the test conditions.

Example 30: CLP1 Increases GRN and Rescues Lysosomal Deficits in a GRN-Heterozygous Mouse Model of FTD CLP1 induces lysosomal biogenesis in vivo through TFEB upregulation and subsequent transcription of lysosomal proteins, such as GRN (Example 10). This provides a therapeutic rationale for using CLP1 in FTD patients with GRN-haploinsufficiency. To further assess the therapeutic effect of CLP1 within this patient-subgroup, we treated GRN-heterozygous mice over a 7-day period and evaluated both GRN-levels as well as lysosomal marker LAMP1 and the autophagosome cargo protein P62. Haploinsufficiency of GRN leads to lysosomal dysfunction and accumulation of lysosomal protein LAMP1 in FTD-TDP patients with GRN mutation (Götzl, 2014). Additionally, increased levels of P62 are observed in FTD patient-derived fibroblasts (Aoki, 2017) as well as in CSF of patients with FTD (Rubino, 2022) as a sign of defective autophagy.

GRN heterozygous (+/−) mice were generated by crossing B6(Cg)-Gmtm1.1Aidi/J (PGRN KO) mice with C57BL/J wild-type mice by The Jackson Laboratory. The GRN+/− mice (9-11 weeks of age) were injected once daily with 0.2 mg/kg of CLP1 subcutaneously in 4.38 mM L-His, 140 mM NaCl, 0.2% Tween-20 and 1500 IU hyaluronidase (pH 6.15). Wild-type mice were used as controls. 12-16 mice were included per condition (n=12-16). The mice were sacrificed at day 8, 24 hours after last injection. Cortical tissue was isolated and the tissue was lysed using a TissueLyser in RIPA lysis buffer containing cOmplete and phosSTOP. Levels of GRN, p62 and LAMP1 were validated by western blotting. All proteins were normalized to beta-actin levels.

Figure 31A:
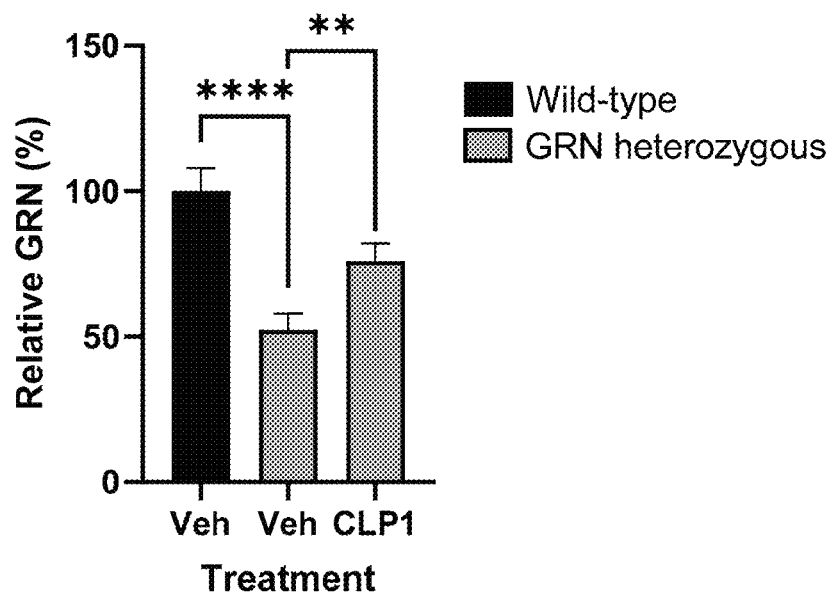
FIG. 31A to FIG. 31C: CLP1 increases GRN and rescues lysosomal deficits in a GRN-heterozygous mouse model of FTD: Daily subcutaneous administration of CLP1 (0.2 mg/kg) for 7 days in GRN heterozygous mice increases GRN levels (FIG. 31A) and normalises lysosomal proteins LAMP1 (FIG. 31B) and p62 (FIG. 31C).
Figure 31B:
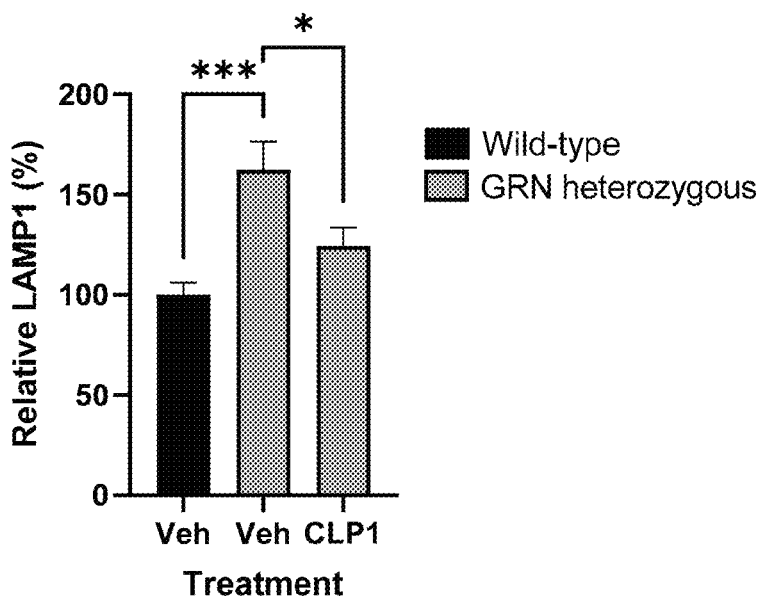
Figure 31C:
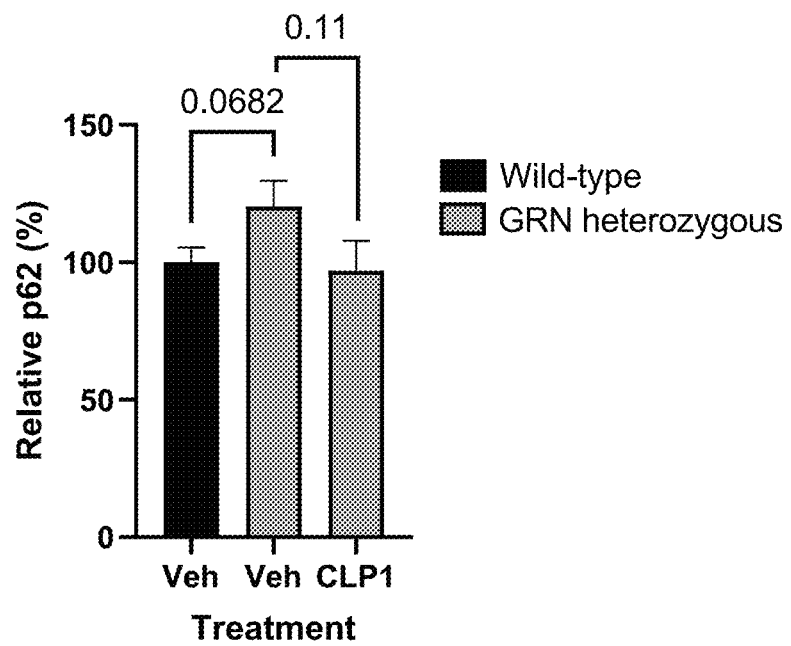

As shown in FIG. 31A to FIG. 31C, the GRN heterozygous (+/−) mice display 50% reduced GRN levels and treatment with CLP1 significantly increased the GRN levels by around 50% compared to vehicle-treated GRN+/− mice (p=0.0093). Likewise, the GRN heterozygous mice show increased levels of both LAMP1 (62%) and p62 (20%), shown in FIG. 31B and FIG. 31C respectively. Treatment with CLP1 showed a tendency to normalize p62-levels (p=0.1156), while reducing LAMP1-levels by 40% (p=0.0268). This demonstrates the therapeutic potential of increasing GRN levels by CLP1, which leads to a more functional lysosomal network resulting in normalized levels of lysosomal proteins.

Example 31: CLP1 Rescues Behavioral Phenotype in the Huntington's Disease Model zQ175

The purpose of the study was to measure the long-term effects of CPX and CLP1 on the zQ175DNs (zQ175DN KI, B6J.zQ175DN KI with ~CAG 190) mouse model of Huntington's disease (HD) (Menalled, 2003) using motoric testing and home cage analysis (HCA). The zQ175 mice have a mutant mouse/human chimeric protein expression in brain at similar levels of normal endogenous huntingtin protein. This generates a slow progression model, mimicking human disease progression with high mHTT levels at late stage (>1 year). Motor output parameters were related with functional and behavioural data generated from the HCA.

Animals

Altogether 60 zQ175DN mice (zQ175DN KI, B6J.zQ175DN KI with ~CAG 190) and 20 aged match wildtype (WT) littermates at the age of 2 months were received from CHDI Foundation, Inc. and were used for experiments. All mice were housed in a temperature (22±1° C.) and humidity (30-50%) controlled environment with a normal light-dark cycle (8:00-20:00). Clean bedding materials covering the floor of the cage were provided and changed as frequently as needed to maintain the bedding dry. This basic environment was enriched with the addition of play tunnels or igloos and wooden nesting material. Food and water were available ad libitum to the mice in their home cages.

Study and Group Information

The experimental animals were divided into 4 groups: WT+vehicle, zQ175+vehicle, zQ175+CPX (13 mg/kg), and zQ175+CLP1 (0.2 mg/kg) with 20 mice per group (n=20).

Treatments were administered via the subcutaneous (SC) route, once a day starting at 3 months of age and continuing until 12 months of age. Following injection, the injection site was monitored for irritation.

Body weight was measured every week starting at 3 months of age until the end of the study. Behavioural tests (rotarod and transverse beam tests) and HCA were performed at 3 (pre-treatment), 6, 9, and 12 months of age.

Rotarod

Mice were tested during the diurnal phase over 2 consecutive days at 3 (pre-treatment), 6, 9 and 12 months of age. Each daily session includes a training trial of 5 min at 4 RPM on the rotarod apparatus (AccuScan Instruments, Columbus, USA). One hour later, the animals were tested for 3 consecutive accelerating trials of 6 min with the speed changing from 0 to 40 RPM over 360 seconds and an inter-trial interval at least 30 min. The latency to fall from the rod is recorded. Mice remaining on the rod for more than 360 seconds were removed and their time scored as 360 seconds.

Transverse Beam Test

Mice were tested during the diurnal phase 3 (pre-treatment), 6, 9 and 12 months of age. The beam test was adapted from the procedure described by Fleming, 2004. Motor performance was measured with a novel beam test adapted from traditional beam-walking tests. The beam was constructed from Plexiglas and consisted of four sections (25 cm each, 1 m total length), each section having a different width. The beam started at a width of 3.5 cm and gradually narrowed to 0.5 in 1 cm increments. Underhanging ledges (1 cm width) were placed 1 cm below the upper surface of the beam. Animals were trained to traverse the length of the beam starting at the widest section and ending at the narrowest, most difficult section. The narrow end of the beam led directly into the animal's home cage. Animals received 2 days of training before testing, and all training was performed without the mesh grid. On the first day, animals received two assisted trials, which involved placing the animal on the beam and positioning the home cage in close proximity to the animal. This encourages forward movement along the beam. After two assisted trials, animals were able to traverse the entire length of the beam unassisted. Day one of training ended after all animals completed five unassisted runs across the entire length of the beam. On day 2 of training, animals were required to run five trials. To increase difficulty further, on the day of the test, a mesh grid (1 cm squares) of corresponding width was placed over the beam surface leaving a ~1 cm space between the grid and the beam surface. The underhanging ledges provided a support or "crutch" for the animal to use when a limb slipped on the grid and permits assessment of a deficit chronically so that the mice do not need to use compensatory motor strategies to complete the task. Animals were videotaped while traversing the grid-surfaced beam for a total of five trials.

Videotapes were viewed and rated in slow motion for errors, number of steps made by each animal, and time to traverse across five trials by an investigator blind to the treatment group. An error was counted when, during a forward movement, a limb (forelimb or hindlimb) slipped through the grid and was visible between the grid and the beam surface. An individual animal could make a maximum of four slips per step. By scoring each limb slip individually, the severity of the error could be measured. For instance, an animal that slipped with three limbs through the grid during a step received an error score of 3, whereas an animal that only slipped one limb through the grid during a step received an error score of 1 for that step. Slips were not counted if the animal was not making a forward movement or when the animal's head was oriented to the left or right of the beam. Error of steps and the time to traverse were measured for WT and zQ175 mice across all five trials and averaged.

Home Cage Analysis zQ175 and WT mice at the age of 2.5 months were placed in home cages at N=4/cage in random groups. RFID chips were introduced to each animal for the purposes of this monitoring. The home cage monitoring was performed on a 48-hour rotation at 3 (pre-treatment), 6, 9 and 12 months of age. All groups of mice (n=8 per group, n=4 per gender) were home cage monitored with ActualHCA™ devices for 48 hours per cage. The following parameters were measured: moving time, isolated time, peripheral time, in center zones time, climbing time, drinking time, moving speed, moving distance, isolation/separation distance, peripheral distance, in center zones distance and body temperature. The parameters measurements were first processed using the HCA software followed by data visualisation using Matlab software (USA).

Tissue Collection

Mice were terminated at the end of the study for tissue sample collection. The mice were first deeply anesthetized with terminal dose of Zoletil, and the cerebrospinal fluid (CSF) was collected from the cisterna magna into Eppendorf microtubes and were frozen on dry ice and stored at −80° C. Blood samples were collected by cardiac puncture. Whole blood was collected into heparin tubes, and plasma was separated by centrifugation (3000 rpm for 15 min) at 4° C. Separated plasma was collected in Eppendorf microtubes, frozen on dry ice and stored at −80° C.

Neuronal 4PlexA Measurements in CSF

Concentrations of glial fibrillary acidic protein (GFAP), tubulin associated unit (Tau), neurofilament light chain protein (Nf-L) and ubiquitin C-terminal hydrolase L1 (UCH-L1) in the CSF were determined using the Simoa Neuronal 4PlexA assay (cat #102153, Quanterix). Paramagnetic carboxylated beads (Quanterix Corp, Boston, MA, USA) were coated with mouse anti-GFAP, Tau, Nf-L or UCH-L1 antibody and incubated for 35 min with the sample and a biotinylated mouse anti-GFAP, Tau, Nf-L or UCH-L1 antibody in the Simoa instrument (Quanterix). The average number of enzymes per bead (AEB) of samples was interpolated onto the calibrator curve constructed by AEB measurements.

Results

Figure 32A:
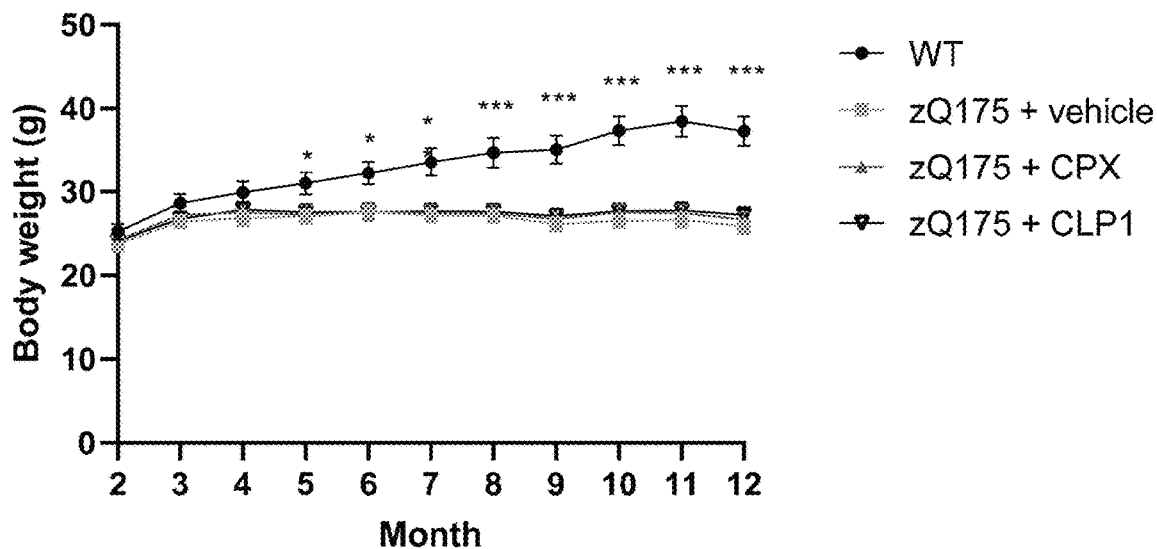
FIG. 32A to FIG. 32I: CLP1 rescues behavioral phenotype in the Huntington's Disease model zQ175: zQ175 mice display reduced bodyweight compared to wild-type littermates and treatment has no effect on bodyweight (FIG. 32A). Latency to fall in rotarod behavioral assessment throughout study (FIG. 32B). At 12 months of age, the latency to fall of the treatment groups (CPX and CLP1) trended higher compared with zQ175+vehicle. Number of errors made in Transverse beam test while traversing (FIG. 32C). CLP1 rescues number of errors made at 12 months of age, which is also significant compared to CPX-treated group. Principal component analysis plot of home-cage analysis data (FIG. 32D) and hierarchical dendrogram analysis (FIG. 32E) demonstrate rescue of behavioural phenotype in zQ175 HD mouse model by CLP1 treatment, whereas CPX treatment also leads to notable rescue. Individual behavior parameters for CPX and CLP1 (FIG. 32F and FIG. 32G respectively). zQ175 mice all display higher NfL levels in CSF and blood compared to WT (FIG. 32H and FIG. 32I) and treatment with CLP1 and CPX show a trend to decrease this.

While wild-type mice increased weight throughout the study, all zQ175 did not. No significant difference was observed between treated zQ175 mice and vehicle-treated zQ175 mice (FIG. 32A), showing that treatments does not affect weight in this HD model.

Figure 32B:
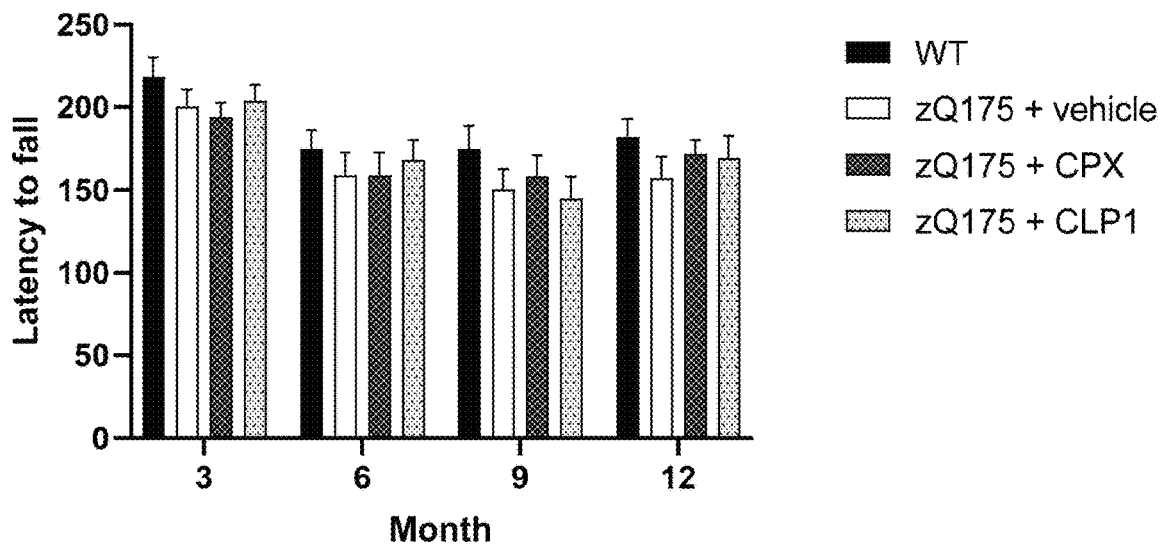

Latency to fall from rotarod generally decreased with increasing age in all groups (FIG. 32B). Latency to fall of vehicle-treated zQ175 trended lower compared with that of the WT control. At 12 months of age, the latency to fall of the treatment groups with CLP1 and CPX trended higher compared with vehicle-treated, but this was not statistically significant. However, this demonstrates a potential effect on motoric function of both CLP1 and CPX.

Figure 32C:
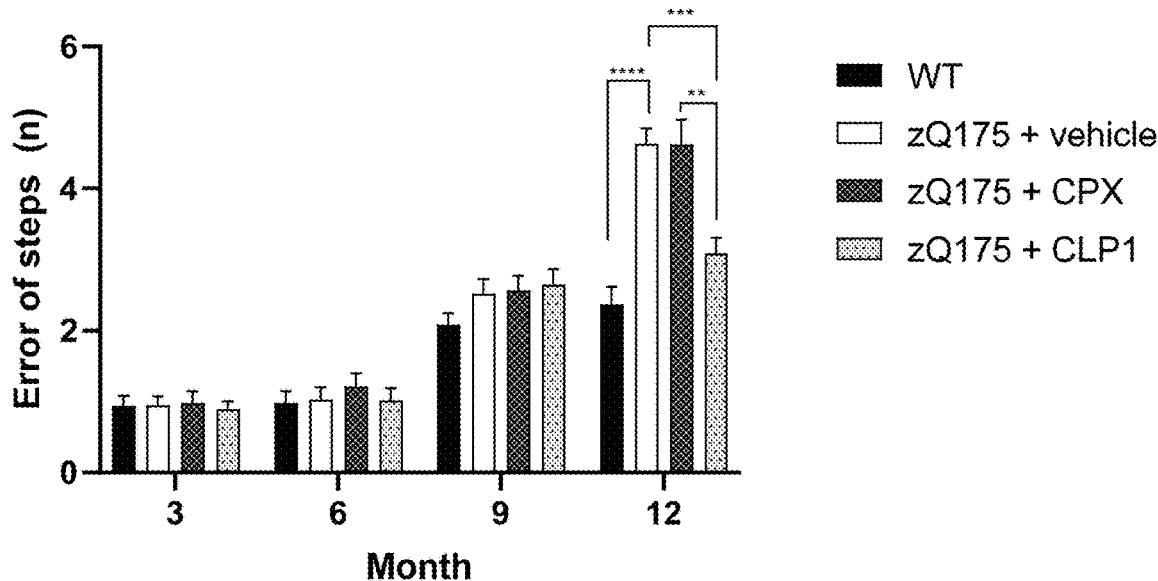

Number of errors made while traversing (transverse beam test, FIG. 32C) increased with increasing age after 9 months of age. Number of errors made by vehicle-treated and CPX-treated zQ175 mice sharply increased from 9 to 12 months of age and was significantly higher compared with WT. Number of errors of CLP1-treated zQ175 mice was not significantly different compared with WT at 12 months of age and demonstrated a complete rescue in this behavioural assessment. The test is very sensitive for demonstrating cortico-striatal function, the circuits underlying motor coordination and performance. This indicates a strong rescue of cortico-striatal pathology by CLP1 in HD disease, and may also be of relevance in other disorders.

Figure 32D:
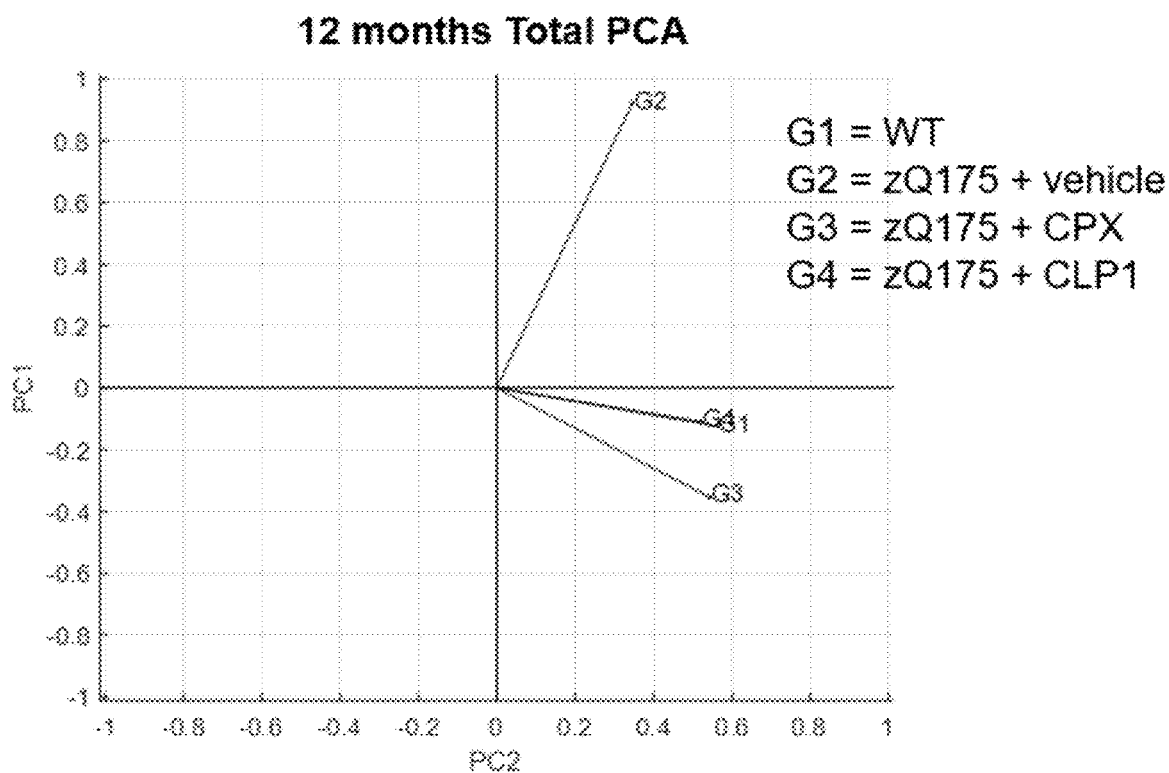
Figure 32E:
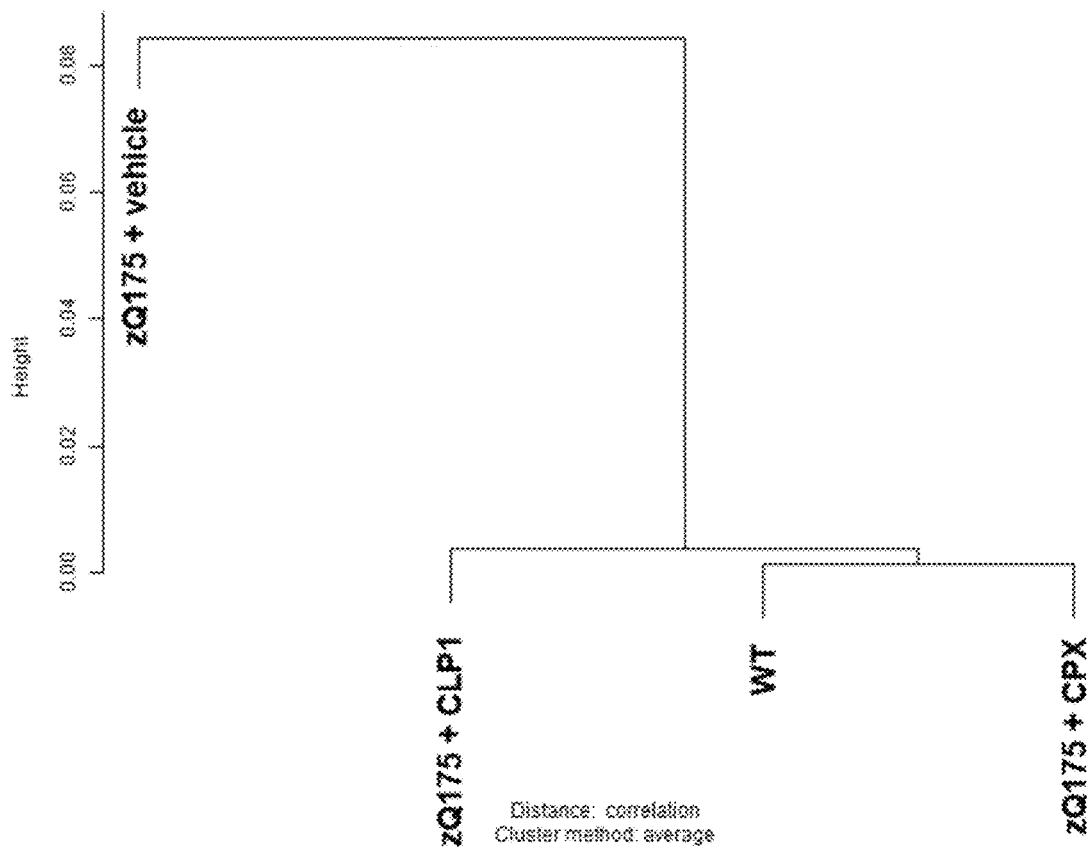

The multiple parameters measured in the Home-cage analysis (HCA) were used to construct a principal component analysis (PCA) (FIG. 32D) and the groups were clustered based on the hierarchical dendrogram analysis into WT-like or Knock-In (KI)-like phenotype (FIG. 32E) to provide a holistic summary of the HCA.

Figure 32F:
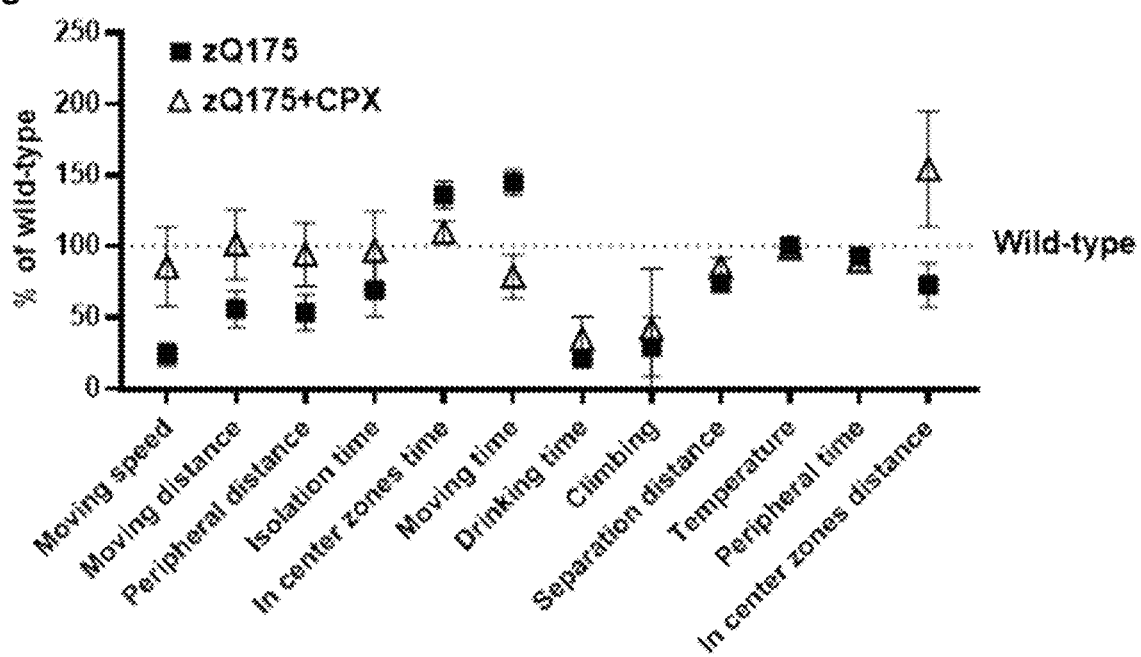
Figure 32G:
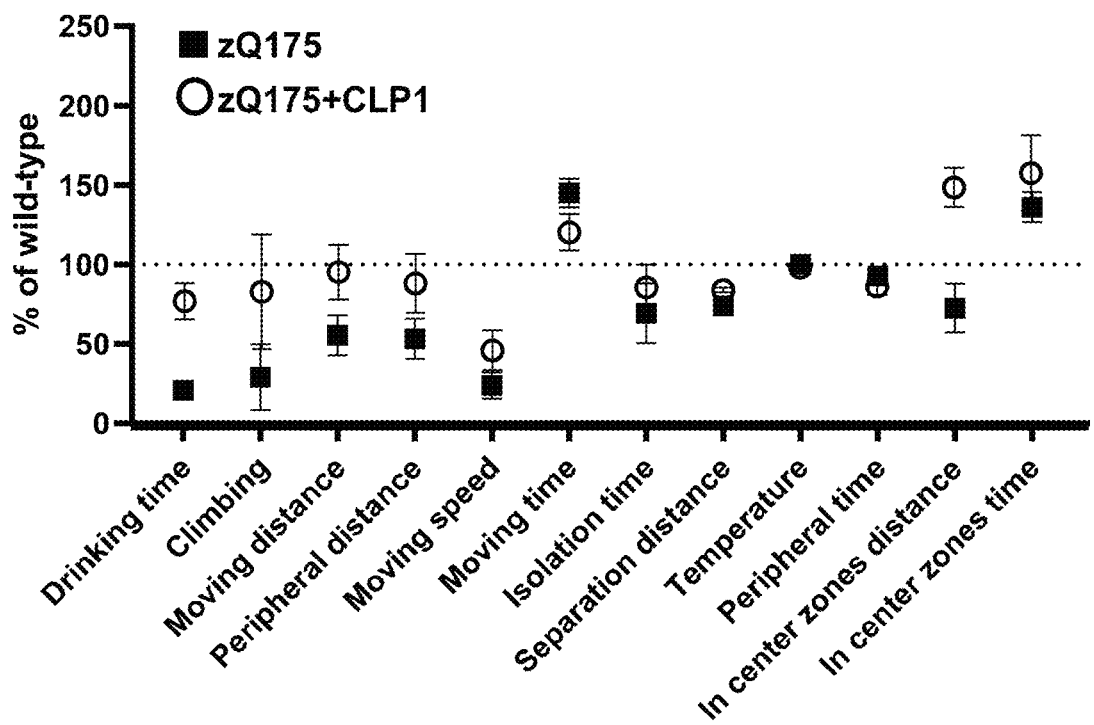

Based on the PCA, no notable pattern was observed until 12 months of age, at which vehicle-treated zQ175 mice clearly differentiated from both WT and CPX and CLP1-treated zQ175 mice. In the PCA, CLP1-treated zQ175 mice clustered on top of WT-mice showing a behavior identical to WT mice while CPX-treated zQ175 clustered very closely to WT mice suggesting almost identical behavior. Likewise, at 12 months of age, CPX and CLP1-treated zQ175 mice clustered with the WT control as WT-like phenotype in the hierarchical dendrogram analysis (p=0.01). Individual behavioral parameters for both CPX and CLP1 treated mice versus WT and zQ175-vehicle group is shown in FIG. 32F and FIG. 32G. In summary, treatment with CPX and CLP1 in HD mice completely rescued phenotype measured on 12 different behavioral parameters in the HCA, demonstrating a potent therapeutic effect by both CPX and CLP1 in this mouse model of HD.

Figure 32H:
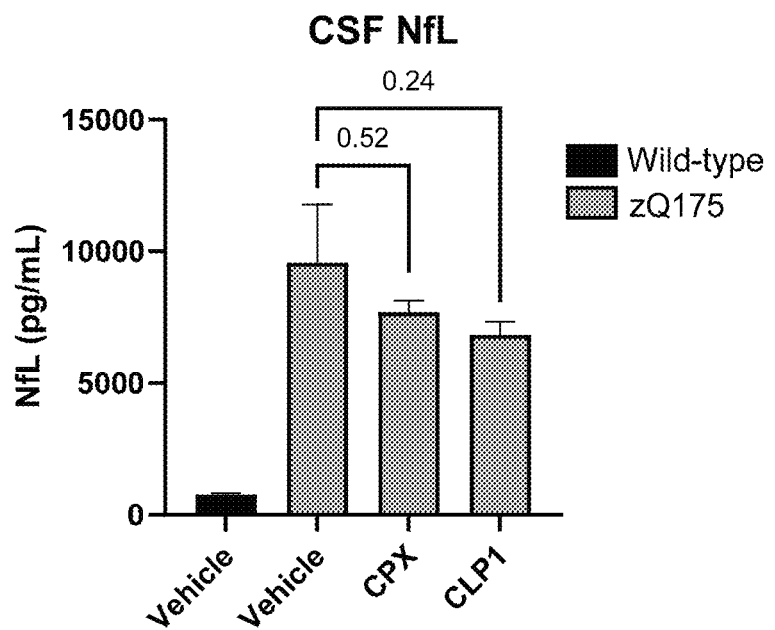
Figure 32I:
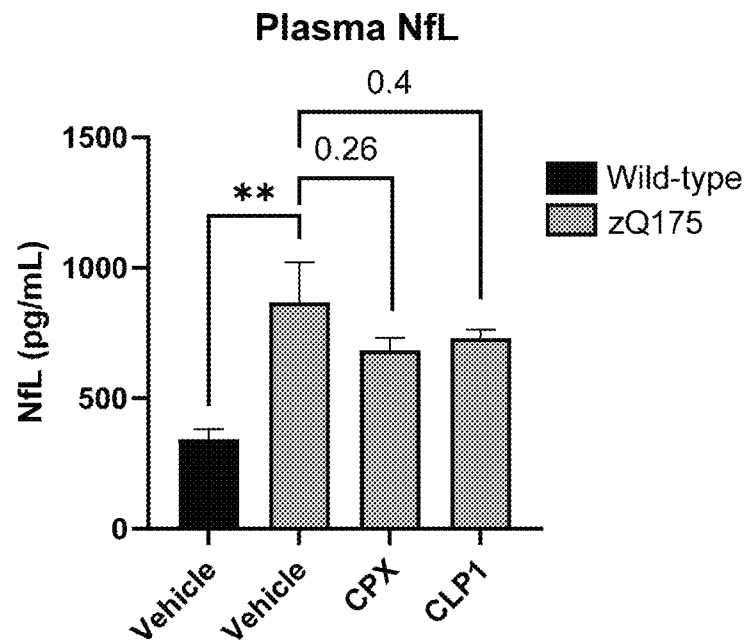

Finally, the concentration of Nf-L in the CSF was measured (FIG. 32H). NfL was significantly elevated in the zQ175 groups compared with the WT control group. However, NfL concentration of the treatment groups trended lower compared with vehicle-treated zQ175. NfL is a clinically validated biomarker of the CSF in HD patients. This demonstrates a potential for using NfL as a biomarker in humans to assess efficacy of CLP1 and CPX. No significant effect was observed on the other markers of GFAP, Tau and UCH-L1 (data not shown).

Example 32: CLP1 Increases GBA in Human IPSC-Derived Dopaminergic Neurons

GBA1 encodes a lysosomal protein important for degradation of lipids and turnover of cellular membranes—a vital function of lysosomes. Monoallelic mutations in GBA1 is found in 5-20% of sporadic PD cases making it the most common (known) genetic risk factor for PD. Mutations within GBA1 confers a 20- to 30-fold increased risk for the development of PD (Stoker, 2018). In addition, biallelic mutations in the GBA1 gene are known to cause the lysosomal disorder Gauchers Disease (GD). Interestingly, GBA1 mutations lead to protein-variants of GCase (protein product of GBA1 gene) that are more prone to degradation, loss of activity or mis-trafficking leading to depletion of GCase in the lysosomal compartment (Do, 2019).

TFEB has been shown to both promote the expression of GBA1, but also enhance folding and trafficking of GCase (Song, 2013). Thus, we evaluated whether treatment with CLP1 could increase GCase levels as a potential therapeutic approach to both GD and PD.

To assess this, human induced-pluripotent stem cells (DANi001-C) were reprogrammed and cultured as according to previous protocol (Chen, 2020). Culturing was continued for 95 days leading to differentiation of hIPSCs into midbrain dopaminergic neurons. On day 95, 6 of the neuronal organoids were treated with either vehicle or CLP1 (n=6) for 4 hours and subsequently lysed in RIPA buffer. TFEB and GBA levels were validated by western blotting using beta-actin as loading control.

Figure 33A:
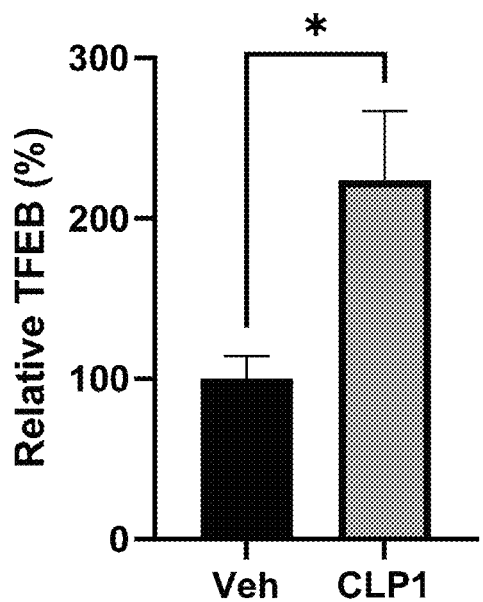
FIG. 33A and FIG. 33B: CLP1 increases GBA in human iPSC-derived dopaminergic neurons: TFEB and GCase levels in hIPSC-derived dopaminergic neurons following treatment with CLP1.
Figure 33B:
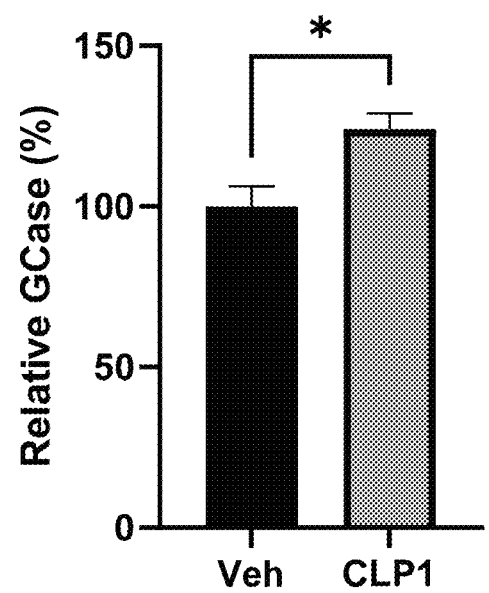

As shown in FIG. 33A, stimulation with CLP1 increases TFEB by 125% (p=0.02) also in FIG. 33B translating into a 25% increase in GCase levels (p=0.013). Taken together, this verify that CLP1 indeed display biological activity in human dopaminergic neurons (those affected in PD among others) in addition to adding to its therapeutic potential in PD patients with GBA1 mutations as well as patients suffering from GD.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims form part may be used as a basis for priority in respect of any subsequent application. The claims of such subsequent application may be directed to any feature or combination of features described herein. They may take the form of product, composition, process, or use claims and may include, by way of example and without limitation, the claims which follow.

BIBLIOGRAPHY

A User's Guide (Advances in Molecular Biology), Grant G. A. ed., Oxford University Press, 2002.
Adler, C. H. & Beach, T. G. Mov Disord 31, 1114-1119, doi:10.1002/mds.26605 (2016).
Alemany, S. et al. Am J Med Genet B Neuropsychiatr Genet 168, 459-470, doi:10.1002/ajmg.b.32341 (2015).
Aoki, Y et al. Brain 140(4):887-897 (2017).
Baum, A. E. et al. Mol Psychiatry 13, 197-207, doi:10.1038/sj.mp.4002012 (2008).
Beach, T. G. et al. Acta Neuropathol 117, 613-634, doi:10.1007/s00401-009-0538-8 (2009).
Beach, T. G. et al. Acta Neuropathol 119, 689-702, doi:10.1007/s00401-010-0664-3 (2010).
Bech, E et al., ACS Med. Chem. Lett. 2018, 9, 577-580.
Beel, S. et al. Mol Neurodegener 13, 55, doi:10.1186/s13024-018-0288-y (2018).
Benito, E. & Barco, A. Trends Neurosci 33, 230-240, doi:10.1016/j.tins.2010.02.001 (2010).
Boland, B. et al. Nat Rev Drug Discov 17, 660-688, doi:10.1038/nrd.2018.109 (2018).
Casarotto, P. C. et alCell 184, 1299-1313 e1219, doi:10.1016/j.cell.2021.01.034 (2021).
Chandrudu et al, Molecules 2013 18(4):4373-4388.
Chaturvedi, R. K. & Beal, M. F. Mol Cell Neurosci 55, 101-114, doi:10.1016/j.mcn.2012.11.011 (2013).
Chen, B. et al. L. T. Biol Psychiatry 50, 260-265, doi:10.1016/s0006-3223(01)01083-6 (2001).
Chen, M. et al. Christoforou, A. et al., Mol Psychiatry 16, 240-242 (2011), https://doi.org/10.1038/mp.2010.25
Conforti, P. et al. Gene Ther 20, 678-685, doi:10.1038/gt.2012.84 (2013).
Do, J. et al. Molecular Neurodegeneration volume 14, Article number: 36 (2019).
Dugovic, C. et al. Neuroreport 11, 627-631, doi:10.1097/00001756-200002280-00038 (2000).
Dwivedi, Y. et al. Arch Gen Psychiatry 60, 804-815, doi:10.1001/archpsyc.60.8.804 (2003).
Finkbeiner, S. et al. Neuron 19, 1031-1047, doi:10.1016/s0896-6273(00)80395-5 (1997).
Fleming, S. et al. Journal of Neuroscience 24(42)-9434-9440 (2004)
Ghosh, A. et al. J Biol Chem 290, 10309-10324, doi:10.1074/jbc.M114.610659 (2015).
Glerup, S. et al. Neuron. 2014 Jun. 4; 82(5):1074-87. doi:10.1016/j.neuron.2014.04.022.
Glerup, S. et al. Mol Psychiatry 21, 1740-1751, doi:10.1038/mp.2016.108 (2016).
Götzl, J. et al. Acta Neuropathologica 127:845-860 (2014).
Guilloux, J. P. et al. Mol Psychiatry 17, 1130-1142, doi:10.1038/mp.2011.113 (2012).
Hermey, G. et al. J Biol Chem 278, 7390-7396, doi:10.1074/jbc.M210851200 (2003).
Isidro-Llobet et al, Chem Rev 2009 109 2455-2504
Kang, H. et al. Oncotarget 8, 48603-48618, doi:10.18632/oncotarget.18122 (2017).

Kurtzhals, P. et al. Nature Reviews Drug Discovery 22:59-80 (2023).
Leloup, N. et al. Nat Commun 9, 2979, doi:10.1038/s41467-018-05405-z (2018).
Ljungberg, M. C. et al. Hum Mol Genet 21, 251-267, doi:10.1093/hmg/ddr492 (2012).
Lynch, M. R. et al. JCI Insight 5, doi:10.1172/jci.insight.142898 (2020).
Ma, Q. et al. JCI Insight 2, doi:10.1172/jci.insight.88995 (2017).
Malik, A. R. et al. Cell Rep 26, 2792-2804 e2796, doi:10.1016/j.celrep.2019.02.027 (2019).
Menalled, L. et al. J Comp Neurol. 465(1):11-26. (2003) doi:10.1002/cne.10776.
Miki, Y et al., Neuropathology, 38, 5, 2018 p 521-528.
Mo, F. et al. Neurosci Lett 608, 6-11, doi:10.1016/j.neulet.2015.09.030 (2015).
Naia, L. et al. Biochem Biophys Res Commun, 483, 1069-1077, doi:10.1016/j.bbrc.2016.07.122 (2017).
Oetjen, S. et al. J Comp Neurol 522, 3386-3402, doi:10.1002/cne.23606 (2014).
Oliveira, J. M. et al. J Neurochem 101, 241-249, doi:10.1111/j.1471-4159.2006.04361.x (2007).
Ollila, H. M. et al. Mol Psychiatry 14, 351-353, doi:10.1038/mp.2008.122 (2009).
Østergaard, S et al., Sci Reports, 2021, 11, 21179; doi.org/10.1038/s41598-021-00654-3.
Overstreet, D. H. Neurosci Biobehav Rev 17, 51-68, doi:10.1016/s0149-7634(05)80230-1 (1993).
Pharmaceutical Formulation: Development of Peptides and Proteins, Frokjaer and Hovgaard eds., Taylor and Francis, 1999.
Pinho, B. R. et al. Free Radic Biol Med 146, 372-382, doi:10.1016/j.freeradbiomed.2019.11.021 (2020).
Pugazhenthi, S. et al. Mol Neurodegen 6, 60, doi:10.1186/1750-1326-6-60 (2011).
Qin, Z. H. et al. J Neurosci 24, 269-281, doi:10.1523/JNEUROSCI.1409-03.2004 (2004).
Reitz, C et al. Transl Psychiatry. 2013 May 14; 3(5):e256. doi: 10.1038/tp.2013.13.
Richner, M. et al., Scandinavian Journal of Pain, vol. 3, no. 3, 2012, pp. 183-184, https://doi.org/10.1016/j.sjpain.2012.05.028.
Rubino, E. et al. Brain Sci 12(10):1414 (2022) doi:10.3390/brainsci12101414.
Sakamoto, K. et al. Neurochem 116, 1-9, doi:10.1111/j.1471-4159.2010.07080.x (2011).
Salaiovc et al., BioRxiv 2021.11.03.466767; doi: https://doi.org/10.1101/2021.11.03.466767.
Savas, J. N. et al. Neuron 87, 764-780, doi:10.1016/j.neuron.2015.08.007 (2015).
Sawa, A. J Mol Med (Berl) 79, 375-381, doi:10.1007/s001090100223 (2001).
Seth, J.et al. BMC Medical Genetics 20:31 (2019)
Shiromani, P. J. et al. Neuropsychopharmacology 1, 127-133, doi:10.1016/0893-133x(88)90004-8 (1988).
Shiromani, P. J. et al. Sleep 14, 116-120 (1991).
Song, W. et al. Human Molecular Genetics 22(10):1994-2009 (2013).
Stoker, B. Pathological Mechanisms and Clinical Aspects of GBA1 Mutation-Associated Parkinson's Disease in Pathological Mechanisms and Clinical Aspects of GBA1 Mutation-Associated Parkinson's Disease Stoker TB, Greenland JC, editors, Codon Publications 2018.
Strand, A. D. et al. J Neurosci 27, 11758-11768, doi:10.1523/JNEUROSCI.2461-07.2007 (2007).
Sugars, K. L. et al. J Biol Chem 279, 4988-4999, doi:10.1074/jbc.M310226200 (2004).
Tanaka, Y. et al. Neuroscience 250, 8-19, doi:10.1016/j.neuroscience.2013.06.049 (2013).
Tao, X. et al. Neuron 20, 709-726, doi:10.1016/s0896-6273(00)81010-7 (1998).
Thompson Ray, M. et al. J Psychiatry Neurosci 36, 195-203, doi:10.1503/jpn.100048 (2011).
van Swieten, J. C. & Heutink, P. Lancet Neurol 7, 965-974, doi:10.1016/S1474-4422(08)70194-7 (2008).
van Witteloostuijn, S et al., ChemMedChem, 2016, 11, 2474-2495.
Walton, M. R. & Dragunow, I. Trends Neurosci 23, 48-53, doi:10.1016/s0166-2236(99)01500-3 (2000).
Wong, Y. C. & Holzbaur, E. L. J Neurosci 34, 1293-1305, doi:10.1523/JNEUROSCI.1870-13.2014 (2014).
Wu, Z. et al. Proc Nati Acad Sci USA 103, 14379-14384, doi:10.1073/pnas.0606714103 (2006).
Yang J et al., Mol Psychiatry. 2021 March; 26(3):927-940. doi: 10.1038/s41380-020-0650-7. Epub 2020 Jan. 27. PMID: 31988435.
Zuccato, C. & Cattaneo, E. 81, 294-330, doi:10.1016/j.pneurobio.2007.01.003 (2007).
WO2017101956
WO2022029281

The invention claimed is:

1. A cyclic lipidated peptide:

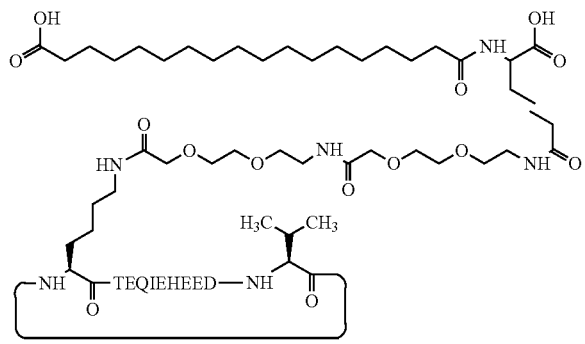

or a salt thereof.

2. The cyclic lipidated peptide according to claim 1.

3. The cyclic lipidated peptide or a salt thereof according to claim 1, wherein γGlu is L-γGlu.

4. The cyclic lipidated peptide or a salt thereof according to claim 1, wherein γGlu is D-γGlu.

5. The salt of the cyclic lipidated peptide according to claim 1.

6. The cyclic lipidated peptide or a salt thereof according to claim 5, wherein γGlu is L-γGlu.

7. The cyclic lipidated peptide or a salt thereof according to claim 5, wherein γGlu is D-γGlu.

8. The salt of the cyclic lipidated peptide according to claim 1, wherein the salt is a pharmaceutically acceptable salt.

9. The cyclic lipidated peptide or a salt thereof according to claim 8, wherein γGlu is L-γGlu.

10. The cyclic lipidated peptide or a salt thereof according to claim 8, wherein γGlu is D-γGlu.

11. A pharmaceutical composition comprising a cyclic lipidated peptide:

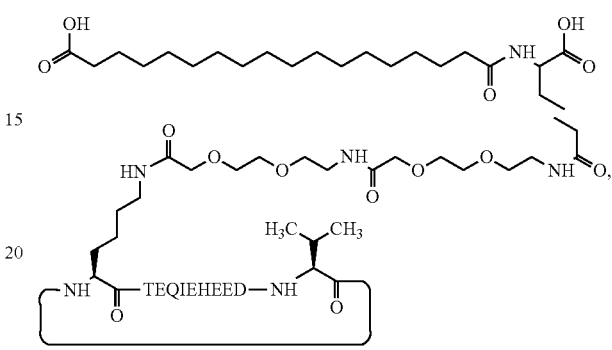

or a pharmaceutically acceptable salt thereof, and a pharmaceutically acceptable carrier.

12. The pharmaceutical composition according to claim 11, wherein γGlu is L-γGlu.

13. The pharmaceutical composition according to claim 11, wherein γGlu is D-γGlu.

* * * * *

SEQUENCE LISTING

```
Sequence total quantity: 63
SEQ ID NO: 1           moltype = AA  length = 11
FEATURE                Location/Qualifiers
REGION                 1..11
                       note = Lipidated cyclic peptide
LIPID                  1
                       note = C18DA-yGlu-OEG-OEG-
source                 1..11
                       mol_type = protein
                       organism = synthetic construct
SEQUENCE: 1
KTEQIEHEED V                                                            11

SEQ ID NO: 2           moltype = AA  length = 11
FEATURE                Location/Qualifiers
REGION                 1..11
                       note = Lipidated cyclic peptide
LIPID                  1
                       note = C18DA-yGlu-OEG-OEG-
source                 1..11
```

```
                         -continued
                    mol_type = protein
                    organism = synthetic construct
SEQUENCE: 2
KTEKVEHEED V                                                        11

SEQ ID NO: 3        moltype = AA   length = 11
FEATURE             Location/Qualifiers
REGION              1..11
                    note = Lipidated cyclic peptide
LIPID               1
                    note = C18DA-yGlu-OEG-OEG-
source              1..11
                    mol_type = protein
                    organism = synthetic construct
SEQUENCE: 3
KTEKIEHEED V                                                        11

SEQ ID NO: 4        moltype = AA   length = 11
FEATURE             Location/Qualifiers
REGION              1..11
                    note = Lipidated cyclic peptide
LIPID               1
                    note = C18DA-yGlu-OEG-OEG-
source              1..11
                    mol_type = protein
                    organism = synthetic construct
SEQUENCE: 4
KTEDVEHEED V                                                        11

SEQ ID NO: 5        moltype = AA   length = 11
FEATURE             Location/Qualifiers
REGION              1..11
                    note = Lipidated cyclic peptide
LIPID               1
                    note = C18DA-yGlu-OEG-OEG-
source              1..11
                    mol_type = protein
                    organism = synthetic construct
SEQUENCE: 5
KTEDIEHEED V                                                        11

SEQ ID NO: 6        moltype = AA   length = 11
FEATURE             Location/Qualifiers
REGION              1..11
                    note = Lipidated cyclic peptide
LIPID               1
                    note = C18DA-yGlu-OEG-OEG-
source              1..11
                    mol_type = protein
                    organism = synthetic construct
SEQUENCE: 6
KTEQVEHEED V                                                        11

SEQ ID NO: 7        moltype = AA   length = 11
FEATURE             Location/Qualifiers
REGION              1..11
                    note = Lipidated cyclic peptide
LIPID               4
                    note = C18DA-yGlu-OEG-OEG-
source              1..11
                    mol_type = protein
                    organism = synthetic construct
SEQUENCE: 7
KTEKVEHEED V                                                        11

SEQ ID NO: 8        moltype = AA   length = 11
FEATURE             Location/Qualifiers
REGION              1..11
                    note = Lipidated cyclic peptide
LIPID               4
                    note = C18DA-yGlu-OEG-OEG-
source              1..11
                    mol_type = protein
                    organism = synthetic construct
SEQUENCE: 8
KTEKIEHEED V                                                        11

SEQ ID NO: 9        moltype = AA   length = 11
FEATURE             Location/Qualifiers
```

```
REGION                  1..11
                        note = Lipidated cyclic peptide
LIPID                   4
                        note = C18DA-yGlu-OEG-OEG-
source                  1..11
                        mol_type = protein
                        organism = synthetic construct SEQUENCE: 9
MTEKVEHEED V                                                               11

SEQ ID NO: 10           moltype = AA   length = 11
FEATURE                 Location/Qualifiers
REGION                  1..11
                        note = Lipidated cyclic peptide
LIPID                   4
                        note = C18DA-yGlu-OEG-OEG-
source                  1..11
                        mol_type = protein
                        organism = synthetic construct SEQUENCE: 10
MTEKIEHEED V                                                               11

SEQ ID NO: 11           moltype = AA   length = 11
FEATURE                 Location/Qualifiers
REGION                  1..11
                        note = Lipidated cyclic peptide
LIPID                   1
                        note = C18DA-yGlu-OEG-OEG-
source                  1..11
                        mol_type = protein
                        organism = synthetic construct SEQUENCE: 11
KTEPVEHEED V                                                               11

SEQ ID NO: 12           moltype = AA   length = 11
FEATURE                 Location/Qualifiers
REGION                  1..11
                        note = Lipidated cyclic peptide
LIPID                   1
                        note = C18DA-yGlu-OEG-OEG-
source                  1..11
                        mol_type = protein
                        organism = synthetic construct SEQUENCE: 12
KTDPVDHDED V                                                               11

SEQ ID NO: 13           moltype = AA   length = 11
FEATURE                 Location/Qualifiers
REGION                  1..11
                        note = Lipidated cyclic peptide
LIPID                   1
                        note = C18-yGlu-OEG-OEG-
source                  1..11
                        mol_type = protein
                        organism = synthetic construct SEQUENCE: 13
KTEPVEHEED V                                                               11

SEQ ID NO: 14           moltype = AA   length = 11
FEATURE                 Location/Qualifiers
REGION                  1..11
                        note = Lipidated cyclic peptide
LIPID                   1
                        note = C14DA-yGlu-OEG-OEG-
source                  1..11
                        mol_type = protein
                        organism = synthetic construct SEQUENCE: 14
KTEPVEHEED V                                                               11

SEQ ID NO: 15           moltype = AA   length = 11
FEATURE                 Location/Qualifiers
REGION                  1..11
                        note = Lipidated cyclic peptide
LIPID                   1
                        note = Cholesterol-OEG-OEG-
source                  1..11
                        mol_type = protein
                        organism = synthetic construct
```

```
SEQUENCE: 15
KTEPVEHEED V                                                                                      11

SEQ ID NO: 16           moltype = AA  length = 11
FEATURE                 Location/Qualifiers
REGION                  1..11
                        note = Lipidated linear peptide
LIPID                   1
                        note = C18DA-yGlu-OEG-OEG-
MOD_RES                 1
                        note = ACETYLATION
MOD_RES                 11
                        note = AMIDATION
source                  1..11
                        mol_type = protein
                        organism = synthetic construct
SEQUENCE: 16
KTEKVEHEED V                                                                                      11

SEQ ID NO: 17           moltype = AA  length = 11
FEATURE                 Location/Qualifiers
REGION                  1..11
                        note = Lipidated linear peptide
LIPID                   1
                        note = C18DA-yGlu-OEG-OEG-
MOD_RES                 1
                        note = ACETYLATION
MOD_RES                 11
                        note = AMIDATION
source                  1..11
                        mol_type = protein
                        organism = synthetic construct
SEQUENCE: 17
KTEKIEHEED V                                                                                      11

SEQ ID NO: 18           moltype = AA  length = 11
FEATURE                 Location/Qualifiers
REGION                  1..11
                        note = Lipidated linear peptide
LIPID                   1
                        note = C18DA-yGlu-OEG-OEG-
MOD_RES                 1
                        note = ACETYLATION
MOD_RES                 11
                        note = AMIDATION
source                  1..11
                        mol_type = protein
                        organism = synthetic construct
SEQUENCE: 18
KTEDVEHEED V                                                                                      11

SEQ ID NO: 19           moltype = AA  length = 11
FEATURE                 Location/Qualifiers
REGION                  1..11
                        note = Lipidated linear peptide
LIPID                   1
                        note = C18DA-yGlu-OEG-OEG-
MOD_RES                 1
                        note = ACETYLATION
MOD_RES                 11
                        note = AMIDATION
source                  1..11
                        mol_type = protein
                        organism = synthetic construct
SEQUENCE: 19
KTEDIEHEED V                                                                                      11

SEQ ID NO: 20           moltype = AA  length = 11
FEATURE                 Location/Qualifiers
REGION                  1..11
                        note = Lipidated linear peptide
LIPID                   1
                        note = C18DA-yGlu-OEG-OEG-
MOD_RES                 1
                        note = ACETYLATION
MOD_RES                 11
                        note = AMIDATION
source                  1..11
                        mol_type = protein
```

```
                        organism = synthetic construct
SEQUENCE: 20
KTEQVEHEED V                                                                        11

SEQ ID NO: 21           moltype = AA   length = 11
FEATURE                 Location/Qualifiers
REGION                  1..11
                        note = Lipidated linear peptide
LIPID                   1
                        note = C18DA-yGlu-OEG-OEG-
MOD_RES                 1
                        note = ACETYLATION
MOD_RES                 11
                        note = AMIDATION
source                  1..11
                        mol_type = protein
                        organism = synthetic construct
SEQUENCE: 21
KTEQIEHEED V                                                                        11

SEQ ID NO: 22           moltype = AA   length = 11
FEATURE                 Location/Qualifiers
REGION                  1..11
                        note = Lipidated linear peptide
MOD_RES                 1
                        note = ACETYLATION
LIPID                   4
                        note = C18DA-yGlu-OEG-OEG-
MOD_RES                 11
                        note = AMIDATION
source                  1..11
                        mol_type = protein
                        organism = synthetic construct
SEQUENCE: 22
KTEKVEHEED V                                                                        11

SEQ ID NO: 23           moltype = AA   length = 11
FEATURE                 Location/Qualifiers
REGION                  1..11
                        note = Lipidated linear peptide
MOD_RES                 1
                        note = ACETYLATION
LIPID                   4
                        note = C18DA-yGlu-OEG-OEG-
MOD_RES                 11
                        note = AMIDATION
source                  1..11
                        mol_type = protein
                        organism = synthetic construct
SEQUENCE: 23
KTEKIEHEED V                                                                        11

SEQ ID NO: 24           moltype = AA   length = 11
FEATURE                 Location/Qualifiers
REGION                  1..11
                        note = Lipidated linear peptide
MOD_RES                 1
                        note = ACETYLATION
LIPID                   4
                        note = C18DA-yGlu-OEG-OEG-
MOD_RES                 11
                        note = AMIDATION
source                  1..11
                        mol_type = protein
                        organism = synthetic construct
SEQUENCE: 24
MTEKVEHEED V                                                                        11

SEQ ID NO: 25           moltype = AA   length = 11
FEATURE                 Location/Qualifiers
REGION                  1..11
                        note = Lipidated linear peptide
MOD_RES                 1
                        note = ACETYLATION
LIPID                   4
                        note = C18DA-yGlu-OEG-OEG-
MOD_RES                 11
                        note = AMIDATION
source                  1..11
```

```
                        mol_type = protein
                        organism = synthetic construct
SEQUENCE: 25
MTEKIEHEED V                                                              11

SEQ ID NO: 26           moltype = AA   length = 11
FEATURE                 Location/Qualifiers
REGION                  1..11
                        note = Lipidated linear peptide
LIPID                   1
                        note = C18DA-yGlu-OEG-OEG-
MOD_RES                 1
                        note = ACETYLATION
MOD_RES                 11
                        note = AMIDATION
source                  1..11
                        mol_type = protein
                        organism = synthetic construct
SEQUENCE: 26
KTEPVEHEED V                                                              11

SEQ ID NO: 27           moltype = AA   length = 15
FEATURE                 Location/Qualifiers
REGION                  1..15
                        note = Lipidated linear peptide
LIPID                   1
                        note = C18DA-yGlu-OEG-OEG-
MOD_RES                 15
                        note = AMIDATION
source                  1..15
                        mol_type = protein
                        organism = synthetic construct
SEQUENCE: 27
KEQEMTEPVE HEEDV                                                          15

SEQ ID NO: 28           moltype = AA   length = 11
FEATURE                 Location/Qualifiers
REGION                  1..11
                        note = Cyclic peptide
source                  1..11
                        mol_type = protein
                        organism = synthetic construct
SEQUENCE: 28
MTEPIEHEED V                                                              11

SEQ ID NO: 29           moltype = AA   length = 11
FEATURE                 Location/Qualifiers
REGION                  1..11
                        note = Cyclic peptide
source                  1..11
                        mol_type = protein
                        organism = synthetic construct
SEQUENCE: 29
MTEPLEHEED V                                                              11

SEQ ID NO: 30           moltype = AA   length = 11
FEATURE                 Location/Qualifiers
REGION                  1..11
                        note = Cyclic peptide
source                  1..11
                        mol_type = protein
                        organism = synthetic construct
SEQUENCE: 30
MTEPAEHEED V                                                              11

SEQ ID NO: 31           moltype = AA   length = 11
FEATURE                 Location/Qualifiers
REGION                  1..11
                        note = Cyclic peptide
source                  1..11
                        mol_type = protein
                        organism = synthetic construct
SEQUENCE: 31
MTEPTEHEED V                                                              11

SEQ ID NO: 32           moltype = AA   length = 11
FEATURE                 Location/Qualifiers
REGION                  1..11
                        note = Cyclic peptide
```

```
source                      1..11
                            mol_type = protein
                            organism = synthetic construct
SEQUENCE: 32
MTEGVHEED V                                                                     11

SEQ ID NO: 33               moltype = AA   length = 11
FEATURE                     Location/Qualifiers
REGION                      1..11
                            note = Cyclic peptide
source                      1..11
                            mol_type = protein
                            organism = synthetic construct
SEQUENCE: 33
MTEDVHEED V                                                                     11

SEQ ID NO: 34               moltype = AA   length = 11
FEATURE                     Location/Qualifiers
REGION                      1..11
                            note = Cyclic peptide
source                      1..11
                            mol_type = protein
                            organism = synthetic construct
SEQUENCE: 34
MTEKVHEED V                                                                     11

SEQ ID NO: 35               moltype = AA   length = 11
FEATURE                     Location/Qualifiers
REGION                      1..11
                            note = Cyclic peptide
source                      1..11
                            mol_type = protein
                            organism = synthetic construct
SEQUENCE: 35
MTEQVHEED V                                                                     11

SEQ ID NO: 36               moltype = AA   length = 11
FEATURE                     Location/Qualifiers
REGION                      1..11
                            note = Cyclic peptide
source                      1..11
                            mol_type = protein
                            organism = synthetic construct
SEQUENCE: 36
MTEQIHEED V                                                                     11

SEQ ID NO: 37               moltype = AA   length = 11
FEATURE                     Location/Qualifiers
REGION                      1..11
                            note = Cyclic peptide
source                      1..11
                            mol_type = protein
                            organism = synthetic construct
SEQUENCE: 37
MTEDIHEED V                                                                     11

SEQ ID NO: 38               moltype = AA   length = 11
FEATURE                     Location/Qualifiers
REGION                      1..11
                            note = Cyclic peptide
source                      1..11
                            mol_type = protein
                            organism = synthetic construct
SEQUENCE: 38
MTEQLHEED V                                                                     11

SEQ ID NO: 39               moltype = AA   length = 11
FEATURE                     Location/Qualifiers
REGION                      1..11
                            note = Cyclic peptide
source                      1..11
                            mol_type = protein
                            organism = synthetic construct
SEQUENCE: 39
MTEDLHEED V                                                                     11

SEQ ID NO: 40               moltype = AA   length = 9
FEATURE                     Location/Qualifiers
REGION                      1..9
```

```
                        note = Cyclic peptide
source                  1..9
                        mol_type = protein
                        organism = synthetic construct
SEQUENCE: 40
TEPVEHEED                                                                  9

SEQ ID NO: 41           moltype = AA  length = 8
FEATURE                 Location/Qualifiers
REGION                  1..8
                        note = Cyclic peptide
source                  1..8
                        mol_type = protein
                        organism = synthetic construct
SEQUENCE: 41
TEPVEHEE                                                                   8

SEQ ID NO: 42           moltype = AA  length = 7
FEATURE                 Location/Qualifiers
REGION                  1..7
                        note = Cyclic peptide
source                  1..7
                        mol_type = protein
                        organism = synthetic construct
SEQUENCE: 42
EPVEHEE                                                                    7

SEQ ID NO: 43           moltype = AA  length = 6
FEATURE                 Location/Qualifiers
REGION                  1..6
                        note = Cyclic peptide
source                  1..6
                        mol_type = protein
                        organism = synthetic construct
SEQUENCE: 43
EPVEHE                                                                     6

SEQ ID NO: 44           moltype = AA  length = 5
FEATURE                 Location/Qualifiers
REGION                  1..5
                        note = Cyclic peptide
source                  1..5
                        mol_type = protein
                        organism = synthetic construct
SEQUENCE: 44
PVEHE                                                                      5

SEQ ID NO: 45           moltype = AA  length = 11
FEATURE                 Location/Qualifiers
REGION                  1..11
                        note = Cyclic peptide
source                  1..11
                        mol_type = protein
                        organism = synthetic construct
SEQUENCE: 45
MTEPVDHDED V                                                              11

SEQ ID NO: 46           moltype = AA  length = 11
FEATURE                 Location/Qualifiers
REGION                  1..11
                        note = Cyclic peptide
source                  1..11
                        mol_type = protein
                        organism = synthetic construct
SEQUENCE: 46
MTDPVDHEED V                                                              11

SEQ ID NO: 47           moltype = AA  length = 11
FEATURE                 Location/Qualifiers
REGION                  1..11
                        note = Cyclic peptide
source                  1..11
                        mol_type = protein
                        organism = synthetic construct
SEQUENCE: 47
MTAPVEHEED V                                                              11

SEQ ID NO: 48           moltype = AA  length = 11
FEATURE                 Location/Qualifiers
```

```
REGION                  1..11
                        note = Cyclic peptide
source                  1..11
                        mol_type = protein
                        organism = synthetic construct
SEQUENCE: 48
MTEPVAHEED V                                                                   11

SEQ ID NO: 49           moltype = AA  length = 11
FEATURE                 Location/Qualifiers
REGION                  1..11
                        note = Cyclic peptide
source                  1..11
                        mol_type = protein
                        organism = synthetic construct
SEQUENCE: 49
MTEPVEHAED V                                                                   11

SEQ ID NO: 50           moltype = AA  length = 11
FEATURE                 Location/Qualifiers
source                  1..11
                        mol_type = protein
                        organism = Homo sapiens
SEQUENCE: 50
MTSPVSHSED V                                                                   11

SEQ ID NO: 51           moltype =   length =
SEQUENCE: 51
000

SEQ ID NO: 52           moltype = AA  length = 7
FEATURE                 Location/Qualifiers
REGION                  1..7
                        note = Variable peptide sequence 2
VARIANT                 2
                        note = Xaa is selected from Pro, Asp, Gln, Lys and Gly
VARIANT                 3
                        note = Xaa is selected from Ile, Leu, Ala, Thr and Val
VARIANT                 6
                        note = Xaa is selected from Glu and Ala
source                  1..7
                        mol_type = protein
                        organism = synthetic construct
SEQUENCE: 52
EXXEHXE                                                                        7

SEQ ID NO: 53           moltype = AA  length = 7
FEATURE                 Location/Qualifiers
REGION                  1..7
                        note = Variable peptide sequence 3
VARIANT                 1
                        note = Xaa is selected from Pro, Asp, Gln, Lys and Gly
VARIANT                 2
                        note = Xaa is selected from Ile, Leu, Ala, Thr and Val
VARIANT                 5
                        note = Xaa is selected from Glu and Ala
source                  1..7
                        mol_type = protein
                        organism = synthetic construct
SEQUENCE: 53
XXEHXED                                                                        7

SEQ ID NO: 54           moltype = AA  length = 8
FEATURE                 Location/Qualifiers
REGION                  1..8
                        note = Variable peptide sequence 4
VARIANT                 3
                        note = Xaa is selected from Pro, Asp, Gln, Lys and Gly
VARIANT                 4
                        note = Xaa is selected from Ile, Leu, Ala, Thr and Val
VARIANT                 7
                        note = Xaa is selected from Glu and Ala
source                  1..8
                        mol_type = protein
                        organism = synthetic construct
SEQUENCE: 54
TEXXEHXE                                                                       8

SEQ ID NO: 55           moltype = AA  length = 8
```

```
FEATURE                 Location/Qualifiers
REGION                  1..8
                        note = Variable peptide sequence 5
VARIANT                 2
                        note = Xaa is selected from Pro, Asp, Gln, Lys and Gly
VARIANT                 3
                        note = Xaa is selected from Ile, Leu, Ala, Thr and Val
VARIANT                 6
                        note = Xaa is selected from Glu and Ala
source                  1..8
                        mol_type = protein
                        organism = synthetic construct
SEQUENCE: 55
EXXEHXED                                                                      8

SEQ ID NO: 56           moltype = AA  length = 8
FEATURE                 Location/Qualifiers
REGION                  1..8
                        note = Variable peptide sequence 6
VARIANT                 1
                        note = Xaa is selected from Pro, Asp, Gln, Lys and Gly
VARIANT                 2
                        note = Xaa is selected from Ile, Leu, Ala, Thr and Val
VARIANT                 5
                        note = Xaa is selected from Glu and Ala
source                  1..8
                        mol_type = protein
                        organism = synthetic construct
SEQUENCE: 56
XXEHXEDV                                                                      8

SEQ ID NO: 57           moltype = AA  length = 9
FEATURE                 Location/Qualifiers
REGION                  1..9
                        note = Variable peptide sequence 7
VARIANT                 1
                        note = Xaa is selected from Met and Lys
VARIANT                 4
                        note = Xaa is selected from Pro, Asp, Gln, Lys and Gly
VARIANT                 5
                        note = Xaa is selected from Ile, Leu, Ala, Thr and Val
VARIANT                 8
                        note = Xaa is selected from Glu and Ala
source                  1..9
                        mol_type = protein
                        organism = synthetic construct
SEQUENCE: 57
XTEXXEHXE                                                                     9

SEQ ID NO: 58           moltype = AA  length = 9
FEATURE                 Location/Qualifiers
REGION                  1..9
                        note = Variable peptide sequence 8
VARIANT                 3
                        note = Xaa is selected from Pro, Asp, Gln, Lys and Gly
VARIANT                 4
                        note = Xaa is selected from Ile, Leu, Ala, Thr and Val
VARIANT                 7
                        note = Xaa is selected from Glu and Ala
source                  1..9
                        mol_type = protein
                        organism = synthetic construct
SEQUENCE: 58
TEXXEHXED                                                                     9

SEQ ID NO: 59           moltype = AA  length = 9
FEATURE                 Location/Qualifiers
REGION                  1..9
                        note = Variable peptide sequence 9
VARIANT                 2
                        note = Xaa is selected from Pro, Asp, Gln, Lys and Gly
VARIANT                 3
                        note = Xaa is selected from Ile, Leu, Ala, Thr and Val
VARIANT                 6
                        note = Xaa is selected from Glu and Ala
source                  1..9
                        mol_type = protein
                        organism = synthetic construct
SEQUENCE: 59
```

```
EXXEHXEDV                                                                      9

SEQ ID NO: 60           moltype = AA  length = 10
FEATURE                 Location/Qualifiers
REGION                  1..10
                        note = Variable peptide sequence 10
VARIANT                 1
                        note = Xaa is selected from Met and Lys
VARIANT                 4
                        note = Xaa is selected from Pro, Asp, Gln, Lys and Gly
VARIANT                 5
                        note = Xaa is selected from Ile, Leu, Ala, Thr and Val
VARIANT                 8
                        note = Xaa is selected from Glu and Ala
source                  1..10
                        mol_type = protein
                        organism = synthetic construct
SEQUENCE: 60
XTEXXEHXED                                                                     10

SEQ ID NO: 61           moltype = AA  length = 10
FEATURE                 Location/Qualifiers
REGION                  1..10
                        note = Variable peptide sequence 11
VARIANT                 3
                        note = Xaa is selected from Pro, Asp, Gln, Lys and Gly
VARIANT                 4
                        note = Xaa is selected from Ile, Leu, Ala, Thr and Val
VARIANT                 7
                        note = Xaa is selected from Glu and Ala
source                  1..10
                        mol_type = protein
                        organism = synthetic construct
SEQUENCE: 61
TEXXEHXEDV                                                                     10

SEQ ID NO: 62           moltype = AA  length = 11
FEATURE                 Location/Qualifiers
REGION                  1..11
                        note = Variable peptide sequence 12
VARIANT                 1
                        note = Xaa is selected from Met and Lys
VARIANT                 4
                        note = Xaa is selected from Pro, Asp, Gln, Lys and Gly
VARIANT                 5
                        note = Xaa is selected from Ile, Leu, Ala, Thr and Val
VARIANT                 8
                        note = Xaa is selected from Glu and Ala
source                  1..11
                        mol_type = protein
                        organism = synthetic construct
SEQUENCE: 62
XTEXXEHXED V                                                                   11

SEQ ID NO: 63           moltype = AA  length = 11
FEATURE                 Location/Qualifiers
REGION                  1..11
                        note = Cyclic peptide CPX
source                  1..11
                        mol_type = protein
                        organism = synthetic construct
SEQUENCE: 63
MTEPVEHEED V                                                                   11
```